US010485811B2

(12) United States Patent
Bouckaert et al.

(10) Patent No.: US 10,485,811 B2
(45) Date of Patent: Nov. 26, 2019

(54) ORALLY AVAILABLE COMPOUNDS, A PROCESS FOR PREPARING THE SAME AND THEIR USES AS ANTI-ADHESIVE DRUGS FOR TREATING *E. COLI* INDUCED INFLAMMATORY BOWEL DISEASES SUCH AS CROHN'S DISEASE

(71) Applicants: CENTRE NATIONAL DE LA RECHERCHE SCIENTIFIQUE, Paris (FR); UNIVERSITE D'AUVERGNE, Villeneuve d'Ascq (FR); UNIVERSITE DES SCIENCES ET TECHNOLOGIES DE LILLE 1, Villeneuve d'Ascq (FR); UNIVERSITE DE NANTES, Nantes (FR); INSERM INSTITUT NATIONAL DE LA SANTE ET DE LA RECHERCHE MEDICALE, Paris (FR); Jean-Eric Michaud, La Roche-Blanche (FR); Pierre-Yohan Michaud, Lannion (FR); Vincent Michaud, Bordeaux (FR)

(72) Inventors: Julie Bouckaert, Kortrijk (BE); Sebastien Gouin, Thouare sur Loire (FR); Adeline Sivignon, Gerzat (FR); Arlette Darfeuille-Michaud, La Roche-Blanche (FR); Rostyslav Bilyy, Lviv (UA); Dimitri Alvarez-Dorta, Nantes (FR); Nao Yamakawa, Haubourdin (FR); Tetiana Dumych, Volyn Oblast (UA)

(73) Assignees: CENTRE NATIONAL DE LA RECHERCHE SCIENTIFIQUE, Paris (FR); UNIVERSITE D'AUVERGNE, Clermont-Ferrand (FR); UNIVERSITE DES SCIENCES ET TECHNOLOGIES DE LILLE 1, Villeneuve d'Ascq (FR); UNIVERSITE DE NANTES, Nantes (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 281 days.

(21) Appl. No.: 15/113,986

(22) PCT Filed: Jan. 23, 2015

(86) PCT No.: PCT/EP2015/051415
§ 371 (c)(1),
(2) Date: Jul. 25, 2016

(87) PCT Pub. No.: WO2015/110609
PCT Pub. Date: Jul. 30, 2015

(65) Prior Publication Data
US 2016/0340445 A1  Nov. 24, 2016

(30) Foreign Application Priority Data

Jan. 24, 2014  (EP) .................................... 14305107

(51) Int. Cl.
| C07H 15/00 | (2006.01) |
| A61K 31/7028 | (2006.01) |
| A61K 31/7056 | (2006.01) |
| A61K 31/706 | (2006.01) |
| A61K 31/724 | (2006.01) |
| C07H 15/04 | (2006.01) |
| A61K 31/7004 | (2006.01) |
| C07H 15/14 | (2006.01) |
| C07H 15/26 | (2006.01) |
| A61K 31/7064 | (2006.01) |
| A61K 31/70 | (2006.01) |
| A61K 45/06 | (2006.01) |
| C08B 37/16 | (2006.01) |
| C08L 5/16 | (2006.01) |

(Continued)

(52) U.S. Cl.
CPC ............ *A61K 31/70* (2013.01); *A61K 9/0053* (2013.01); *A61K 31/7004* (2013.01); *A61K 31/706* (2013.01); *A61K 31/7028* (2013.01); *A61K 31/7056* (2013.01); *A61K 31/7064* (2013.01); *A61K 31/724* (2013.01); *A61K 45/06* (2013.01); *A61K 47/549* (2017.08); *C07D 309/10* (2013.01); *C07D 309/14* (2013.01); *C07D 405/12* (2013.01); *C07D 405/14* (2013.01); *C07H 7/02* (2013.01); *C07H 15/00* (2013.01); *C07H 15/04* (2013.01); *C07H 15/14* (2013.01); *C07H 15/26* (2013.01); *C08B 37/0012* (2013.01); *C08B 37/0015* (2013.01); *C08L 5/16* (2013.01)

(58) Field of Classification Search
None
See application file for complete search history.

(56) References Cited

FOREIGN PATENT DOCUMENTS

EP      2 377 883 A1    10/2011

OTHER PUBLICATIONS

Gouin, S. G., Wellens, A., Bouckaert, J., & Kovensky, J. (2009). Synthetic multimeric heptyl mannosides as potent antiadhesives of uropathogenic *Escherichia coli*. ChemMedChem, 4(5), 749-755. (Year: 2009).*

(Continued)

*Primary Examiner* — Dale R Miller
(74) *Attorney, Agent, or Firm* — Young & Thompson

(57) ABSTRACT

Orally available compounds, a process for preparing the same and their uses as anti-adhesive drugs for treating *E. coli* induced inflammatory bowel diseases such as crohn's disease.

5 Claims, 9 Drawing Sheets

(51) Int. Cl.
   *A61K 9/00*    (2006.01)
   *C07H 7/02*    (2006.01)
   *C07D 405/14*  (2006.01)
   *C07D 309/10*  (2006.01)
   *C07D 309/14*  (2006.01)
   *C07D 405/12*  (2006.01)
   *A61K 47/54*   (2017.01)

(56) References Cited

OTHER PUBLICATIONS

Ichikawa, M., Woods, A. S., Mo, H., Goldstein, I. J., & Ichikawa, Y. (2000). Simple preparation of multi-valent cyclodextrin-carbohydrate conjugates. Tetrahedron: Asymmetry, 11(2), 389-392. (Year: 2000).*
Gao, Y., Eguchi, A., Kakehi, K., & Lee, Y. C. (2004). Efficient preparation of glycoclusters from silsesquioxanes. Organic letters, 6(20), 3457-3460. (Year: 2004).*
Kitano, H., Ishino, Y., & Yabe, K. (2001). Dehydration effect on the recognition of amphiphiles with many pendent mannose residues by concanavalin A. Langmuir, 17(8), 2312-2316. (Year: 2001).*
Ichikawa, Y., & Lee, Y. C. (1990). Synthesis of a branched glycopeptide derivative containing terminal D-mannose 6-phosphate residues. Carbohydrate research, 198(2), 235-246. (Year: 1990).*
Albumin From Bovine Serum, Product Information Sheet, Sigma-Aldrich, 2013 (Year: 2013).*
Noriko Nagahori et al: "Inhibition of Adhesion of Type 1 Fimbriated *Escherichia coli* to Highly Mannosylated Ligands Shin-Ichiro Nishimura, [b]", Chembiochem, vol. 50, No. 3, Jan. 1, 2002 (Jan. 1, 2002), pp. 836-844, XP055094204.
H. Takekawa et al: "Novel Carbohydrate-binding Activity of Pancreatic Trypsins to N-Linked Glycans of Glycoproteins", Journal of Biological Chemistry, vol. 281, No. 13, Jan. 17, 2006 (Jan. 17, 2006), pp. 8528-8538, XP055109787, ISSN: 0021-9258, DOI: 10.1074/jbc.M513773200.
Sarfati S R et al: "Synthesis of Uridine and 2'-Deoxyuridine Mono- and Tri-Phosphates Alkylated in Position 5 by Glycosides of Alpha-D-Mannose and N-Acetyl-Beta-D-Glucosamine: DNA and RNA Monomers With Tethered Lectin Targets", Journal of the Chemical Society, Perkin Transactions 1, Royal Society of Chemistry, GB, No. 4, Jan. 1, 1990 (Jan. 1, 1990), pp. 1065-1070, XP009062137, ISSN: 0300-922X, DOI: 10.1039/P19900001065.
Durette P L et al: "Structure-Activity Relationships of Aminoalkyl and -Aryl Glycosides Having Insulin-Like Activity", Journal of Medicinal Chemistry, American Chemical Society, vol. 21, No. 9, Jan. 1, 1978 (Jan. 1, 1978), pp. 854-859, XP002464168, ISSN: 0022-2623, DOI: 10.1021/JM00207A003.
Koji Tagawa et al: "Recognition of Novel Amphiphiles with Many Pendent Mannose Residues by Con A +", Bioconjugate Chemistry, vol. 10, No. 3, May 1, 1999 (May 1, 1999), pp. 354-360, XP055109945, ISSN: 1043-1802, DOI: 10.1021/bc980083x.
Labsky J: "Binding of d-mannose to poly(2-hydroxyethyl methacrylate) hydrogels by azo coupling", Biomaterials, Elsevier Science Publishers BV., Barking, GB, vol. 24, No. 22, Oct. 1, 2003 (Oct. 1, 2003), pp. 4031-4036, XP004434245, ISSN: 0142-9612, DOI: 10.1016/S0142-9612(03)00313-2.
Sami Brument et al: "Thiazolylaminomannosides as Potent Antiadhesives of Type 1 Piliated *Escherichia coli* Isolated from Crohn's Disease Patients", Journal of Medicinal Chemistry, vol. 56, No. 13, Jul. 11, 2013 (Jul. 11, 2013), pp. 5395-5406, XP055109883, ISSN: 0022-2623, DOI: 10.1021/jm400723n.
International Search Report, dated Jun. 25, 2015, from corresponding PCT application.
EP Search Report, dated Mar. 26, 2014, from corresponding EP application.

* cited by examiner

Ileum

Colon

FIGURE 7A
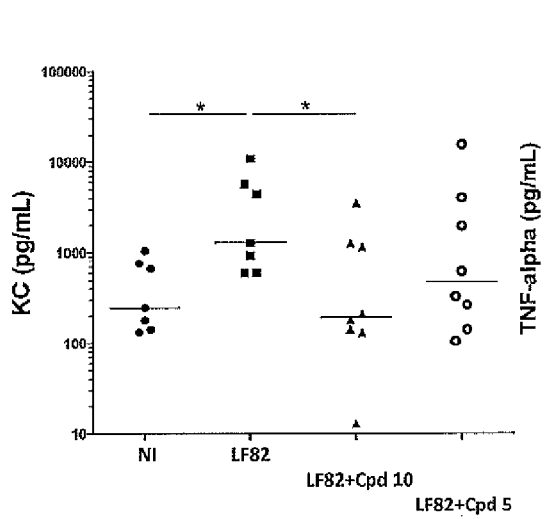
FIGURE 7B
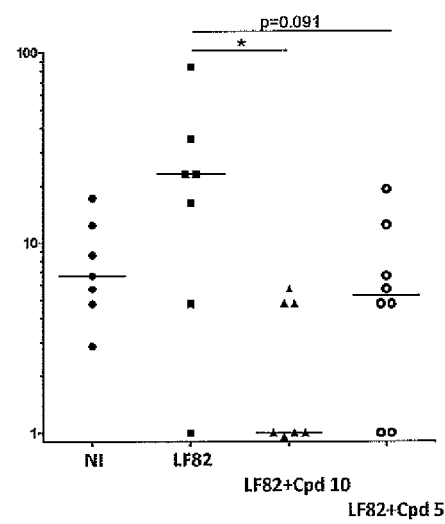
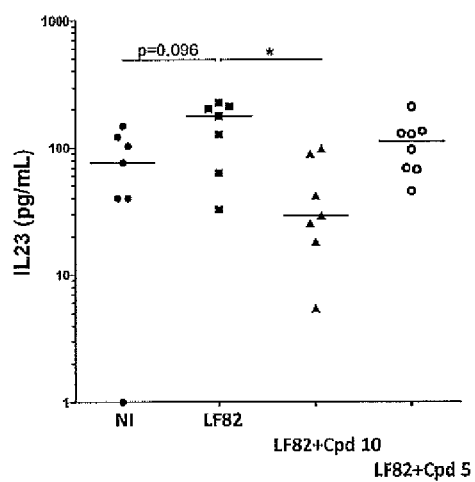
FIGURE 7C t test (in comparison with LF82 adhesion in absence of any compounds)
a : p<0.05
b : p<0.01
c : p<0.001 t test in comparison with the LF82-infected group

ORALLY AVAILABLE COMPOUNDS, A PROCESS FOR PREPARING THE SAME AND THEIR USES AS ANTI-ADHESIVE DRUGS FOR TREATING *E. COLI* INDUCED INFLAMMATORY BOWEL DISEASES SUCH AS CROHN'S DISEASE

The present invention relates to orally available compounds, a process for preparing the same and their uses as anti-adhesive drugs for treating *E. coli* induced inflammatory bowel diseases such as crohn's disease.

Crohn's disease is a chronic and lifelong disease which affects 4 millions of people worldwide with a prevalence of about 100 cases per 100,000 individuals. It has a major impact on the quality of life, extending into the old age and 80% of patients will require surgery. Crohn's disease represents an important economic impact on the healthcare system and the economy as a whole, with direct costs ($18,022-18,932 per year for patients living in the US, "Inflammatory bowel disease-attributable costs and cost-effective strategies in the united states: a review" K. T. Park, MD, and Dorsey Bass, MD, IBD 2011) and indirect costs because of the effect on employability.

Crohn's disease is characterized by an aberrant immune response occurring in a genetically predisposed host in response to microbes and/or microbial compounds. Adherent-Invasive *E. coli* (AIEC) bacteria are found abnormally associated with the ileal mucosa in 36.4% of the Crohn's disease patients with an ileal involvement. As these bacteria possess invasive, anti-phagocytic and pro-inflammatory properties, this is of a crucial importance to elaborate a strategy to eradicate AIEC bacteria from the digestive tract, in inhibiting the bacterial adhesion. The role of type 1 fimbriae was well established in these *E. coli* strains associated with Crohn's disease. It has been shown that the ileum of CD patients is abnormally colonized by *E. coli* bacteria in results from overexpression of carcinoembryonic antigen-related cell adhesion molecule 6 (CEACAM6) acting as receptors for *E. coli* adhesion via type 1 pili. Bacterial adhesion to intestinal epithelial cells is mediated by the FimH adhesin on the tip of the type 1 pili from the bacteria. Several amino acid substitutions modify type 1 pili FimH adhesin affinity for various mannose residues (Bouckaert, Berglund, Schembri, Christiansen and Klemm, FimH-mediated autoaggregation of *Escherichia coli*. Mol Microbiol, 2001. 41.1419-30, Sokurenko, Schembri, Trintchina, Kjaergaard, Hasty and Klemm, Valency conversion in the type 1 fimbrial adhesin of *Escherichia coli*. Mol Microbiol, 2001. 41.675-86), under conditions of shear force. The AIEC reference strain LF82 expresses type 1 pili variant with four amino acid substitutions (V27A; N70S; S78N; T158P) that could favour the binding of the bacteria to the abnormally expressed CEACAM6 receptor in CD patients. The host/bacteria crosstalk in the context of host susceptibility to CD can be mimicked using CEABAC10 transgenic mouse expressing human CEACAM6 receptor. In this model, it has been reported that AIEC infected CEABAC10 mice develop severe colitis and are abundantly colonized by bacteria only when AIEC bacteria express type 1 pili.

The specificity of FimH lectin has been identified by Bouckaert (Bouckaert, J. et al., *Mol. Microbiol.* 2006, 61(6), 1556-68) and Wellens et al., (Wellens, A. et al., *PloS One* 2008, 3(4), e2040). The FimH adhesin has been structurally and functionally characterized and a series of inhibitors with nanomolar afinities has been developed (Bouckaert, J., Berglund, J. et al. *Mol. Microbiol.* 2005, 55(2), 441-55; Gouin, S. G. et al., *ChemMedChem.* 2009, 5, 749-755). It has been demonstrated that alkyl α-D-manoside are effectively inhibiting binding of *E. coli* to its human cell targets (US2008171706). Heptyl α-D-mannoside (HM) is still one of the best monomeric mannose-based inhibitors of FimH to date in vitro.

However, HM is ineffective in vivo, probably due to its amphiphilic nature, allowing its insertion in biological membranes.

One objective of the present invention is to provide monomeric mannose derivatives liable to constitute a treatment of pathologies induced by type 1 fimbriated *E. coli*, in particular inflammatory bowel disease, more particularly Crohn's disease.

Another aim of the present invention is to provide monomeric mannose derivatives being active in vivo towards inflammatory bowel disease, especially Crohn's disease.

Still another aim of the present invention is to provide monomeric mannose derivatives, which are able to be administrated per os.

The present invention relates to a compound of the following formula (I):

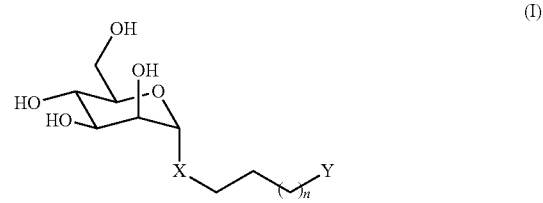

wherein:
X represents NH, O, S or $CH_2$;
n represents an integer being equal to 3, 4, 5, 6 or 7, n being in particular equal to 5;
Y represents a group selected from:

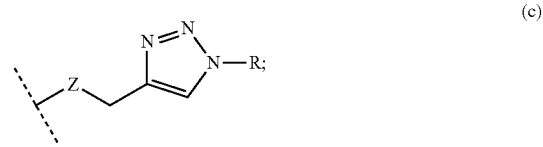

Z representing O or S;
R representing:
  H
  a linear or branched ($C_1$-$C_7$)-alkyl, in particular methyl, ethyl, isopropyl or isobutyl,
  a linear or branched ($C_2$-$C_7$)-alkenyl,
  a linear or branched ($C_2$-$C_7$)-alkynyl,
  a ($C_3$-$C_7$)-cycloalkyl,
  a ($C_5$-$C_7$)-cycloalkenyl,
  a ($C_3$-$C_7$)-heterocycloalkyl, a (C$_5$-C$_7$)-heterocycloalkenyl,
an aryl, said aryl being an aromatic or heteroaromatic group,
an alkyl aryl, wherein the aryl is an aromatic or heteroaromatic group,
a CO—(C$_1$-C$_7$)-alkyl,
a CO-aryl, wherein aryl is an aromatic or heteroaromatic group,
a CO$_2$H,
a CO$_2$—(C$_1$-C$_7$)-alkyl,
a CONH—(C$_1$-C$_7$)-alkyl,
CF$_3$,
adamantyl,
CHRa—NH$_2$, wherein Ra represents the side chain of a proteinogenic amino acid,
a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a β-cyclodextrin of the following formula:

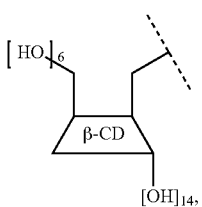
(d)

said (C$_1$-C$_7$)-alkyl, (C$_2$-C$_7$)-alkenyl, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl, CO-aryl and cyclodextrin being substituted or not by one or more substituent(s), each independently selected from:
  a linear or branched (C$_1$-C$_7$)-alkyl,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl,
  an aryl, wherein the aryl is an aromatic or heteroaromatic group
  an alkyl aryl, wherein the aryl is an aromatic or heteroaromatic group,
  a CHO,
  a CO—(C$_1$-C$_7$)-alkyl,
  a CO-aryl, wherein aryl is an aromatic or heteroaromatic group,
  a CO$_2$H,
  a CO$_2$—(C$_1$-C$_7$)-alkyl,
  a CONH—(C$_1$-C$_7$)-alkyl,
  a halogen selected from the group comprising F, Cl, Br, and I,
  CF$_3$,
  OR$_a$, wherein R$_a$ represents:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NR$_b$R$_c$, wherein R$_b$ and R$_c$ represent independently from each other:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NO$_2$,
  CN;
provided that when R represents CHRa—NH$_2$, then Y can only represent the following group (a):

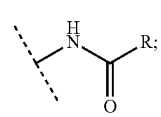
(a)

for use in the treatment or the prevention of inflammatory bowel disease, in particular Crohn disease or ulcerative colitis.

The present invention also relates to a compound of the following formula (I):

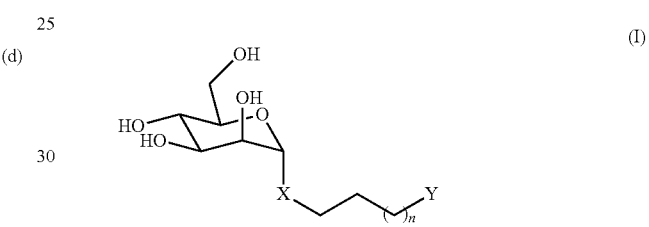
(I)

wherein:
X represents NH, O, S or CH$_2$;
n represents an integer being equal to 3, 4, 5, 6 or 7, n being in particular equal to 5;
Y represents a group selected from:

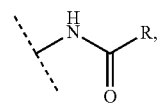
(a)

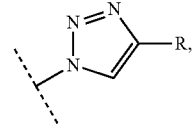
(b)

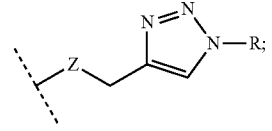
(c)

Z representing O, S or NH;
R representing:
  H
  a linear or branched (C$_1$-C$_7$)-alkyl, in particular methyl, ethyl, isopropyl or isobutyl,
  a group of formula —(CH$_2$)$_i$—X'—(CH$_2$)$_j$—H, wherein X' represents O, S or NH, i is an integer from 1 to 7, and j is an integer from 0 to 7, said group being in particular —CH$_2$—O—CH$_3$, a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, said aryl being an aromatic or heteroaromatic group,
an alkyl aryl, wherein the aryl is an aromatic or heteroaromatic group,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
$CF_3$,
adamantyl,
$CHRa$—$NH_2$, wherein Ra represents the side chain of a proteinogenic amino acid,
a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a cyclodextrin of one of the following formulae:

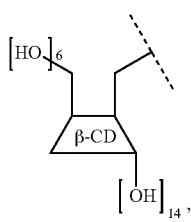

(d)

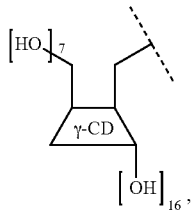

(e)

said $(C_1-C_7)$-alkyl, group of formula —$(CH_2)_i$—X'—$(CH_2)_j$—H, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl, CO-aryl and cyclodextrin being substituted or not by one or more substituent(s), each independently selected from:
a linear or branched $(C_1-C_7)$-alkyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, wherein the aryl is an aromatic or heteroaromatic group
an alkyl aryl, wherein the aryl is an aromatic or heteroaromatic group,
a CHO,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
a halogen selected from the group comprising F, Cl, Br, and I,
$CF_3$,
$OR_a$, wherein $R_a$ represents:
  H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NR_bR_c$, wherein $R_b$ and $R_c$ represent independently from each other:
  H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NO_2$,
CN,
$SO_3H$ or one of its salts, in particular $SO_3Na$;
and its pharmaceutically acceptable salts,
provided that when R represents $CHRa$—$NH_2$, then Y can only represent the following group (a):

for use in the treatment or the prevention of inflammatory bowel disease, in particular Crohn disease or ulcerative colitis.

By linear $(C_1-C_7)$ alkyl group is meant a group such as methyl, ethyl, propyl, butyl, pentyl, hexyl or heptyl.

By branched alkyl group is meant an alkyl group as defined above bearing substituents selected from the list of linear alkyl groups defined above, said linear alkyl group being also liable to be branched.

By linear $(C_2-C_7)$ alkenyl group is meant a linear hydrocarbon group constituted by 2 to 7 carbon atoms, with one or more carbon-carbon double bond(s).

By branched alkenyl group is meant an alkenyl group as defined above bearing substituents selected from the list of linear alkyl groups defined above, said linear alkyl group being also liable to be branched.

By linear $(C_2-C_7)$ alkynyl group is meant a linear hydrocarbon group constituted by 2 to 7 carbon atoms, with one or more carbon-carbon triple bond(s).

By branched alkynyl group is meant an alkynyl group as defined above bearing substituents selected from the list of linear alkyl groups defined above, said linear alkyl group being also liable to be branched.

By $(C_3-C_7)$-cycloalkyl group is meant a group such as cyclopropyl, cyclobutyl, cyclopentyl, cyclohexyl or cycloheptyl.

By $(C_5-C_7)$-cycloalkenyl group is meant a cyclic hydrocarbon group constituted by 5 to 7 carbon atoms, with one or more carbon-carbon double bond(s).

By $(C_3-C_7)$-heterocycloalkyl group is meant a $(C_3-C_7)$-cyclic group having at least one non-carbon atom in the ring.

By $(C_5-C_7)$-heterocycloalkenyl group is meant a heterocyclic group constituted by 5 to 7 carbon atoms, with one or more double bond(s).

The term "aryl" refers to any functional group or substituent derived from a simple aromatic ring, aforesaid aromatic ring comprising from 6 to 16 carbon atoms.

The term "heteroaromatic" refers to a compound comprising from 5 to 16 atoms, having the characteristics of an aromatic compound whilst having at least one non-carbon atom in the ring, aforesaid non-carbon atom being in particular N, S or O.

By alkyl aryl group is meant a linear or branched alkyl group as defined above, which is substituted by an aryl group.

By

is meant that the atom At is bound through a covalent bond to another atom or group that is not represented.

For instance, considering:

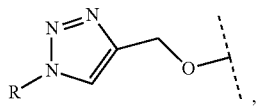

by

is meant that the oxygen atom is bound to another atom or group through a covalent bond involving aforesaid oxygen atom.

By "proteinogenic amino acid" is meant amino acids that are precursors to proteins, such as alanine, arginine, asparagine, aspartic acid, cysteine, glutamine, glutamic acid, glycine, histidine, isoleucine, leucine, lysine, methionine, phenylalanine, proline, pyrrolysine, selenocysteine, serine, threonine, tryptophan, tyrosine and valine.

By "side chain of an amino acid" is meant the group $S_c$ as defined hereafter: $H_2NCHS_cCOOH$.

The amino acid residue of formula —CHRa—$NH_2$ is of configuration L or D, in particular of configuration L.

The above-mentioned definitions apply to the entire specification.

Interestingly, the inventors have found that compounds of the invention are not only able to inhibit bacterial binding to uroepithelial cells, but also to inhibit bacterial binding to intestinal epithelial cells.

In an advantageous embodiment of the use according to the invention, the compound of formula (I) is of particular formula (I-1), wherein R is $R_1$, $R_1$ representing:
H
a linear or branched ($C_1$-$C_7$)-alkyl, in particular isopropyl,
a linear or branched ($C_2$-$C_7$)-alkenyl,
a linear or branched ($C_2$-$C_7$)-alkynyl,
a ($C_3$-$C_7$)-cycloalkyl,
a ($C_5$-$C_7$)-cycloalkenyl,
a ($C_3$-$C_7$)-heterocycloalkyl,
a ($C_5$-$C_7$)-heterocycloalkenyl,
an aryl, said aryl being an aromatic or heteroaromatic group,
an alkyl aryl, wherein the aryl is an aromatic or heteroaromatic group,
a CO—($C_1$-$C_7$)-alkyl,
a CO-aryl, wherein aryl is an aromatic or heteroaromatic group,
a $CO_2H$,
a $CO_2$—($C_1$-$C_7$)-alkyl,
a CONH—($C_1$-$C_7$)-alkyl,
$CF_3$,
adamantly,
CHRa—$NH_2$, wherein Ra represents the side chain of a proteinogenic amino acid,
$R_1$ representing in particular:
a linear ($C_1$-$C_7$)-alkyl, more particularly methyl, ethyl, propyl or butyl, optionally substituted by a —OH and/or a —$NH_2$ group,
a branched ($C_3$-$C_7$)-alkyl, more particularly isopropyl or isobutyl,
a ($C_3$-$C_7$)-heterocycloalkyl, more particularly a pyrrolidine,
an aryl, said aryl being an aromatic or heteroaromatic group, more particularly a phenyl, a pyridinyl, a pyrrole or an imidazole, optionally substituted by a —OH, a —$NH_2$ or a —$SO_3Na$ group,
an alkyl aryl, wherein the aryl is an aromatic or heteroaromatic group, more particularly a benzyl, a phenethyl or an ethyl imidazolyl, optionally substituted by a —OH or a —$NH_2$ group,
CHRa—$NH_2$, wherein Ra represents the side chain of a proteinogenic amino acid, in particular alanine, serine, proline, phenylalanine, cysteine or histidine.

In an advantageous embodiment of the use according to the invention, the compound of formula (I) is of particular formula (I-1), wherein R is $R_1$, $R_1$ representing:
H
a linear or branched ($C_1$-$C_7$)-alkyl, in particular isopropyl,
a group of formula —$(CH_2)_i$—X'—$(CH_2)_j$—H, wherein X' represents O, S or NH, i is an integer from 1 to 7, and j is an integer from 0 to 7, said group being in particular —$CH_2$—O—$CH_3$,
a linear or branched ($C_2$-$C_7$)-alkenyl,
a linear or branched ($C_2$-$C_7$)-alkynyl,
a ($C_3$-$C_7$)-cycloalkyl,
a ($C_5$-$C_7$)-cycloalkenyl,
a ($C_3$-$C_7$)-heterocycloalkyl,
a ($C_5$-$C_7$)-heterocycloalkenyl,
an aryl, said aryl being an aromatic or heteroaromatic group,
an alkyl aryl, wherein the aryl is an aromatic or heteroaromatic group,
a CO—($C_1$-$C_7$)-alkyl,
a CO-aryl, wherein aryl is an aromatic or heteroaromatic group,
a $CO_2H$,
a $CO_2$—($C_1$-$C_7$)-alkyl,
a CONH—($C_1$-$C_7$)-alkyl,
$CF_3$,
adamantly,
CHRa—$NH_2$, wherein Ra represents the side chain of a proteinogenic amino acid,
$R_1$ representing in particular:
a linear ($C_1$-$C_7$)-alkyl, more particularly methyl, ethyl, propyl or butyl, optionally substituted by a —OH and/or a —$NH_2$ group, a group of formula —CH$_2$—O—CH$_3$, optionally substituted by a pyridinyl, a branched (C$_3$-C$_7$)-alkyl, more particularly isopropyl or isobutyl, a (C$_3$-C$_7$)-heterocycloalkyl, more particularly a pyrrolidine, an aryl, said aryl being an aromatic or heteroaromatic group, more particularly a phenyl, a pyridinyl, a pyrrole or an imidazole, optionally substituted by a —OH, a —NH$_2$ or a —SO$_3$Na group, an alkyl aryl, wherein the aryl is an aromatic or heteroaromatic group, more particularly a benzyl, a phenethyl or an ethyl imidazolyl, optionally substituted by a —OH or a —NH$_2$ group, CHRa—NH$_2$, wherein Ra represents the side chain of a proteinogenic amino acid, in particular alanine, serine, proline, phenylalanine, cysteine or histidine.

In an advantageous embodiment, the present invention relates to the use according to the invention of a compound of formula (I-1), wherein Y represents:

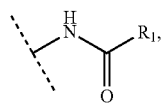

(a)

of following formula (I-1a):

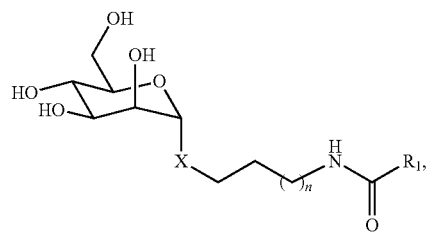

(I-1a)

X, R$_1$ and n being as defined above,

R$_1$ representing in particular a linear or branched (C$_1$-C$_7$)-alkyl, more particularly isopropyl.

In an advantageous embodiment, the present invention relates to the use according to the invention of a compound of formula (I-1), wherein Y represents:

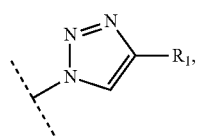

(b)

of following formula (I-1b):

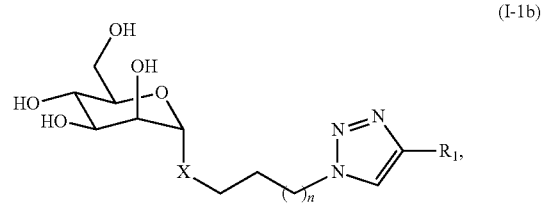

(I-1b)

X, R$_1$ and n being as defined above.

In an advantageous embodiment, the present invention relates to the use according to the invention of a compound of formula (I-1), wherein Y represents:

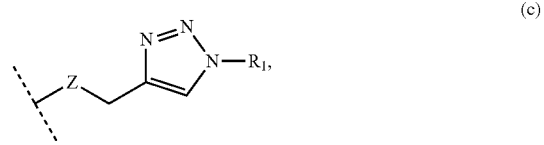

(c)

of following formula (I-1c):

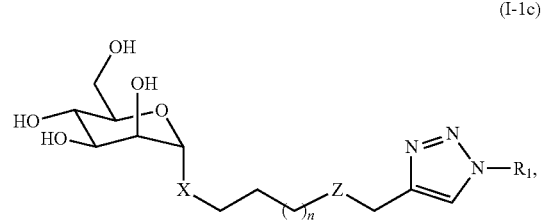

(I-1c)

X, Z, R$_1$ and n being as defined above.

In an advantageous embodiment of the use according to the invention, the compound of formula (I) is of particular formula (I-2), wherein R is R$_2$, R$_2$ representing a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly β-cyclodextrin of the following formula:

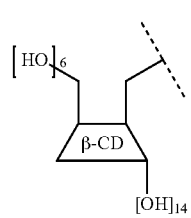

(d)

In an advantageous embodiment of the use according to the invention, the compound of formula (I) is of particular formula (I-2), wherein R is R$_2$, R$_2$ representing a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a β-cyclodextrin of the following formula:

(d)

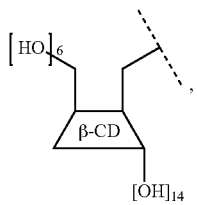

(e)

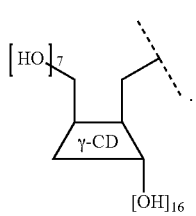

As indicated above, R is in the case of the formula (I-2) a cyclodextrin.

In an advantageous embodiment, the present invention relates to the use according to the invention of a compound of formula (I-2), wherein Y represents:

(c)

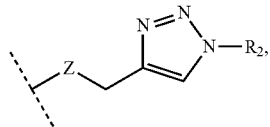

of following formula (I-2c):

(I-2c)

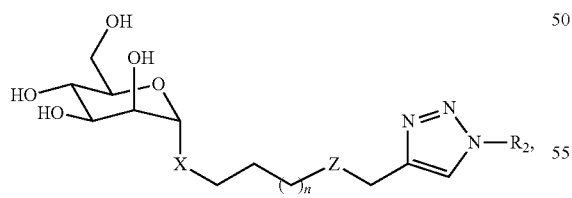

X, R$_2$, n and Z being as defined above.

In an advantageous embodiment of the use according to the invention, the compound of formula (I) is of particular formula (I-2c), wherein X represents O or S, in particular S.

In an advantageous embodiment of the use according to the invention, the compound of formula (I) is of particular formula (I-2c), wherein R$_2$ represents:

(d)

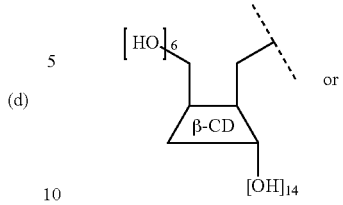

In an advantageous embodiment of the use according to the invention, the compound of formula (I) is of particular formula (I-2c), X represents O or S, in particular S, and wherein R$_2$ represents:

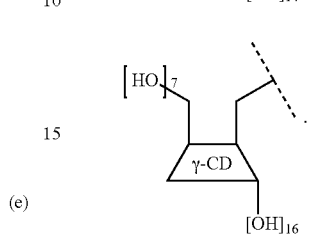

Z being in particular O.

In an advantageous embodiment of the use according to the invention, the compound of formula (I-1) is of following formula (I-1a-1):

(I-1a-1)

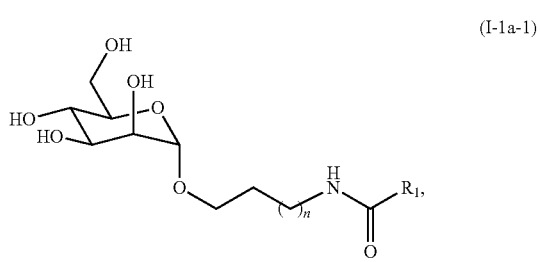

R$_1$ and n being as defined above.

In an advantageous embodiment of the use according to the invention, the compound of formula (I-1) is of following formula (I-1a-2):

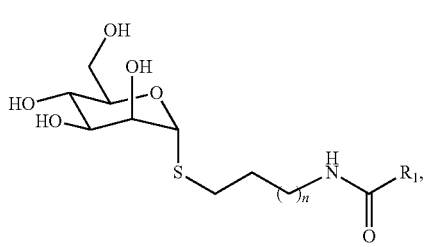
(I-1a-2)

In an advantageous embodiment of the use according to the invention, the compound of formula (I-1) is of following formula (I-1a-3):

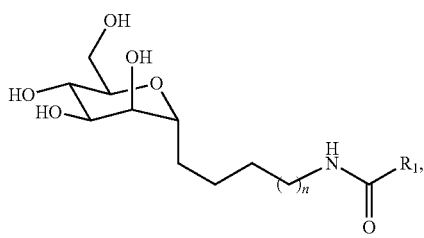
(I-1a-3)

$R_1$ and n being as defined above.

In an advantageous embodiment of the use according to the invention, the compound of formula (I-1) is of following formula (I-1a-4):

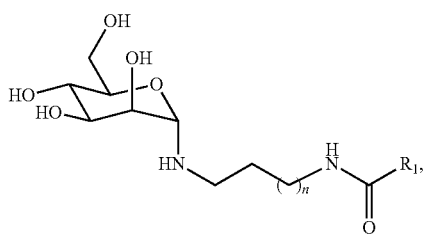
(I-1a-4)

$R_1$ and n being as defined above.

In an advantageous embodiment of the use according to the invention, the compound of formula (I-1) is of following formula (I-1b-1):

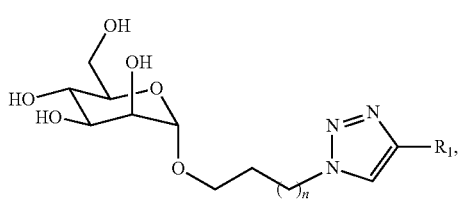
(I-1b-1)

$R_1$ and n being as defined above.

In an advantageous embodiment of the use according to the invention, the compound of formula (I-1) is of following formula (I-1b-2):

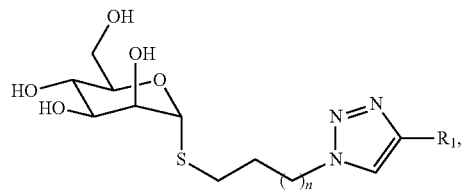
(I-1b-2)

$R_1$ and n being as defined above.

In an advantageous embodiment of the use according to the invention, the compound of formula (I-1) is of following formula (I-1b-3):

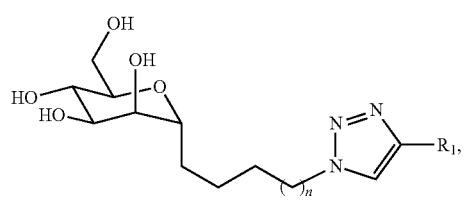
(I-1b-3)

$R_1$ and n being as defined above.

In an advantageous embodiment of the use according to the invention, the compound of formula (I-1) is of following formula (I-1b-4):

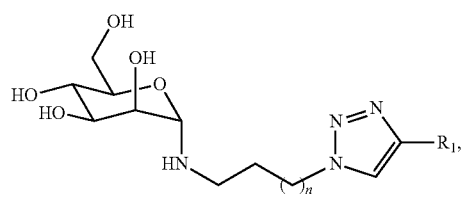
(I-1b-4)

$R_1$ and n being as defined above.

In an advantageous embodiment of the use according to the invention, the compound of formula (I-1) is of following formula (I-1c-1):

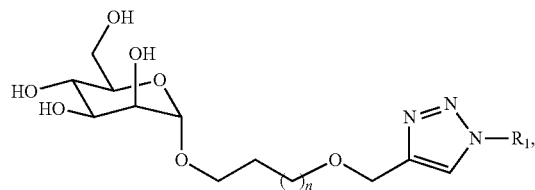
(I-1c-1)

$R_1$ and n being as defined above.

In an advantageous embodiment of the use according to the invention, the compound of formula (I-1) is of following formula (I-1c-2):

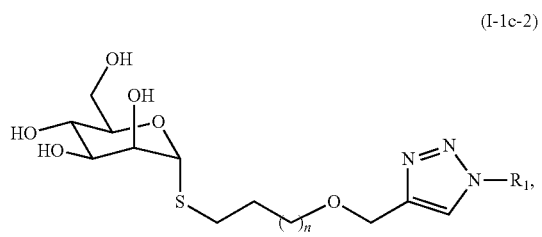
(I-1c-2)

$R_1$ and n being as defined above.

In an advantageous embodiment of the use according to the invention, the compound of formula (I-1) is of following formula (I-1c-3):

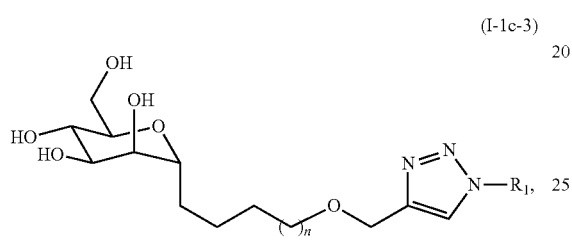
(I-1c-3)

$R_1$ and n being as defined above.

In an advantageous embodiment of the use according to the invention, the compound of formula (I-1) is of following formula (I-1c-4):

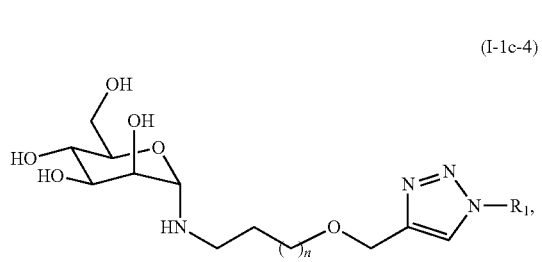
(I-1c-4)

$R_1$ and n being as defined above.

In an advantageous embodiment of the use according to the invention, the compound of formula (I-1) is of following formula (I-1c-5):

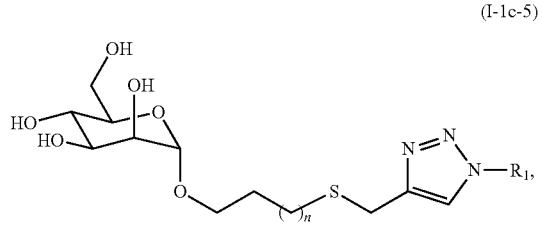
(I-1c-5)

$R_1$ and n being as defined above.

In an advantageous embodiment of the use according to the invention, the compound of formula (I-1) is of following formula (I-1c-6):

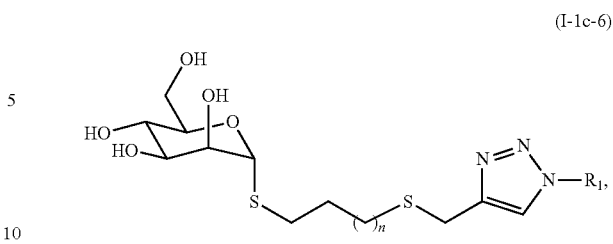
(I-1c-6)

$R_1$ and n being as defined above.

In an advantageous embodiment of the use according to the invention, the compound of formula (I-1) is of following formula (I-1c-7):

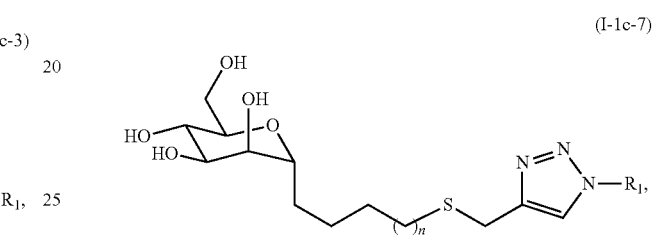
(I-1c-7)

$R_1$ and n being as defined above.

In an advantageous embodiment of the use according to the invention, the compound of formula (I-1) is of following formula (I-1c-8):

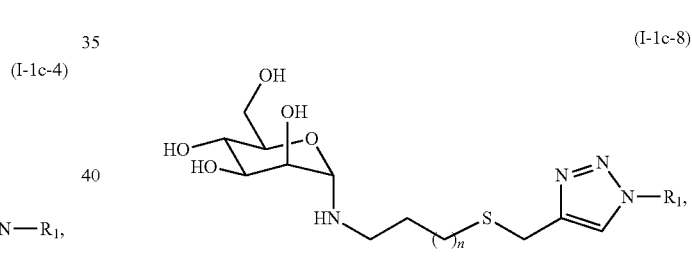
(I-1c-8)

$R_1$ and n being as defined above.

In an advantageous embodiment, the present invention relates to the use according to the invention of a compound of formula (I-1a-1), (I-1a-2), (I-1a-3), (I-1a-4), (I-1b-1), (1-1b-2), (I-1b-3), (I-1b-4), (I-1c-1), (I-1c-2), (I-1c-3), (I-1c-4), (I-1c-5), (I-1c-6), (I-1c-7) or (I-1c-8), wherein $R_1$ represents:

- a linear ($C_1$-$C_7$)-alkyl, more particularly methyl, ethyl, propyl or butyl, optionally substituted by a —OH and/or a —$NH_2$ group,
- a branched ($C_3$-$C_7$)-alkyl, more particularly isopropyl or isobutyl,
- a ($C_3$-$C_7$)-heterocycloalkyl, more particularly a pyrrolidine,
- an aryl, said aryl being an aromatic or heteroaromatic group, more particularly a phenyl, a pyridinyl, a pyrrole or an imidazole, optionally substituted by a —OH, a —$NH_2$ or a —$SO_3Na$ group,
- an alkyl aryl, wherein the aryl is an aromatic or heteroaromatic group, more particularly a benzyl, a phenethyl or an ethyl imidazolyl, optionally substituted by a —OH or a —$NH_2$ group, CHRa—NH₂, wherein Ra represents the side chain of a proteinogenic amino acid, in particular alanine, serine, proline, phenylalanine, cysteine or histidine.

In an advantageous embodiment of the use according to the invention, the compound of formula (I-2) is of following formula (I-2a-1):

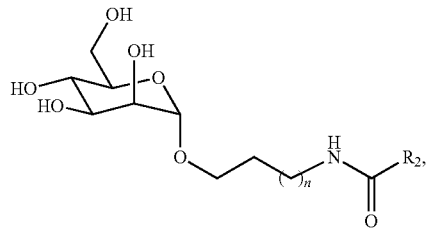
(I-2a-1)

R₂ and n being as defined above.

In an advantageous embodiment of the use according to the invention, the compound of formula (I-2) is of following formula (I-2a-2):

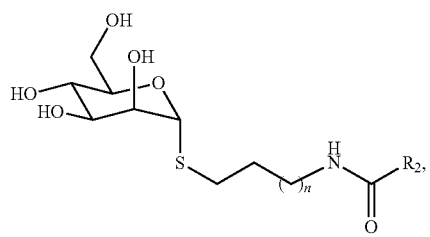
(I-2a-2)

R₂ and n being as defined above.

In an advantageous embodiment of the use according to the invention, the compound of formula (I-2) is of following formula (I-2a-3):

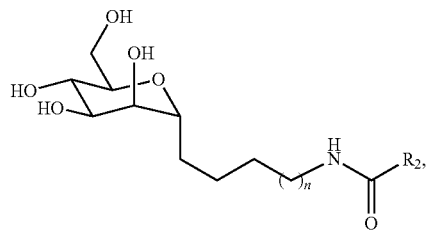
(I-2a-3)

R₂ and n being as defined above.

In an advantageous embodiment of the use according to the invention, the compound of formula (I-2) is of following formula (I-2a-4):

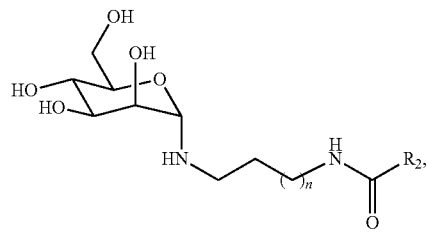
(I-2a-4)

R₂ and n being as defined above.

In an advantageous embodiment of the use according to the invention, the compound of formula (I-2) is of following formula (I-2b-1):

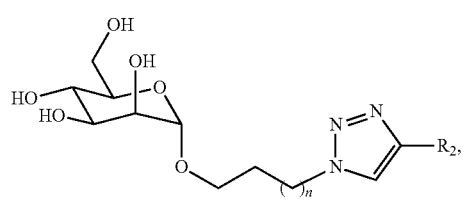
(I-2b-1)

R₂ and n being as defined above.

In an advantageous embodiment of the use according to the invention, the compound of formula (I-2) is of following formula (I-2b-2):

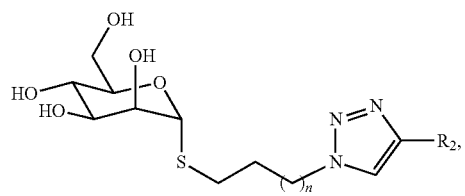
(I-2b-2)

R₂ and n being as defined above.

In an advantageous embodiment of the use according to the invention, the compound of formula (I-2) is of following formula (I-2b-3):

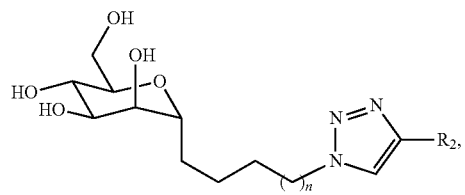
(I-2b-3)

R₂ and n being as defined above.

In an advantageous embodiment of the use according to the invention, the compound of formula (I-2) is of following formula (I-2b-4):

(I-2b-4)

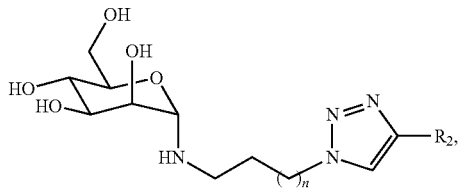

$R_a$ and n being as defined above.

In an advantageous embodiment of the use according to the invention, the compound of formula (I-2) is of following formula (I-2c-1):

(I-2c-1)

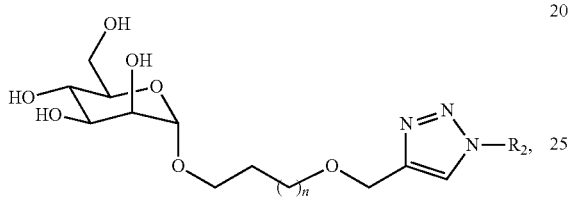

$R_2$ and n being as defined above.

In an advantageous embodiment of the use according to the invention, the compound of formula (I-2) is of following formula (I-2c-2):

(I-2c-2)

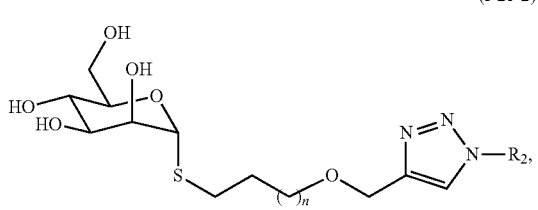

$R_2$ and n being as defined above.

In an advantageous embodiment of the use according to the invention, the compound of formula (I-2) is of following formula (I-2c-3):

(I-2c-3)

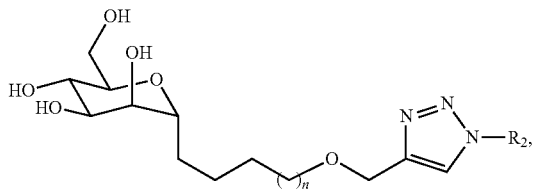

$R_2$ and n being as defined above.

In an advantageous embodiment of the use according to the invention, the compound of formula (I-2) is of following formula (I-2c-4):

(I-2c-4)

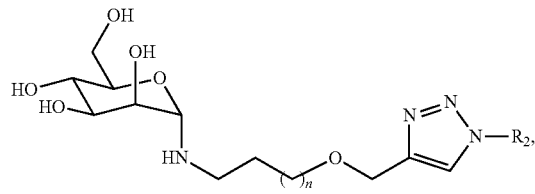

$R_2$ and n being as defined above.

In an advantageous embodiment of the use according to the invention, the compound of formula (I-2) is of following formula (I-2c-5):

(I-2c-5)

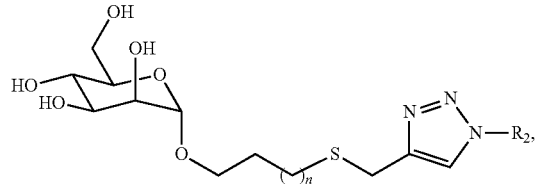

$R_2$ and n being as defined above.

In an advantageous embodiment of the use according to the invention, the compound of formula (I-2) is of following formula (I-2c-6):

(I-2c-6)

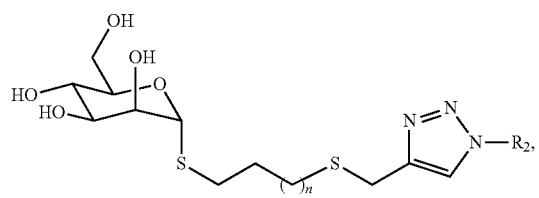

$R_2$ and n being as defined above.

In an advantageous embodiment of the use according to the invention, the compound of formula (I-2) is of following formula (I-2c-7):

(I-2c-7)

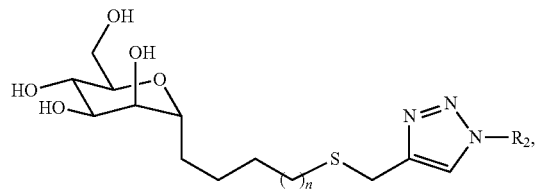

$R_2$ and n being as defined above.

In an advantageous embodiment of the use according to the invention, the compound of formula (I-2) is of following formula (I-2c-8):

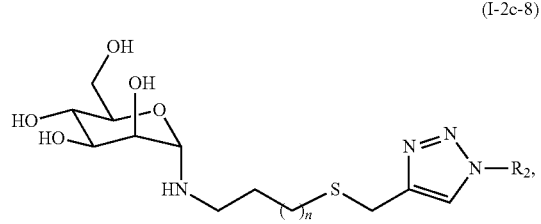

(I-2c-8)

$R_2$ and n being as defined above.

In an advantageous embodiment, the present invention relates to the use according to the invention of a compound of formula (I-1a-1), (I-1a-2), (I-1a-3), (I-1a-4), (I-1b-1), (I-1b-2), (I-1b-3), (I-1b-4), (I-1c-1), (I-1c-2), (I-1c-3), (I-1c-4), (I-1c-5), (I-1c-6), (I-1c-7), (I-1c-8), (I-2a-1), (I-2a-2), (I-2a-3), (I-2a-4), (I-2b-1), (I-2b-2), (I-2b-3), (I-2b-4), (I-2c-1), (I-2c-2), (I-2c-3), (I-2c-4), (I-2c-5), (I-2c-6), (I-2c-7) or (I-2c-8), wherein n is equal to 5.

In an advantageous embodiment, the present invention relates to the use according to the invention of a compound of formula (I) selected from the group consisting of:

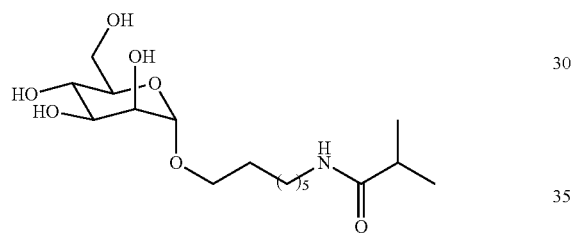

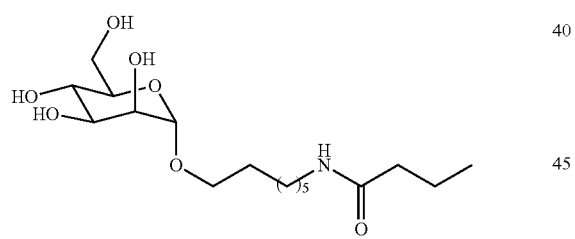

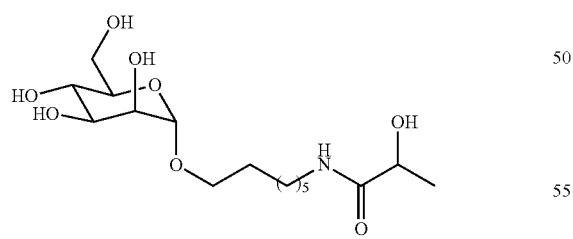

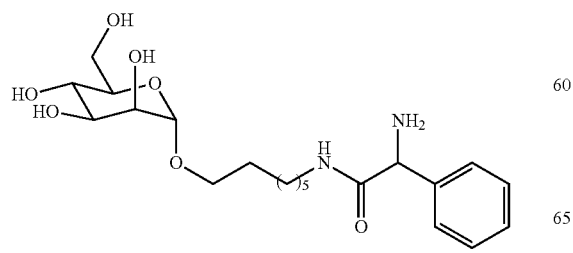

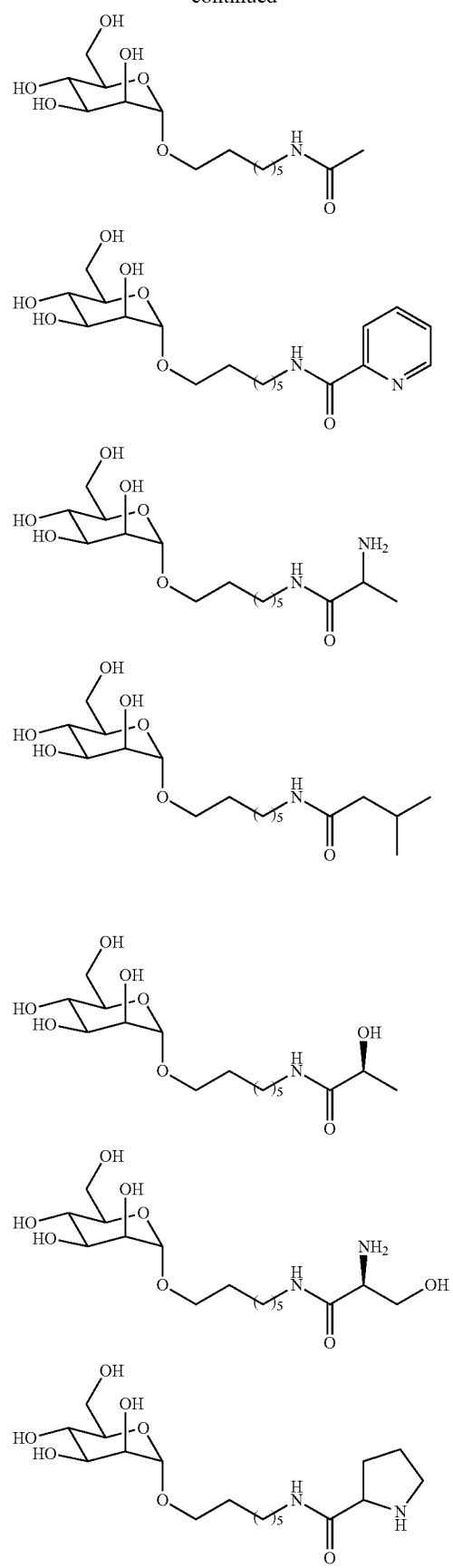

-continued
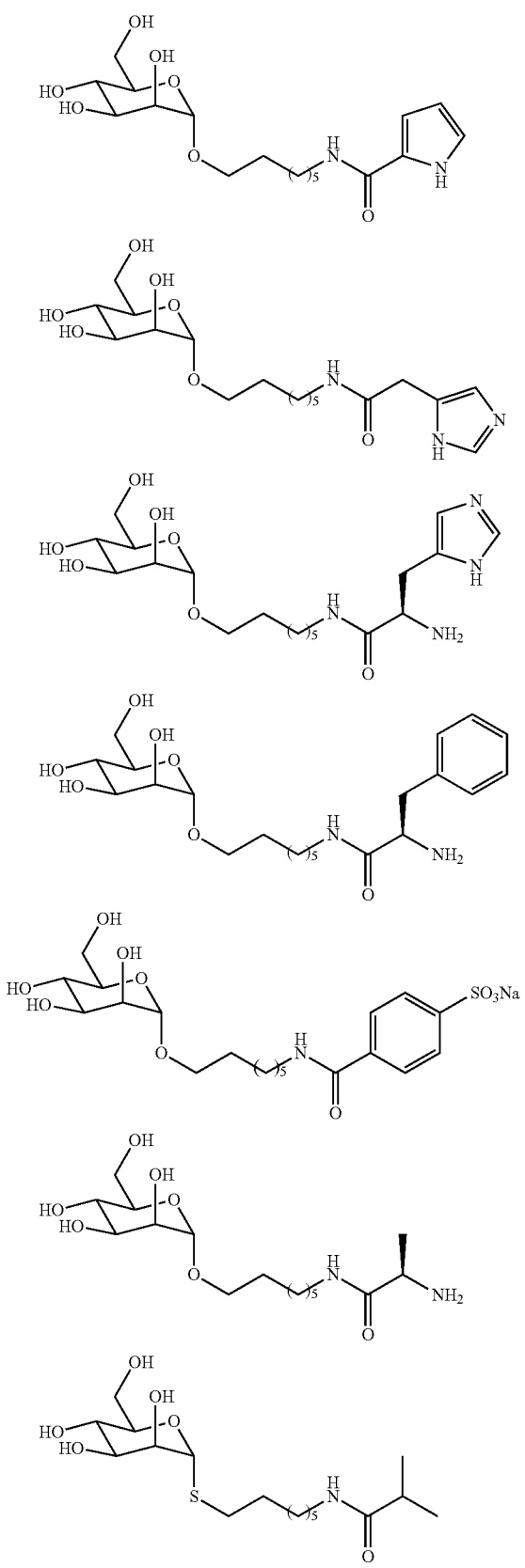
-continued
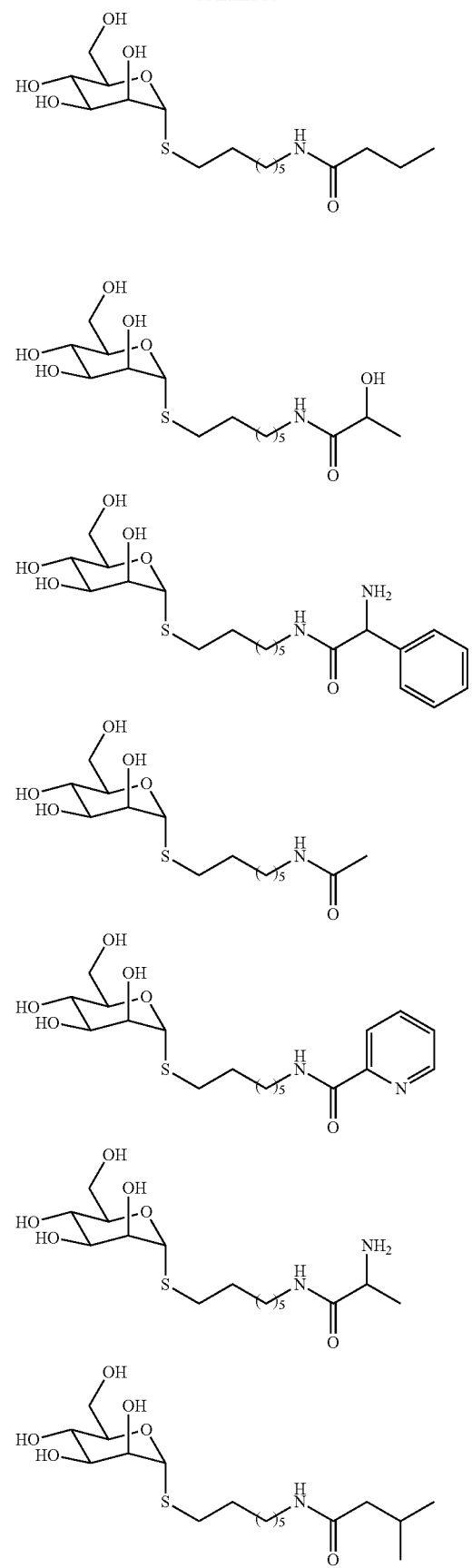

25
-continued
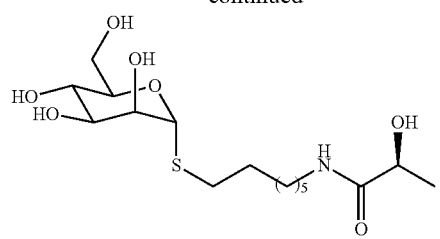
26
-continued
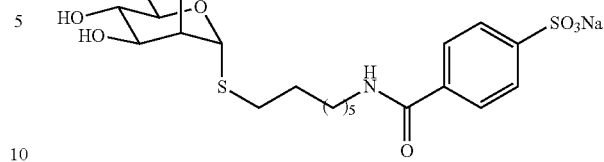
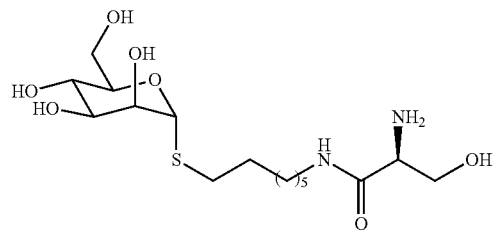
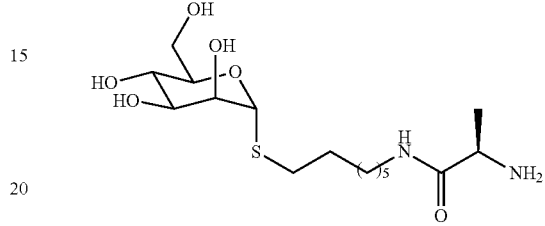
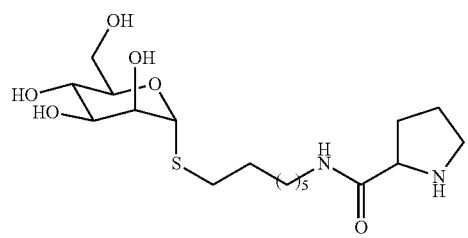
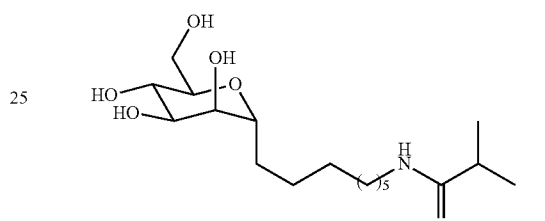
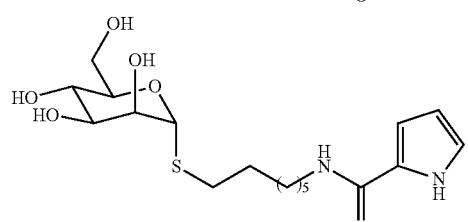
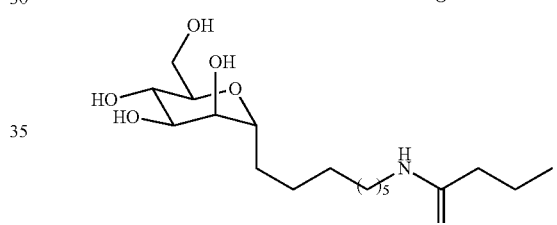
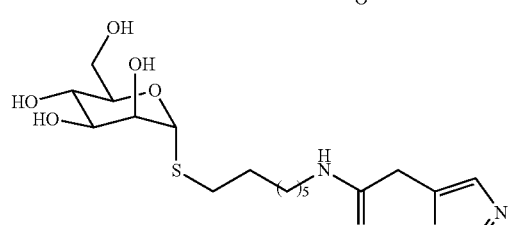
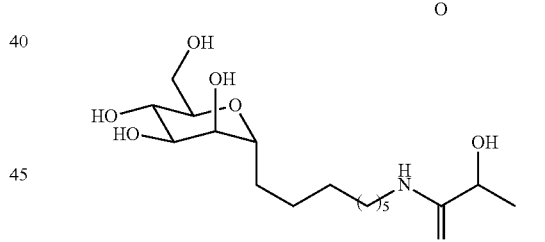
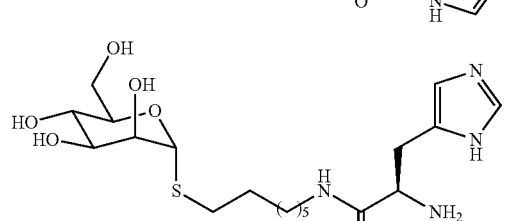
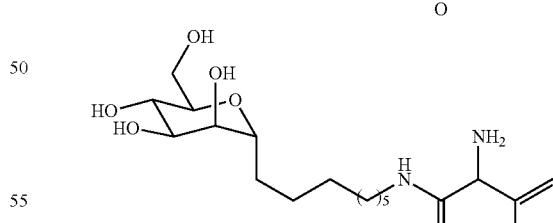
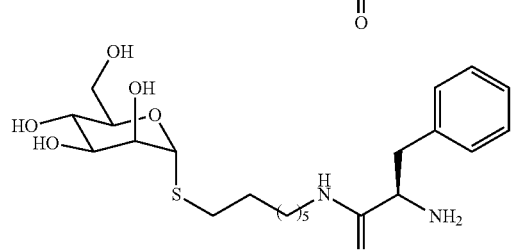
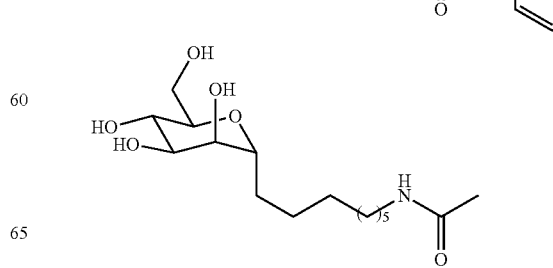

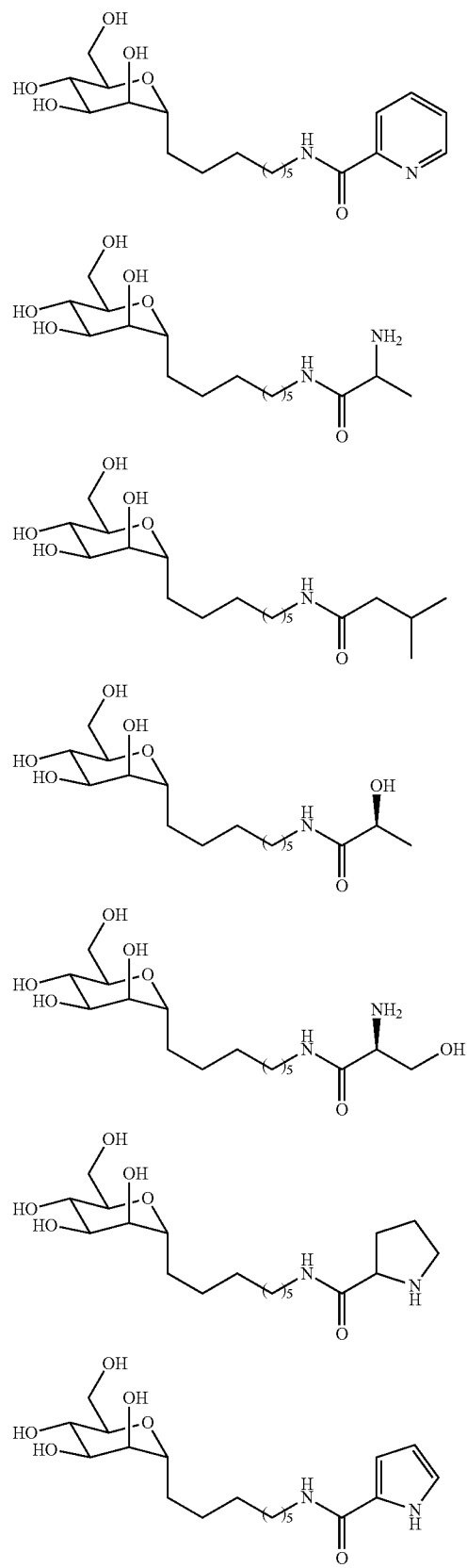
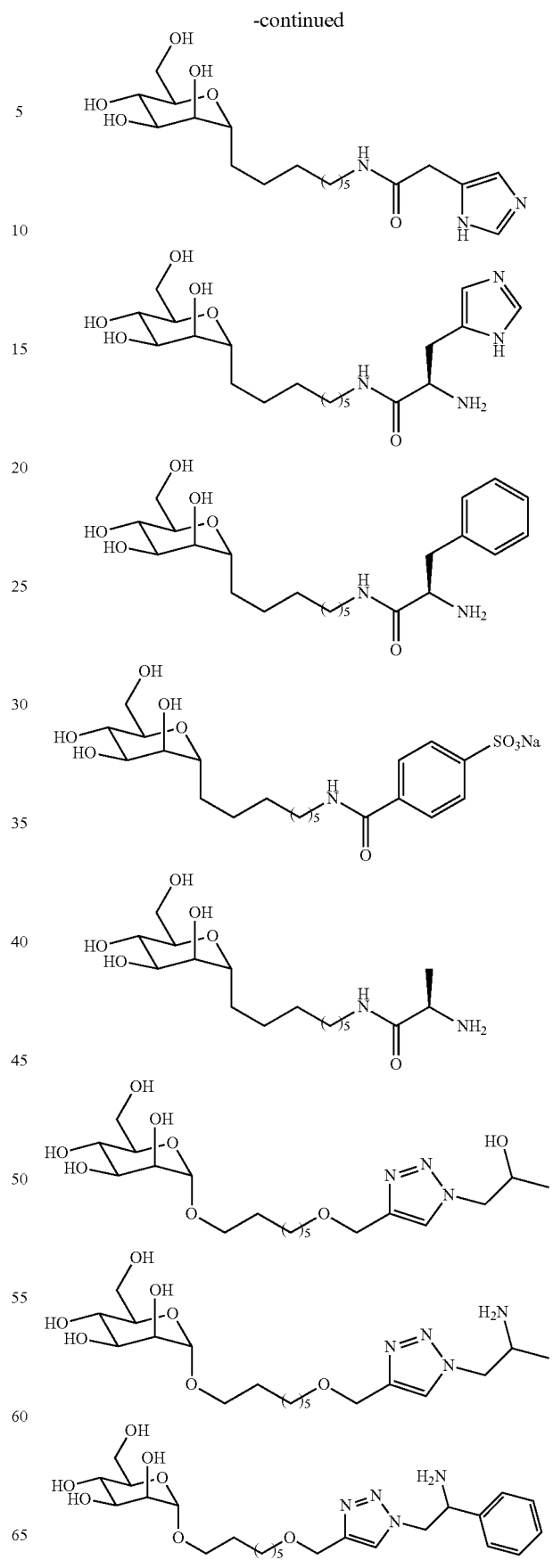

29
-continued
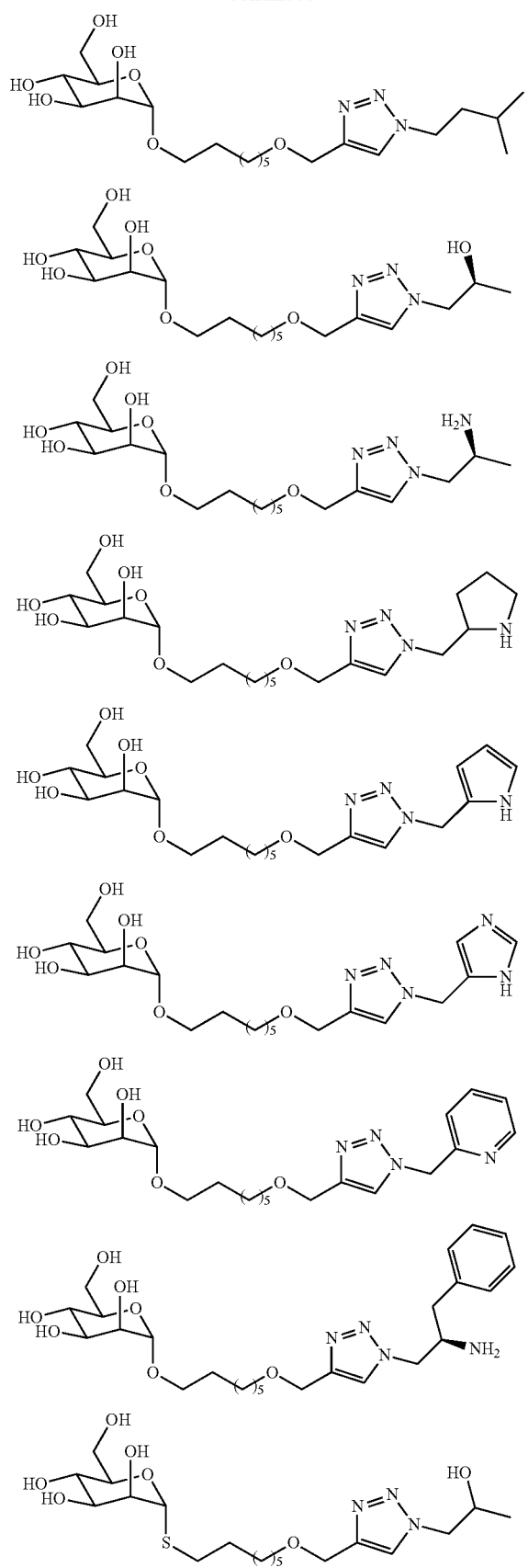
30
-continued
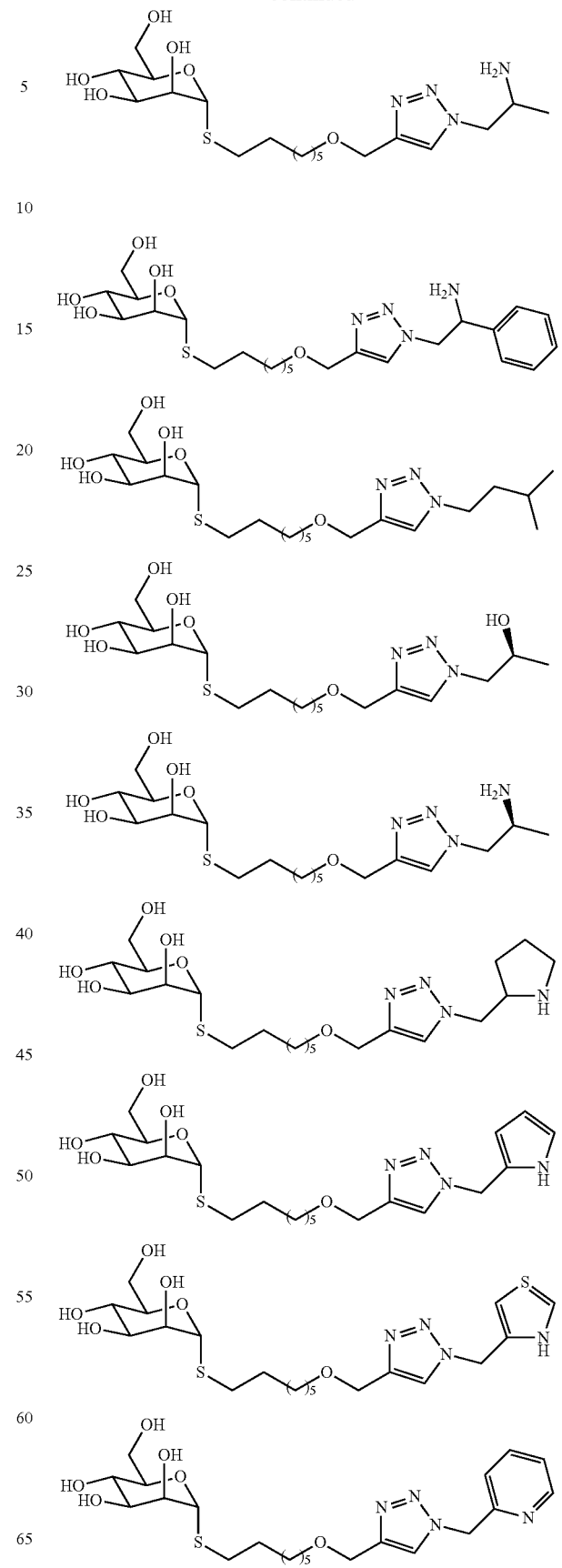

31
-continued
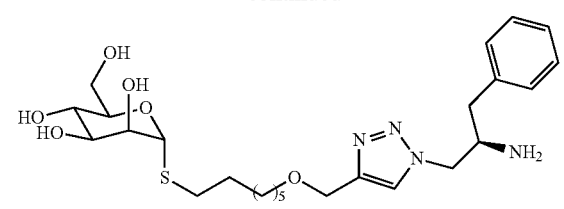
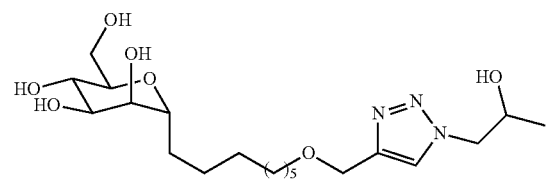
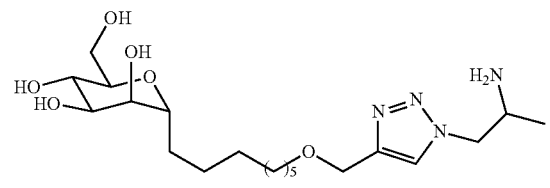
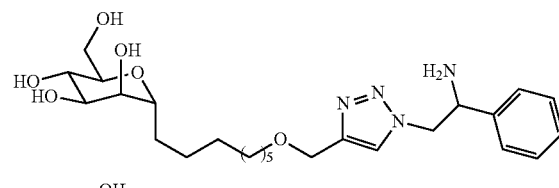
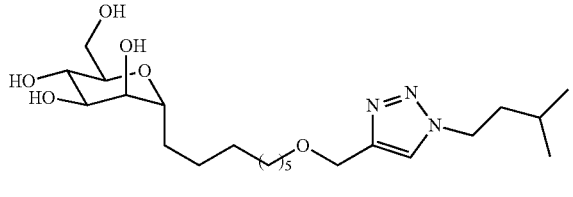
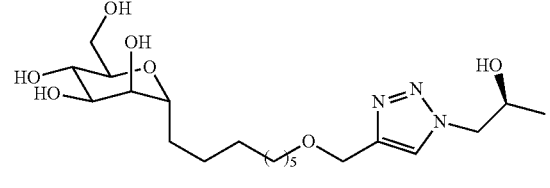
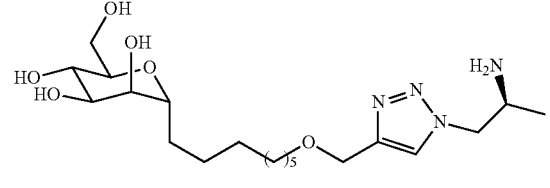
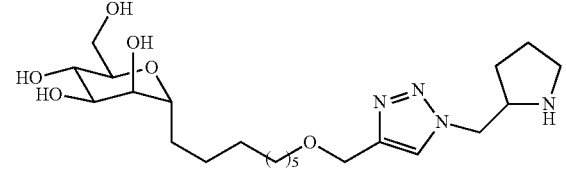
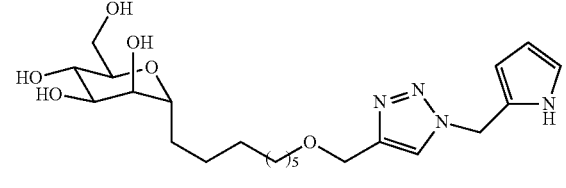
32
-continued
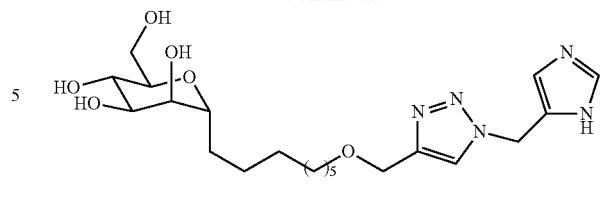
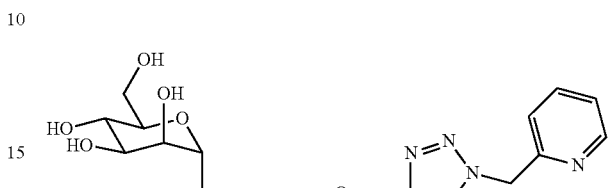
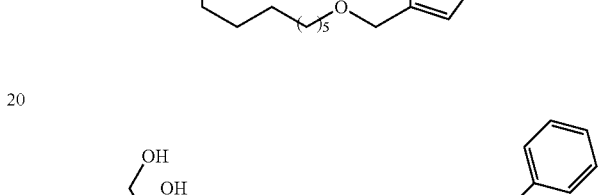
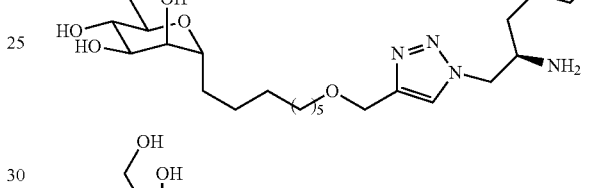
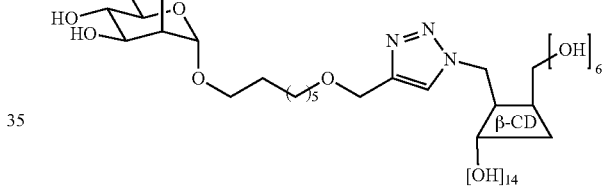
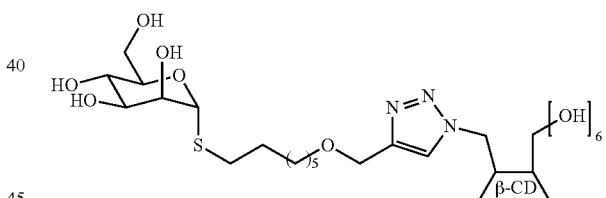
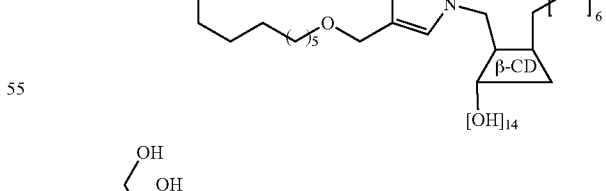
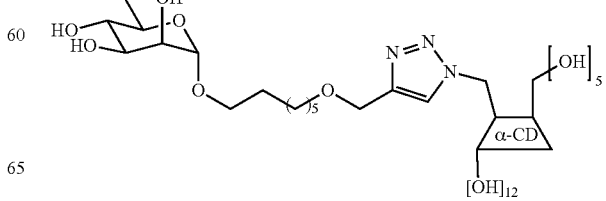

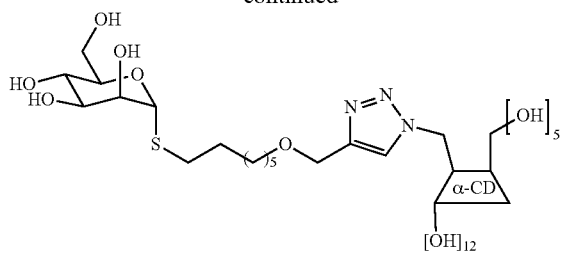

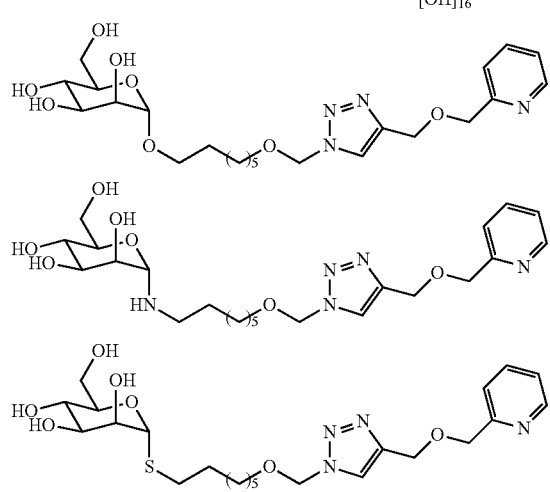

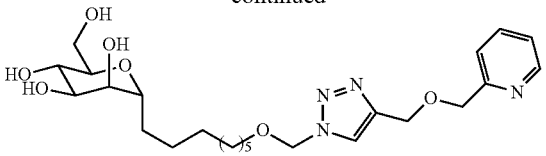

and their pharmaceutically acceptable salts.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutamic acid, glutaric acid, glycerophosphoric acid, glycolic acid, hippuric acid, isobutyric acid, lactobionic acid, lauric acid, maleic acid, malonic acid, mandelic acid, naphthalene-1,5-disulfonic acid, naphthalene-2-sulfonic acid, nicotinic acid, oleic acid, palmitic acid, pamoic acid, proprionic acid, pyroglutamic acid, sebacic acid, stearic acid, tartaric acid, thiocyanic acid, trifluoroacetic acid, undecylenic acid, and the like.

Base-addition salts include those derived from ammonium, potassium, sodium and, quaternary ammonium hydroxides, such as for example, tetramethyl ammonium hydroxide.

In an advantageous embodiment, the present invention relates to the use according to the invention of a compound of formula (I) of one of the following formulae:

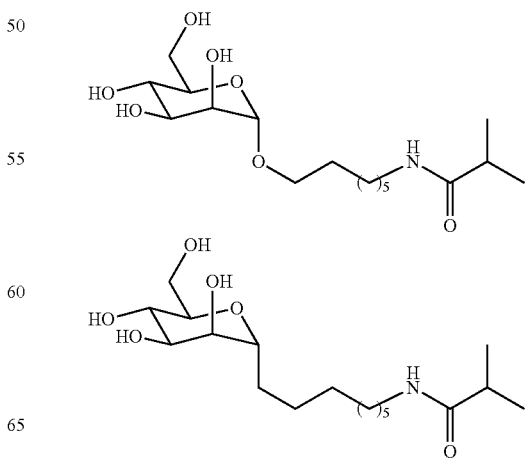

It is noted that the following compound is active in humans, in the treatment or the prevention of inflammatory bowel disease, in particular Crohn disease or ulcerative colitis:

In another aspect, the present invention relates to a new compound of the following formula (I-0):

(I-0)

wherein:
X represents NH, O, S or $CH_2$;
n represents an integer being equal to 3, 4, 5, 6 or 7, n being in particular equal to 5;
Y represents a group selected from:

(a)

(b)

(c)

Z representing O or S;
R representing:
   H
   a linear or branched ($C_1$-$C_7$)-alkyl, in particular isopropyl,
   a linear or branched ($C_2$-$C_7$)-alkenyl,
   a linear or branched ($C_2$-$C_7$)-alkynyl,
   a ($C_3$-$C_7$)-cycloalkyl,
   a ($C_5$-$C_7$)-cycloalkenyl,
   a ($C_3$-$C_7$)-heterocycloalkyl,
   a ($C_5$-$C_7$)-heterocycloalkenyl,
   an aryl, said aryl being an aromatic or heteroaromatic group,
   an alkyl aryl, wherein the aryl is an aromatic or heteroaromatic group,
   a CO—($C_1$-$C_7$)-alkyl,
   a CO-aryl, wherein aryl is an aromatic or heteroaromatic group,
   a $CO_2H$,
   a $CO_2$—($C_1$-$C_7$)-alkyl,
   a CONH—($C_1$-$C_7$)-alkyl,
   $CF_3$,
   adamantyl,
   CHRa—$NH_2$, wherein Ra represents the side chain of a proteinogenic amino acid,
   a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated JP-cyclodextrins and alkylated γ-cyclodextrins, said cyclodextrin being more particularly β-cyclodextrin, even more particularly a β-cyclodextrin of the following formula:

(d)

said ($C_1$-$C_7$)-alkyl, ($C_2$-$C_7$)-alkenyl, ($C_2$-$C_7$)-alkynyl, ($C_3$-$C_7$)-cycloalkyl, ($C_5$-$C_7$)-cycloalkenyl, ($C_3$-$C_7$)-heterocycloalkyl, ($C_5$-$C_7$)-heterocycloalkenyl, CO—($C_1$-$C_7$)-alkyl, $CO_2$—($C_1$-$C_7$)-alkyl, CONH—($C_1$-$C_7$)-alkyl, aryl, alkyl aryl, CO-aryl and cyclodextrin being substituted or not by one or more substituent(s), each independently selected from:
   a linear or branched ($C_1$-$C_7$)-alkyl,
   a linear or branched ($C_2$-$C_7$)-alkenyl,
   a linear or branched ($C_2$-$C_7$)-alkynyl,
   a ($C_3$-$C_7$)-cycloalkyl,
   a ($C_5$-$C_7$)-cycloalkenyl,
   a ($C_3$-$C_7$)-heterocycloalkyl,
   a ($C_5$-$C_7$)-heterocycloalkenyl,
   an aryl, wherein the aryl is an aromatic or heteroaromatic group
   an alkyl aryl, wherein the aryl is an aromatic or heteroaromatic group,
   a CHO,
   a CO—($C_1$-$C_7$)-alkyl,
   a CO-aryl, wherein aryl is an aromatic or heteroaromatic group,
   a $CO_2H$, a CO₂—(C₁-C₇)-alkyl,
a CONH—(C₁-C₇)-alkyl,
a halogen selected from the group comprising F, Cl, Br, and I,
CF₃,
OR$_a$, wherein R$_a$ represents:
  H, a linear or branched (C₁-C₇)-alkyl, a (C₃-C₇)-cycloalkyl, CO—(C₁-C₇)-alkyl, or CO-aryl, wherein aryl is an aromatic or heteroaromatic group,
NR$_b$R$_c$, wherein R$_b$ and R$_c$ represent independently from each other.
  H, a linear or branched (C₁-C₇)-alkyl, a (C₃-C₇)-cycloalkyl, CO—(C₁-C₇)-alkyl, or CO-aryl, wherein aryl is an aromatic or heteroaromatic group,
NO₂,
CN;

provided that when R represents CHRa—NH₂, then Y can only represent the following group (a):

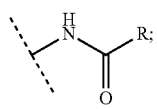
(a)

with the proviso that said compound is not of the following structure:

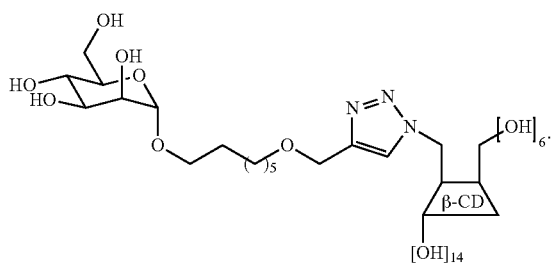

In another aspect, the present invention relates to a new compound of the following formula (I-0)):

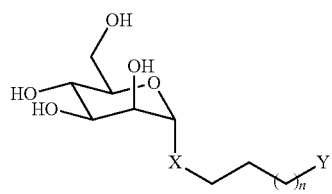
(I-0)

wherein:
X represents NH, O, S or CH₂;
n represents an integer being equal to 3, 4, 5, 6 or 7, n being in particular equal to 5;
Y represents a group selected from:

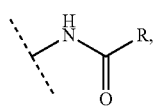
(a)

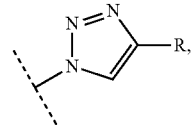
(b)

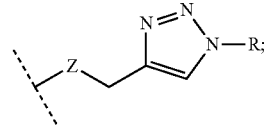
(c)

Z representing O, S or NH;
R representing:
  H
  a linear or branched (C₁-C₇)-alkyl, in particular methyl, ethyl, isopropyl or isobutyl,
  a group of formula —(CH₂)$_i$—X'—(CH₂)$_j$—H, wherein X' represents O, S or NH, i is an integer from 1 to 7, and j is an integer from 0 to 7, said group being in particular —CH₂—O—CH₃,
  a linear or branched (C₂-C₇)-alkenyl,
  a linear or branched (C₂-C₇)-alkynyl,
  a (C₃-C₇)-cycloalkyl,
  a (C₅-C₇)-cycloalkenyl,
  a (C₃-C₇)-heterocycloalkyl,
  a (C₅-C₇)-heterocycloalkenyl,
  an aryl, said aryl being an aromatic or heteroaromatic group,
  an alkyl aryl, wherein the aryl is an aromatic or heteroaromatic group,
  a CO—(C₁-C₇)-alkyl,
  a CO-aryl, wherein aryl is an aromatic or heteroaromatic group,
  a CO₂H,
  a CO₂—(C₁-C₇)-alkyl,
  a CONH—(C₁-C₇)-alkyl,
  CF₃,
  adamantyl,
  CHRa—NH₂, wherein Ra represents the side chain of a proteinogenic amino acid,
  a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a cyclodextrin of one of the following formulae:

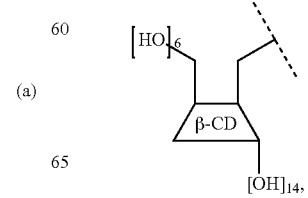
(d)

-continued

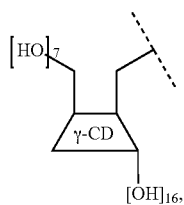
(e)

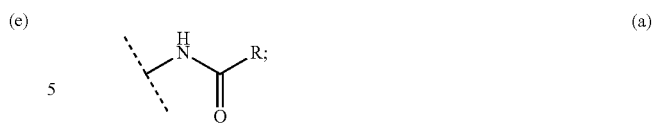
(a)

said $(C_1-C_7)$-alkyl, group of formula —$(CH_2)_i$—X'—$(CH_2)_j$—H, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl, CO-aryl and cyclodextrin being substituted or not by one or more substituent(s), each independently selected from:

a linear or branched $(C_1-C_7)$-alkyl, a linear or branched $(C_2-C_7)$-alkenyl, a linear or branched $(C_2-C_7)$-alkynyl, a $(C_3-C_7)$-cycloalkyl, a $(C_5-C_7)$-cycloalkenyl, a $(C_3-C_7)$-heterocycloalkyl, a $(C_5-C_7)$-heterocycloalkenyl, an aryl, wherein the aryl is an aromatic or heteroaromatic group an alkyl aryl, wherein the aryl is an aromatic or heteroaromatic group, a CHO, a CO—$(C_1-C_7)$-alkyl, a CO-aryl, wherein aryl is an aromatic or heteroaromatic group, a $CO_2H$, a $CO_2$—$(C_1-C_7)$-alkyl, a CONH—$(C_1-C_7)$-alkyl, a halogen selected from the group comprising F, Cl, Br, and I, $CF_3$, $OR_a$, wherein $R_a$ represents:

H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group, $NR_bR_c$, wherein $R_b$ and $R_c$ represent independently from each other:

H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group, $NO_2$,

CN, $SO_3H$ or one of its salts, in particular $SO_3Na$;

and its pharmaceutically acceptable salts, provided that when R represents $CHR_a$—$NH_2$, then Y can only represent the following group (a):

with the proviso that said compound is not of one of the following structures:

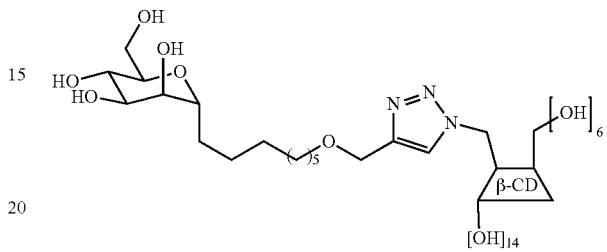

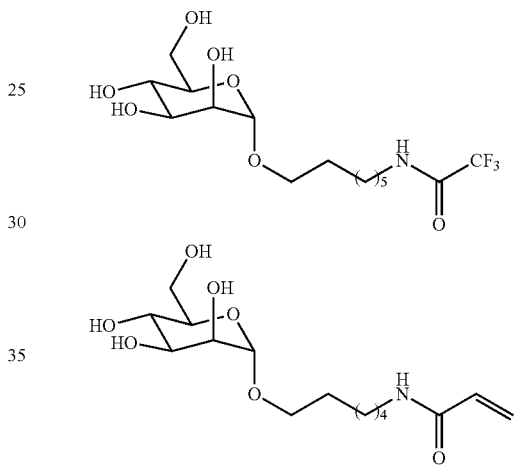

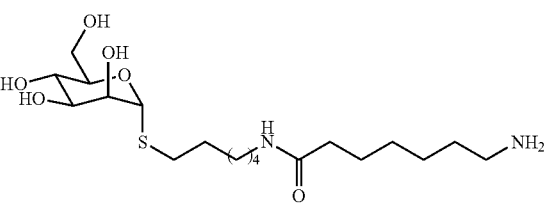

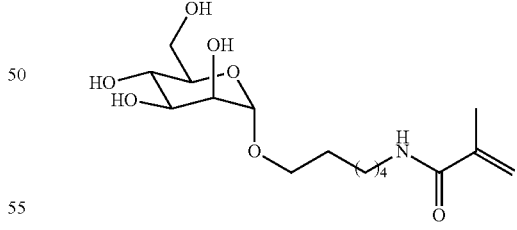

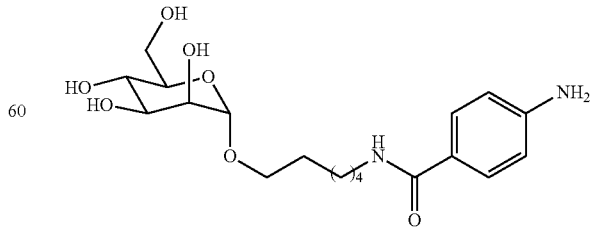

and its salts.

In an advantageous embodiment, the present invention relates to a new compound of the following formula (I-1):

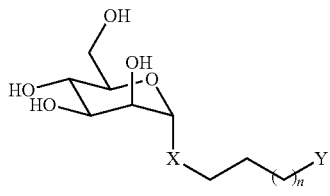

wherein:
X represents NH, O, S or CH$_2$;
n represents an integer comprised from 3 to 7, n being in particular equal to 5;
Y represents a group selected from:

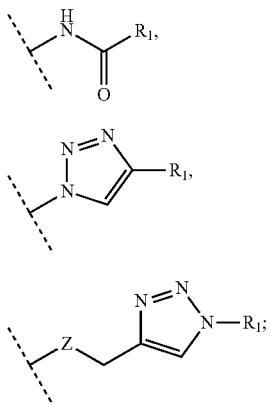

Z representing O or S;
R$_1$ representing:
H
a linear or branched (C$_1$-C$_7$)-alkyl, in particular isopropyl,
a linear or branched (C$_2$-C$_7$)-alkenyl,
a linear or branched (C$_2$-C$_7$)-alkynyl,
a (C$_3$-C$_7$)-cycloalkyl,
a (C$_5$-C$_7$)-cycloalkenyl,
a (C$_3$-C$_7$)-heterocycloalkyl,
a (C$_5$-C$_7$)-heterocycloalkenyl,
an aryl, said aryl being an aromatic or heteroaromatic group,
an alkyl aryl, wherein the aryl is an aromatic or heteroaromatic group,
a CO—(C$_1$-C$_7$)-alkyl,
a CO-aryl, wherein aryl is an aromatic or heteroaromatic group,
a CO$_2$H,
a CO$_2$—(C$_1$-C$_7$)-alkyl,
a CONH—(C$_1$-C$_7$)-alkyl,
—CF$_3$,
adamantyl,
CHRa—NH$_2$, wherein Ra represents the side chain of a proteinogenic amino acid,
said (C$_1$-C$_7$)-alkyl, (C$_2$-C$_7$)-alkenyl, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl and CO-aryl being substituted or not by one or more substituent(s), each independently selected from:
a linear or branched (C$_1$-C$_7$)-alkyl,
a linear or branched (C$_2$-C$_7$)-alkenyl,
a linear or branched (C$_2$-C$_7$)-alkynyl,
a (C$_3$-C$_7$)-cycloalkyl,
a (C$_5$-C$_7$)-cycloalkenyl,
a (C$_3$-C$_7$)-heterocycloalkyl,
a (C$_5$-C$_7$)-heterocycloalkenyl,
an aryl, wherein the aryl is an aromatic or heteroaromatic group
an alkyl aryl, wherein the aryl is an aromatic or heteroaromatic group,
a CHO,
a CO—(C$_1$-C$_7$)-alkyl,
a CO-aryl, wherein aryl is an aromatic or heteroaromatic group,
a CO$_2$H,
a CO$_2$—(C$_1$-C$_7$)-alkyl,
a CONH—(C$_1$-C$_7$)-alkyl,
a halogen selected from the group comprising F, Cl, Br, and I,
CF$_3$,
OR$_a$, wherein R$_a$ represents:
H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
NR$_b$R$_c$, wherein R$_b$ and R$_c$ represent independently from each other:
H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
NO$_2$,
—CN;
provided that when R$_1$ represents CHRa—NH$_2$, then Y can only represent the following group (a):

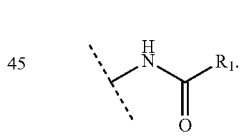

In an advantageous embodiment, the present invention relates to a new compound of the following formula (I-1):

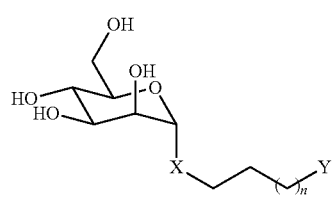

wherein:
X represents NH, O, S or CH$_2$;
n represents an integer being equal to 3, 4, 5, 6 or 7, n being in particular equal to 5;

Y represents a group selected from:

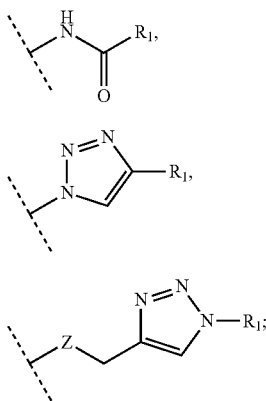

Z representing O, S or NH;
R$_1$ representing:
  H
  a linear or branched (C$_1$-C$_7$)-alkyl, in particular methyl, ethyl, isopropyl or isobutyl,
  a group of formula —(CH$_2$)$_i$—X'—(CH$_2$)$_j$—H, wherein X' represents O, S or NH, i is an integer from 1 to 7, and j is an integer from 0 to 7, said group being in particular —CH$_2$—O—CH$_3$,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl,
  an aryl, said aryl being an aromatic or heteroaromatic group,
  an alkyl aryl, wherein the aryl is an aromatic or heteroaromatic group,
  a CO—(C$_1$-C$_7$)-alkyl,
  a CO-aryl, wherein aryl is an aromatic or heteroaromatic group,
  a CO$_2$H,
  a CO$_2$—(C$_1$-C$_7$)-alkyl,
  a CONH—(C$_1$-C$_7$)-alkyl,
  CF$_3$,
  adamantyl,
  CHRa—NH$_2$, wherein Ra represents the side chain of a proteinogenic amino acid,
said (C$_1$-C$_7$)-alkyl, group of formula —(CH$_2$)$_i$—X'—(CH$_2$)$_j$—H, (C$_2$-C$_7$)-alkenyl, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl and CO-aryl being substituted or not by one or more substituent(s), each independently selected from:
  a linear or branched (C$_1$-C$_7$)-alkyl,
  a linear or branched (C$_2$-C$_7$)-alkenyl,
  a linear or branched (C$_2$-C$_7$)-alkynyl,
  a (C$_3$-C$_7$)-cycloalkyl,
  a (C$_5$-C$_7$)-cycloalkenyl,
  a (C$_3$-C$_7$)-heterocycloalkyl,
  a (C$_5$-C$_7$)-heterocycloalkenyl,
  an aryl, wherein the aryl is an aromatic or heteroaromatic group
  an alkyl aryl, wherein the aryl is an aromatic or heteroaromatic group,
  a CHO,
  a CO—(C$_1$-C$_7$)-alkyl,
  a CO-aryl, wherein aryl is an aromatic or heteroaromatic group,
  a CO$_2$H,
  a CO$_2$—(C$_1$-C$_7$)-alkyl,
  a CONH—(C$_1$-C$_7$)-alkyl,
  a halogen selected from the group comprising F, Cl, Br, and I,
  CF$_3$,
  OR$_a$, wherein R$_a$ represents:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NR$_b$R$_c$, wherein R$_b$ and R$_c$ represent independently from each other:
    H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,
  NO$_2$,
  CN,
  SO$_3$H or one of its salts, in particular SO$_3$Na;
and its pharmaceutically acceptable salts,
provided that when R$_1$ represents CHRa—NH$_2$, then Y can only represent the following group (a):

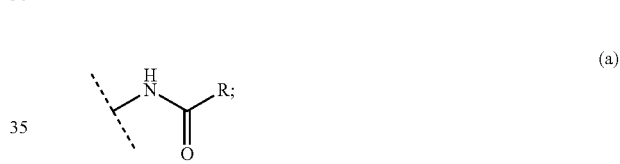

with the proviso that said compound is not of one of the following structures:

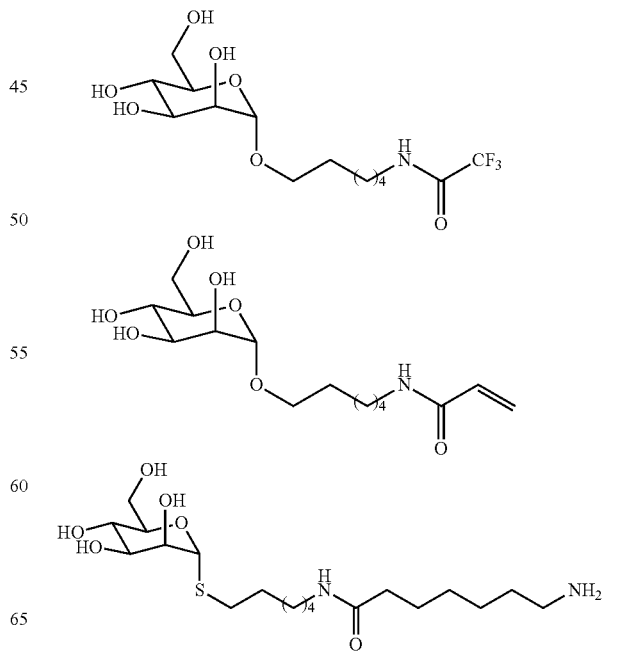

-continued

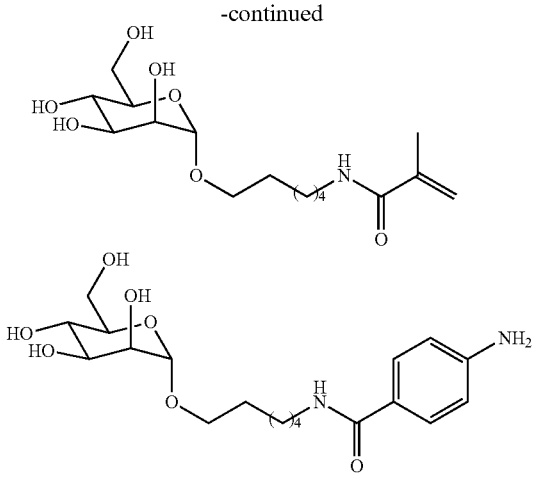

and its salts.

In an advantageous embodiment, the present invention relates to a new compound of formula (I-0) or (I-1), wherein R or $R_1$ represents:
- a linear ($C_1$-$C_7$)-alkyl, more particularly methyl, ethyl, propyl or butyl, optionally substituted by a —OH and/or a —$NH_2$ group,
- a branched ($C_3$-$C_7$)-alkyl, more particularly isopropyl or isobutyl,
- a ($C_3$-$C_7$)-heterocycloalkyl, more particularly a pyrrolidine,
- an aryl, said aryl being an aromatic or heteroaromatic group, more particularly a phenyl, a pyridinyl, a pyrrole or an imidazole, optionally substituted by a —OH, a —$NH_2$ or a —$SO_3Na$ group,
- an alkyl aryl, wherein the aryl is an aromatic or heteroaromatic group, more particularly a benzyl, a phenethyl or an ethyl imidazolyl, optionally substituted by a —OH or a —$NH_2$ group,
- CHRa—$NH_2$, wherein Ra represents the side chain of a proteinogenic amino acid, in particular alanine, serine, proline, phenylalanine, cysteine or histidine.

In an advantageous embodiment, the present invention relates to a new compound of formula (I-0), of particular formula (I-2):

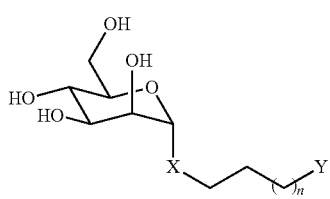

wherein:
X represents NH, O, S or $CH_2$;
n represents an integer being equal to 3, 4, 5, 6 or 7, n being in particular equal to 5;

Y represents a group selected from:

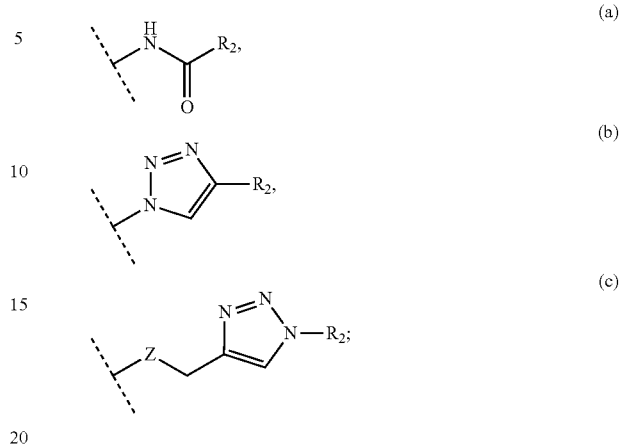

Z representing O, S or NH;
$R_2$ representing a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a β-cyclodextrin of the following formula:

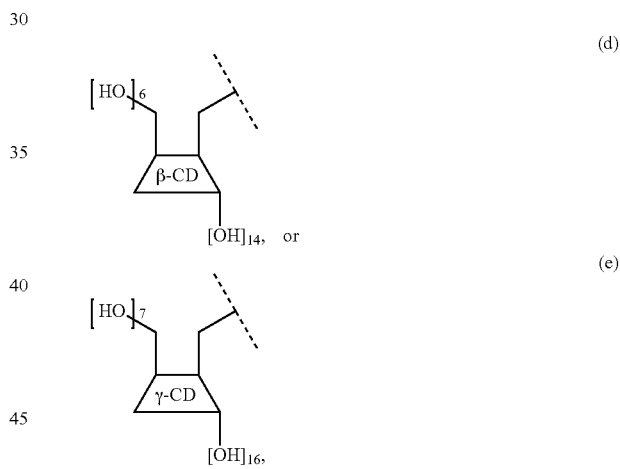

said cyclodextrin being substituted or not by one or more substituent(s), each independently selected from:
- a linear or branched ($C_1$-$C_7$)-alkyl,
- a linear or branched ($C_2$-$C_7$)-alkenyl,
- a linear or branched ($C_2$-$C_7$)-alkynyl,
- a ($C_3$-$C_7$)-cycloalkyl,
- a ($C_5$-$C_7$)-cycloalkenyl,
- a ($C_3$-$C_7$)-heterocycloalkyl,
- a ($C_5$-$C_7$)-heterocycloalkenyl,
- an aryl, wherein the aryl is an aromatic or heteroaromatic group
- an alkyl aryl, wherein the aryl is an aromatic or heteroaromatic group,
- a CHO,
- a CO—($C_1$-$C_7$)-alkyl,
- a CO-aryl, wherein aryl is an aromatic or heteroaromatic group,
- a $CO_2H$,
- a $CO_2$—($C_1$-$C_7$)-alkyl,
- a CONH—($C_1$-$C_7$)-alkyl, a halogen selected from the group comprising F, Cl, Br, and I,

CF$_3$,

OR$_a$, wherein R$_a$ represents:

H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group, NR$_b$R$_c$, wherein R$_b$ and R$_c$ represent independently from each other:

H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group,

NO$_2$,

CN;

with the proviso that said compound is not of the following structure:

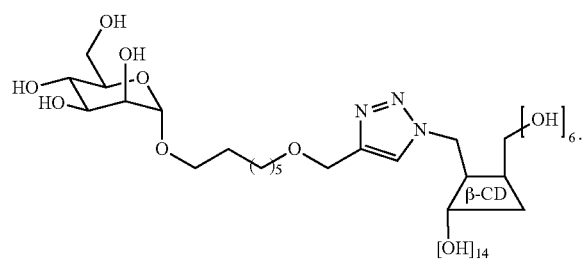

In an advantageous embodiment, the present invention relates to a compound of formula (I-0) or (I-1), wherein Y represents:

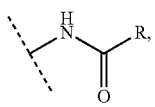

(a)

of following formula (I-1a):

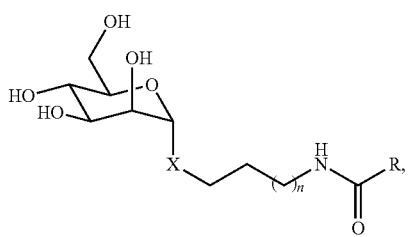

(I-1a)

X, R and n being as defined above,

R being R$_1$ as defined above when said compound is of formula (I-1),

R representing in particular a linear or branched (C$_1$-C$_7$)-alkyl, more particularly isopropyl.

In an advantageous embodiment, the present invention relates to a new compound of formula (I-1a):

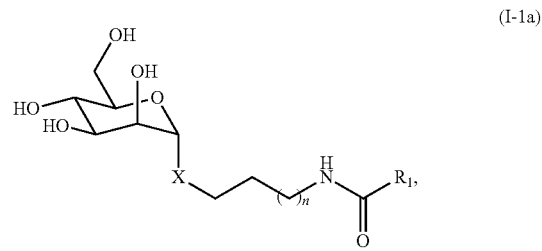

(I-1a)

wherein X and n being as defined above,

R$_1$ representing:

H a linear or branched (C$_1$-C$_7$)-alkyl, in particular methyl, ethyl, isopropyl or isobutyl, a group of formula —(CH$_2$)$_i$—X'—(CH$_2$)$_j$—H, wherein X' represents O, S or NH, i is an integer from 1 to 7, and j is an integer from 0 to 7, said group being in particular —CH$_2$—O—CH$_3$, a linear or branched (C$_2$-C$_7$)-alkynyl, a (C$_3$-C$_7$)-cycloalkyl, a (C$_5$-C$_7$)-cycloalkenyl, a (C$_3$-C$_7$)-heterocycloalkyl, a (C$_5$-C$_7$)-heterocycloalkenyl, an aryl, said aryl being an aromatic or heteroaromatic group, an alkyl aryl, wherein the aryl is an aromatic or heteroaromatic group, a CO—(C$_1$-C$_7$)-alkyl, a CO-aryl, wherein aryl is an aromatic or heteroaromatic group, a CO$_2$H, a CO$_2$—(C$_1$-C$_7$)-alkyl, a CONH—(C$_1$-C$_7$)-alkyl, adamantyl, CHRa—NH$_2$, wherein Ra represents the side chain of a proteinogenic amino acid, said (C$_1$-C$_7$)-alkyl, group of formula —(CH$_2$)$_i$—(CH$_2$)$_j$—H, (C$_2$-C$_7$)-alkynyl, (C$_3$-C$_7$)-cycloalkyl, (C$_5$-C$_7$)-cycloalkenyl, (C$_3$-C$_7$)-heterocycloalkyl, (C$_5$-C$_7$)-heterocycloalkenyl, CO—(C$_1$-C$_7$)-alkyl, CO$_2$—(C$_1$-C$_7$)-alkyl, CONH—(C$_1$-C$_7$)-alkyl, aryl, alkyl aryl and CO-aryl being substituted or not by one or more substituent(s), each independently selected from:

a linear or branched (C$_1$-C$_7$)-alkyl, a linear or branched (C$_2$-C$_7$)-alkynyl, a (C$_3$-C$_7$)-cycloalkyl, a (C$_5$-C$_7$)-cycloalkenyl, a (C$_3$-C$_7$)-heterocycloalkyl, a (C$_5$-C$_7$)-heterocycloalkenyl, an aryl, wherein the aryl is an aromatic or heteroaromatic group an alkyl aryl, wherein the aryl is an aromatic or heteroaromatic group, a CHO, a CO—(C$_1$-C$_7$)-alkyl, a CO-aryl, wherein aryl is an aromatic or heteroaromatic group, a CO$_2$H, a CO$_2$—(C$_1$-C$_7$)-alkyl, a CONH—(C$_1$-C$_7$)-alkyl, a halogen selected from the group comprising F, Cl, Br, and I,

CF$_3$,

OR$_a$, wherein R$_a$ represents:

H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group, NR$_b$R$_c$, wherein R$_b$ and R$_c$ represent independently from each other:

H, a linear or branched (C$_1$-C$_7$)-alkyl, a (C$_3$-C$_7$)-cycloalkyl, CO—(C$_1$-C$_7$)-alkyl, or CO-aryl, wherein aryl is an aromatic or heteroaromatic group, at least one of R$_b$ and R$_c$ representing CO—(C$_1$-C$_7$)-alkyl, or CO-aryl,

NO$_2$,

CN,

SO$_3$H or one of its salts, in particular SO$_3$Na.

In an advantageous embodiment, the present invention relates to a new compound of formula (I-0) or (I-1), wherein Y represents:

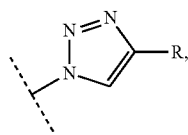
(b)

of following formula (I-1b):

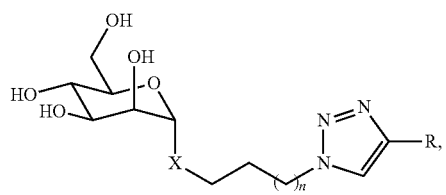
(I-1b)

X, n and R being as defined above,

R being R$_1$ as defined above when said compound is of formula (I-1).

In an advantageous embodiment, the present invention relates to a new compound of formula (I-0) or (I-1), wherein Y represents:

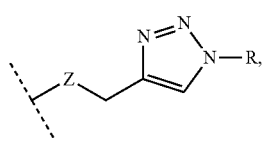
(c)

Z being as defined above, of following formula (I-1c):

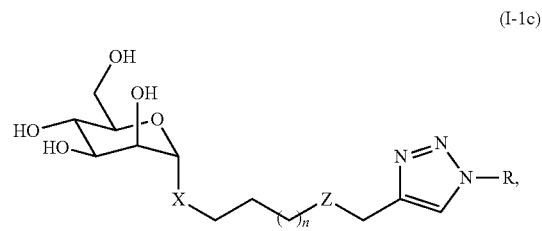
(I-1c)

X, n, Z and R being as defined above,

R being R$_1$ as defined above when said compound is of formula (I-1).

In an advantageous embodiment, the present invention relates to a new compound of formula (I-2), wherein Y represents:

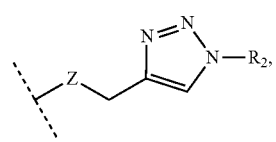
(c)

of following formula (I-2c):

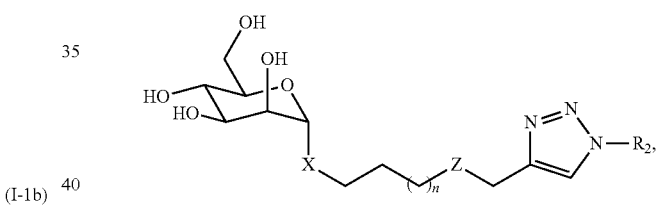
(I-2c)

X, R$_2$, n and Z being as defined above.

In an advantageous embodiment, the new compound of formula (I) is of particular formula (I-2c), wherein X represents O or S, in particular S.

In an advantageous embodiment, the new compound of formula (I) is of particular formula (I-2c), wherein R$_2$ represents:

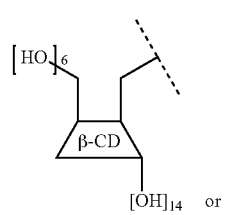
(d)

or

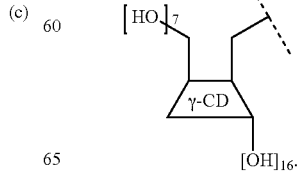
(e)

In an advantageous embodiment, the new compound of formula (I) is of particular formula (I-2c), X represents O or S, in particular S, and wherein $R_2$ represents:

(d)
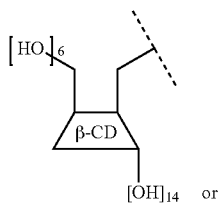

or (e)
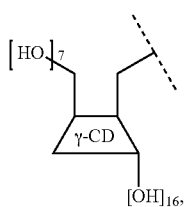

Z being in particular O.

In an advantageous embodiment, the present invention relates to a new compound of formula (I-1), of following formula (I-1a-1):

(I-1a-1)
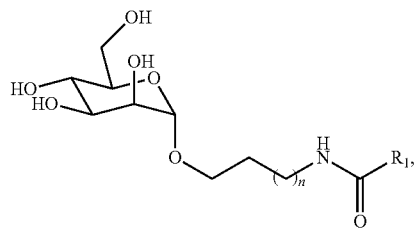

$R_1$ and n being as defined above.

In an advantageous embodiment, the present invention relates to a new compound of formula (I-1), of following formula (I-1a-2):

(I-1a-2)
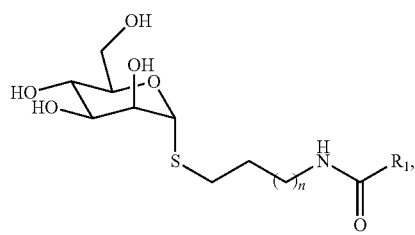

$R_1$ and n being as defined above.

In an advantageous embodiment, the present invention relates to a new compound of formula (I-1), of following formula (I-1a-3):

(I-1a-3)
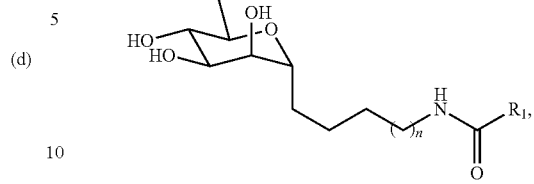

$R_1$ and n being as defined above.

In an advantageous embodiment, the present invention relates to a new compound of formula (I-1), of following formula (I-1a-4):

(I-1a-4)
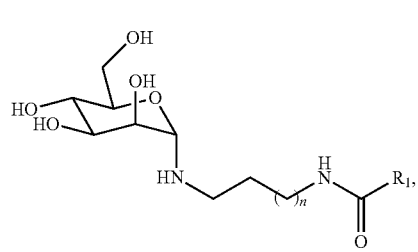

$R_1$ and n being as defined above.

In an advantageous embodiment, the present invention relates to a new compound of formula (I-1), of following formula (I-1b-1):

(I-1b-1)
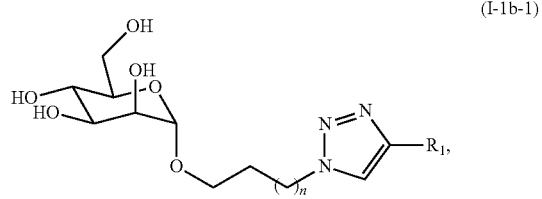

$R_1$ and n being as defined above.

In an advantageous embodiment, the present invention relates to a new compound of formula (I-1), of following formula (I-1b-2):

(I-1b-2)
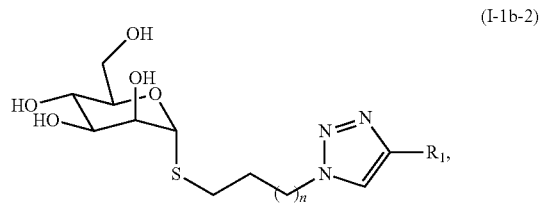

$R_1$ and n being as defined above.

In an advantageous embodiment, the present invention relates to a new compound of formula (I-1), of following formula (I-1b-3):

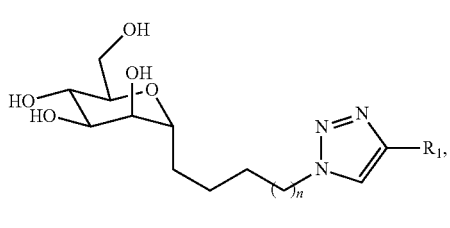
(I-1b-3)

$R_1$ and n being as defined above.

In an advantageous embodiment, the present invention relates to a new compound of formula (I-1), of following formula (I-1b-4):

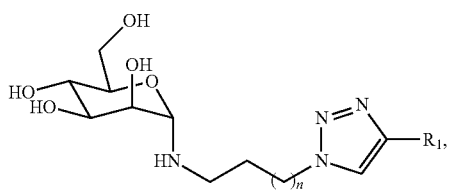
(I-1b-4)

$R_1$ and n being as defined above.

In an advantageous embodiment, the present invention relates to a new compound of formula (I-1), of following formula (I-1c-1):

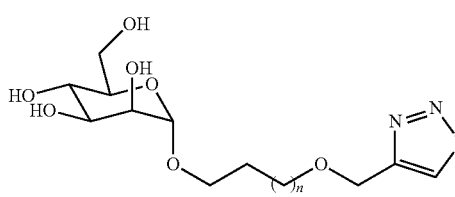
(I-1c-1)

$R_1$ and n being as defined above.

In an advantageous embodiment, the present invention relates to a new compound of formula (I-1), of following formula (I-1c-2):

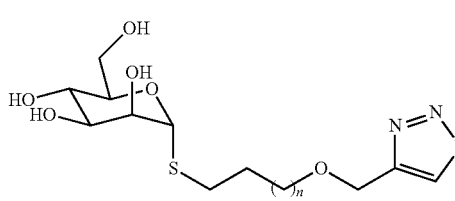
(I-1c-2)

$R_1$ and n being as defined above.

In an advantageous embodiment, the present invention relates to a new compound of formula (I-1), of following formula (I-1c-3):

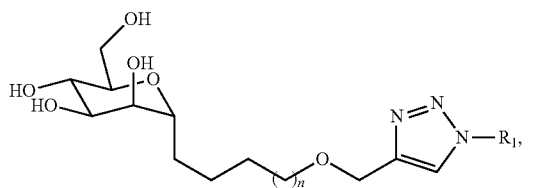
(I-1c-3)

$R_1$ and n being as defined above.

In an advantageous embodiment, the present invention relates to a new compound of formula (I-1), of following formula (I-1c-4):

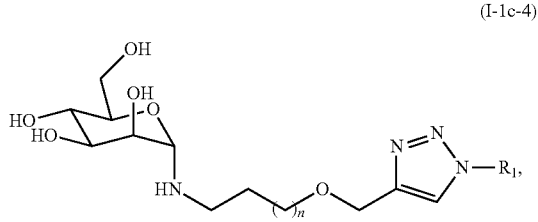
(I-1c-4)

$R_1$ and n being as defined above.

In an advantageous embodiment, the present invention relates to a new compound of formula (I-1), of following formula (I-1c-5):

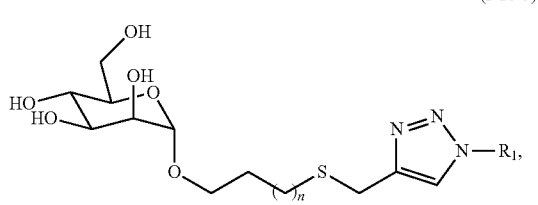
(I-1c-5)

$R_1$ and n being as defined above.

In an advantageous embodiment, the present invention relates to a new compound of formula (I-1), of following formula (I-1c-6):

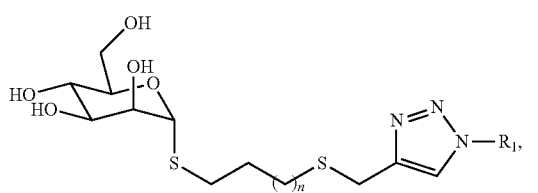
(I-1c-6)

$R_1$ and n being as defined above.

In an advantageous embodiment, the present invention relates to a new compound of formula (I-1), of following formula (I-1c-7):

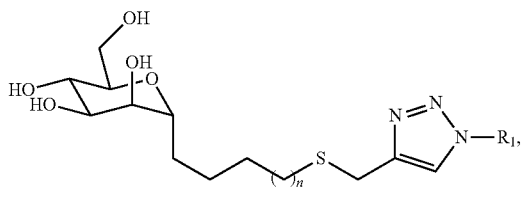

(I-1c-7)

In an advantageous embodiment, the present invention relates to a new compound of formula (I-1), of following formula (I-1c-8):

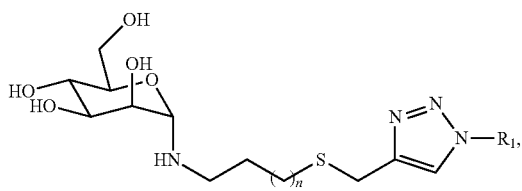

(I-1c-8)

$R_1$ and n being as defined above.

In an advantageous embodiment, the present invention relates to a new compound of formula (I-1a-1), (I-1a-2), (I-1a-3), (I-1a-4), (I-1b-1), (I-1b-2), (I-1b-3), (I-1b-4), (I-1c-1), (I-1c-2), (I-1c-3), (I-1c-4), (I-1c-5), (I-1c-6), (I-1c-7) or (I-1c-8), wherein $R_1$ represents:
- a linear ($C_1$-$C_7$)-alkyl, more particularly methyl, ethyl, propyl or butyl, optionally substituted by a —OH and/or a —$NH_2$ group,
- a branched ($C_3$-$C_7$)-alkyl, more particularly isopropyl or isobutyl,
- a ($C_3$-$C_7$)-heterocycloalkyl, more particularly a pyrrolidine,
- an aryl, said aryl being an aromatic or heteroaromatic group, more particularly a phenyl, a pyridinyl, a pyrrole or an imidazole, optionally substituted by a —OH, a —$NH_2$ or a —$SO_3Na$ group,
- an alkyl aryl, wherein the aryl is an aromatic or heteroaromatic group, more particularly a benzyl, a phenethyl or an ethyl imidazolyl, optionally substituted by a —OH or a —$NH_2$ group,
- CHRa—$NH_2$, wherein Ra represents the side chain of a proteinogenic amino acid, in particular alanine, serine, proline, phenylalanine, cysteine or histidine.

In an advantageous embodiment, the present invention relates to a new compound of formula (I-2), of following formula (I-2a-1):

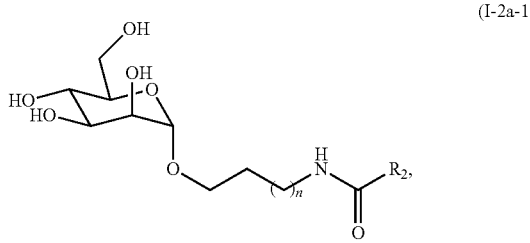

(I-2a-1)

$R_2$ and n being as defined above.

In an advantageous embodiment, the present invention relates to a new compound of formula (I-2), of following formula (I-2a-2):

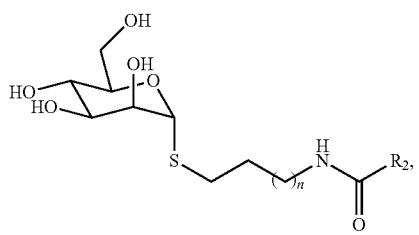

(I-2a-2)

$R_2$ and n being as defined above.

In an advantageous embodiment, the present invention relates to a new compound of formula (I-2), of following formula (I-2a-3):

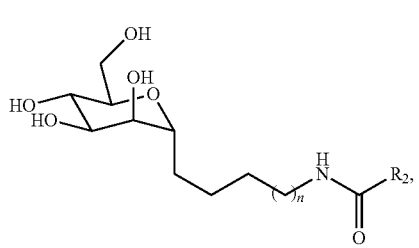

(I-2a-3)

$R_2$ and n being as defined above.

In an advantageous embodiment, the present invention relates to a new compound of formula (I-2), of following formula (I-2a-4):

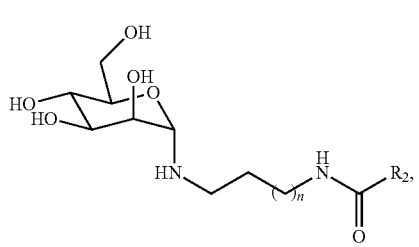

(I-2a-4)

$R_2$ and n being as defined above.

In an advantageous embodiment, the present invention relates to a new compound of formula (I-2), of following formula (I-2b-1):

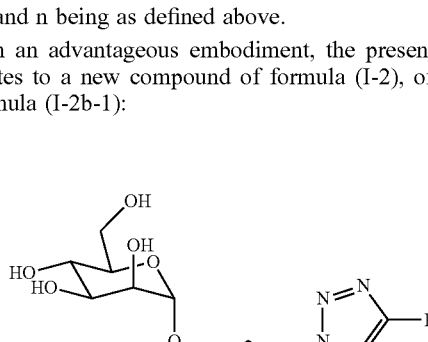

(I-2b-1)

$R_2$ and n being as defined above.

In an advantageous embodiment, the present invention relates to a new compound of formula (I-2), of following formula (I-2b-2):

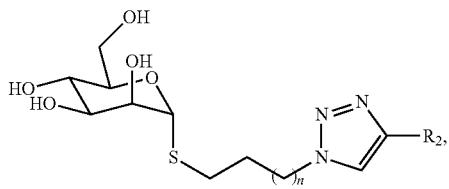
(I-2b-2)

$R_2$ and n being as defined above.

In an advantageous embodiment, the present invention relates to a new compound of formula (I-2), of following formula (I-2b-3):

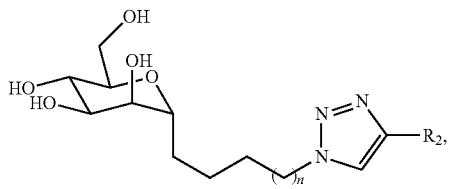
(I-2b-3)

$R_2$ and n being as defined above.

In an advantageous embodiment, the present invention relates to a new compound of formula (I-2), of following formula (I-2b-4):

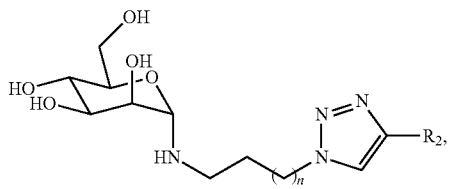
(I-2b-4)

$R_2$ and n being as defined above.

In an advantageous embodiment, the present invention relates to a new compound of formula (I-2), of following formula (I-2c-1):

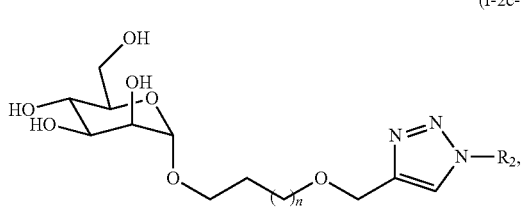
(I-2c-1)

$R_2$ and n being as defined above.

In an advantageous embodiment, the present invention relates to a new compound of formula (I-2), of following formula (I-2c-2):

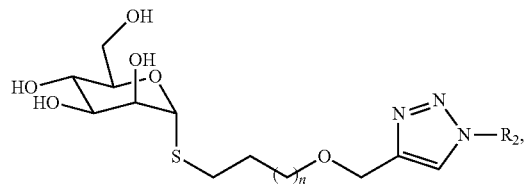
(I-2c-2)

$R_2$ and n being as defined above.

In an advantageous embodiment, the present invention relates to a new compound of formula (I-2), of following formula (I-2c-3):

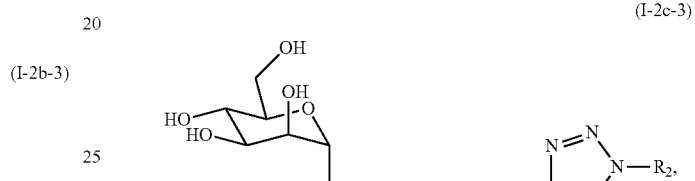
(I-2c-3)

$R_2$ and n being as defined above.

In an advantageous embodiment, the present invention relates to a new compound of formula (I-2), of following formula (I-2c-4):

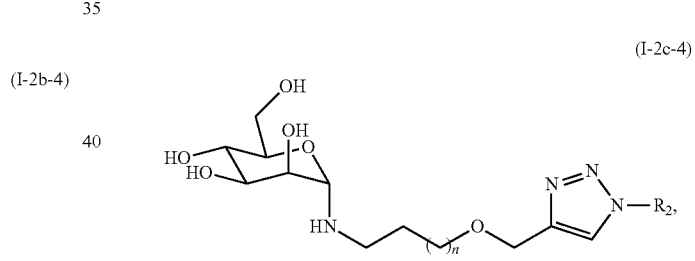
(I-2c-4)

$R_2$ and n being as defined above.

In an advantageous embodiment, the present invention relates to a new compound of formula (I-2), of following formula (I-2c-5):

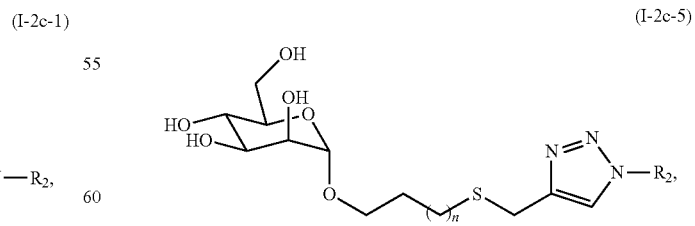
(I-2c-5)

$R_2$ and n being as defined above.

In an advantageous embodiment, the present invention relates to a new compound of formula (I-2), of following formula (I-2c-6):

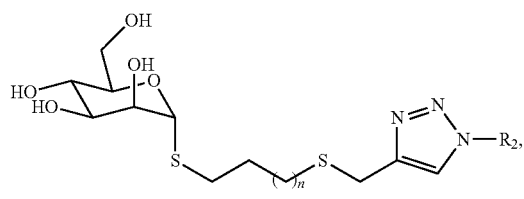

$R_2$ and n being as defined above.

In an advantageous embodiment, the present invention relates to a new compound of formula (I-2), of following formula (I-2c-7):

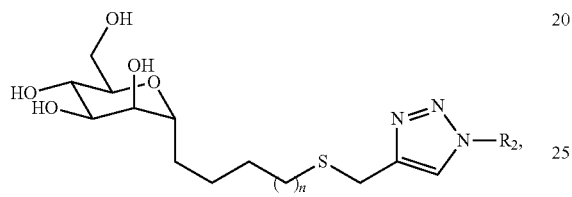

$R_2$ and n being as defined above.

In an advantageous embodiment, the present invention relates to a new compound of formula (I-2), of following formula (I-2c-8):

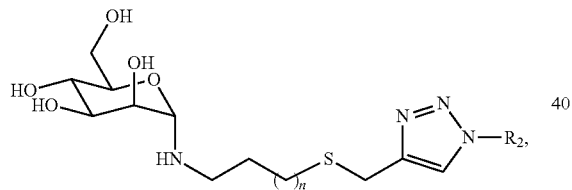

$R_2$ and n being as defined above.

In an advantageous embodiment, the present invention relates to a new compound of formula (I-1a-1)(I-1a-2)(I-1a-3), (I-1c-4), (I-1c-5), (I-1c-6), (I-1c-7), (I-1-8), (I-2a-1), (I-2a-2), (I-2a-3), (I-2a-4), (I-2b-1), (I-2b-2), (I-2b-3), (I-2b-4), (I-2c-1), (I-2c-2), (I-2c-3), (I-2c-4), (I-2c-5), (I-2c-6), (I-2c-7) or (I-2c-8), wherein n is equal to 5.

In an advantageous embodiment, the present invention relates to a new compound of formula (I-0) or (I-1), selected from the group consisting of

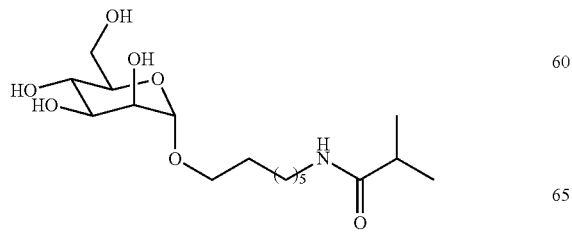

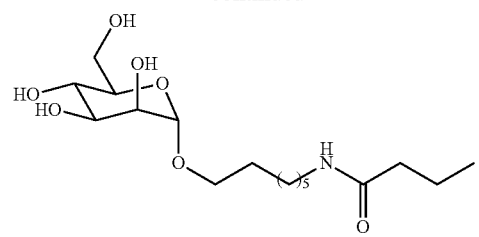

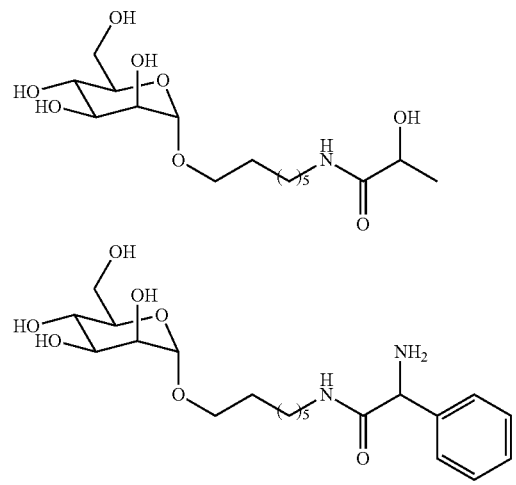

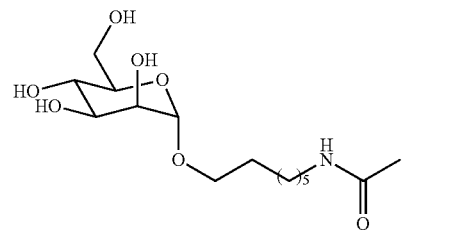

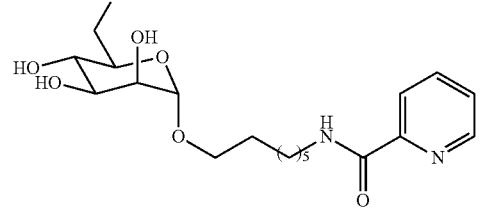

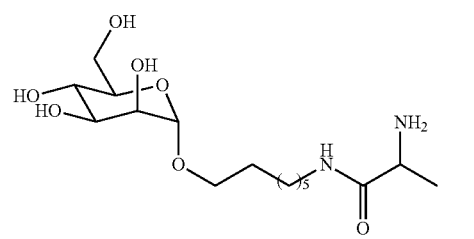

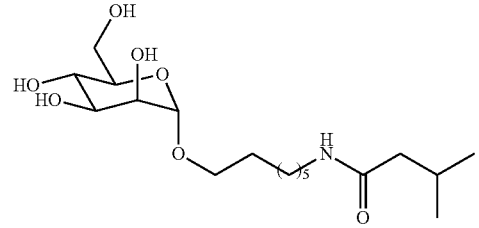

-continued
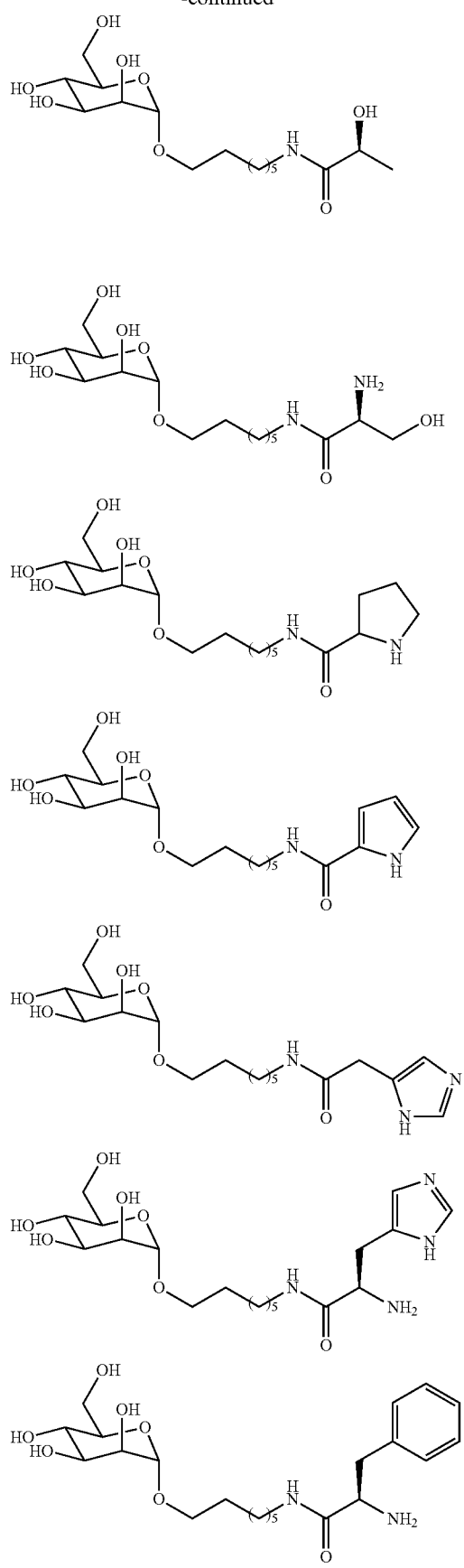
-continued
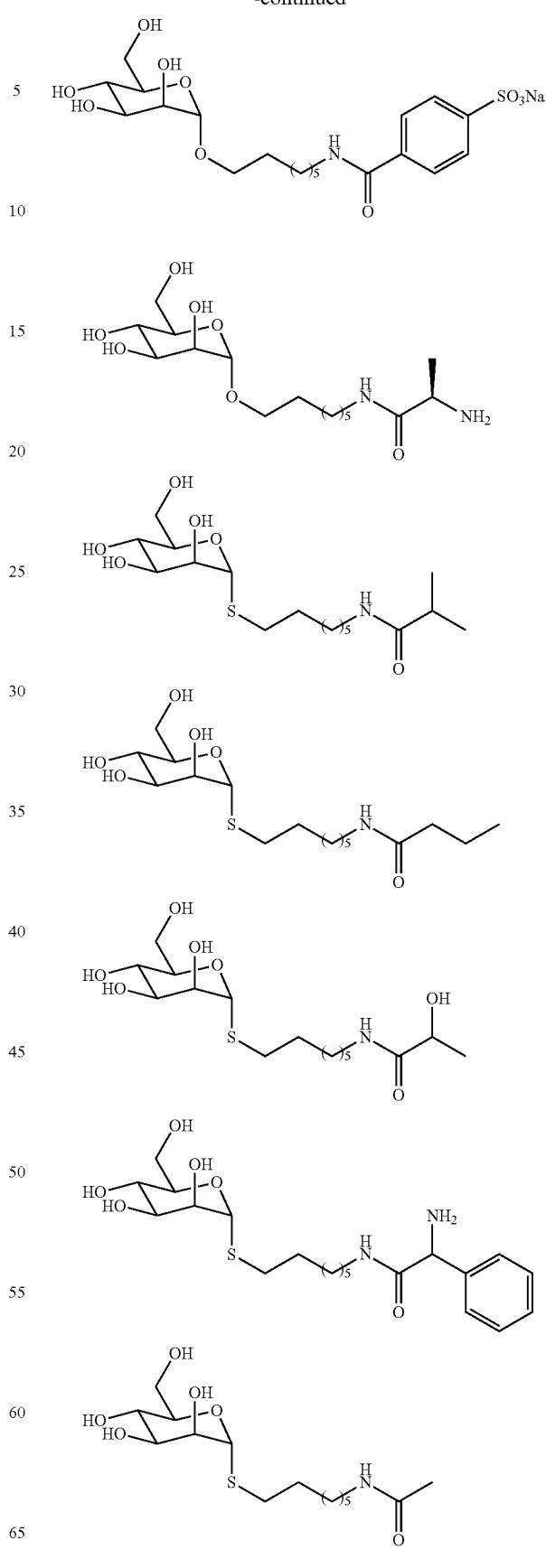

-continued
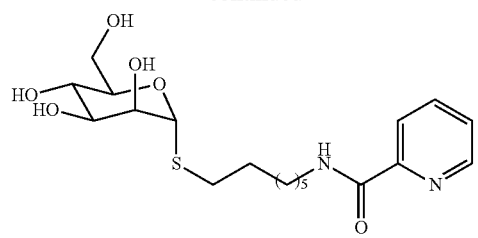
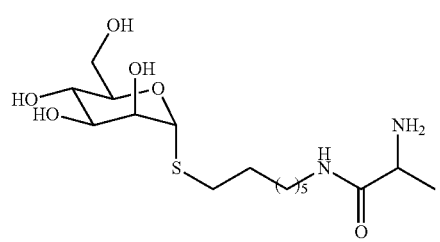
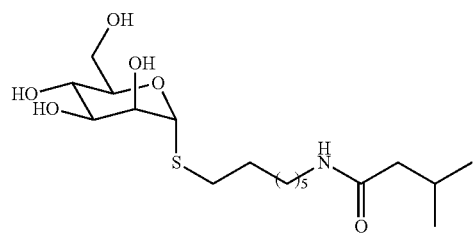
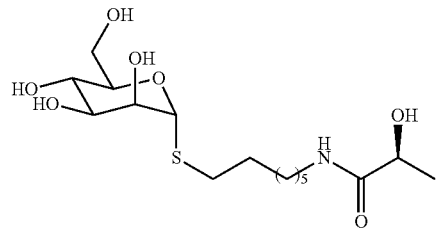
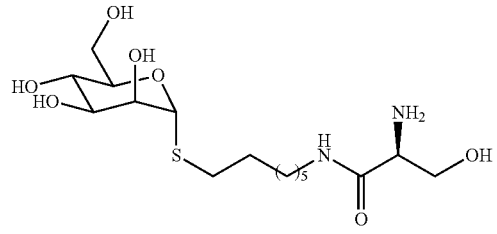
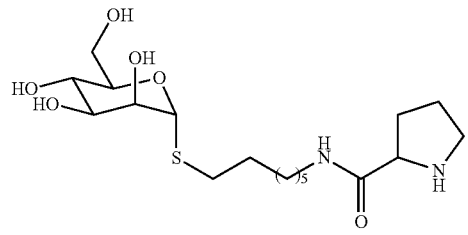
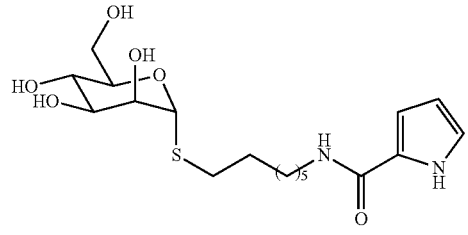
-continued
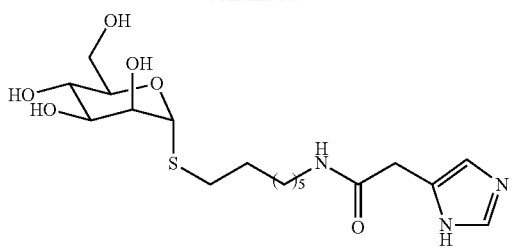
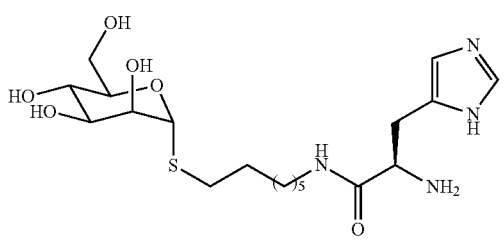
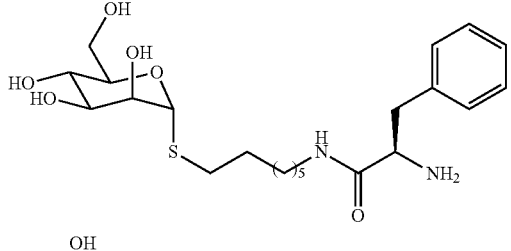
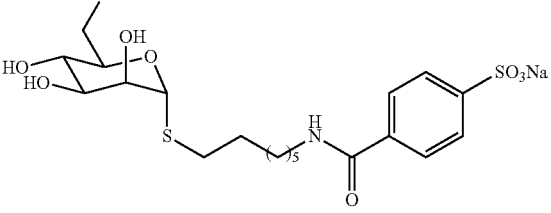
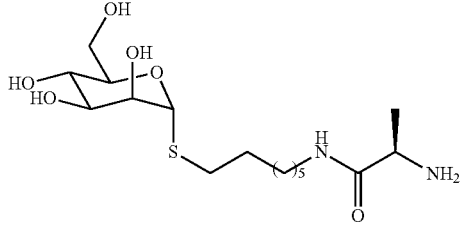
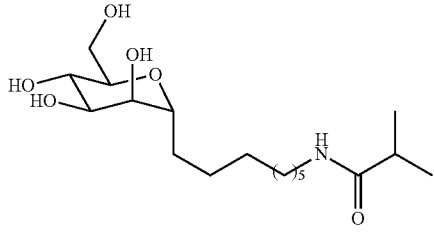
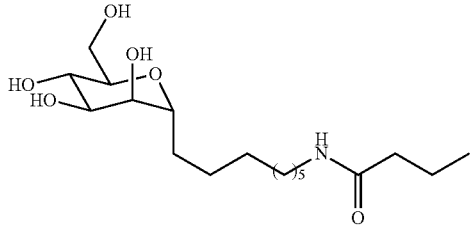

-continued
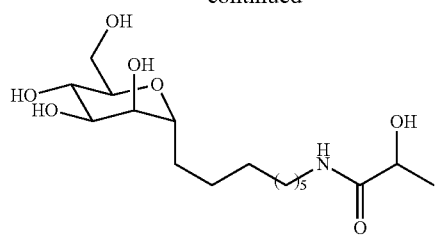
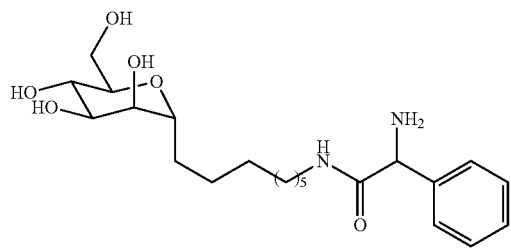
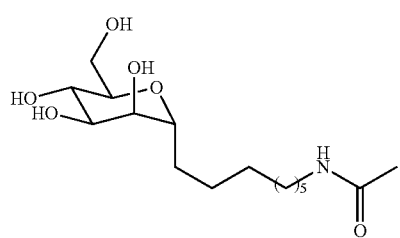
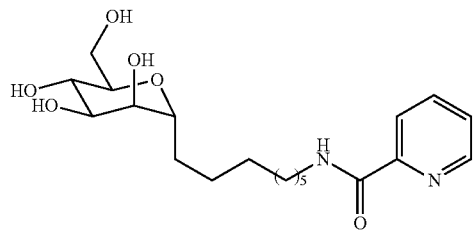
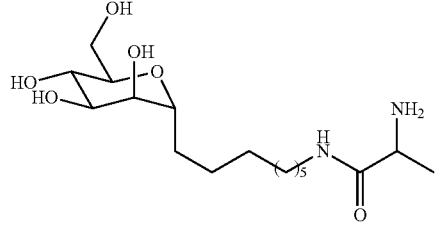
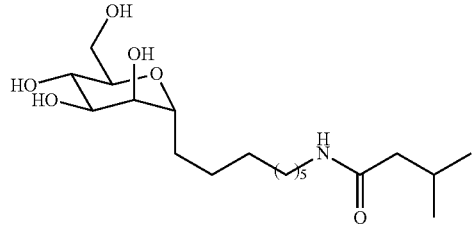
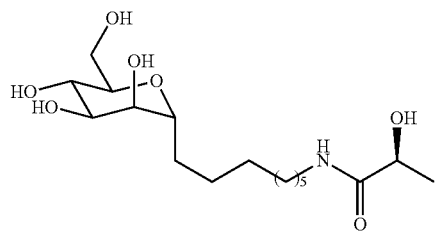
-continued
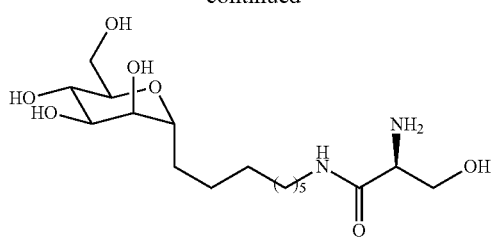
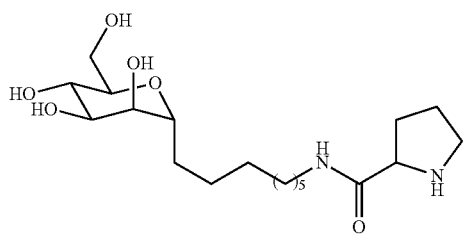
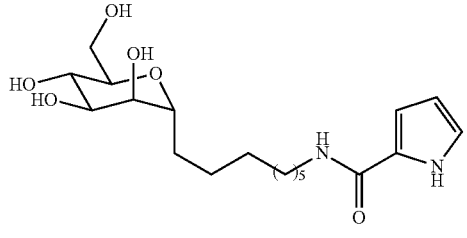
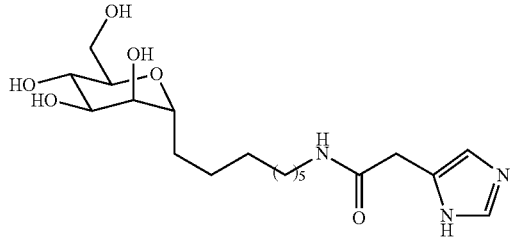
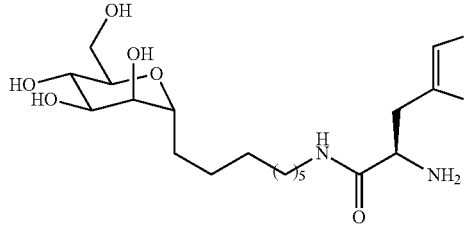
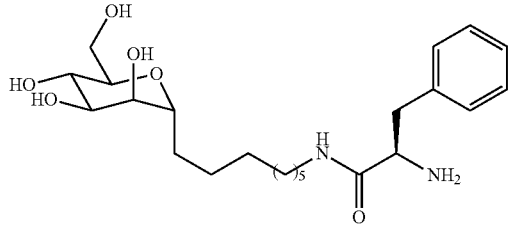
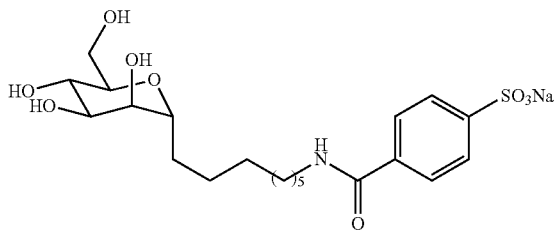

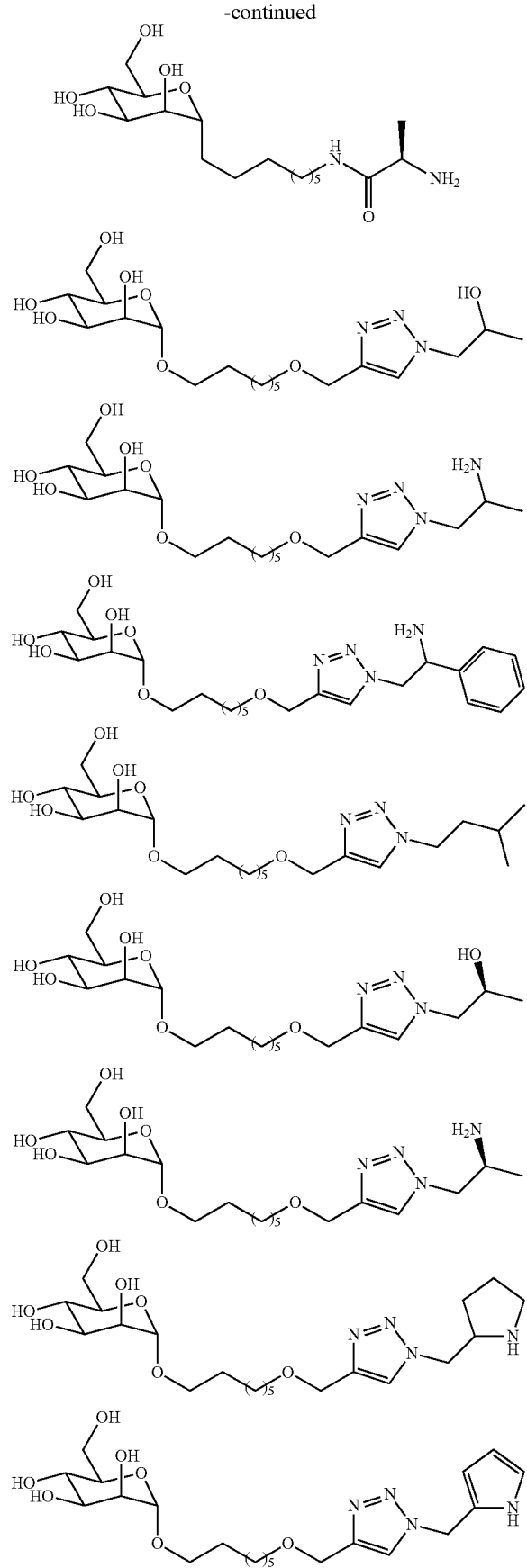
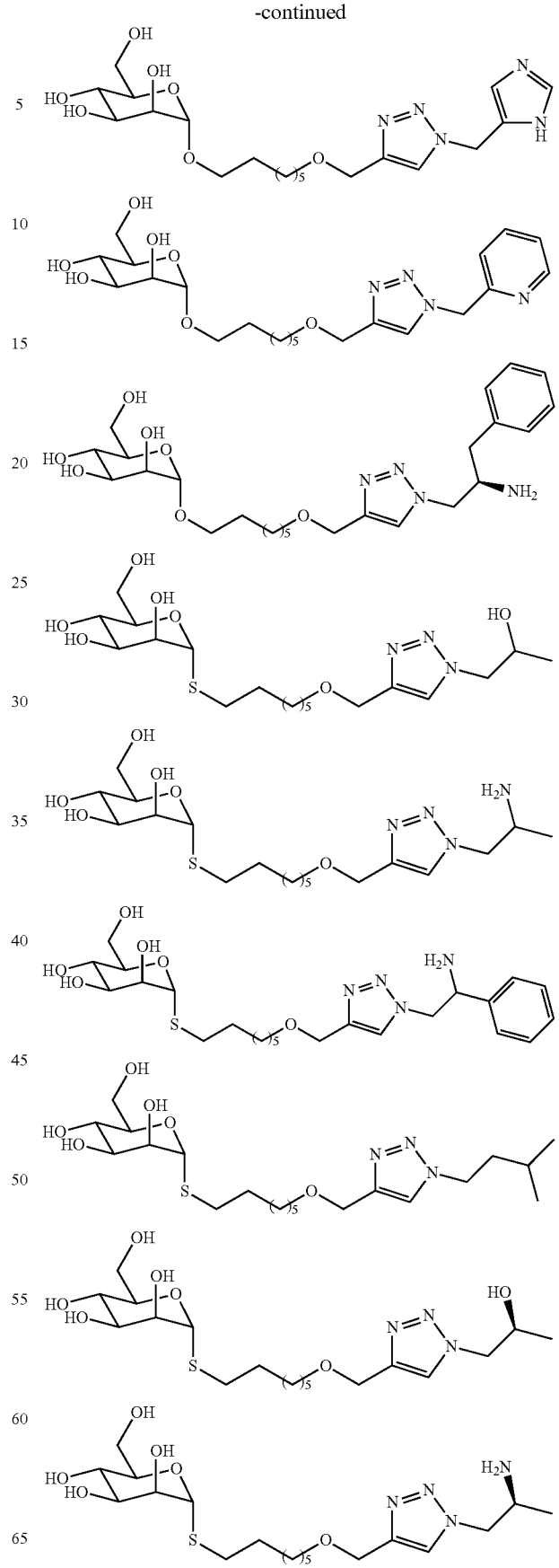

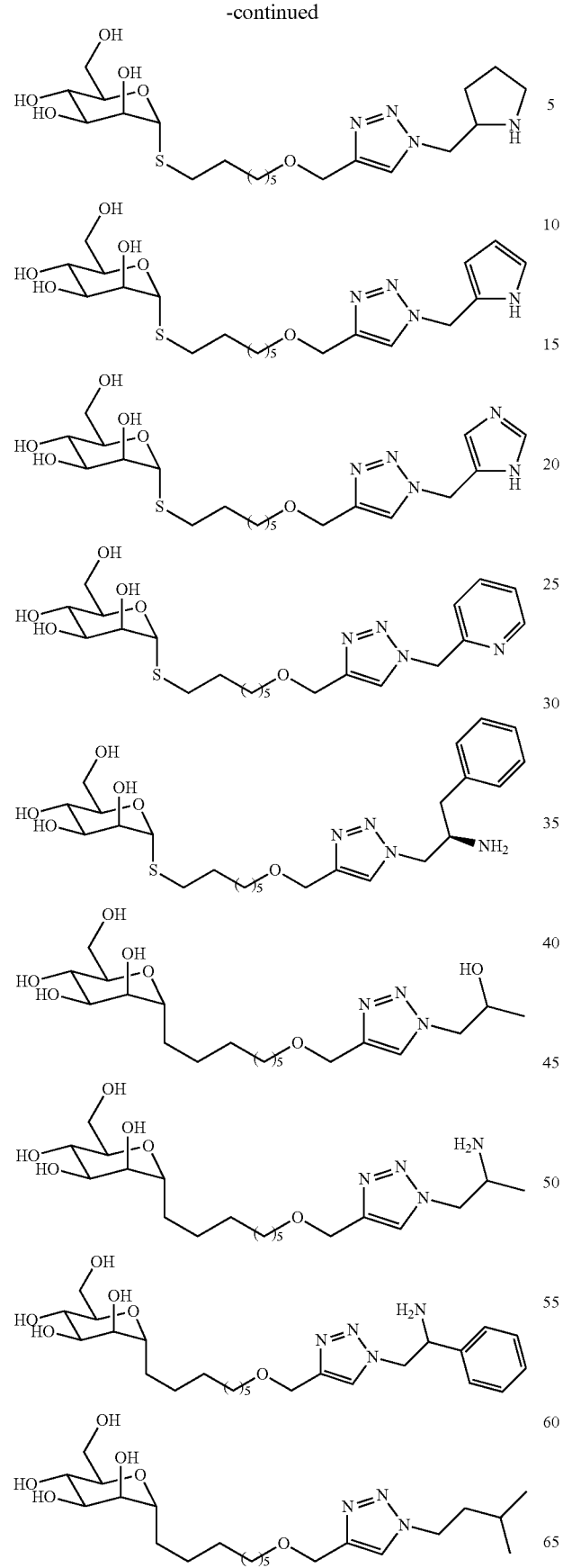
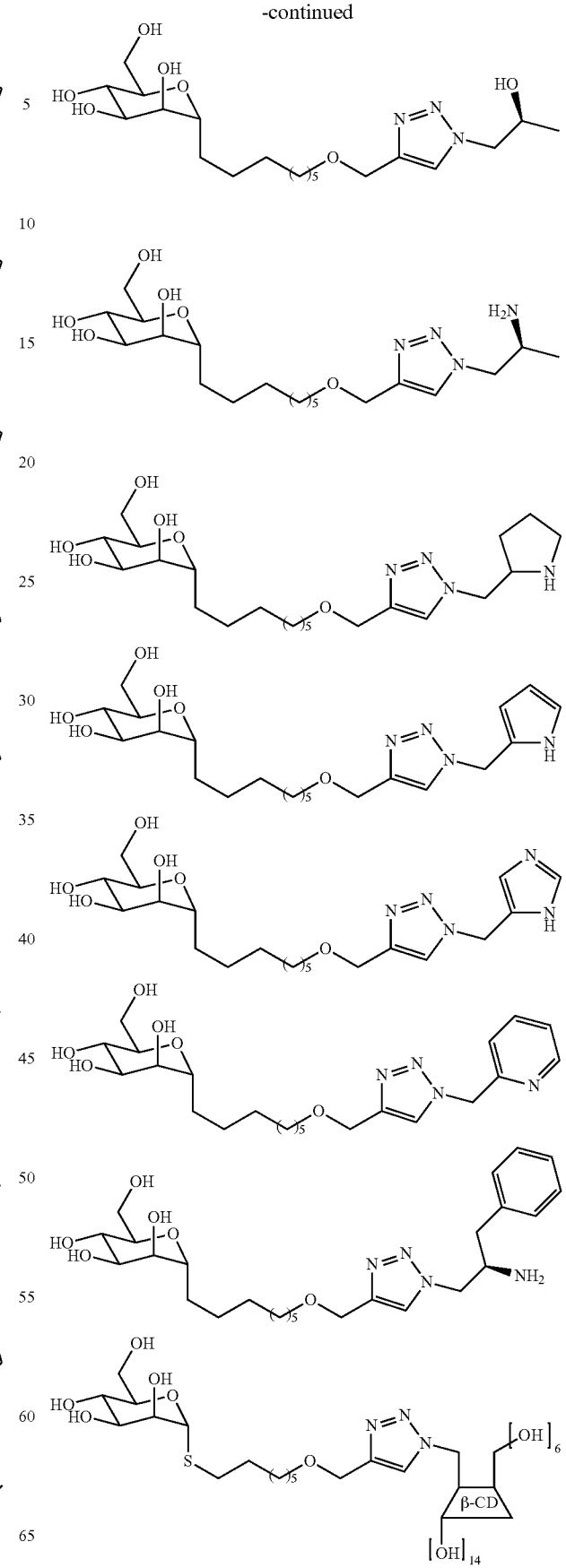

-continued
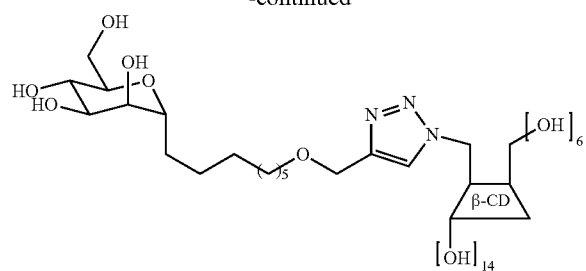
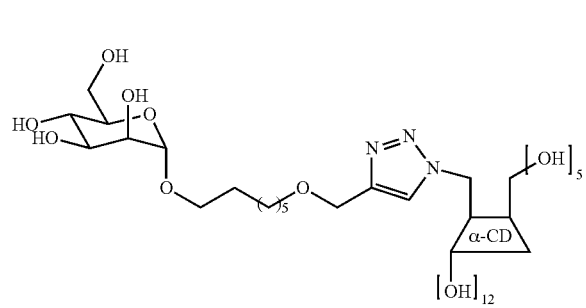
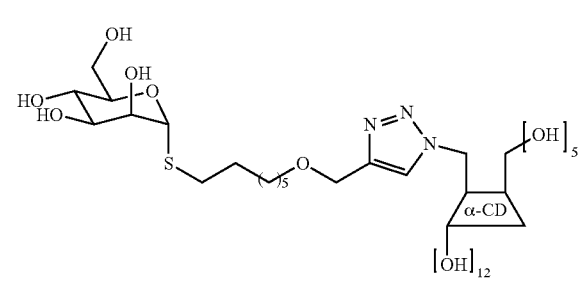
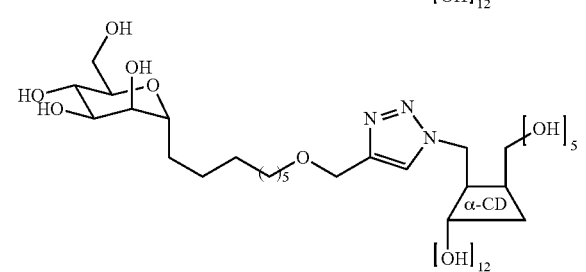
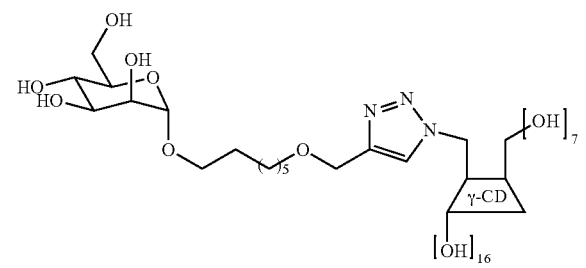
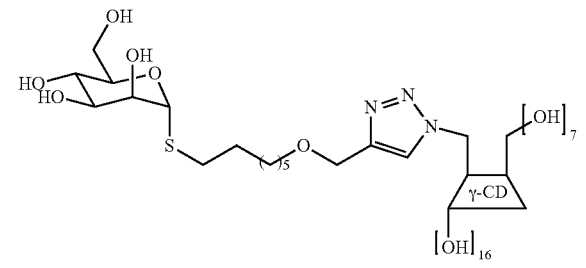
-continued
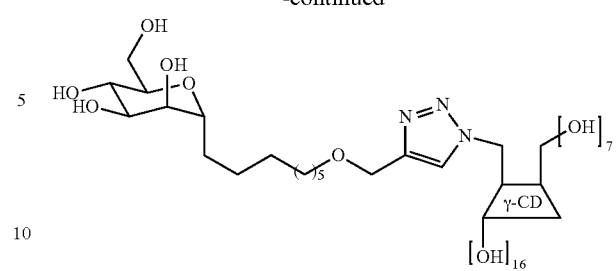
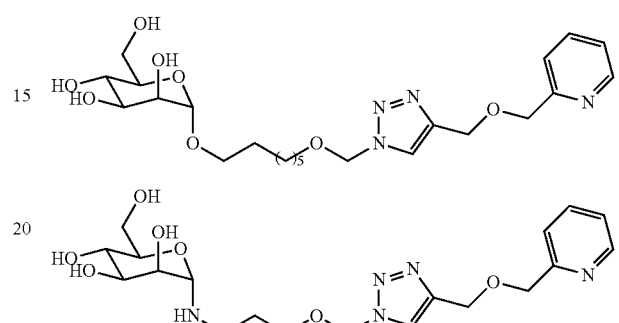
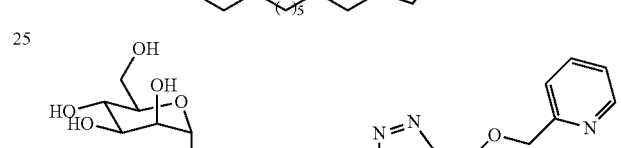
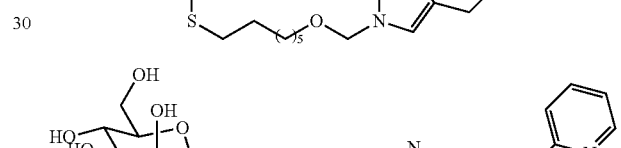
and their salts, in particular their pharmaceutically acceptable salts.
In an advantageous embodiment, the present invention relates to a new compound of formula (I) of one of the following formulae:
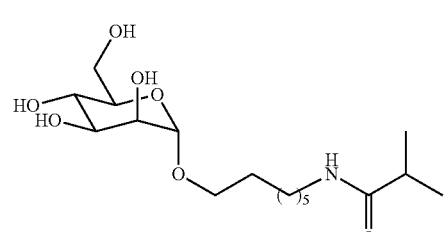
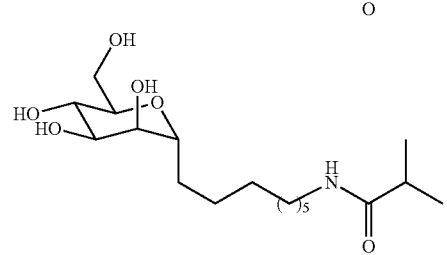

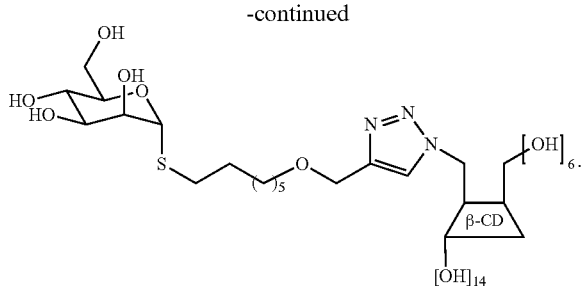

In another aspect, the present invention relates to a pharmaceutical composition comprising, as active substance, a compound of formula (I-0) or (I-1), in particular (I-1a-1), (I-1a-2)(I-1a-3)(I-1a-4), (I-1c-5), (I-1c-6), (I-1c-7), (I-1c-8), (I-2a-1), (I-2a-2), (I-2a-3), (I-2a-4), (I-2b-1), (I-2b-2), (I-2b-3), (I-2b-4), (I-2c-1), (I-2c-2), (I-2c-3), (I-2c-4), (I-2c-5), (I-2c-6), (I-2c-7) or (I-2c-8), as defined above, in association with a pharmaceutically acceptable vehicle.

In another aspect, the present invention relates to a pharmaceutical composition comprising, as active substance, a compound of formula (I) of one of the following formulae:

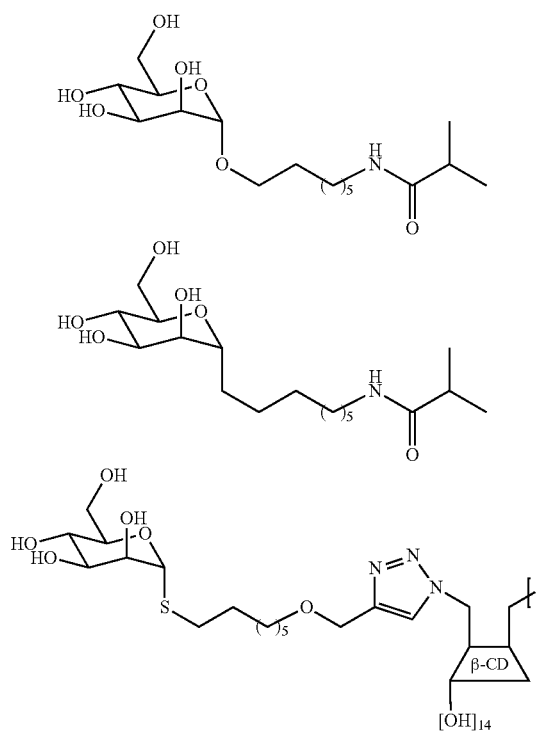

in association with a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semi-synthetic glycerides or polyethylene glycols.

The compositions can also be aerosols. For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical composition, said composition being in a form administrable by at least one route selected from the group consisting of oral, intravenous, subcutaneous, nasal, inhalatory, intramuscular, intraperitoneal and suppository, in particular oral or intravenous route.

In an advantageous embodiment, the present invention relates to a pharmaceutical composition, administrable by oral route at a dose comprised from about 0.1 mg/kg to about 100 mg/kg of body weight.

In an advantageous embodiment, the present invention relates to a pharmaceutical composition, under a form liable to be administrable by oral route, under the form of a unit dose comprised from 5 mg to 7500 mg, in particular from 10 mg to 2000 mg, in particular from 50 to 1000 mg.

Said pharmaceutical composition can be administered 1 to 4 times per day, preferably 2 or 3 times per day.

In an advantageous embodiment, the present invention relates to a pharmaceutical composition, administrable by intravenous route at a dose comprised from about 10 g/kg to about 10 mg/kg.

In an advantageous embodiment, the present invention relates to a pharmaceutical composition, under a form liable to be administrable by intravenous, under the form of a unit dose comprised from 0.1 mg to 1000 mg, in particular from 10 mg to 1000 mg, in particular from 10 to 500 mg, in particular from 10 to 100 mg.

Said pharmaceutical composition can be administered 1 to 4 times per day, preferably 2 or 3 times per day.

In another aspect, the present invention relates to a vaccine composition comprising, as active substance, a compound of formula (I-0) or (I-1), in particular (I-1a-1), (I-1a-2), (I-1a-3), (I-1a-4), (I-1b-1), (I-1b-2), (I-1b-3), (I-1b-4), (I-c-1), (c-1-2), (I-1c-3), (I-10-4), (I-1c-5), (I-1c-6), (I-1c-7), (I-1c-8), (I-2a-1), (I-2a-2), (I-2a-3), (I-2a-4), (I-2b-1), (I-2b-2), (I-2b-3), (I-2b-4), (I-2c-1), (I-2c-2), (I-2c-3), (I-2c-4), (I-2c-5), (I-2c-6), (I-2c-7) or (I-2c-8), as described above, in association with a pharmaceutically acceptable adjuvant.

In another aspect, the present invention relates to a vaccine composition comprising, as active substance, a compound of formula (I) of one of the following formulae:

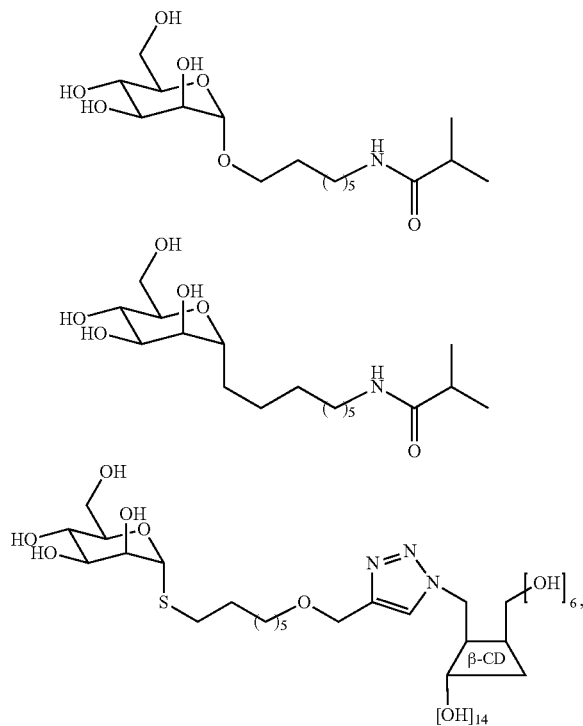

in association with a pharmaceutically acceptable adjuvant.

By "adjuvant" is meant any substance that enhances the immune response to an antigen. Adjuvants useful in the vaccine composition according to the present invention include mineral compounds including mineral salts such as calcium or aluminium salts, mineral or non-mineral oils, bacterial products, liposomes, saponins, iscoms and biodegradable microparticles. Well known adjuvants include Quil A, Marcol 52, Montanide 103 and pluronic polymers, such as L121 (BASF, N.J.).

The vaccine composition may include other adjuvants, including adjuvants in liquid form. Such other adjuvants that may be used include squalene, Adjuvant 65 (containing peanut oil, mannide monooleate and aluminium monostearate), surfactants such as hexadecylamine, octadecylamine, lysolecithin, dimethyl-dioctadecylammonium bromide, N,N-dioctradecyl-N,N'-bis(2-hydroxyethyl)-propanediamine, methoxy-hexadecylglycerol and pluronic polyols, polyanions such as pyran, dextran sulfate, polyacrylic acid and carbopol, peptides and amino acids such as muramyl dipeptide, demethylglycine, tuftsin and trehalose dimycolate, Adju-Phos, Algal Glucan, Algammulin, aluminium salts including aluminium hydroxide (Al(OH)$_3$), aluminium phosphate (AlPO$_4$), Alhydrogel, Antigen Formulation, Avridine, Bay R1005, Calcitriol, Calcium Phosphate, Calcium Phosphate Gel, Cholera Holotoxin (CT), Cholera Toxin B Subunit (CTB), CRL1005, DDA, DHEA, DMPC, DMPG, DOC/Alum Complex, Gamma Inulin, Gerbu Adjuvant, GMDP, Imiquimod, ImmTher, Interferon-gamma, Iscoprep 7.0.3, Loxoribine, LT-OA or LT Oral Adjuvant, MF59, Mannan, MONTANIDE ISA 51, MONTANIDE ISA 720, MPL, MTP-PE, MTP-PE, Murametide, Murapalmitine, D-Murapalmitine, NAGO, Nonionic Surfactant Vesicles, Pleuran, PLGA, PGA and PLA, PMMA, PODDS, Poly Ra: Poly rU, Polyphosphazene, Polysorbate 80, Protein Cochleates, QS-21, Rehydragel HPA, Rehydragel LV, S-28463, SAF-1, Sclavo Peptide, Sendai Proteoliposomes, Sendai-Containing Lipid Matrices, Span 85, Specol, Stearyl Tyrosine, Theramide, Threonyl-MDP and Ty Particles.

In another aspect, the present invention relates to a pharmaceutical composition comprising, in combination with a pharmaceutically acceptable vehicle:

at least one compound of formula (I-0) or (1-1), in particular (I-1a-1), (I-1a-2), (I-1a-3), (I-1a-4), (I-1b-1), (I-1b-2), (I-1b-3), (I-1b-4), (I-1-1), (I-1c-2), (I-1c-3), (I-1c-4), (I-1c-5), (I-1c-6), (I-1c-7), (I-1c-8), (I-2a-1), (I-2a-2), (I-2a-3), (I-2a-4), (I-2b-1), (I-2b-2), (1-2b-3), (I-2b-4), (I-2c-1), (I-2c-2), (I-2c-3), (I-2c-4), (I-2c-5), (I-2c-6), (I-2c-7) or (I-2c-8), as defined above, and at least one compound selected from the group consisting of antibiotics, anti-inflammatory compounds, glucocorticoids, immunosuppressive compounds and anti-TNF-alpha therapies, said pharmaceutical composition being used for simultaneous or separate use or use spread over time intended for the treatment or the prevention of inflammatory bowel disease, in particular Crohn disease or ulcerative colitis.

In another aspect, the present invention relates to a pharmaceutical composition comprising, in combination with a pharmaceutically acceptable vehicle:

at least one compound of one of the following formulae:

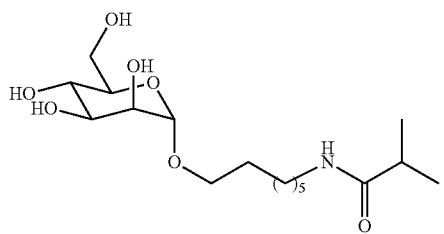

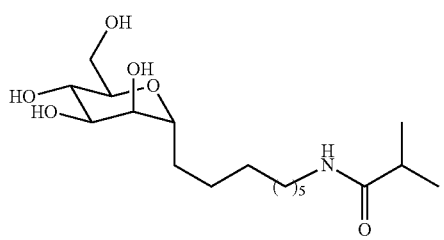

-continued

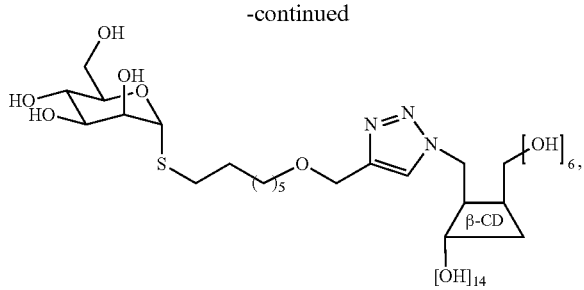

and
at least one compound selected from the group consisting of antibiotics, anti-inflammatory compounds, glucocorticoids, immunosuppressive compounds and anti-TNF-alpha therapies,
said pharmaceutical composition being used for simultaneous or separate use or use spread over time intended for the treatment or the prevention of inflammatory bowel disease, in particular Crohn disease or ulcerative colitis.

In another aspect, the present invention relates to a process of preparation of a compound of formula (I-1):

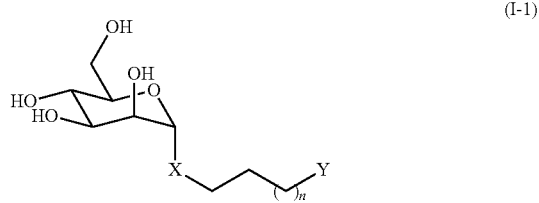

(I-1)

wherein:
X represents NH, O, S or $CH_2$;
n represents an integer being equal to 3, 4, 5, 6 or 7, n being in particular equal to 5;
Y represents a group selected from:

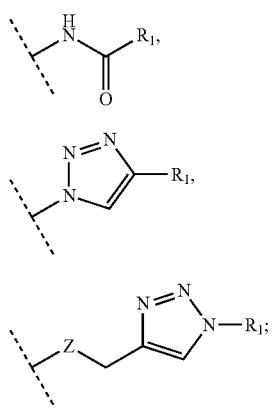

(a)

(b)

(c)

Z representing O or S;
$R_1$ representing:
H
a linear or branched $(C_1-C_7)$-alkyl, in particular isopropyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, said aryl being an aromatic or heteroaromatic group,
an alkyl aryl, wherein the aryl is an aromatic or heteroaromatic group,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
$CF_3$,
adamantyl,
CHRa—$NH_2$, wherein Ra represents the side chain of a proteinogenic amino acid,
said $(C_1-C_7)$-alkyl, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl and CO-aryl being substituted or not by one or more substituent(s), each independently selected from:
a linear or branched $(C_1-C_7)$-alkyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, wherein the aryl is an aromatic or heteroaromatic group
an alkyl aryl, wherein the aryl is an aromatic or heteroaromatic group,
a CHO,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
a halogen selected from the group comprising F, Cl, Br, and I,
$CF_3$,
$OR_a$, wherein $R_a$ represents:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NR_bR_c$, wherein $R_b$ and $R_c$ represent independently from each other:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NO_2$,
—CN,
provided that when $R_1$ represents CHRa—$NH_2$, then Y can only represent the following group (a):

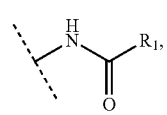

(a)

comprising the following steps:
when Y represents:

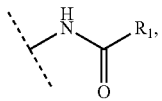
(a)

reaction between a compound of formula (1a):

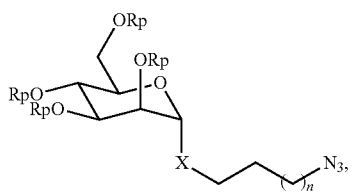
(1a)

wherein Rp represents an ad hoc hydroxyl protecting group,
and a compound of formula (2a):

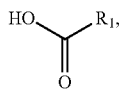
(2a)

in presence of triphenylphosphine, a coupling agent and optionally 1-hydroxybenzotriazole (HOBt) or 1-hydroxy-7-aza-benzotriazole (HOAt),
to obtain a compound of formula (3a):

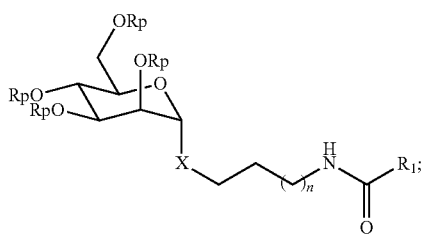
(3a)

cleavage of the Rp protecting groups of said compound of formula (3a), to obtain a compound of formula (I-1) wherein Y represents (a), of following formula (I-1a):

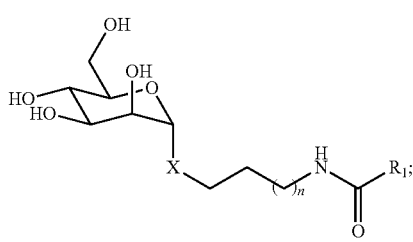
(I-1a)

when Y represents:

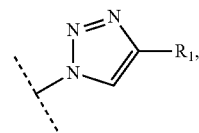
(b)

reaction between a compound of formula (1b):

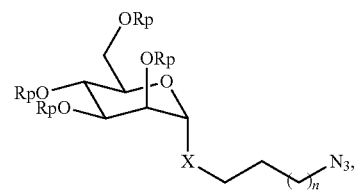
(1b)

and a compound of formula (2b):

(2b)

to obtain a compound of formula (3b):

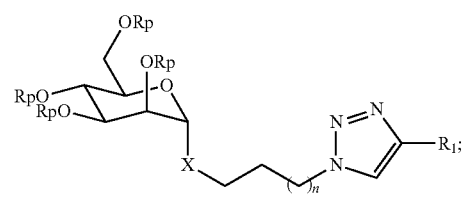
(3b)

cleavage of the Rp protecting groups of said compound of formula (3b), to obtain a compound of formula (I-1) wherein Y represents (b), of following formula (I-1b):

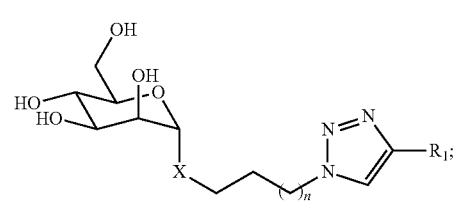
(I-1b)

when Y represents:

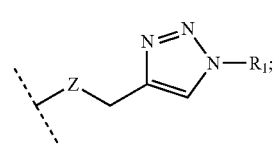
(c)

reaction between a compound of formula (1c):

(1c)

and a compound of formula (2b):

(2c)

$N_3 \diagdown R_1$, to obtain a compound of formula (3b):

(3c)

cleavage of the Rp protecting groups of said compound of formula (3c), to obtain a compound of formula (I-1) wherein Y represents (c), of following formula (I-1c):

(I-1c)

In another aspect, the present invention relates to a process of preparation of a compound of formula (I-0):

(I-0)

wherein:
X represents NH, O, S or $CH_2$;
n represents an integer being equal to 3, 4, 5, 6 or 7, n being in particular equal to 5;

Y represents a group selected from:

(a)

(b)

(c)

Z representing O, S or NH;
R representing:
  H
  a linear or branched ($C_1$-$C_7$)-alkyl, in particular methyl, ethyl, isopropyl or isobutyl,
  a group of formula —$(CH_2)_i$—X'—$(CH_2)_j$—H, wherein X' represents O, S or NH, i is an integer from 1 to 7, and j is an integer from 0 to 7, said group being in particular —$CH_2$—O—$CH_3$,
  a linear or branched ($C_2$-$C_7$)-alkenyl,
  a linear or branched ($C_2$-$C_7$)-alkynyl,
  a ($C_3$-$C_7$)-cycloalkyl,
  a ($C_5$-$C_7$)-cycloalkenyl,
  a ($C_3$-$C_7$)-heterocycloalkyl,
  a ($C_5$-$C_7$)-heterocycloalkenyl,
  an aryl, said aryl being an aromatic or heteroaromatic group,
  an alkyl aryl, wherein the aryl is an aromatic or heteroaromatic group,
  a CO—($C_1$-$C_7$)-alkyl,
  a CO-aryl, wherein aryl is an aromatic or heteroaromatic group,
  a $CO_2H$,
  a $CO_2$—($C_1$-$C_7$)-alkyl,
  a CONH—($C_1$-$C_7$)-alkyl,
  $CF_3$,
  adamantyl,
  $CHRa$—$NH_2$, wherein Ra represents the side chain of a proteinogenic amino acid,
  a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a cyclodextrin of one of the following formulae:

(d)

-continued (e)

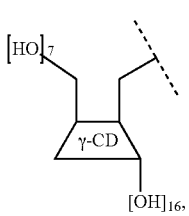

said $(C_1-C_7)$-alkyl, group of formula —$(CH_2)_i$—X'—$(CH_2)_j$—H, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl, CO-aryl and cyclodextrin being substituted or not by one or more substituent(s), each independently selected from:

- a linear or branched $(C_1-C_7)$-alkyl,
- a linear or branched $(C_2-C_7)$-alkenyl,
- a linear or branched $(C_2-C_7)$-alkynyl,
- a $(C_3-C_7)$-cycloalkyl,
- a $(C_5-C_7)$-cycloalkenyl,
- a $(C_3-C_7)$-heterocycloalkyl,
- a $(C_5-C_7)$-heterocycloalkenyl,
- an aryl, wherein the aryl is an aromatic or heteroaromatic group
- an alkyl aryl, wherein the aryl is an aromatic or heteroaromatic group,
- a CHO,
- a CO—$(C_1-C_7)$-alkyl,
- a CO-aryl, wherein aryl is an aromatic or heteroaromatic group,
- a $CO_2H$,
- a $CO_2$—$(C_1-C_7)$-alkyl,
- a CONH—$(C_1-C_7)$-alkyl,
- a halogen selected from the group comprising F, Cl, Br, and I,
- $CF_3$,
- $OR_a$, wherein $R_a$ represents:
    - H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
- $NR_bR_c$, wherein $R_b$ and $R_c$ represent independently from each other:
    - H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
- $NO_2$,
- CN,
- $SO_3H$ or one of its salts, in particular $SO_3Na$;

and its pharmaceutically acceptable salts,
provided that when R represents $CHR_a$—$NH_2$, then Y can only represent the following group (a):

(a)

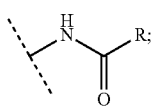

with the proviso that said compound is not of one of the following structures:

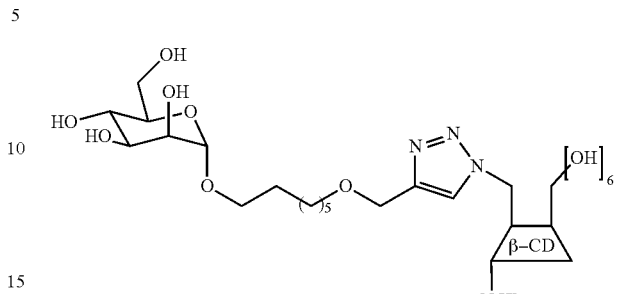

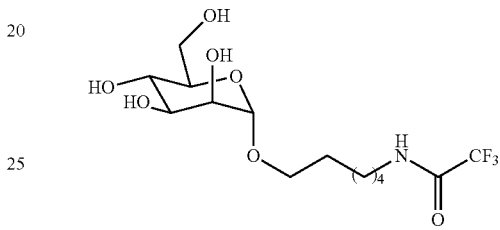

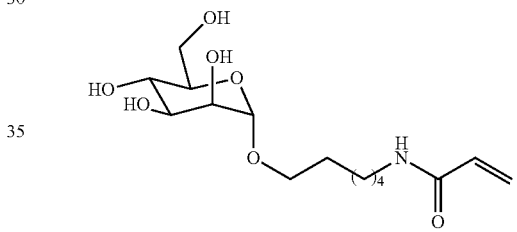

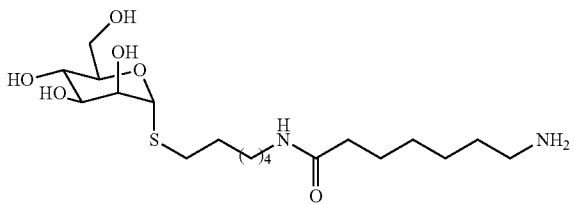

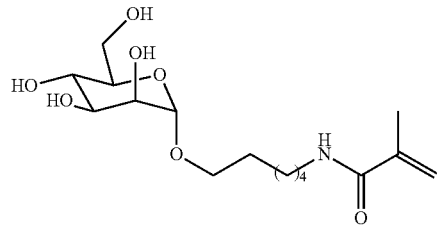

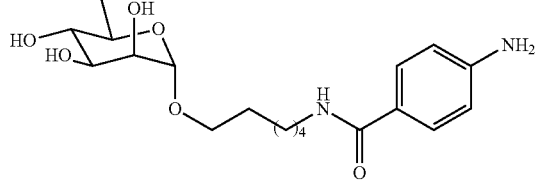

and its salts, comprising the following steps:

when Y represents:

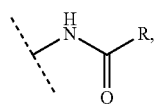

(a)

reaction between a compound of formula (1a):

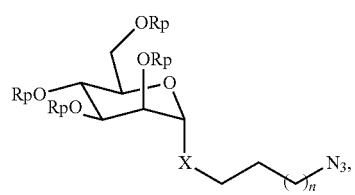

(1a)

wherein Rp represents an ad hoc hydroxyl protecting group, and a compound of formula (2a):

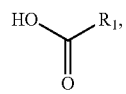

(2a)

wherein $R_1$ is a group R that is optionally protected by one or more ad hoc protecting groups, in presence of triphenylphosphine, a coupling agent and optionally 1-hydroxybenzotriazole (HOBt) or 1-hydroxy-7-aza-benzotriazole (HOAt), to obtain a compound of formula (3a):

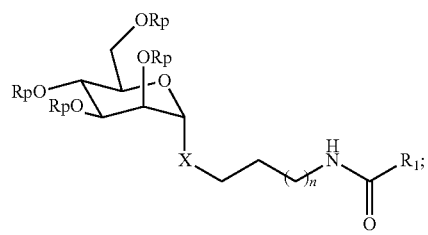

(3a)

cleavage of the Rp protecting groups and of the optional protecting groups of $R_1$ in said compound of formula (3a), to obtain a compound of formula (I-0) wherein Y represents (a), of following formula (I-0a):

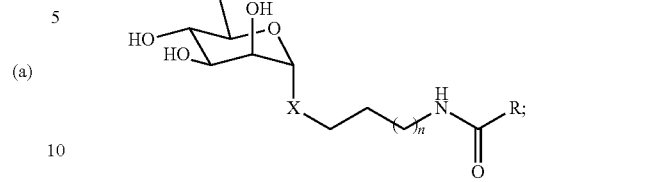

(I-0a)

when Y represents:

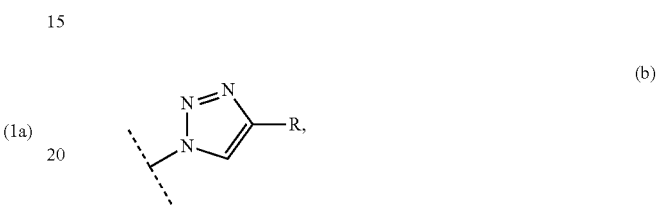

(b)

reaction between a compound of formula (1b):

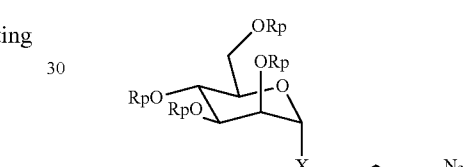

(1b)

and a compound of formula (2b):

(2b)

wherein $R_1$ is a group R that is optionally protected by one or more ad hoc protecting groups, to obtain a compound of formula (3b):

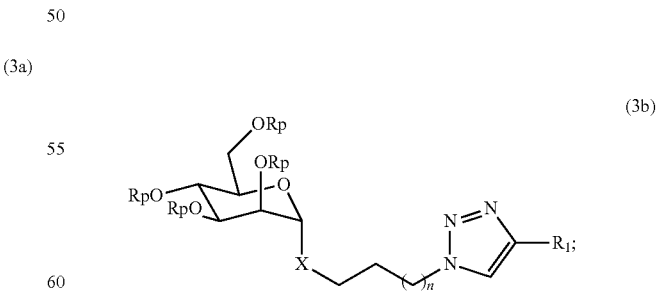

(3b)

cleavage of the Rp protecting groups and of the optional protecting groups of $R_1$ in said compound of formula (3b), to obtain a compound of formula (I-0) wherein Y represents (b), of following formula (I-0b):

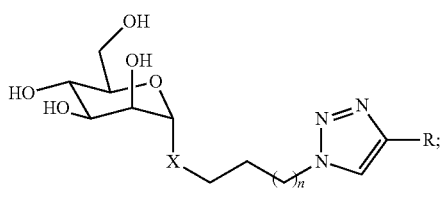 (I-0b)

when Y represents:

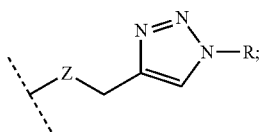 (c)

reaction between a compound of formula (1c):

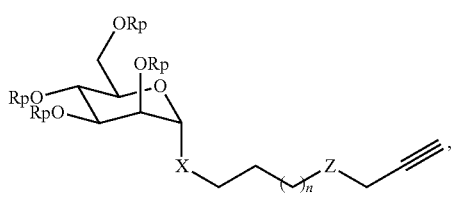 (1c)

and a compound of formula (2b):

 (2c)

wherein $R_1$ is a group R that is optionally protected by one or more ad hoc protecting groups, to obtain a compound of formula (3b):

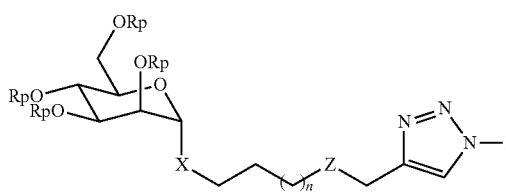 (3c)

cleavage of the Rp protecting groups and of the optional protecting groups of $R_1$ in said compound of formula (3c), to obtain a compound of formula (I-0) wherein Y represents (c), of following formula (I-0c):

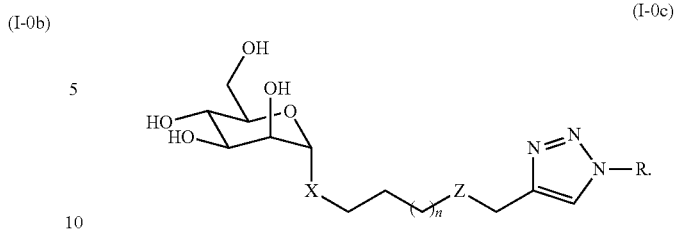 (I-0c)

By "ad hoc hydroxyl protecting group" is meant a group intended to protect an hydroxyl group against undesirable reactions during synthetic procedures. Commonly used hydroxyl protecting groups are disclosed in Greene, "Protective Groups In Organic Synthesis" (John Wiley & Sons, New York (1981). Hydroxyl protecting groups comprise methoxymethyl, tetrahydropyranyl, t-butyl, allyl, benzyl, t-butyldimethylsilyl, 1-butyldiphenylsilyl, acetyl, pivaloyl and benzoyl groups, in particular acetyl group.

By "coupling agent" is meant a compound enabling the reaction between an amine containing compound and an acid containing compound to form an amide bond. Examples of suitable coupling agents are peptide coupling agents well known by the persons skilled in the art, in particular dicyclohexylcarbodiimide (DCC), diisopropylcarbodiimide (DIC), O-Benzotriazole-N,N,N',N'-tetramethyluronium-hexafluoro-phosphate (HBTU), 1-[Bis(dimethylamino)methylene]-1H-1,2,3-triazolo[4,5-b]pyridinium 3-oxide hexafluorophosphate (HATU), O-(7-Azabenzotriazole-1-yl)-N,N,N',N-tetramethyluronium tetrafluoroborate (TATU), O-(Benzotriazol-1-yl)-N,N,N',N'-tetramethyluronium tetrafluoroborate (TBTU), Benzotriazole-1-yl-oxy-tris-(dimethylamino)-phosphonium hexafluorophosphate (BOP), (Benzotriazol-1-yloxy)tripyrrolidinophosphonium hexafluorophosphate (PyBOP), where the preferred agent is DIC.

The present invention also relates to a compound of the following formula (I):

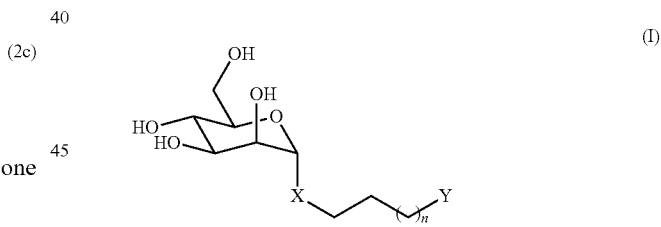 (I)

wherein:
X represents NH, O, S or $CH_2$;
n represents an integer being equal to 3, 4, 5, 6 or 7, n being in particular equal to 5;
Y represents a group selected from:

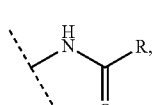 (a)

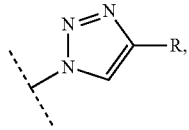 (b)

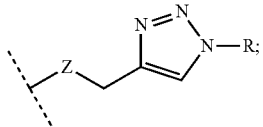

Z representing O or S;
R representing:
H
a linear or branched $(C_1-C_7)$-alkyl, in particular methyl, ethyl, isopropyl or isobutyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, said aryl being an aromatic or heteroaromatic group,
an alkyl aryl, wherein the aryl is an aromatic or heteroaromatic group,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
$CF_3$,
adamantyl,
$CHRa-NH_2$, wherein Ra represents the side chain of a proteinogenic amino acid,
a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a β-cyclodextrin of the following formula:

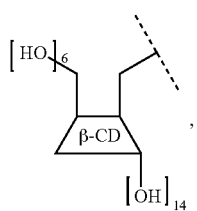

said $(C_1-C_7)$-alkyl, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl, CO-aryl and cyclodextrin being substituted or not by one or more substituent(s), each independently selected from:
a linear or branched $(C_1-C_7)$-alkyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, wherein the aryl is an aromatic or heteroaromatic group
an alkyl aryl, wherein the aryl is an aromatic or heteroaromatic group,
a CHO,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
a halogen selected from the group comprising F, Cl, Br, and I,
$CF_3$,
$OR_a$, wherein $R_a$ represents:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NR_bR_b$, wherein $R_b$ and $R_c$ represent independently from each other:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NO_2$,
CN;
provided that when R represents $CHRa-NH_2$, then Y can only represent the following group (a):

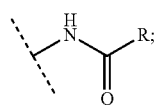

for use in the treatment or the prevention of pathologies belonging to the group consisting of:
urinary tract infections, in particular painful bladder syndrome and cystitis, more particularly interstitial cystitis, and
urinary tract infections in patients with a metabolic disease correlated with enhanced apoptosis, in particular diabetes.

The present invention also relates to a compound of the following formula (I):

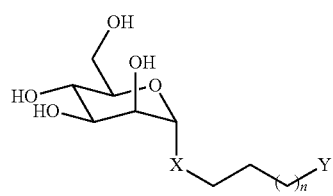

wherein:
X represents NH, O, S or $CH_2$;
n represents an integer being equal to 3, 4, 5, 6 or 7, n being in particular equal to 5;
Y represents a group selected from:

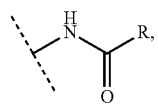

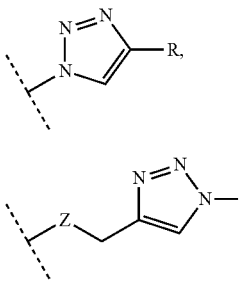

(b)

(c)

Z representing O, S or NH;
R representing:
  H
  a linear or branched $(C_1-C_7)$-alkyl, in particular methyl, ethyl, isopropyl or isobutyl,
  a group of formula $—(CH_2)_i—X'—(CH_2)_j—H$, wherein X' represents O, S or NH, i is an integer from 1 to 7, and j is an integer from 0 to 7, said group being in particular $—CH_2—O—CH_3$,
  a linear or branched $(C_2-C_7)$-alkenyl,
  a linear or branched $(C_2-C_7)$-alkynyl,
  a $(C_3-C_7)$-cycloalkyl,
  a $(C_5-C_7)$-cycloalkenyl,
  a $(C_3-C_7)$-heterocycloalkyl,
  a $(C_5-C_7)$-heterocycloalkenyl,
  an aryl, said aryl being an aromatic or heteroaromatic group,
  an alkyl aryl, wherein the aryl is an aromatic or heteroaromatic group,
  a $CO—(C_1-C_7)$-alkyl,
  a CO-aryl, wherein aryl is an aromatic or heteroaromatic group,
  a $CO_2H$,
  a $CO_2—(C_1-C_7)$-alkyl,
  a $CONH—(C_1-C_7)$-alkyl,
  $CF_3$,
  adamantyl,
  $CHRa—NH_2$, wherein Ra represents the side chain of a proteinogenic amino acid,
  a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a cyclodextrin of one the following formulae:

(d)

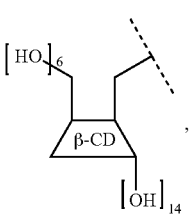

(e)

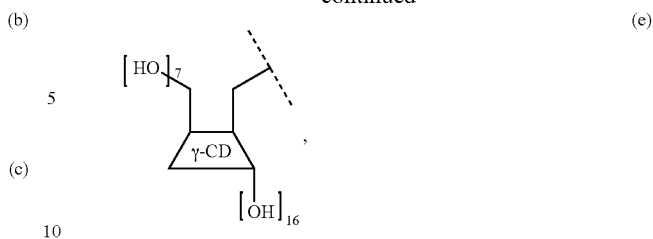

said $(C_1-C_7)$-alkyl, group of formula $—(CH_2)_i—X'—(CH_2)_j—H$, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, $CO—(C_1-C_7)$-alkyl, $CO_2—(C_1-C_7)$-alkyl, $CONH—(C_1-C_7)$-alkyl, aryl, alkyl aryl, CO-aryl and cyclodextrin being substituted or not by one or more substituent(s), each independently selected from:
  a linear or branched $(C_1-C_7)$-alkyl,
  a linear or branched $(C_2-C_7)$-alkenyl,
  a linear or branched $(C_2-C_7)$-alkynyl,
  a $(C_3-C_7)$-cycloalkyl,
  a $(C_5-C_7)$-cycloalkenyl,
  a $(C_3-C_7)$-heterocycloalkyl,
  a $(C_5-C_7)$-heterocycloalkenyl,
  an aryl, wherein the aryl is an aromatic or heteroaromatic group
  an alkyl aryl, wherein the aryl is an aromatic or heteroaromatic group,
  a CHO,
  a $CO—(C_1-C_7)$-alkyl,
  a CO-aryl, wherein aryl is an aromatic or heteroaromatic group,
  a $CO_2H$,
  a $CO_2—(C_1-C_7)$-alkyl,
  a $CONH—(C_1-C_7)$-alkyl,
  a halogen selected from the group comprising F, Cl, Br, and I,
  $CF_3$,
  $OR_a$, wherein $R_a$ represents:
    H, a linear or branched $(C_1-C_7)$-alkyl, a $(C_3-C_7)$-cycloalkyl, $CO—(C_1-C_7)$-alkyl, or CO-aryl, wherein aryl is an aromatic or heteroaromatic group,
  $NR_bR_c$, wherein $R_b$ and $R_c$ represent independently from each other:
    H, a linear or branched $(C_1-C_7)$-alkyl, a $(C_3-C_7)$-cycloalkyl, $CO—(C_1-C_7)$-alkyl, or CO-aryl, wherein aryl is an aromatic or heteroaromatic group,
  $NO_2$,
  CN,
  $SO_3H$ or one of its salts, in particular $SO_3Na$;
and its pharmaceutically acceptable salts,
provided that when R represents $CHRa—NH_2$, then Y can only represent the following group (a):

(a)

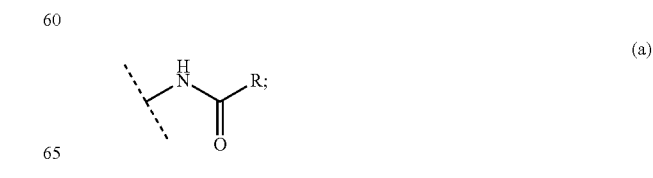

with the proviso that said compound is not of the following structure:

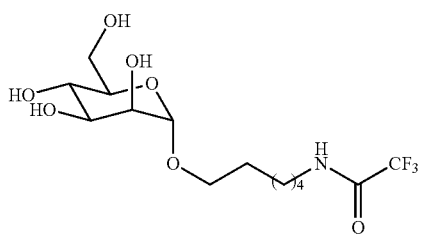

for use in the treatment or the prevention of pathologies belonging to the group consisting of:
- urinary tract infections, in particular painful bladder syndrome and cystitis, more particularly interstitial cystitis, and
- urinary tract infections in patients with a metabolic disease correlated with enhanced apoptosis, in particular diabetes.

In an advantageous embodiment of the use according to the invention, the compound of formula (I) is of particular formula (I-1), wherein R is $R_1$, $R_1$ representing:
- H
- a linear or branched $(C_1-C_7)$-alkyl, in particular isopropyl,
- a linear or branched $(C_2-C_7)$-alkenyl,
- a linear or branched $(C_2-C_7)$-alkynyl,
- a $(C_3-C_7)$-cycloalkyl,
- a $(C_5-C_7)$-cycloalkenyl,
- a $(C_3-C_7)$-heterocycloalkyl,
- a $(C_5-C_7)$-heterocycloalkenyl,
- an aryl, said aryl being an aromatic or heteroaromatic group,
- an alkyl aryl, wherein the aryl is an aromatic or heteroaromatic group,
- a CO—$(C_1-C_7)$-alkyl,
- a CO-aryl, wherein aryl is an aromatic or heteroaromatic group,
- a $CO_2H$,
- a $CO_2$—$(C_1-C_7)$-alkyl,
- a CONH—$(C_1-C_7)$-alkyl,
- $CF_3$,
- adamantly,
- $CHRa$—$NH_2$, wherein Ra represents the side chain of a proteinogenic amino acid, $R_1$ representing in particular:
- a linear $(C_1-C_7)$-alkyl, more particularly methyl, ethyl, propyl or butyl, optionally substituted by a —OH and/or a —$NH_2$ group,
- a branched $(C_3-C_7)$-alkyl, more particularly isopropyl or isobutyl,
- a $(C_3-C_7)$-heterocycloalkyl, more particularly a pyrrolidine,
- an aryl, said aryl being an aromatic or heteroaromatic group, more particularly a phenyl, a pyridinyl, a pyrrole or an imidazole, optionally substituted by a —OH, a —$NH_2$ or a —$SO_3Na$ group,
- an alkyl aryl, wherein the aryl is an aromatic or heteroaromatic group, more particularly a benzyl, a phenethyl or an ethyl imidazolyl, optionally substituted by a —OH or a —$NH_2$ group,
- $CHRa$—$NH_2$, wherein Ra represents the side chain of a proteinogenic amino acid, in particular alanine, serine, proline, phenylalanine, cysteine or histidine.

In an advantageous embodiment, the present invention relates to the use according to the invention of a compound of formula (I-1), wherein Y represents:

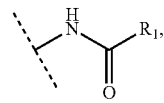

(a)

of following formula (I-1a):

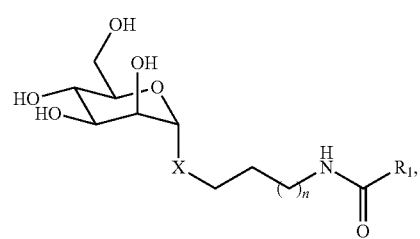

(I-1a)

X, $R_1$ and n being as defined above,
$R_1$ representing in particular a linear or branched $(C_1-C_7)$-alkyl, more particularly isopropyl.

In an advantageous embodiment, the present invention relates to the use according to the invention of a compound of formula (I-1), wherein Y represents:

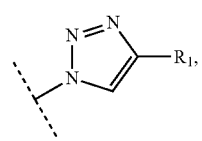

(b)

of following formula (I-1b):

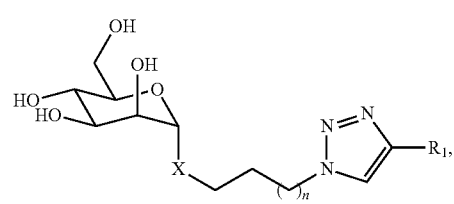

(I-1b)

X, $R_1$ and n being as defined above.

In an advantageous embodiment, the present invention relates to the use according to the invention of a compound of formula (I-1), wherein Y represents:

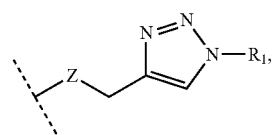

(c)

of following formula (I-1c):

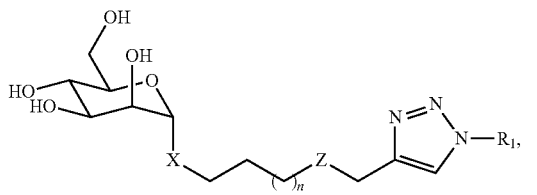

X, Z, $R_1$ and n being as defined above.

In an advantageous embodiment of the use according to the invention, the compound of formula (I) is of particular formula (I-2), wherein R is $R_2$, $R_2$ representing a cyclodextrin, said cyclodextrin being in particular chosen from α-cyclodextrin (α-CD), β-cyclodextrin (β-CD), γ-cyclodextrin (γ-CD) and their derivatives, in particular alkylated α-cyclodextrins, alkylated β-cyclodextrins and alkylated γ-cyclodextrins, said cyclodextrin being more particularly a β-cyclodextrin, even more particularly a β-cyclodextrin of the following formula:

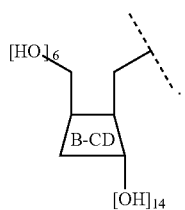

(d)

In an advantageous embodiment, the present invention relates to the use according to the invention of a compound of formula (I-2), wherein Y represents:

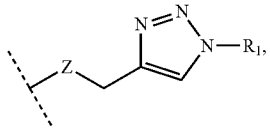

(c)

of following formula (I-2c):

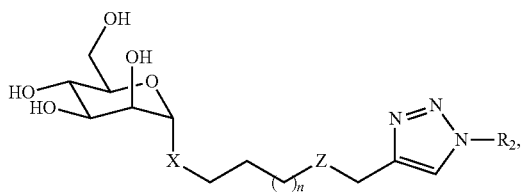

X, $R_2$, n and Z being as defined above.

In an advantageous embodiment of the use according to the invention, the compound of formula (I-1) is of following formula (I-1a-1):

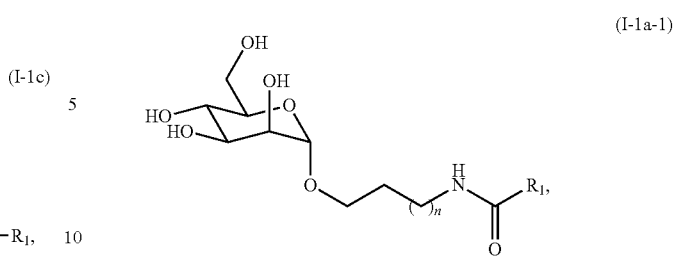

$R_1$ and n being as defined above.

In an advantageous embodiment of the use according to the invention, the compound of formula (I-1) is of following formula (I-1a-2):

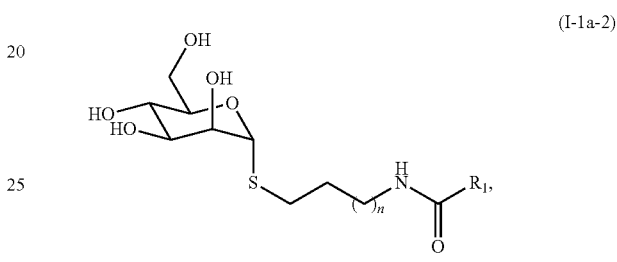

$R_1$ and n being as defined above.

In an advantageous embodiment of the use according to the invention, the compound of formula (I-1) is of following formula (I-1a-3):

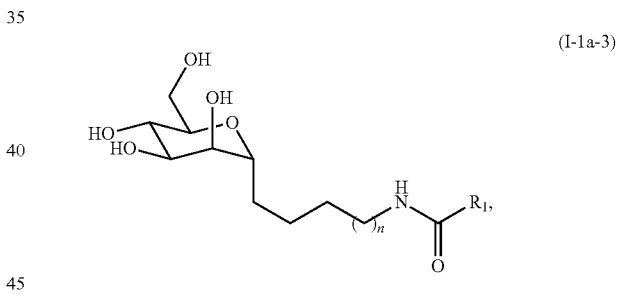

$R_1$ and n being as defined above.

In an advantageous embodiment of the use according to the invention, the compound of formula (I-1) is of following formula (I-1a-4):

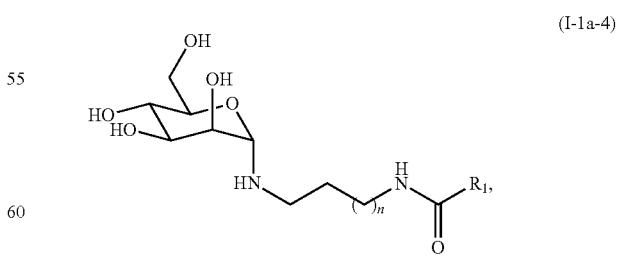

$R_1$ and n being as defined above.

In an advantageous embodiment of the use according to the invention, the compound of formula (I-1) is of following formula (I-1b-1):

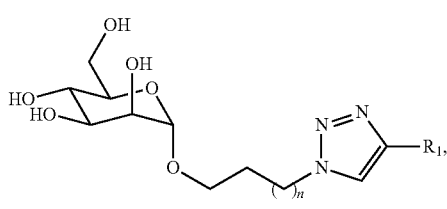
(I-1b-1)

$R_1$ and n being as defined above.

In an advantageous embodiment of the use according to the invention, the compound of formula (I-1) is of following formula (I-1b-2):

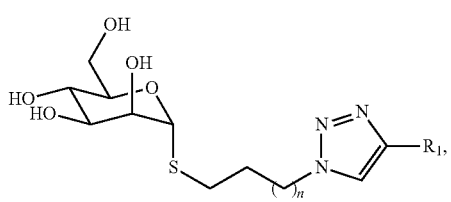
(I-1b-2)

$R_1$ and n being as defined above.

In an advantageous embodiment of the use according to the invention, the compound of formula (I-1) is of following formula (I-1b-3):

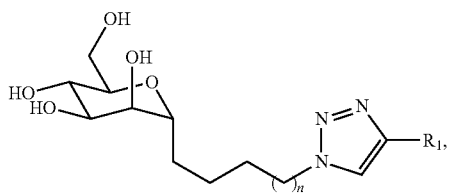
(I-1b-3)

$R_1$ and n being as defined above.

In an advantageous embodiment of the use according to the invention, the compound of formula (I-1) is of following formula (I-1b-4):

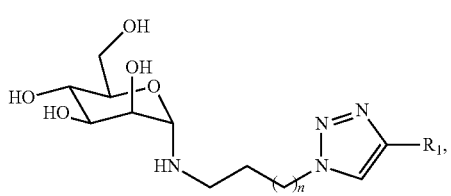
(I-1b-4)

$R_1$ and n being as defined above.

In an advantageous embodiment of the use according to the invention, the compound of formula (I-1) is of following formula (I-1c-1):

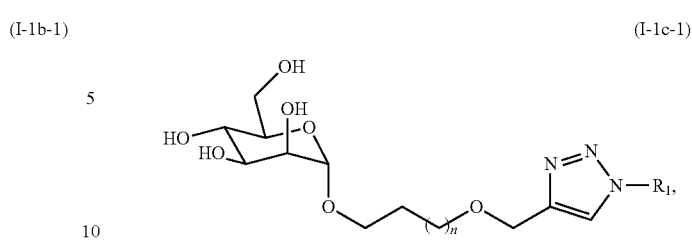
(I-1c-1)

$R_1$ and n being as defined above.

In an advantageous embodiment of the use according to the invention, the compound of formula (I-1) is of following formula (I-1c-2):

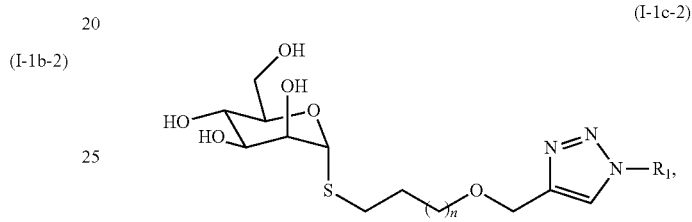
(I-1c-2)

$R_1$ and n being as defined above.

In an advantageous embodiment of the use according to the invention, the compound of formula (I-1) is of following formula (I-1c-3):

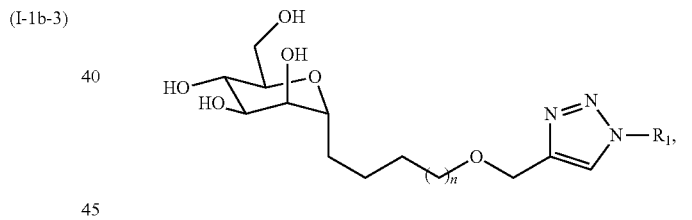
(I-1c-3)

$R_1$ and n being as defined above.

In an advantageous embodiment of the use according to the invention, the compound of formula (I-1) is of following formula (I-1c-4):

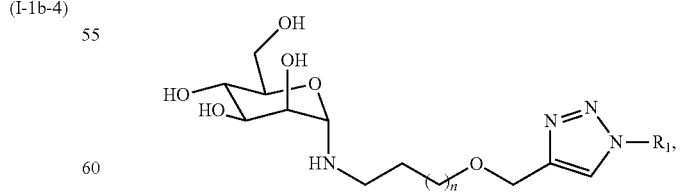
(I-1c-4)

$R_1$ and n being as defined above.

In an advantageous embodiment of the use according to the invention, the compound of formula (I-1) is of following formula (I-1c-5):

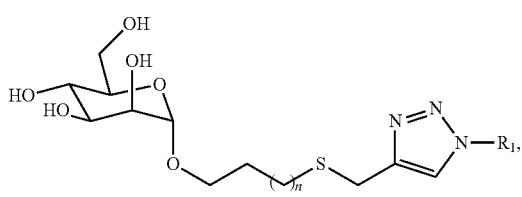

$R_1$ and n being as defined above.

In an advantageous embodiment of the use according to the invention, the compound of formula (I-1) is of following formula (I-1c-6):

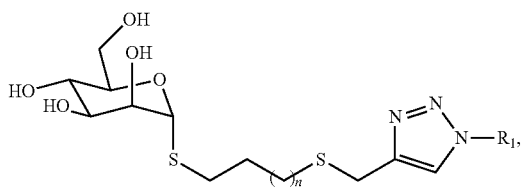

$R_1$ and n being as defined above.

In an advantageous embodiment of the use according to the invention, the compound of formula (I-1) is of following formula (I-1c-7):

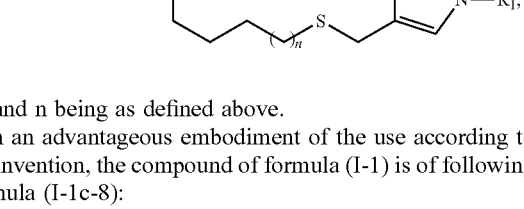

$R_1$ and n being as defined above.

In an advantageous embodiment of the use according to the invention, the compound of formula (I-1) is of following formula (I-1c-8):

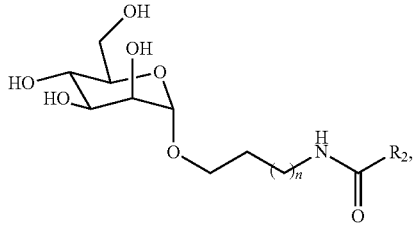

$R_1$ and n being as defined above.

In an advantageous embodiment, the present invention relates to the use according to the invention of a compound of formula (I-1a-1), (I-1a-2), (I-1a-3), (I-1a-4), (I-1b-1), (I-1b-2), (I-1-3), (I-1b-4), (I-1c-1), (I-1c-2), (I-1c-3), (I-1c-4), (I-1c-5), (I-1c-6), (I-1c-7) or (I-1c-8), wherein $R_1$ represents:

- a linear $(C_1\text{-}C_7)$-alkyl, more particularly methyl, ethyl, propyl or butyl, optionally substituted by a —OH and/or a —NH$_2$ group,
- a branched $(C_3\text{-}C_7)$-alkyl, more particularly isopropyl or isobutyl,
- a $(C_3\text{-}C_7)$-heterocycloalkyl, more particularly a pyrrolidine,
- an aryl, said aryl being an aromatic or heteroaromatic group, more particularly a phenyl, a pyridinyl, a pyrrole or an imidazole, optionally substituted by a —OH, a —NH$_2$ or a —SO$_3$Na group,
- an alkyl aryl, wherein the aryl is an aromatic or heteroaromatic group, more particularly a benzyl, a phenethyl or an ethyl imidazolyl, optionally substituted by a —OH or a —NH$_2$ group,
- CHRa—NH$_2$, wherein Ra represents the side chain of a proteinogenic amino acid, in particular alanine, serine, proline, phenylalanine, cysteine or histidine.

In an advantageous embodiment of the use according to the invention, the compound of formula (I-2) is of following formula (I-2a-1):

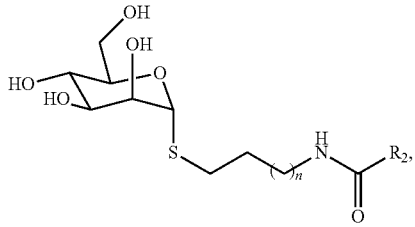

$R_2$ and n being as defined above.

In an advantageous embodiment of the use according to the invention, the compound of formula (I-2) is of following formula (I-2a-2):

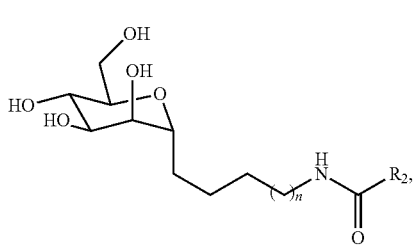

$R_2$ and n being as defined above.

In an advantageous embodiment of the use according to the invention, the compound of formula (I-2) is of following formula (I-2a-3):

$R_2$ and n being as defined above.

In an advantageous embodiment of the use according to the invention, the compound of formula (I-2) is of following formula (I-2a-4):

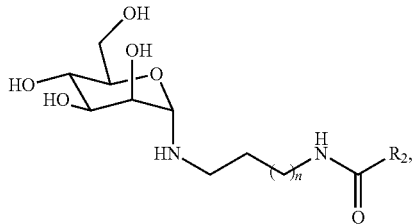
(I-2a-4)

$R_2$ and n being as defined above.

In an advantageous embodiment of the use according to the invention, the compound of formula (I-2) is of following formula (I-2b-1):

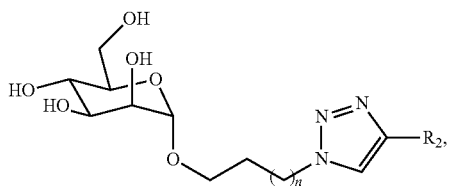
(I-2b-1)

$R_2$ and n being as defined above.

In an advantageous embodiment of the use according to the invention, the compound of formula (I-2) is of following formula (I-2b-2):

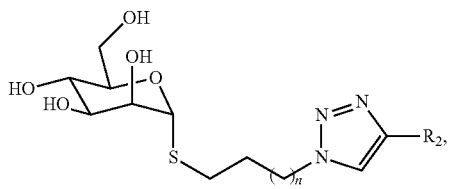
(I-2b-2)

$R_2$ and n being as defined above.

In an advantageous embodiment of the use according to the invention, the compound of formula (I-2) is of following formula (I-2b-3):

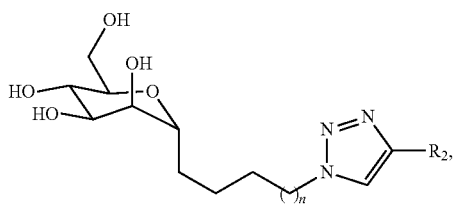
(I-2b-3)

$R_2$ and n being as defined above.

In an advantageous embodiment of the use according to the invention, the compound of formula (I-2) is of following formula (I-2b-4):

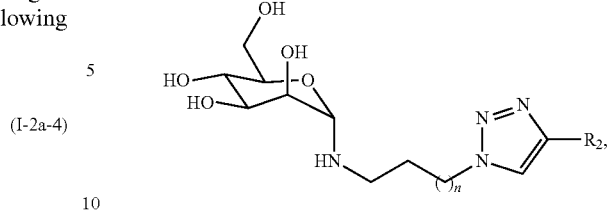
(I-2b-4)

$R_2$ and n being as defined above.

In an advantageous embodiment of the use according to the invention, the compound of formula (I-2) is of following formula (I-2c-1):

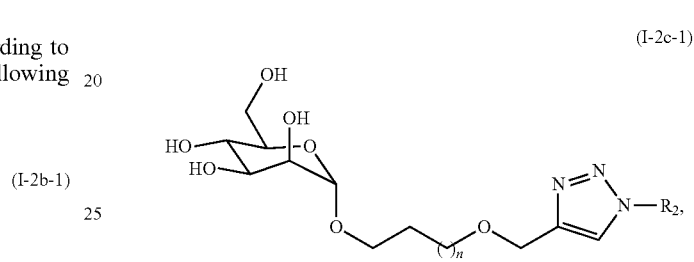
(I-2c-1)

$R_2$ and n being as defined above.

In an advantageous embodiment of the use according to the invention, the compound of formula (I-2) is of following formula (I-2c-2):

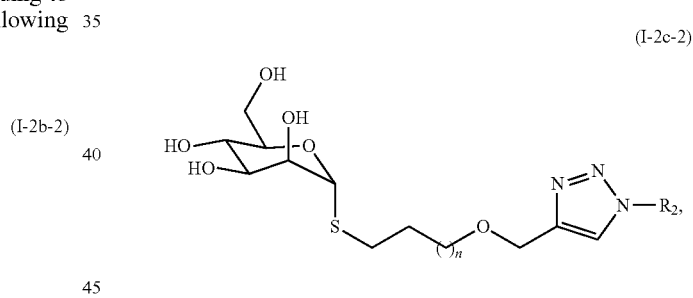
(I-2c-2)

$R_2$ and n being as defined above.

In an advantageous embodiment of the use according to the invention, the compound of formula (I-2) is of following formula (I-2c-3):

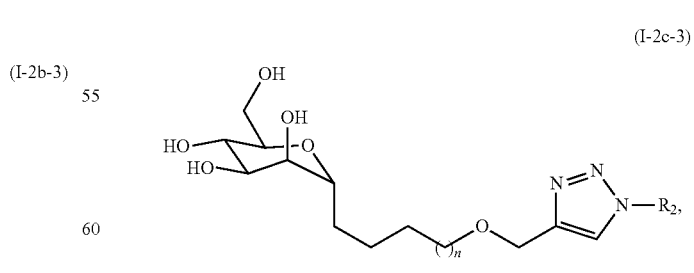
(I-2c-3)

$R_2$ and n being as defined above.

In an advantageous embodiment of the use according to the invention, the compound of formula (I-2) is of following formula (I-2c-4):

(I-2c-4)

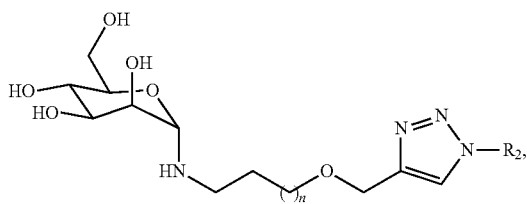

R$_2$ and n being as defined above.

In an advantageous embodiment of the use according to the invention, the compound of formula (I-2) is of following formula (I-2c-5):

(I-2c-5)

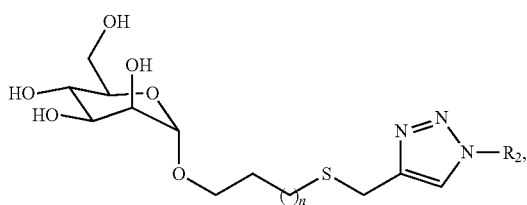

R$_2$ and n being as defined above.

In an advantageous embodiment of the use according to the invention, the compound of formula (I-2) is of following formula (I-2c-6):

(I-2c-6)

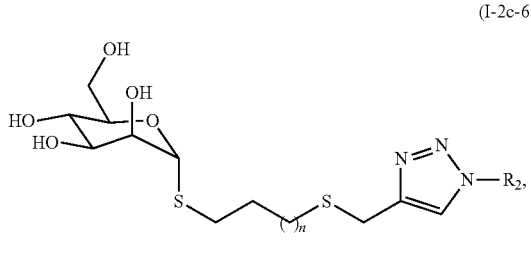

R$_2$ and n being as defined above.

In an advantageous embodiment of the use according to the invention, the compound of formula (I-2) is of following formula (I-2c-7):

(I-2c-7)

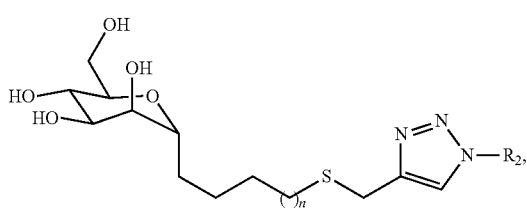

R$_2$ and n being as defined above.

In an advantageous embodiment of the use according to the invention, the compound of formula (I-2) is of following formula (I-2c-8):

(I-2c-8)

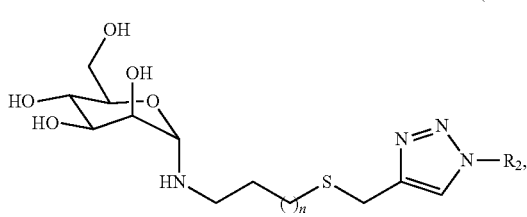

R$_2$ and n being as defined above.

In an advantageous embodiment, the present invention relates to the use according to the invention of a compound of formula (I-1a-1), (I-1a-2), (I-1a-3), (I-1a-4), (I-1b-1), (I-1b-2), (I-1b-3), (I-1b-4), (I-1c-1), (I-1c-2), (I-1c-3), (I-1c-4), (I-1c-5), (I-1c-6), (I-1c-7), (I-1c-8), (I-2a-1), (I-2a-2), (I-2a-3), (I-2a-4), (I-2b-1), (I-2b-2), (I-2b-3), (I-2b-4), (I-2c-1), (I-2c-2), (I-2c-3), (I-2c-4), (I-2c-5), (I-2c-6), (I-2c-7) or (I-2c-8), wherein n is equal to 5.

In an advantageous embodiment, the present invention relates to the use according to the invention of a compound of formula (I) selected from the group consisting of:

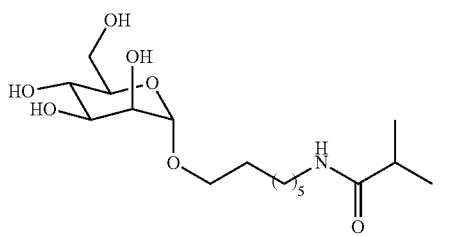

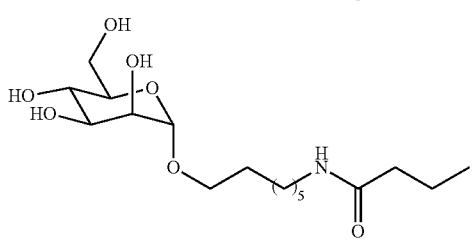

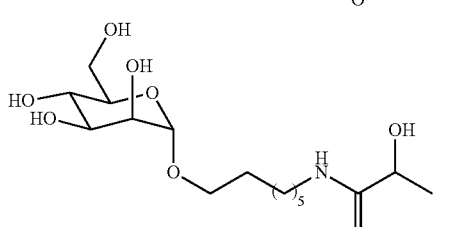

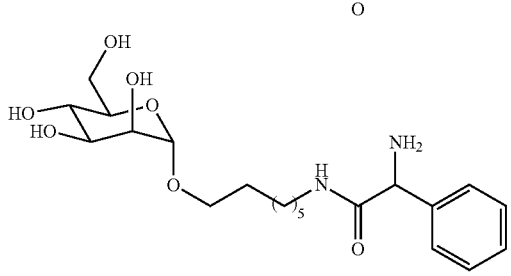

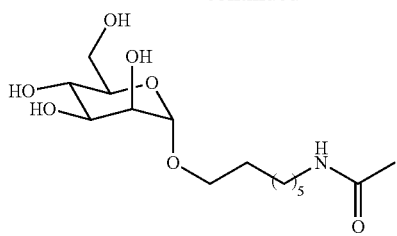
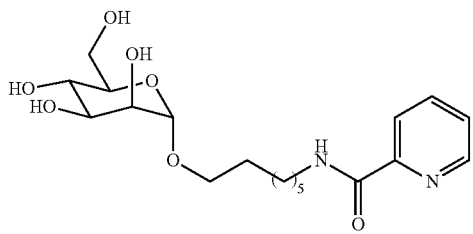
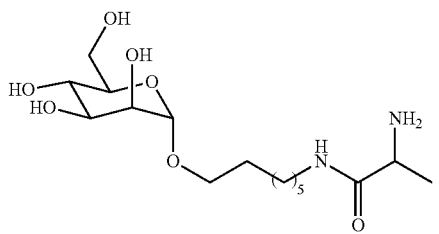
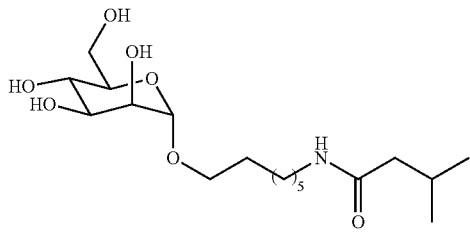
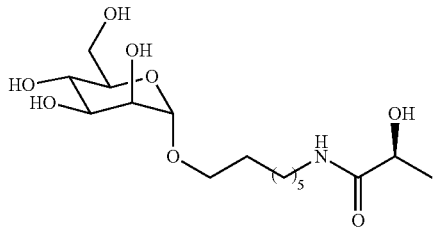
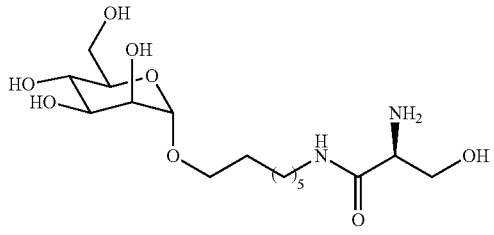
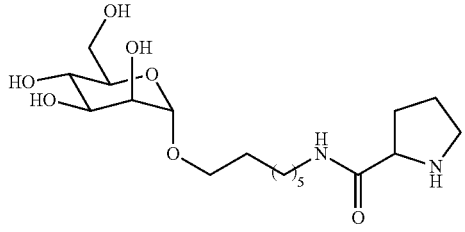
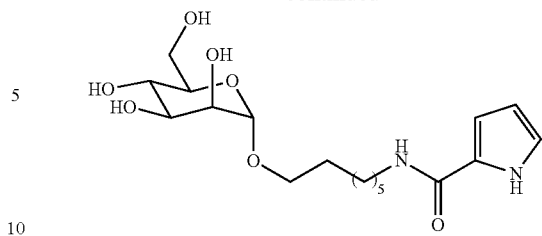
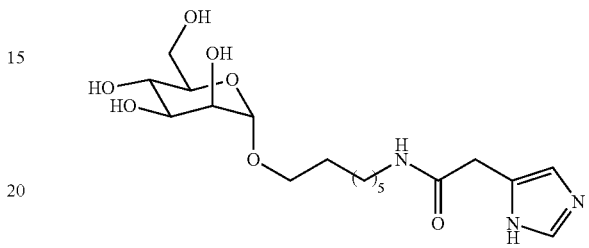
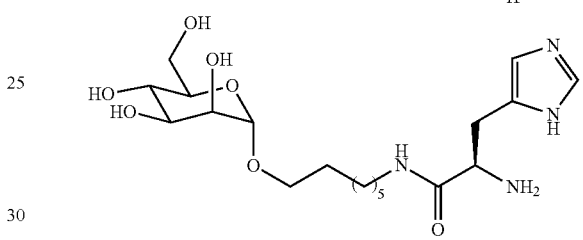
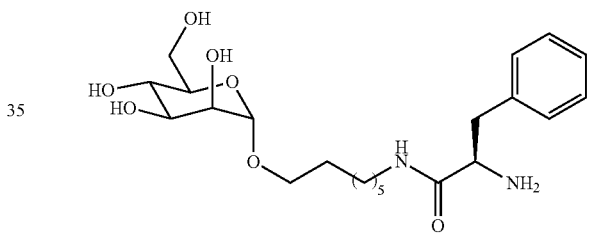
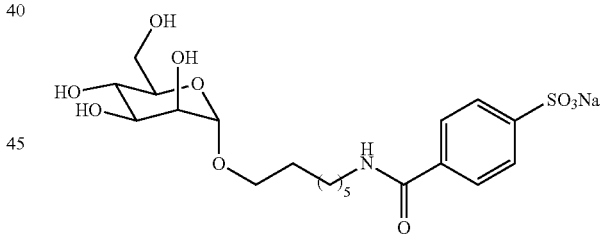
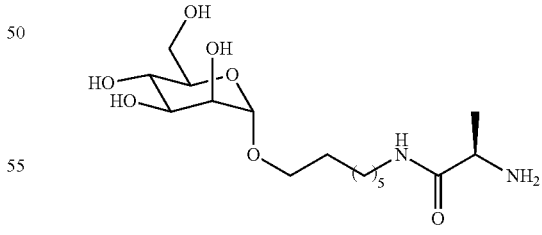
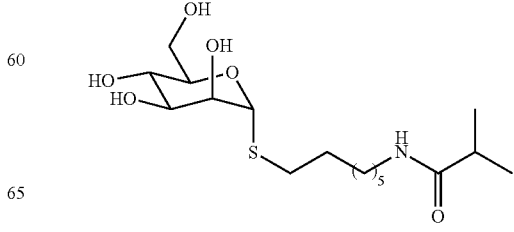

107
-continued
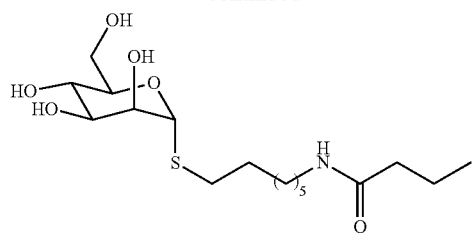
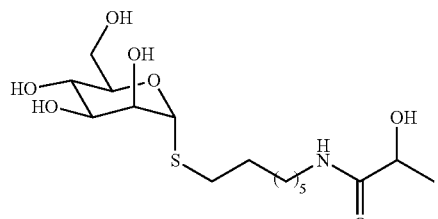
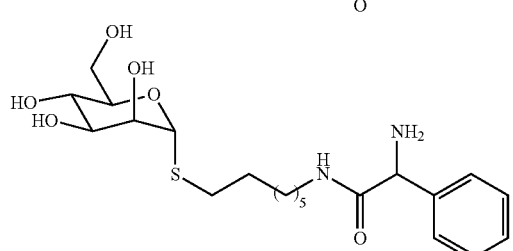
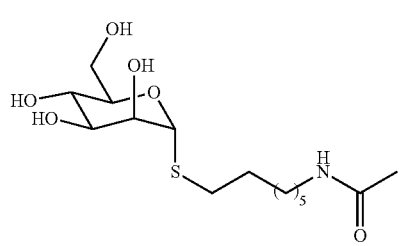
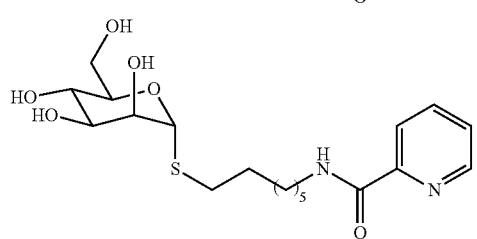
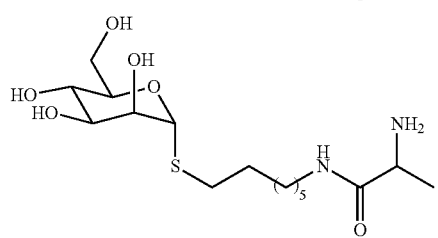
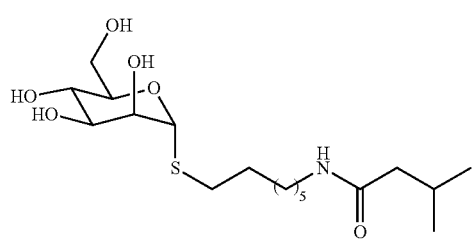
108
-continued
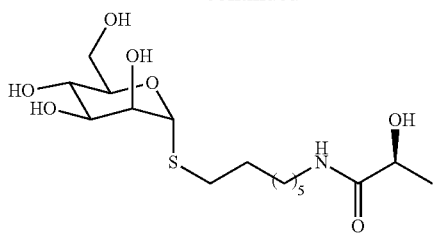
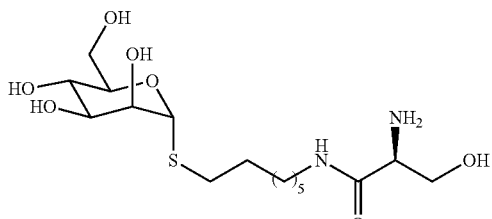
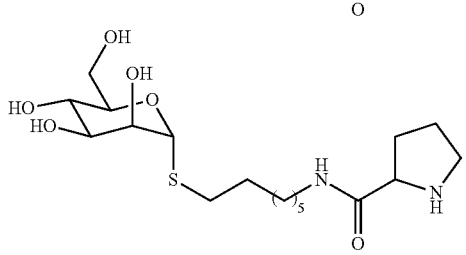
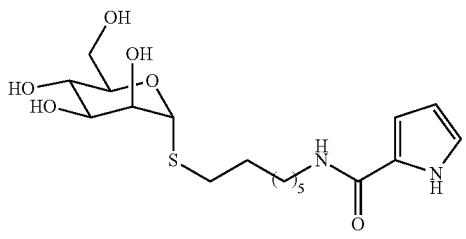
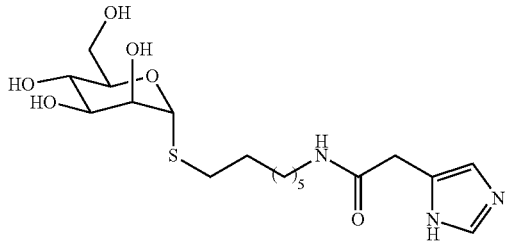
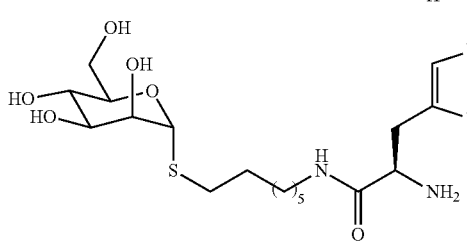
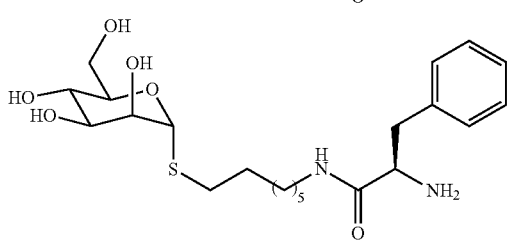

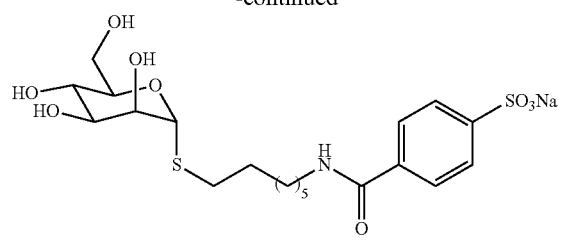
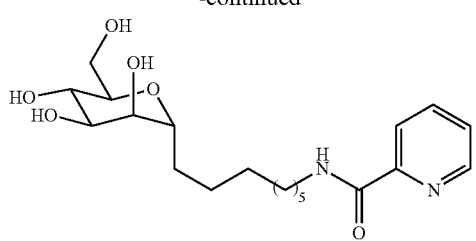
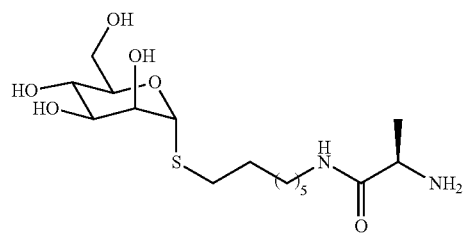
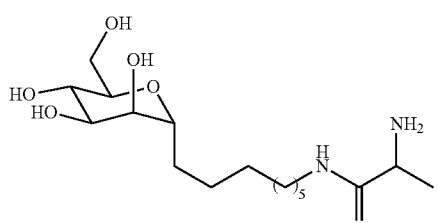
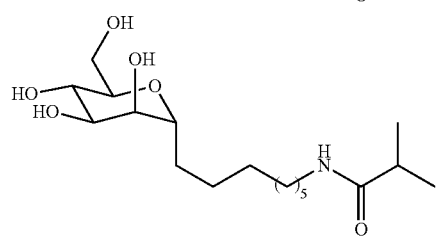
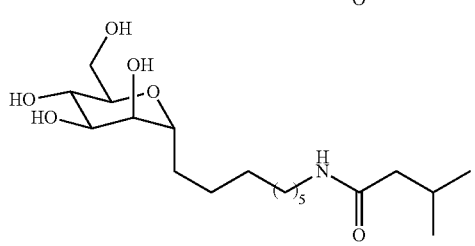
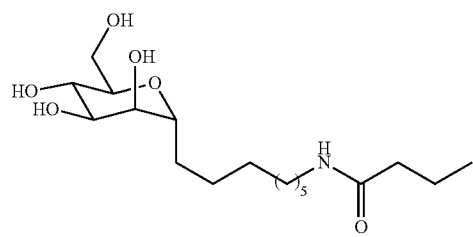
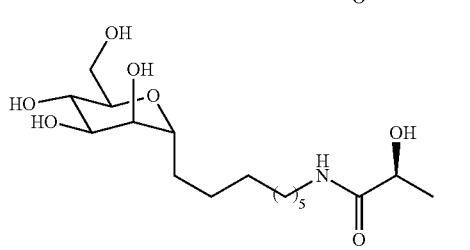
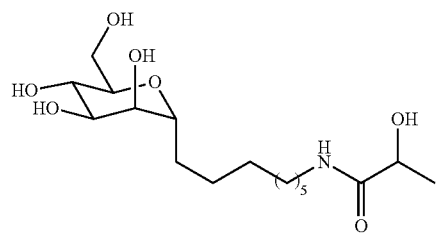
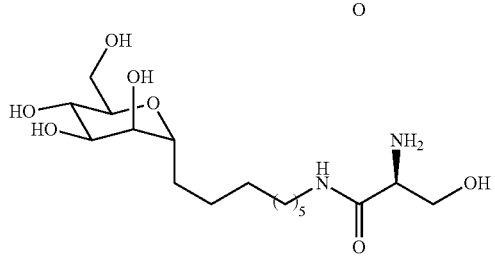
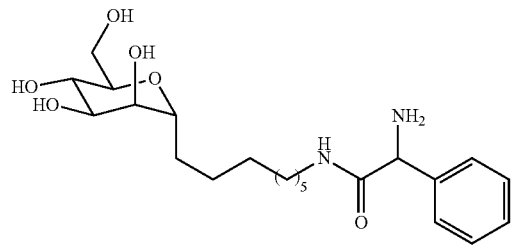
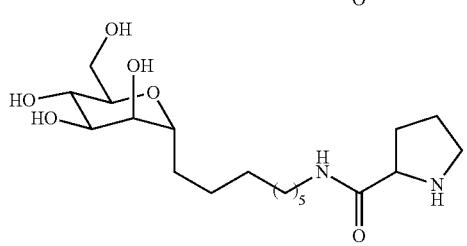
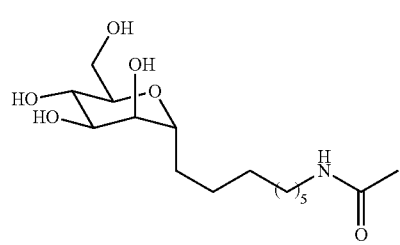
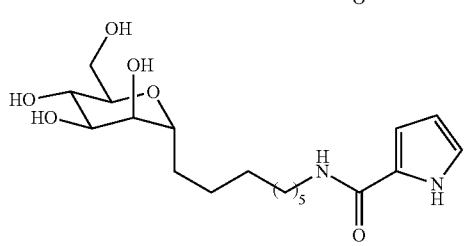

-continued
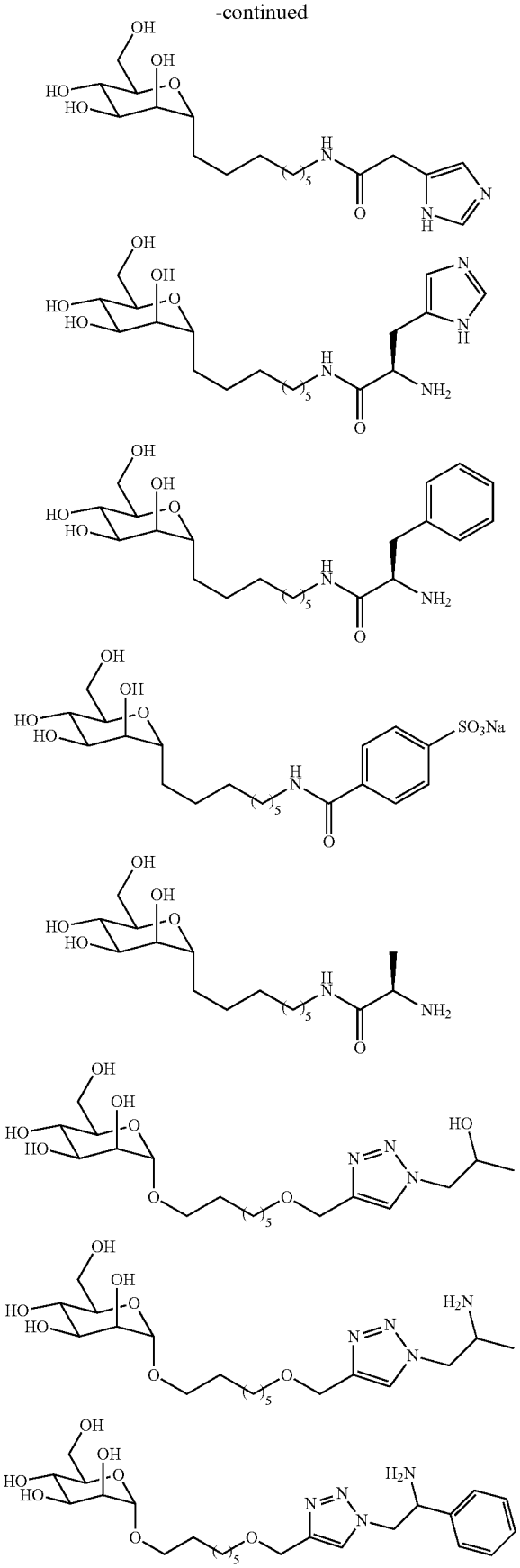
-continued
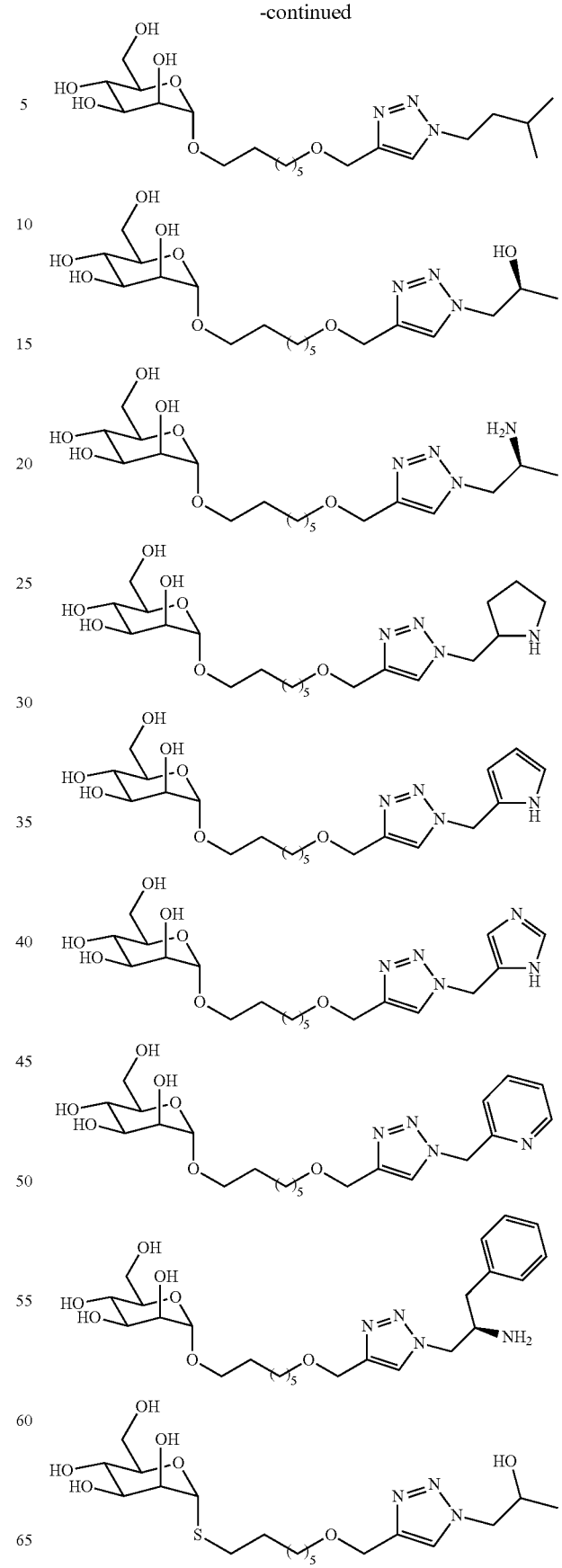

113
-continued
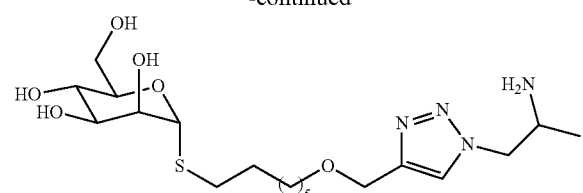
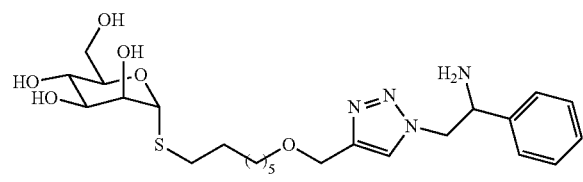
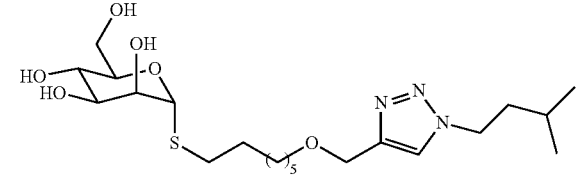
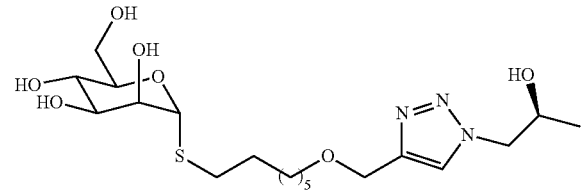
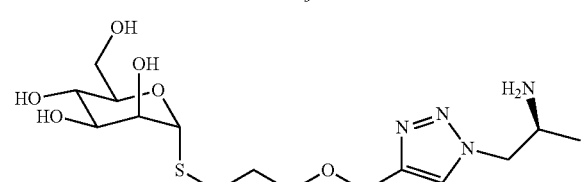
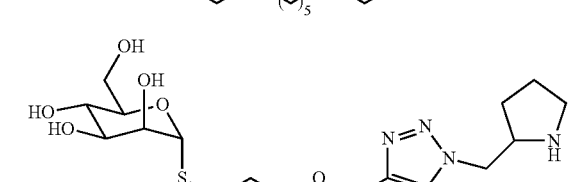
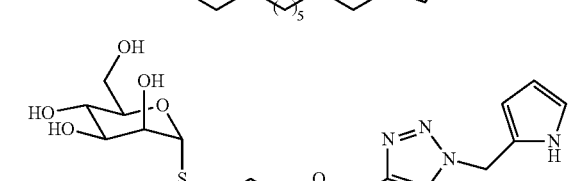
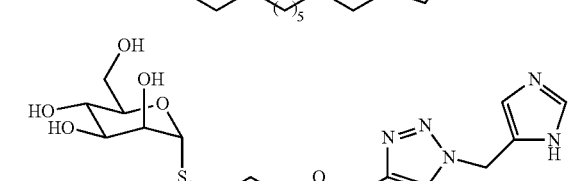
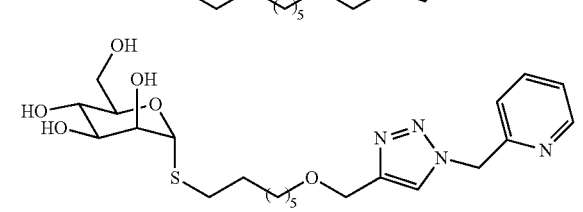
114
-continued
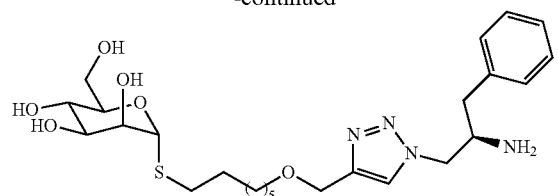
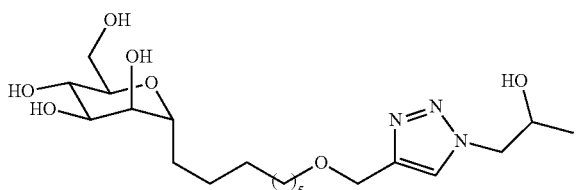
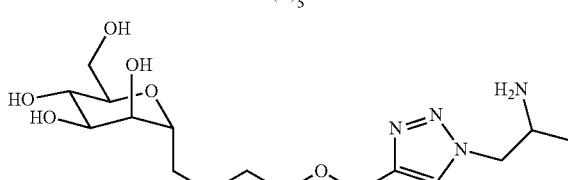
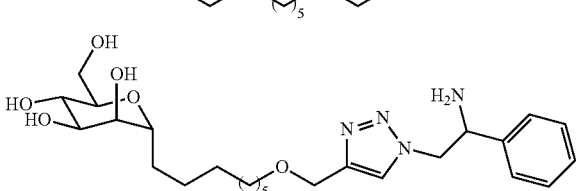
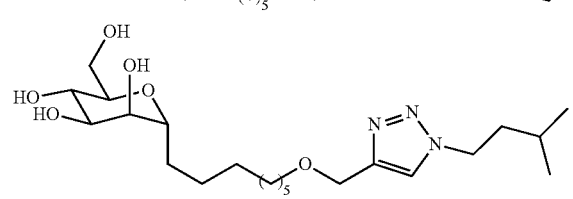
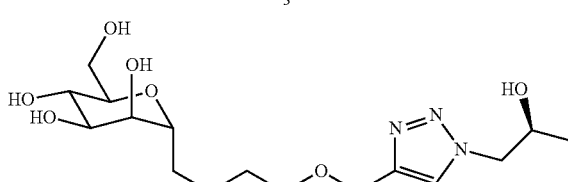
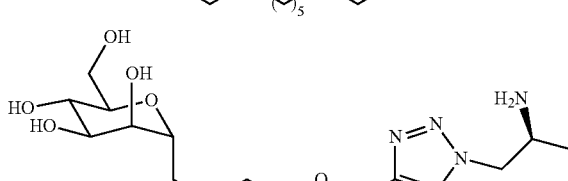
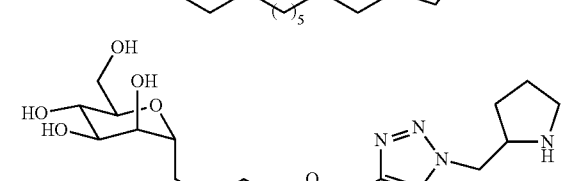
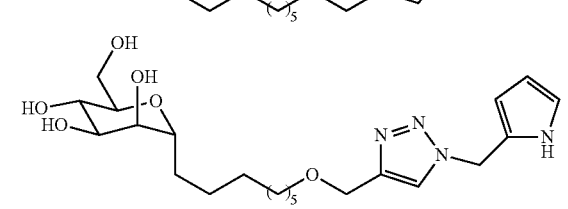

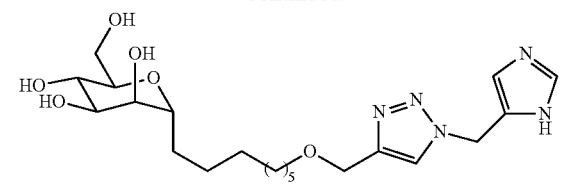
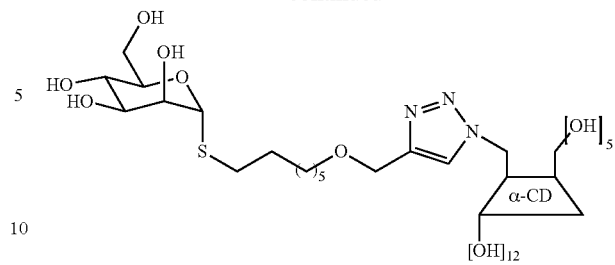
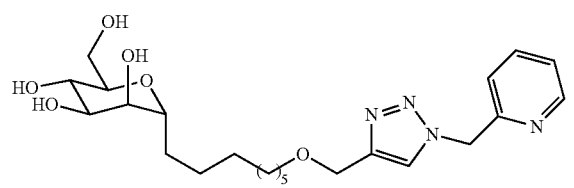
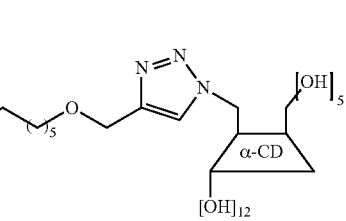
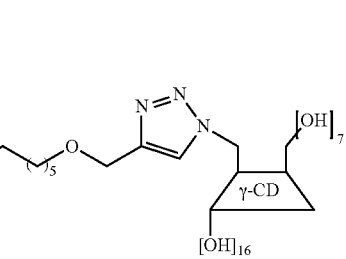
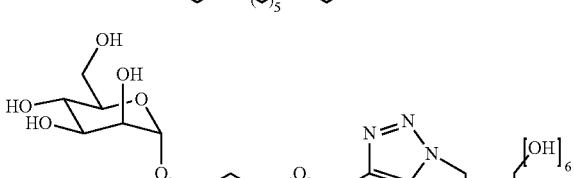
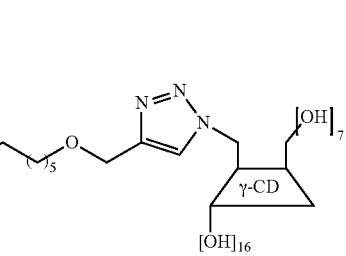
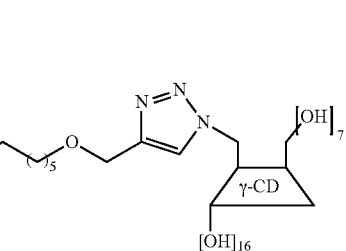
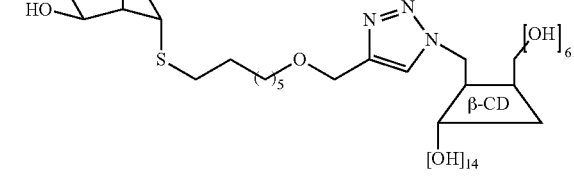
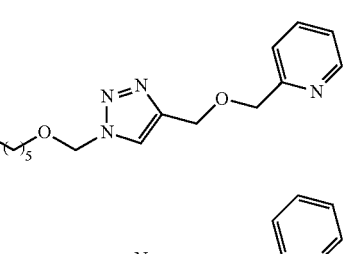
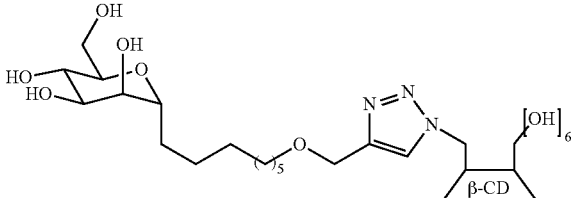
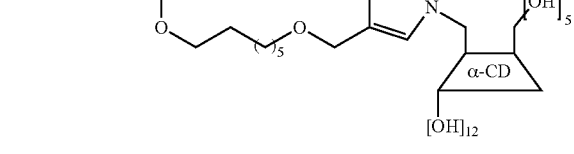

-continued

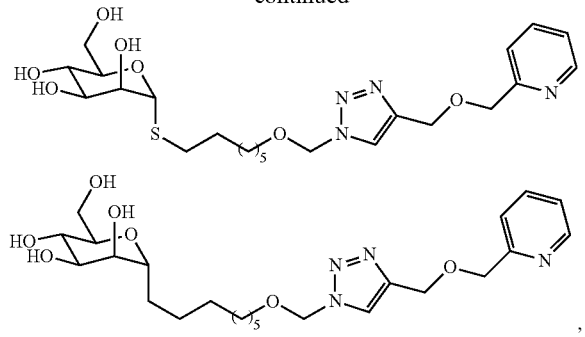

and their salts, in particular their pharmaceutically acceptable salts.

Figure 4A:
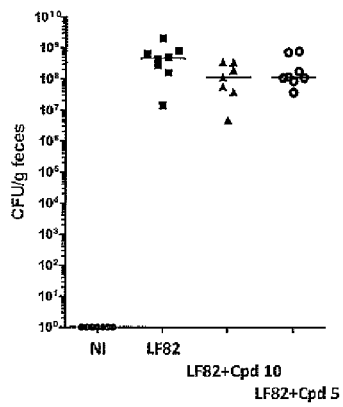
FIG. 4 presents the bacterial colonization in feces (FIGS. 4A, 4B and 4C) and Disease Activity Index score (DAI) (D) at respectively day 1, 3 and 4 post-infection of CEABAC10 mice infected with $10^9$ AIEC LF82 at day 0. Two oral administrations of monovalent compounds 5 and 10 were realized at a dose of 10 mg/kg.
Figure 4B:
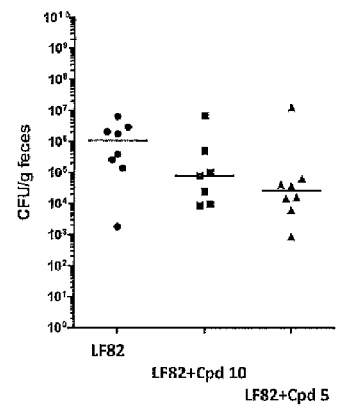
Figure 4C:
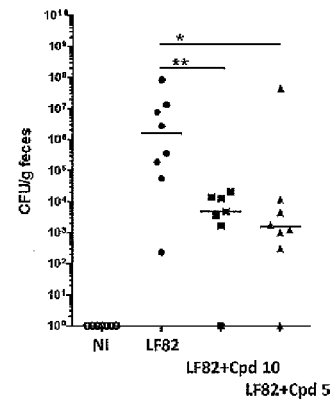

For FIGS. 4A to 4C, each point represents the number of colony forming units (CFU) of AIEC LF82 per gram of feces for each mouse. Horizontal red bars represent medians.

Figure 4D:
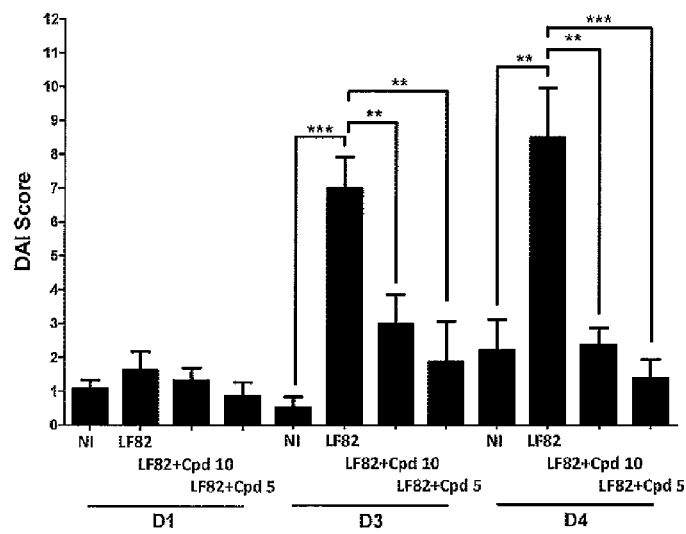

FIG. 4D presents DAI scores, expressed as means±sem. NI: non-infected. *: $p<0.05$; : $p<0.01$; *: $p<0.001$ (t test, in comparison with LF82 group).

Figure 5A:
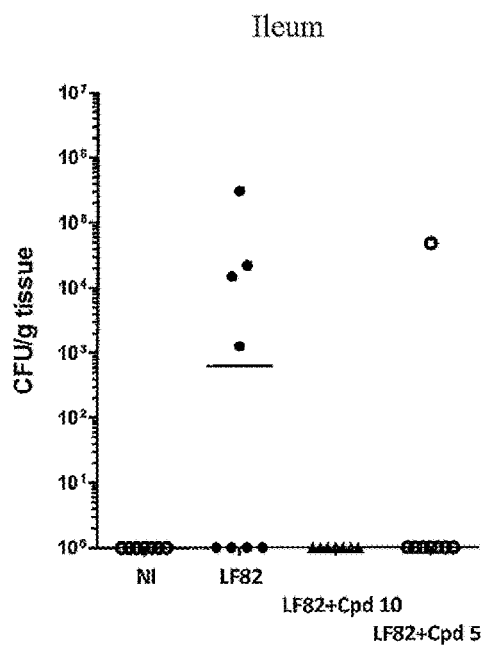
Figure 5B:
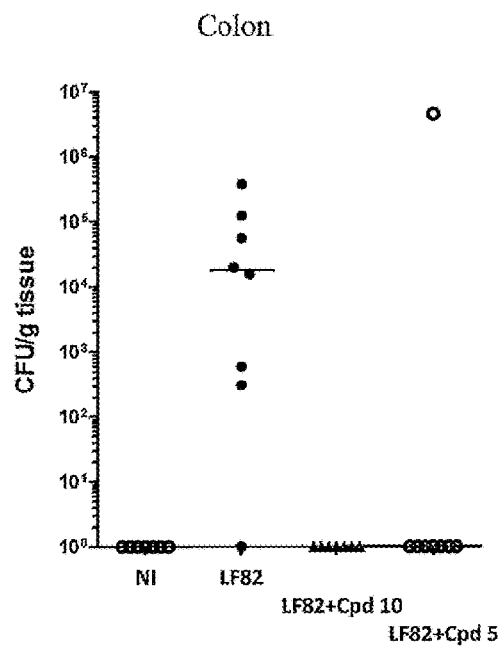

FIG. 5 presents the assessment of bacteria-associated to the ileum (FIG. 5A) and to the colon (FIG. 5B) of CEABAC10 mice infected with AIEC LF82 after oral treatment with monovalent compounds 5 and 10 (day 4 post-infection). Mice were orally challenged with $10^9$ bacteria at day 0 (D0) and monovalent compounds were administrated two times at a dose of 10 mg/kg. Each point represents the number of colony forming units (CFU) of AIEC LF82 per gram of feces for each mouse, horizontal bars represent medians. NI: non-infected mice.

Figure 6:
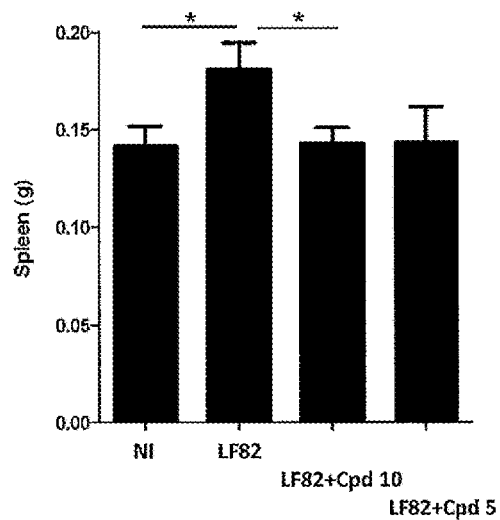

FIG. 6 presents the weight of spleens of AIEC LF82-infected CEABAC10 mice after oral treatment with monovalent compounds 5 and 10 at day 4 post-infection. Mice were orally challenged with $10^9$ bacteria at day 0 (D0) and monovalent compounds were administrated two times at a dose of 10 mg/kg. Results are expressed as means±sem. NI: non-infected. *: $p<0.05$ (t test).

FIG. 7 presents the contents in pro-inflammatory cytokines KC (FIG. 7A), TNF-α (FIG. 7B) and IL-23 (FIG. 7C) secreted by colonic mucosa at day 4 post-infection of CEABAC10 mice infected with AIEC LF82 after oral treatment with monovalent compounds 5 and 10. Mice were orally challenged with $10^9$ bacteria at day 0 (D0) and monovalent compounds were administrated two times at a dose of 10 mg/kg. Each point represents the level of secreted cytokines in pg/mL, for one mouse. Horizontal bars represent medians. *: $p<0.05$ (t test).

Figure 8:
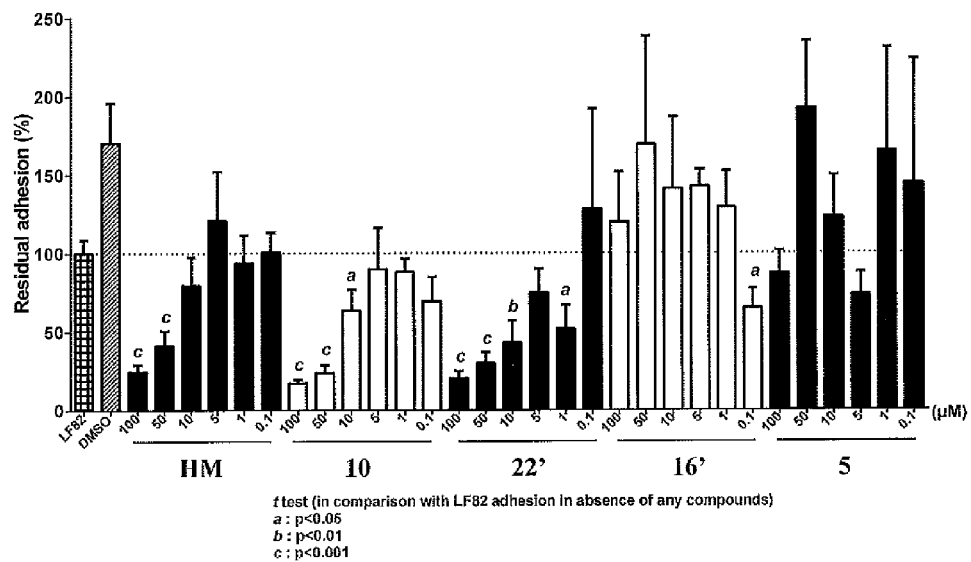

FIG. 8 presents the residual adhesion of LF82 bacteria on T84 cells in a post-incubation assay. Results are expressed in percentage of residual considering 100% as adhesion of LF82 AIEC (infected control) without any inhibitory compound (tested molecule). Different concentrations of anti-FimH molecules are tested: 0.1, 1, 5, 10, 50 and 100 μM. T test=Student: a: $p<0.05$, b: $p<0.01$, c: $p<0.001$.

Figure 9A:
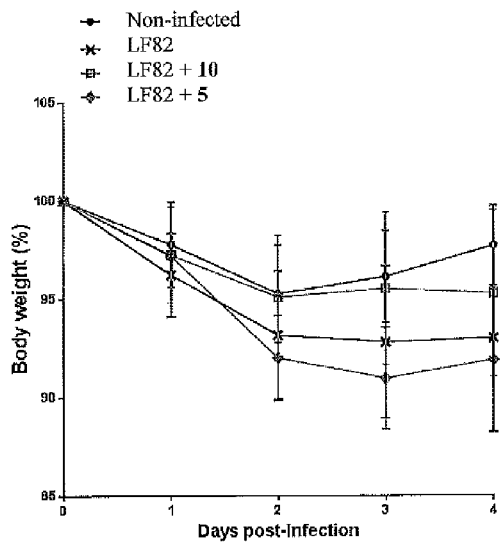

FIG. 9A presents the body weight of CEABAC10 transgenic mice uninfected or infected with AIEC LF82 measured at D=1, D=2, D=3 and D=4 days post infection.

Non-infected=Non infected mice (negative control); LF82=Infected mice with the LF82 AIEC strain (positive control); LF82+10, LF82+5=Infected mice with the LF82 AIEC strain treated with molecules tested at 10 mg/kg.

Figure 9B:
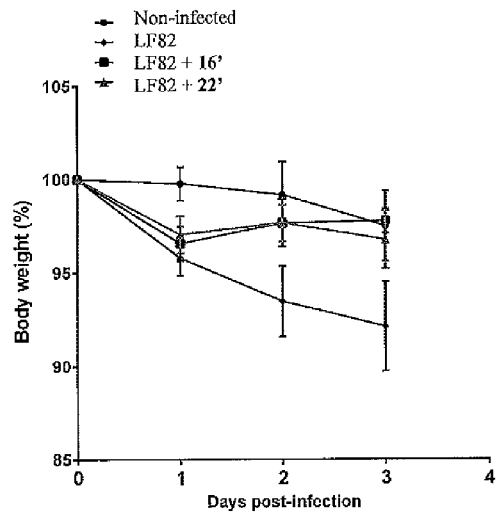

FIG. 9B presents the body weight of CEABAC10 transgenic mice uninfected or infected with AIEC LF82 measured at D=1, D=2, D=3 and D=4 days post infection.

Non-infected=Non infected mice (negative control); LF82=Infected mice with the LF82 AIEC strain (positive control); LF82+16', LF82+22'=Infected mice with the LF82 AIEC strain treated with molecules tested at 10 mg/kg.

Figure 10:
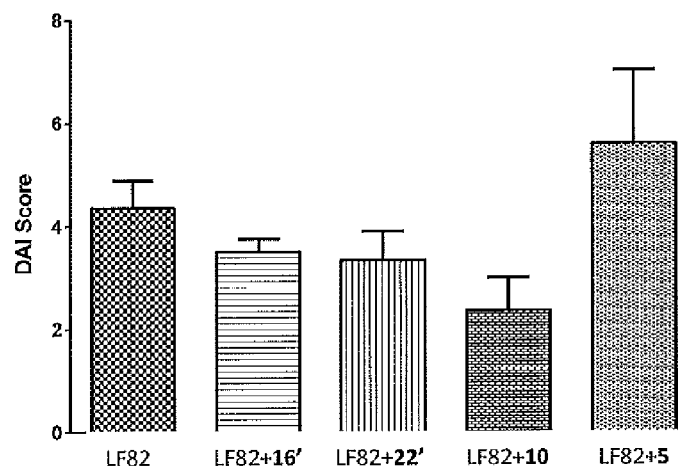

FIG. 10 presents the DAI (Disease Activity Index) measured at D=3 days post infection.

LF82=Infected mice with the LF82 AIEC strain (positive control); LF82+16', LF82+22', LF82+10, LF82+5=Infected mice with the LF82 AIEC strain treated with molecules tested at 10 mg/kg.

Figure 11:
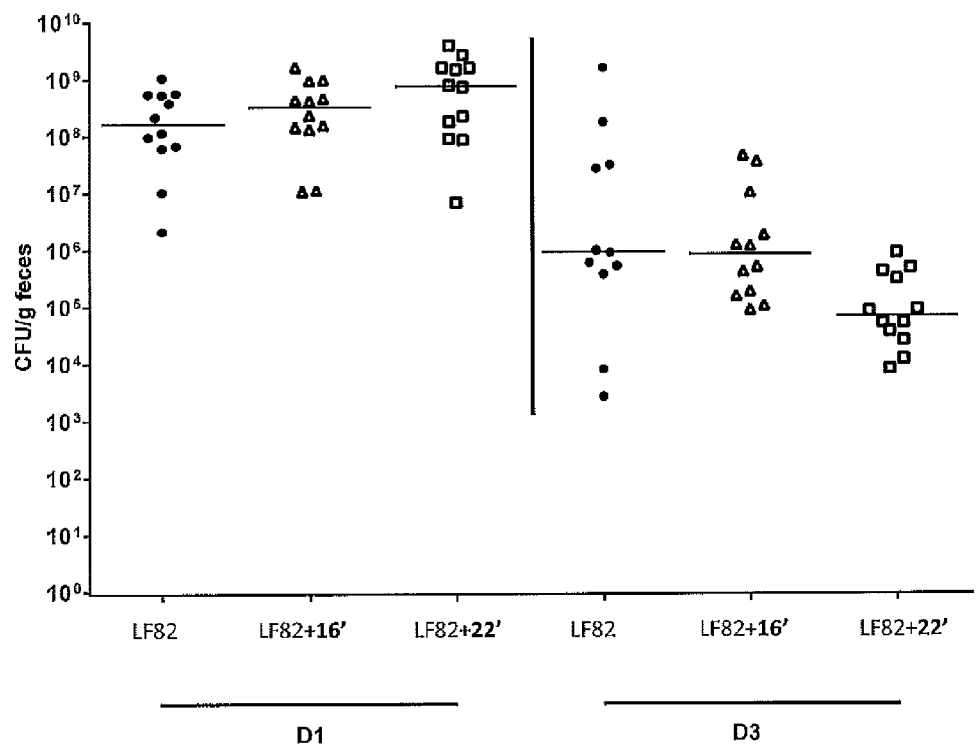

FIG. 11 presents the colony forming units (CFU) measured per gram of feces at D=1 and D=3 days.

NI=Non infected mice (negative control); LF82=Infected mice with the LF82 AIEC strain (positive control); LF82+16', LF82+22'=Infected mice with the LF82 AIEC strain treated with molecules tested at 10 mg/kg. Median value is indicated in horizontal line.

Figure 12:
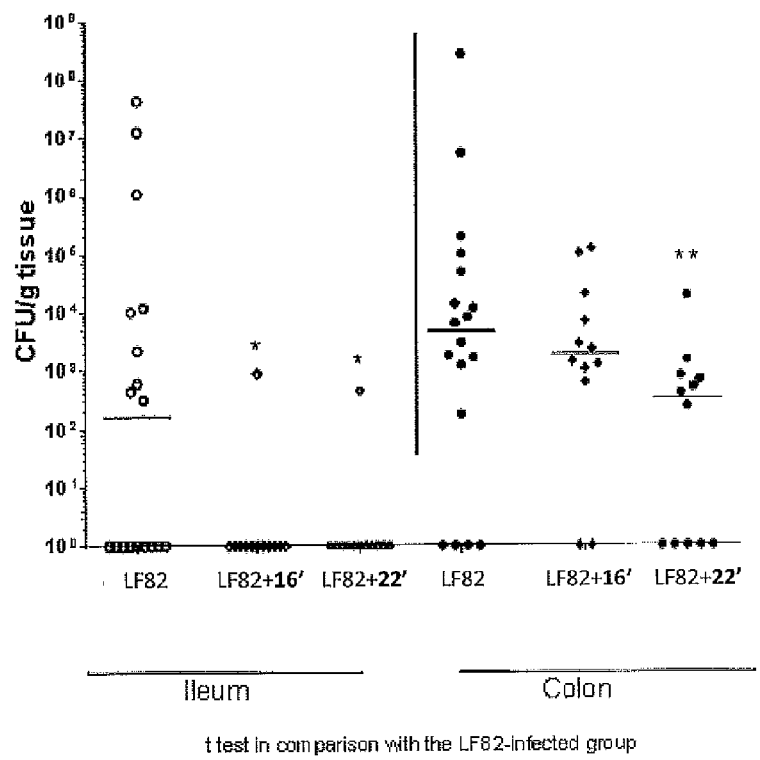

FIG. 12 presents the colony forming units (CFU) measured per gram of ileum and colon (mucosa) after D=3 days.

LF82=Infected mice with the LF82 AIEC strain (positive control); LF82+16', LF82+22'=Infected mice with the LF82 AIEC strain treated with molecules tested at 10 mg/kg. Median value is indicated in horizontal line.

Figure 13:
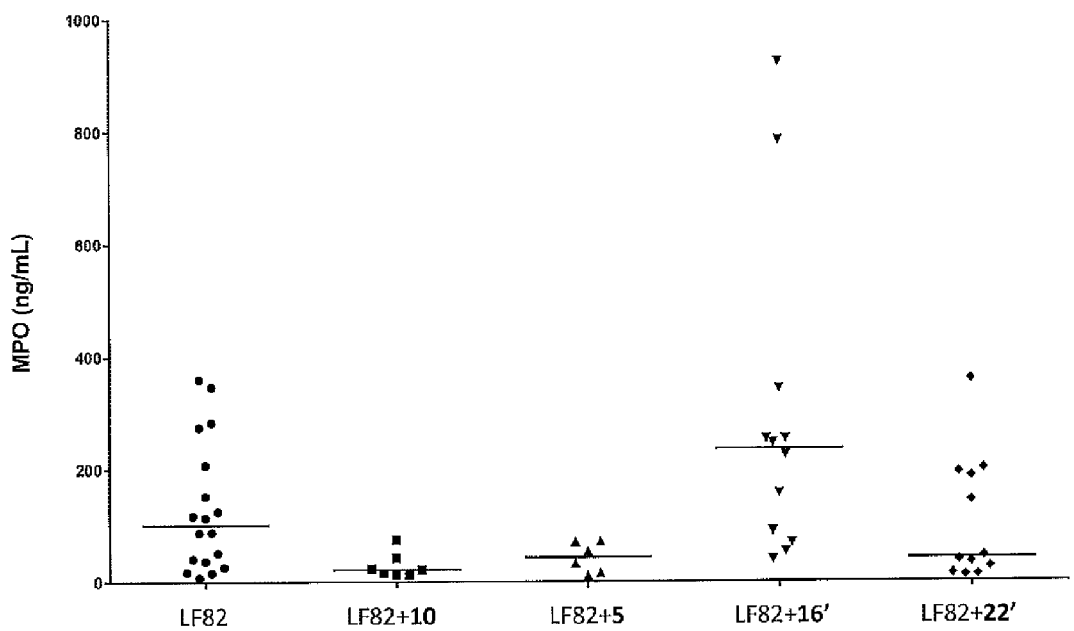

FIG. 13 presents the Myelopexoridase activity (MPO) assessment in intestinal tissue from CEABAC10 mice measured in ng/mL.

LF82=Infected mice with the LF82 AIEC strain (positive control); LF82+10, LF82+5, LF82+16', LF82+22'=Infected mice with the LF82 AIEC strain treated with molecules tested at 10 mg/kg. Median value is indicated in horizontal line. T test=Student: *$p<0.05$, $P<0.01$, *$p<0.001$.

Figure 14A:
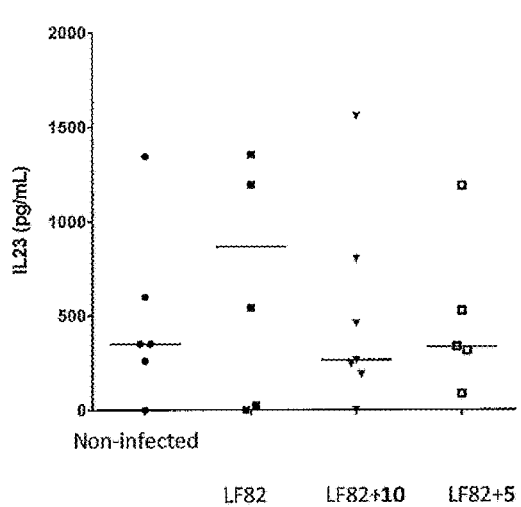

FIG. 14A presents the IL-23 assessment in blood from CEABAC10 mice measured in pg/mL.

Non-infected=non infected mice (negative control); LF82=Infected mice with the LF82 AIEC strain (positive control); LF82+10, LF82+5=Infected mice with the LF82 AIEC strain treated with molecules tested at 10 mg/kg. Median value is indicated in horizontal line. T test=Student: *p<0.05, P<0.01, *p<0.001.

Figure 14B:
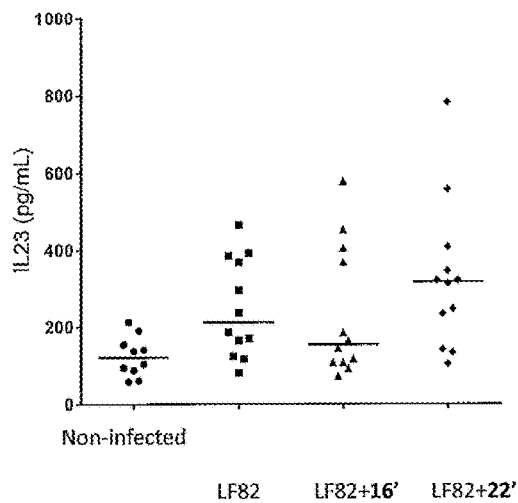

FIG. 14B presents the IL-23 assessment in blood from CEABAC10 mice measured in pg/mL.

Non-infected=non infected mice (negative control); LF82=Infected mice with the LF82 AIEC strain (positive control); LF82+16', LF82+22'=Infected mice with the LF82 AIEC strain treated with molecules tested at 10 mg/kg. Median value is indicated in horizontal line. T test=Student: *p<0.05, P<0.01, *p<0.001.

Figure 15A:
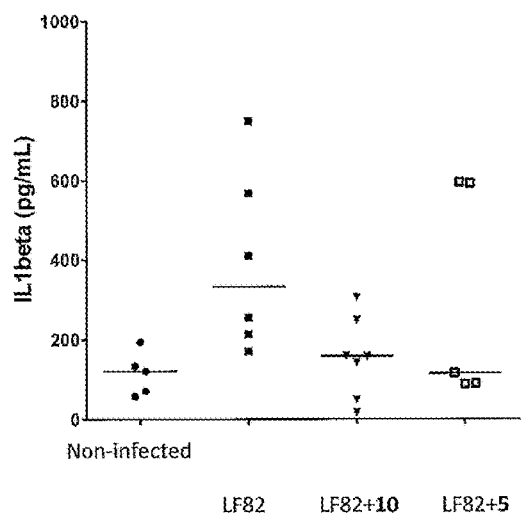

FIG. 15A presents the IL-1beta assessment in blood from CEABAC10 mice measured in pg/mL.

Non-infected=non infected mice (negative control); LF82=Infected mice with the LF82 AIEC strain (positive control); LF82+10, LF82+5=Infected mice with the LF82 AIEC strain treated with molecules tested at 10 mg/kg. Median value is indicated in horizontal line. T test=Student: *p<0.05, P<0.01, *p<0.001

Figure 15B:
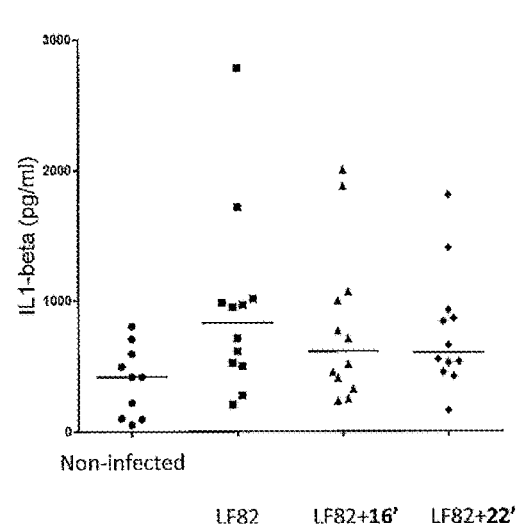

FIG. 15B presents the IL-1beta assessment in blood from CEABAC10 mice measured in pg/mL.

Non-infected=non infected mice (negative control); LF82=Infected mice with the LF82 AIEC strain (positive control); LF82+16', LF82+DA22'=Infected mice with the LF82 AIEC strain treated with molecules tested at 10 mg/kg. Median value is indicated in horizontal line. T test=Student: *p<0.05, P<0.01, *p<0.001.

EXAMPLES

A. Synthesis of Monovalent Heptylmannoside Cyclodextrin Compounds

Example 1: Synthesis of Compound 5

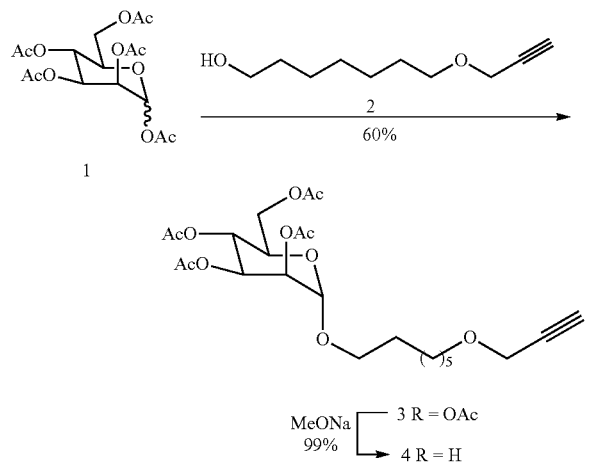

8-Oxaundec-10-ynyl 2,3,4,6-tetra-O-acetyl-α-D-mannopyranoside 3

Mannosyl pentaacetate 1 (229 mg, 0.587 mmol), compound 2 (150 mg, 0.882 mmol) and silver trifluoroacetate (194 mg, 0.878 mmol) were dissolved in dry dichloromethane (3 mL). A solution of $SnCl_4$ 1M in dichloromethane (585 μL) was added and the mixture was stirred at rt for 3 h under argon atmosphere. The solution was diluted in dichloromethane (10 mL) and washed with $NaHCO_3$ satd. (2×10 mL). The organic layer was dried, filtered and evaporated under reduced pressure. The residue was chromatographied on silica gel with ethyl acetate-cyclohexane (2-8) to (3-7) to afford 3 as a colorless oil (128 mg, 44%). Analytical data were identical as previously described [Gouin, S. G.; Wellens, A.; Bouckaert, J.; Kovensky, J. *ChemMedChem.* 2009, 5, 749-755].

8-Oxaundec-10-ynyl-α-D-mannopyranoside 4

3 (400 mg, 800 μmol) was dissolved in MeOH (10 mL). A solution of freshly prepared sodium methanolate 1M in methanol (500 μL) was added and the mixture was stirred at rt for 4 h. Amberlyst IR120 ($H^+$) was added and the mixture stirred until pH reached 5. The resin was filtered off and the solution was evaporated to dryness leading to unprotected product 4 (263 mg, 99%).

$[α]_D$=+96 (c=0.2, MeOH); $^1$H NMR (300 MHz, $CD_3OD$) δ=4.76 (1H, d, J=1.6 Hz, H-1), 4.14 (2H, d, J=2.4 Hz, $OCH_2C$), 3.82-3.80 (2H, m, H-2, H-3), 3.75-3.69 (3H, m, H-5, 2×H-6), 3.64 (1H, t, J=9.3 Hz, H-4), 2.84 (1H, t, CCH), 1.61-1.55 (4H, br, 2×$CH_2$), 1.39 (6H, br, 6×$CH_2$); $^{13}$C NMR (125 MHz, $D_2O$): δ=102.4 (C1), 76.5 (CCH), 75.5, 73.5, 73.1, 71.8 (C-2, -3, -4, -5), 69.4 ($CH_2O$), 59.6 ($CH_2CCH$), 31.4, 31.3, 31.1, 28.1, 28.0 ($CH_2$); HRMS (ES+): Found 355.1732 $C_{16}H_{28}O_7Na$ requires 355.1733.

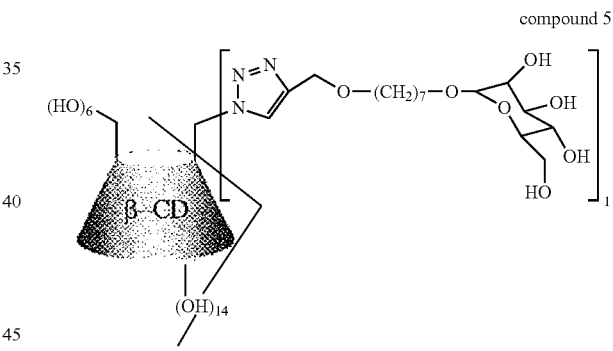

compound 5

Alkynyl-saccharide 4 (29 mg, 87 μmol) and mono-6-azido-6-deoxy-beta-cyclodextrin (50 mg, 43 μmol) were dissolved in a DMF/$H_2O$ mixture (2/0.5 mL). Copper sulfate (6.9 mg, 43 μmol) and sodium ascorbate (17 mg, 86 μmol) were added and the mixture was stirred at 70° C. for 30 minutes under μW irradiation. Ethylenediamine tetraacetic acid trisodium salt (50 mg, 127 μmol) was added and the mixture was stirred for 10 minutes at rt. The mixture was evaporated under reduced pressure and the residue purified by preparative HPLC leading to compound 5 (33 mg, 51%) as a white powder after lyophilisation.

$[α]_D$=+130 (c=0.1, MeOH); Tr=17 min; $^1$H NMR (500 MHz, $D_2O$) δ=8.23 (1H, s, $H_{triazol}$), 5.51, 5.36, 5.30 (7H, 3 s, H-$1^{I-VII}$), 5.15 (1H, s, H-$1^{HM}$), 4.20-3.20 (54H, br, H-2, -3, -4, -5, -6, $^{I-VII}$, H-2, -3, -4, -5, -$6^{HM}$, O—$CH_2$-triazol, 2×$CH_2$), 1.72, 1.65, 1.47 (10H, br, (×$CH_2$), $^{13}$C NMR (125 MHz, $D_2O$): δ=146.1 (C=$CH_{triazol}$), 123.8 (CH=$Ch_{triazol}$), 102.1, 101.8, 99.9 (C$1^{I-VII}$, C$1^{HM}$), 83.1, 81.7, 80.9, 80.3 (C$4^{I-VII}$), 72.1, 71.0, 70.4, 68.6, 67.0, 66.5, 63.0, 60.7, 59.8, 58.8 (C2, -3, -$5^{I-VII}$, C$6^{II-VII}$, C2, -3, -4, -5, -$6^{HM}$, $CH_2O$), 51.5 (C6'), 29.1, 28.5, 28.0, 25.7, 25.1 (CH$_2$); HRMS (ES+): Found 1514.5564 C$_{58}$H$_{97}$N$_3$O$_{41}$Na requires 1514.5495.

B. Synthesis of Mannosyl-O-Heptylamides

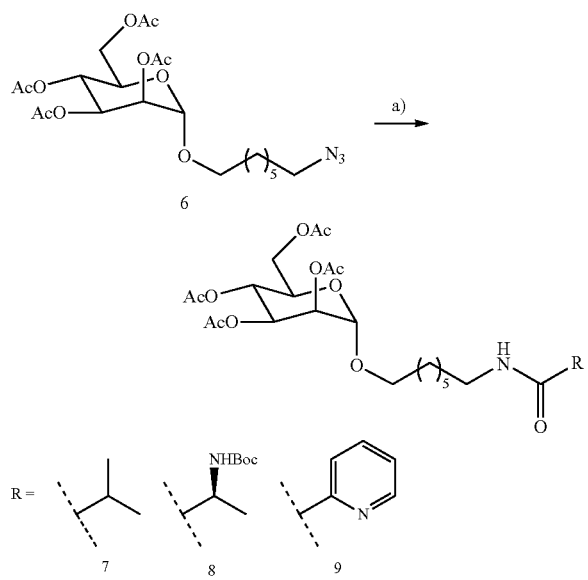

a) Carboxylic acid, HOBt, DIC, PH$_3$P, THF, 0° C. → rt

General Procedure A: "One Pot" Staudinger-Amide Coupling:

The azide-functionalized carbohydrate (1 equiv.) and the carboxylic acid (1.8 equiv.) were combined with HOBt (1.8 equiv.) in a flask and dried for more than 1 h in vacuo. This mixture was dissolved in dry THF (25 ml/mmol azide) under nitrogen and cooled to 0° C. Then DIC (1.8 equiv.) was added and the solution was stirred for 10 min, followed by the addition of Ph$_3$P (1.8 equiv.) and stirring for 1 h at 0° C. Then the reaction mixture was stirred overnight at room temperature, diluted with water (50 mL) and extracted twice with ethyl acetate (30 mL). The combined organic phases were washed with brine, dried with MgSO$_4$ and the mixture was filtered and concentrated under reduced pressure. The crude product was purified by silica gel chromatography.

Example 2: Compound 7

According to the general procedure A, mannosyl azide 6 (50 mg, 0.099 mmol), isobutyric acid (16 mg, 0.178 mmol, 1.8 equiv.), HOBt (24 mg, 0.178 mmol, 1.8 equiv.), DIC (28 μL, 0.178 mmol, 1.8 equiv.) and Ph$_3$P (47 mg, 0.178 mmol, 1.8 equiv.) were allowed to react in THF (2.5 mL). The crude product was purified by silica gel column chromatography (EtOAc/petroleum ether, 70:30→EtOAc as eluents) to give the amide 7 (42 mg, 0.079 mmol, 80%) as an oil.

[α]$_D$=+71 (c=0.81 in CHCl$_3$)

$^1$H NMR (300 MHz, CDCl$_3$): δ=1.12 (6H, d, J=6.9 Hz, 2×CH$_3$-isobutyric acid), 1.28-1.59 (10H, m), 1.97 (3H, s, AcO), 2.02 (3H, s, AcO), 2.08 (3H, s, AcO), 2.13 (3H, s, AcO), 2.31 (1H, m, CH, isobutyric acid), 3.21 (2H, m, H-7'), 3.41 (1H, m, H-1'a), 3.65 (1H, m, H-1'b), 3.95 (1H, ddd, J$_{5,4}$=9.5 Hz, J$_{5,6b}$=5.3 Hz, J$_{5,6a}$=2.5 Hz, H-5), 4.10 (1H, dd, J$_{6a,6b}$=12.2 Hz, J$_{6a,5}$=2.5 Hz, H-6a), 4.25 (1H, dd, J$_{6b,6a}$=12.2 Hz, J$_{6b,5}$=5.3 Hz, H-6a), 4.77 (1H, d, J$_{1,2}$=1.7 Hz, H-1), 5.20 (1H, dd, J$_{2,3}$=3.3 Hz, J$_{2,1}$=1.7 Hz, H-2), 5.24 (1H, dd, J$_{4,3}$=10.1 Hz, J$_{4,5}$=9.6 Hz, H-4), 5.32 (1H, dd, J$_{3,4}$=10.1 Hz, J$_{3,2}$=3.3 Hz, H-3), 5.60 (1H, bs, NH).

$^{13}$C NMR (100.6 MHz, CDCl$_3$): δ=19.6 (2×CH$_3$, isobutyric acid), 20.6 (2×CH$_3$, 2×AcO), 20.7 (CH$_3$, AcO), 20.8 (CH$_3$, AcO), 25.8 (CH$_2$), 26.6 (CH$_2$), 28.8 (CH$_2$), 29.0 (CH$_2$), 29.5 (CH$_2$), 35.6 (CH, isobutyric acid), 39.2 (CH$_2$, C-7'), 62.5 (CH, C-6), 66.2 (CH), 68.3 (CH, CH$_2$, C-5, C-1'), 69.1 (CH), 69.6 (CH, C-2), 97.5 (CH, C-1), 169.7 (C, AcO), 169.9 (C, AcO), 170.1 (C, AcO), 170.6 (C, AcO), 176.8 (C, amide).

MS (CI, NH$_3$): m/z 549 [M+NH$_3$]$^+$.

Example 3: Compound 8

According to the general procedure A, mannosyl azide 6 (50 mg, 0.099 mmol), N-Boc-L-alanine (34 mg, 0.178 mmol, 1.8 equiv.), HOBt (24 mg, 0.178 mmol, 1.8 equiv.), DIC (28 μL, 0.178 mmol, 1.8 equiv.) and Ph$_3$P (47 mg, 0.178 mmol, 1.8 equiv.) were allowed to react in THF (2.5 mL). The crude product was purified by silica gel column chromatography (EtOAc/petroleum ether, 70:30→EtOAc as eluents) to give the amide 8 (35 mg, 0.055 mmol, 56%) as an oil.

[α]$_D$=+54 (c=0.92 in CHCl$_3$)

$^1$H NMR (300 MHz, CDCl$_3$): δ=1.33 (3H, d, J=7.0 Hz, CH$_3$-alanine), 1.25-1.76 (10H, m), 1.44 (3H, s, N-Boc), 2.00 (3H, s, AcO), 2.05 (3H, s, AcO), 2.10 (3H, s, AcO), 2.16 (3H, s, AcO), 3.24 (2H, t, J=6.6 Hz, H-7'), 3.43 (1H, m, H-1'a), 3.67 (1H, m, H-1'b), 3.97 (1H, ddd, J$_{5,4}$=8.2 Hz, J$_{5,6b}$=5.3 Hz, J$_{5,6a}$=2.5 Hz, H-5), 4.11 (1H, dd, J$_{6a,6b}$=12.1 Hz, J$_{6a,5}$=2.4 Hz, H-6a), 4.12 (1H, m, CH-alanine), 4.28 (1H, dd, J$_{6b,6a}$=12.1 Hz, J$_{6b,5}$=5.3 Hz, H-6a), 4.79 (1H, d, J, =1.6 Hz, H-1), 5.03 (1H, bs, NH), 5.22 (1H, dd, J$_{2,3}$=3.1 Hz, J$_{2,1}$=1.6 Hz, H-2), 5.27 (1H, dd, J$_{4,3}$=10.0 Hz, J$_{4,5}$=8.2 Hz, H-4), 5.34 (1H, dd, J$_{3,4}$=10.0 Hz, J$_{3,2}$=3.3 Hz, H-3), 6.19 (1H, bs, NH).

$^{13}$C NMR (100.6 MHz, CDCl$_3$): δ=18.4 (CH$_3$, alanine), 20.7 (CH$_3$, AcO), 20.72 (2×CH$_3$, AcO), 20.9 (CH$_3$, AcO), 25.8 (CH$_2$), 26.5 (CH$_2$), 28.3 (3×CH$_3$, N-Boc), 28.8 (CH$_2$), 29.0 (CH$_2$), 29.3 (CH$_2$), 39.4 (CH$_2$, C-7'), 50.1 (C, N-Boc), 62.5 (CH, C-6), 66.2 (CH, C-1'), 68.4 (2×CH), 69.1 (CH), 69.7 (CH, C-2), 97.5 (CH, C-1), 155.5 (C, amide), 169.7 (C, AcO), 170.0 (C, AcO), 170.1 (C, AcO), 170.6 (C, AcO), 172.4 (C, N-Boc).

MS (CI, NH3): m/z 633 [M]+

HRMS (MALDI, DHB): m/z calcd for C29H48N2O13Na [M+Na]+: 655.3049. found: 655.3026.

Example 4: Compound 9

According to the general procedure A, mannosyl azide 6 (50 mg, 0.099 mmol), picolinic acid (22 mg, 0.178 mmol, 1.8 equiv.), HOBt (24 mg, 0.178 mmol, 1.8 equiv.), DIC (28 μL, 0.178 mmol, 1.8 equiv.) and Ph$_3$P (47 mg, 0.178 mmol, 1.8 equiv.) were allowed to react in THF (2.5 mL). The crude product was purified by silica gel column chromatography (EtOAc/petroleum ether, 70:30→EtOAc as eluents) to give the amide 9 (43 mg, 0.076 mmol, 77%) as an oil.

[α]$_D$=+61 (c=1.03 in CHCl$_3$)

$^1$H NMR (300 MHz, CDCl$_3$): 1.30-1.69 (10H, m), 1.98 (3H, s, AcO), 2.03 (3H, s, AcO), 2.09 (3H, s, AcO), 2.14 (3H, s, AcO), 3.39 (1H, m, H-1'a), 3.46 (2H, q, J=6.8 Hz, H-7'), 3.66 (1H, m, H-1'b), 3.97 (1H, ddd, J$_{5,4}$=9.5 Hz, J$_{5,6b}$=5.2 Hz, J$_{5,6a}$=2.3 Hz, H-5), 4.09 (1H, dd, J$_{6a,6b}$=12.2 Hz, J$_{6a,5}$=2.3 Hz, H-6a), 4.28 (1H, dd, J$_{6b,6a}$=12.2 Hz, J$_{6b,5}$=5.2 Hz, H-6a), 4.79 (1H1H, d, J$_{1,2}$ 1.6 Hz, H-1), 5.22

(1H, dd, $J_{2,3}$=3.3 Hz, $J_{2,1}$=1.6 Hz, H-2), 5.26 (1H, dd, $J_{4,3}$=9.8 Hz, $J_{4,5}$=9.6 Hz, H-4), 5.34 (1H, dd, $J_{3,4}$=9.8 Hz, $J_{3,2}$=3.3 Hz, H-3), 7.41 (1H, ddd, J=7.6 Hz, J=4.8 Hz, J=1.3 Hz, picolinic), 7.84 (1H, ddd, J=7.6 Hz, J=7.6 Hz, J=1.7 Hz, picolinic), 8.08 (1H, bs, NH), 8.19 (1H, bd, J=7.8 Hz, picolinic), 8.54 (1H, ddd, J=4.7 Hz, J=1.7 Hz, J=0.9 Hz, picolinic).

$^{13}$C NMR (100.6 MHz, CDCl$_3$): δ=20.7 (CH$_3$, AcO), 20.71 (2×CH$_3$, AcO), 20.9 (CH$_3$, AcO), 26.0 (CH$_2$), 26.8 (CH$_2$), 29.0 (CH$_2$), 29.1 (CH$_2$), 29.5 (CH$_2$), 39.4 (CH$_2$, C-7'), 62.5 (CH, C-6), 66.2 (CH, C-1'), 68.3 (CH), 68.4 (CH), 69.1 (CH), 69.7 (CH, C-2), 97.5 (CH, C-1), 122.3 (CH, picolinic acid), 126.1 (CH, picolinic acid), 137.5 (CH, picolinic acid), 147.8 (CH, picolinic acid), 149.9 (C, picolinic acid), 164.0 (C, amide), 169.7 (C, AcO), 169.9 (C, AcO), 170.1 (C, AcO), 170.6 (C, AcO).

MS (CI, NH3): m/z (%): 567 [M]+

HRMS (MALDI, DHB): m/z calcd for C27H38N2O11Na [M+Na]+: 598.2368. found: 5892374.

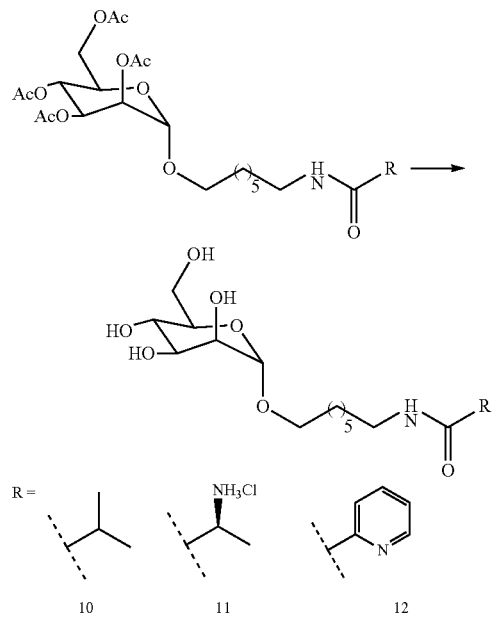

i. NaOMe, MeOH, rt, ii. Amberlite IR120 (H), iii. TFA-DCM, 0° C. vi. HCl ac. (for N—Boc protected compound 8).

General Procedure B: O-Acetyl Deprotection According to Zemplén Conditions

The protected glycosyl amide (1 equiv.) was dissolved in dry MeOH (30 mL) and sodium methoxide (1 M solution in MeOH, 10% per AcO) was added. The mixture was stirred for 4 h, neutralized with Amberlite IR120 (H), filtered and the solvents evaporated to dryness. The substrate was dissolved in water and subjected to lyophilization.

General Procedure C: N-Boc Deprotection with Trifluoroacetic Acid

The Boc-protected amine was dissolved in DCM (2 mL/mmol) and TFA (2 mL/mmol) was added at 0° C. The mixture was stirred for 1 h, evaporated to dryness and co-evaporated with H$_2$O (3 times) and 0.5 N HCl (3 times). The substrate was dissolved in water and subjected to lyophilization.

Example 5: Compound 10

According to the general procedure B, using the amide 7 (81 mg, 0.128 mmol) as starting material, the derivative 10 was obtained after lyophilization (41 mg, 0.113 mmol, 93%), as an amorphous white solid.

[α]$_D$=+48.1 (c=1.32 in MeOD).

$^1$H NMR (300 MHz, MeOD): δ=1.10 (6H, d, J=6.9 Hz, 2×CH$_3$-isobutyric acid), 1.29-1.64 (10H, m), 2.42 (1H, m, CH-isobutyric acid), 3.15 (2H, t, J=6.9 Hz, C-7'), 3.41 (1H, m, H-1a'), 3.52 (1H, ddd, $J_{5,4}$=9.2 Hz, $J_{5,6b}$=5.6 Hz, $J_{5,6a}$=2.4 Hz, H-5), 3.61 (1H, dd, $J_{4,3}$=9.4 Hz, $J_{4,5}$=9.2 Hz, H-4), 3.67-3.75 (3H, m), 3.78 (1H, dd, $J_{2,3}$=3.3 Hz, $J_{2,1}$=1.7 Hz, H-2), 3.82 (1H, dd, $J_{6b,6a}$=11.9 Hz, $J_{6b,5}$=2.5 Hz, H-6b), 4.73 (1H, d, $J_{1,2}$=1.7 Hz, H-1).

$^{13}$C NMR (100.6 MHz, MeOD): δ=20.0 (2×CH$_3$, 2×CH$_3$-isobutyric acid), 27.2 (CH$_2$), 27.8 (CH$_2$), 30.1 (CH$_2$), 30.4 (CH$_2$), 30.5 (CH$_2$), 36.3 (CH, CH-isobutyric acid), 40.2 (CH$_2$, C-7'), 62.9 (CH, C-6), 68.5 (CH), 68.6 (CH), 72.2 (CH, C-5), 72.6 (CH, C-1'), 74.6 (CH, C-2), 101.5 (CH, C-1), 180.0 (C, amide).

MS (CI, NH$_3$): m/z 364 [M+H]$^+$

Example 6: Compound 11

According to the general procedure B and C, using the amide 8 (81 mg, 0.128 mmol) as starting material, the alanine derivative 11 was obtained after lyophilization (41 mg, 0.102 mmol, 80%), in form of ammonium chloride salt, as an amorphous white solid.

[α]$_D$=+39.6 (c=1.21 in D$_2$O).

$^1$H NMR (300 MHz, D$_2$O): δ=1.12-1.48 (10H, m), 1.36 (3H, d, J=7.1 Hz, CH$_3$-alanine), 3.08 (2H, m, H-1'), 3.33-3.77 (8H, m), 3.87 (2H, q, J=7.1 Hz, CH-alanine), 4.67 (1H, bs, H-1).

$^{13}$C NMR (100.6 MHz, D$_2$O): δ=16.6 (CH$_3$, alanine), 24.9 (CH$_2$), 25.2 (CH$_2$), 25.9 (CH$_2$), 28.0 (CH$_2$), 31.2 (CH$_2$), 39.5 (CH$_2$, C-7'), 60.9 (CH, C-6), 61.8 (CH, C-1'), 66.8 (CH, alanine), 67.9 (CH, C-5), 70.1 (CH), 70.7 (CH), 72.7 (CH, C-2), 99.7 (CH, C-1), 170.5 (C, amide).

HRMS (MALDI, DHB): m/z calcd for C$_{16}$H$_{32}$N$_2$O$_7$Na [M+Na]+: 387.2107. found: 387.2119.

Example 7: Compound 12

According to the general procedure B, using the amide 9 (25 mg, 0.048 mmol) as starting material, the picolinic derivative 12 was obtained after lyophilization (19 mg, 0.048 mmol, quantitative) as an amorphous white solid.

[α]$_D$=+47.1 (c=1.81 in MeOH)

$^1$H NMR (300 MHz, MeOD): 1.34-1.68 (10H, m), 3.40 (1H, m, H-1'a), 3.42 (2H, t, J=7.0 Hz, H-7'), 3.52 (1H, ddd, $J_{5,4}$=9.4 Hz, $J_{5,6b}$=5.4 Hz, $J_{5,6a}$=2.4 Hz, H-5), 3.62 (1H, dd, $J_{4,3}$=9.4 Hz, $J_{4,5}$=9.2 Hz, H-4), 3.68-3.76 (3H, m, H-3, H-6a, H-1'b), 3.78 (1H, dd, $J_{2,3}$=3.2 Hz, $J_{2,1}$=1.6 Hz, H-2), 3.82 (1H, dd, $J_{6a,6b}$=11.8 Hz, $J_{6b,5}$=2.4 Hz, H-6b), 4.73 (1H, d, $J_{1,2}$=1.6 Hz, H-1), 7.41 (1H, ddd, J=7.6 Hz, J=4.8 Hz, J=1.3 Hz, picolinic), 7.53 (1H, ddd, J=7.6 Hz, J=4.8 Hz, J=1.3 Hz, picolinic), 7.95 (1H, ddd, J=7.7 Hz, J=7.7 Hz, J=1.7 Hz, picolinic), 8.08 (1H, ddd, J=7.8 Hz, J=1.1 Hz, J=1.1 Hz, picolinic), 8.68 (1H, ddd, J=4.7 Hz, J=1.7 Hz, J=1.1 Hz, picolinic).

$^{13}$C NMR (100.6 MHz, MeOD): δ=23.5 (CH$_2$), 27.3 (CH$_2$), 28.0 (CH$_2$), 30.2 (CH$_2$), 30.5 (CH$_2$), 40.4 (CH$_2$, C-7'), 62.9 (CH, C-6), 68.5 (CH, C-1'), 68.6 (CH), 72.2 (CH), 72.6 (CH), 74.5 (CH, C-2), 101.5 (CH, C-1), 123.0

(CH, picolinic acid), 127.6 (CH, picolinic acid), 138.7 (CH, picolinic acid), 149.7 (CH, picolinic acid), 151.1 (C, picolinic acid), 166.6 (C, amide).

MS (CI, NH$_3$): m/z 399 [M+H]+

HRMS (MALDI, DHB): m/z calcd for C$_{42}$H$_{48}$O$_5$ [M+Na]+: 421.1945. found: 421.1965.

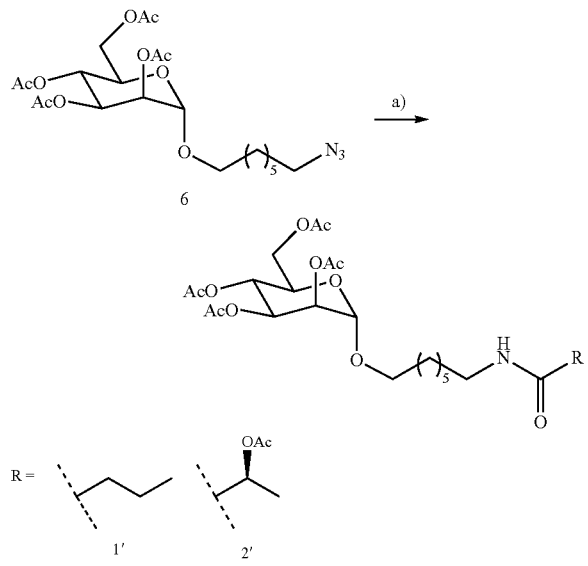

a) Carboxylic acid, HOBt, DIC, PH$_3$P, THF, 0° C. → rt

Example 8: Compound 1'

According to the general procedure A, mannosyl azide 6 (100 mg, 0.205 mmol), n-butyric acid (32 μL, 0.369 mmol, 1.8 equiv.), HOBt (50 mg, 0.369 mmol, 1.8 equiv.), DIC (57 μL, 0.369 mmol, 1.8 equiv.) and Ph$_3$P (97 mg, 0.369 mmol, 1.8 equiv.) were allowed to react in DCM (5 mL). The crude product was purified by silica gel column chromatography (EtOAc/diethyl ether, 80:20 as eluents) to give the amide 1' (47 mg, 0.088 mmol, 43%) as an oil.

$[\alpha]_D$=+37.5 (c=0.62 in CHCl$_3$)

$^1$H NMR (300 MHz, CDCl$_3$): δ=0.94 (3H, t, J=7.4 Hz, CH$_3$-butyric acid), 1.28-1.61 (10H, m), 1.66 (2H, m, CH$_2$-butyric acid), 1.99 (3H, s, AcO), 2.04 (3H, s, AcO), 2.10 (3H, s, AcO), 2.14 (2H, m, CH$_2$-butyric acid), 2.15 (3H, s, AcO), 3.24 (2H, m, H-7'), 3.44 (1H, m, H-1'a), 3.67 (1H, m, H-1'b), 3.97 (1H, ddd, J$_{5,4}$=9.5 Hz, J$_{5,6b}$=5.4 Hz, J$_{5,6a}$=2.5 Hz, H-5), 4.11 (1H, dd, J$_{6a,6b}$=12.3 Hz, J$_{6a,5}$=2.5 Hz, H-6a), 4.28 (1H, dd, J$_{6b,6a}$=12.3 Hz, J$_{6b,5}$=5.4 Hz, H-6a), 4.79 (1H, d, J$_{1,2}$=1.6 Hz, H-1), 5.22 (1H, dd, J$_{2,3}$=3.2 Hz, J$_{2,1}$=1.7 Hz, H-2), 5.27 (1H, dd, J$_{4,3}$=10.1 Hz, J$_{4,5}$=9.6 Hz, H-4), 5.34 (1H, dd, J$_{3,4}$=10.1 Hz, J$_{3,2}$=3.3 Hz, H-3), 5.55 (1H, bs, NH).

$^{13}$C NMR (100.6 MHz, CDCl$_3$): δ=13.7 (CH$_3$, butyric acid), 19.1 (CH$_2$, butyric acid), 20.61 (2×CH$_3$, 2×AcO), 20.66 (CH$_3$, AcO), 20.8 (CH$_3$, AcO), 25.8 (CH$_2$), 26.6 (CH$_2$), 28.8 (CH$_2$), 29.0 (CH$_2$), 29.4 (CH$_2$), 38.7 (CH$_2$, butyric acid), 39.3 (CH$_2$, C-7'), 62.4 (CH, C-6), 66.1 (CH), 68.3 (CH, CH$_2$, C-5, C-1'), 69.1 (CH), 69.6 (CH, C-2), 97.4 (CH, C-1), 169.7 (C, AcO), 169.9 (C, AcO), 170.1 (C, AcO), 170.6 (C, AcO), 172.9 (C, amide).

MS (CI, NH$_3$): m/z 532 [M+H]$^+$

HRMS (ESI): m/z calcd for C$_{25}$H$_{41}$NO$_{11}$Na [M+Na]$^+$: 554.2577. found: 554.2571.

Example 9: Compound 2'

According to the general procedure A, mannosyl azide 6 (100 mg, 0.205 mmol), O-acetyllactic acid (81 mg, 0.615 mmol, 3 equiv.), HOBt (83 mg, 0.615 mmol, 3 equiv.), DIC (95 μL, 0.615 mmol, 3 equiv.) and Ph$_3$P (97 mg, 0.615 mmol, 3 equiv.) were allowed to react in DCM (5.1 mL). The crude product was purified by silica gel column chromatography (EtOAc/petroleum ether, 80:20→EtOAc as eluents) to give the amide 2' (72 mg, 0.125 mmol, 61%) as a colorless oil.

$[\alpha]_D$=+53.9 (c=0.52 in CHCl$_3$)

$^1$H NMR (300 MHz, CDCl$_3$): δ=1.26-1.34 (8H, m), 1.42 (3H, d, J=6.9 Hz, CH$_3$-lactic acid), 1.52 (2H, m), 1.95 (3H, s, AcO), 2.00 (3H, s, AcO), 2.06 (3H, s, AcO), 2.10 (3H, s, AcO), 2.12 (3H, s, AcO), 3.23 (2H, q, J=6.7 Hz, H-7'), 3.40 (1H, m, H-1'a), 3.64 (1H, m, H-1'b), 3.93 (1H, ddd, J$_{5,4}$=9.3 Hz, J$_{5,6b}$=5.2 Hz, J$_{5,6a}$=2.3 Hz, H-5), 4.07 (1H, dd, J$_{6a,6b}$=12.3 Hz, J$_{6a,5}$=2.4 Hz, H-6a), 4.24 (1H, dd, J$_{6b,6a}$=12.3 Hz, J$_{6b,5}$=5.3 Hz, H-6a), 4.76 (1H, d, J$_{1,2}$=1.6 Hz, H-1), 5.13 (1H, q, J=6.7 Hz, CH-lactic acid), 5.18 (1H, dd, J$_{2,3}$=3.2 Hz, J$_{2,1}$=1.6 Hz, H-2), 5.23 (1H, dd, J$_{4,3}$=10.0 Hz, J$_{4,5}$=9.3 Hz, H-4), 5.34 (1H, dd, J$_{3,4}$=10.0 Hz, J$_{3,2}$=3.3 Hz, H-3), 6.18 (1H, bs, NH).

$^{13}$C NMR (100.6 MHz, CDCl$_3$): δ=17.8 (CH$_3$, CH$_3$-lactic acid), 20.61 (2×CH$_3$, 2×AcO), 20.65 (CH$_3$, AcO), 20.8 (CH$_3$, AcO), 21.0 (CH$_3$, AcO), 25.8 (CH$_2$), 26.5 (CH$_2$), 28.8 (CH$_2$), 29.0 (CH$_2$), 29.3 (CH$_2$), 39.1 (CH$_2$, C-7'), 62.4 (CH$_2$, C-6), 66.1 (CH, C-5), 68.3 (CH, CH$_2$, C-3, C-1'), 69.1 (CH, C-4), 69.6 (CH, C-2), 70.6 (CH, CH-lactic acid), 97.4 (CH, C-1), 169.4 (C, AcO), 169.7 (C, AcO), 169.9 (C, AcO), 170.0 (C, AcO), 170.2 (C, AcO), 170.6 (C, amide).

MS (CI, NH$_3$): m/z 576 [M]$^+$

HRMS (MALDI, DHB): m/z calcd for C$_{26}$H$_{41}$NO$_{13}$Na [M+Na]$^+$: 598.2470. found: 598.2471.

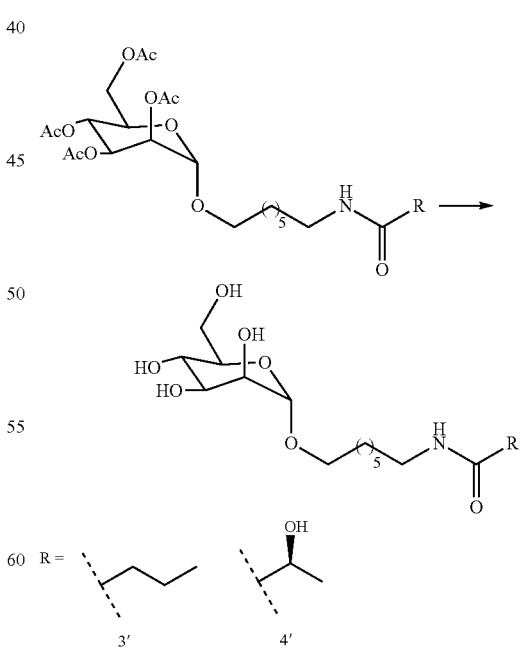

i. NaOMe, MeOH, rt, ii. Amberlite IR120 (H).

Example 10: Compound 3'

According to the general procedure B, using the amide 1' (47 mg, 0.088 mmol) as starting material, the derivative 3' was obtained after lyophilization (31 mg, 0.085 mmol, 97%) as an amorphous white solid.

$[\alpha]_D$=+59.3 (c=1.19 in MeOD).

$^1$H NMR (300 MHz, MeOD): δ=0.95 (3H, d, J=7.4 Hz, CH$_3$-butyric acid), 1.30-1.70 (12H, m), 2.16 (2H, t, J=7.4 Hz, CH$_2$-butyric acid), 3.17 (2H, t, J=6.9 Hz, C-7'), 3.43 (1H, m, H-1a'), 3.53 (1H, ddd, J$_{5,4}$=9.3 Hz, J$_{5,6b}$=5.8 Hz, J$_{5,6a}$=2.4 Hz, H-5), 3.62 (1H, dd, J$_{4,3=9.5}$ Hz, J$_{4,5}$=9.2 Hz, H-4), 3.68-3.76 (3H, m, H-3, H-6a, H-1'b), 3.79 (1H, dd, J$_{2,3}$=3.2 Hz, J$_{2,1}$=1.7 Hz, H-2), 3.82 (1H, dd, J$_{6b,6a}$=11.8 Hz, J$_{6b,5}$=2.3 Hz, H-6b), 4.73 (1H, bs, H-1).

$^{13}$C NMR (100.6 MHz, MeOD): δ=13.96 (CH$_3$, CH$_3$-butyric acid), 20.0 (CH$_3$, CH$_3$-butyric acid), 27.2 (CH$_2$), 27.9 (CH$_2$), 30.1 (CH$_2$), 30.4 (CH$_2$), 30.5 (CH$_2$), 39.0 (CH$_2$, CH$_2$-butyric acid), 40.3 (CH$_2$, C-7'), 62.9 (CH, C-6), 68.5 (CH, C-1'), 68.6 (CH, C-4), 72.3 (CH, C-5), 72.6 (CH, C-3), 74.6 (CH, C-2), 101.5 (CH, C-1), 176.5 (C, amide).

MS (CI, NH$_3$): m/z 364 [M+H]$^+$

HRMS (MALDI, DHB): m/z calcd for C$_{17}$H$_{33}$N$_1$O$_7$Na [M+Na]$^+$: 386.2149. found: 386.2151.

Example 11: Compound 4'

According to the general procedure B, using the amide 2' (42 mg, 0.073 mmol) as starting material, the butyric derivative 4' was obtained after lyophilization (28 mg, 0.069 mmol, 94%) as an amorphous white solid.

$[\alpha]_D$=+20.7 (c=0.83 in MeOH).

$^1$H NMR (400 MHz, MeOD): δ=1.29-1.41 (8H, m), 1.33 (3H, d, J=6.8 Hz, CH$_3$-lactic acid), 1.53 (1H, m), 1.59 (1H, m), 3.21 (2H, t, J=7.1 Hz, H-7'), 3.42 (1H, m, H-1a'), 3.52 (11, ddd, J$_{5,4}$=9.5 Hz, J$_{5,6b}$=5.7 Hz, J$_{5,6a}$=2.3 Hz, H-5), 3.61 (1H, dd, J$_{4,5}$=9.5 Hz, J$_{4,3}$=9.5 Hz, H-4), 3.67-3.76 (3H, m, H-1'b, H-3, H-6a), 3.78 (1H, dd, J$_{2,3}$=3.2 Hz, J$_{2,1}$=1.8 Hz, H-2), 3.82 (1H, dd, J$_{6b,6a}$=11.8 Hz, J$_{6b,5}$=2.3 Hz, H-6b), 4.10 (1H, q, J=6.8 Hz, CH-lactic acid), 4.73 (1H, d, J$_{1,2}$=1.4 Hz, H-1).

$^{13}$C NMR (100.6 MHz, MeOD): δ=21.3 (CH$_3$, CH$_3$-lactic acid), 27.2 (CH$_2$), 27.8 (CH$_2$), 30.1 (CH$_2$), 30.4 (CH$_2$), 30.5 (CH$_2$), 39.9 (CH$_2$, C-7'), 62.9 (CH, C-6), 68.5 (CH, C-5), 68.7 (CH, C-1'), 69.1 (CH), 72.3 (CH), 72.7 (CH, C-2), 74.5 (CH, CH-lactic acid), 101.5 (CH, C-1), 177.7 (C, amide).

MS (CI, NH$_3$): m/z 424 [M+NH$_3$]$^+$

HRMS (ESI): m/z calcd for C$_{16}$H$_{31}$NO$_8$Na [M+Na]$^+$: 388,4128. found: 388,4132.

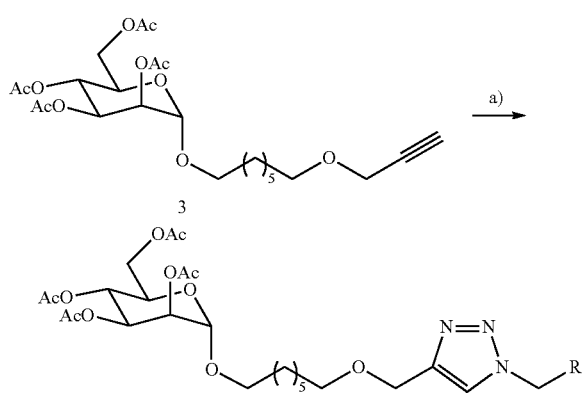

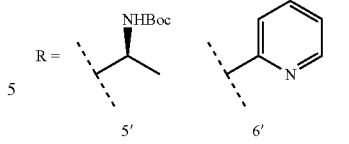

a) (R)—N—Boc-1-azidopropan-2-amine or 2-(azidomethy)pyridine, CuSO$_4$, VitC Na, 1,4-dioxane-H$_2$O, 50° C.

Example 12: Compound 5'

To a solution of mannosyl alkine 3 (100 mg, 0.200 mmol) and (R)—N-Boc-1-azidopropan-2-amine (60 mg, 0.300 mmol) in a mixture 3:1 of 1,4-dioxane-H$_2$O (4 ml) were added CuSO$_4$ (6 mg, 0.040 mmol) and VitC Na (16 mg, 0.080 mmol) and the mixture was warmed up at 50° C. After 8 h, the mixture was concentrated and the crude was purified by silica gel column chromatography (hexanes/AcOEt: 50/50→10/90 as eluents) to give the triazol 5' (128 mg, 0.183 mmol, 91%) as a colorless oil.

$[\alpha]_D$=+63 (c=0.68 in CHCl$_3$)

1H NMR (400 MHz, CDCl$_3$): 1.08 (3H, d, J=6.8 Hz, propylamine), 1.24-1.30 (6H, m), 1.34 (9H, s, Boc), 1.52 (4H, m), 1.91 (3H, s, AcO), 1.96 (3H, s, AcO), 2.01 (3H, s, AcO), 2.07 (3H, s, AcO), 3.37 (11, m, H-1'a), 3.44 (2H, t, J=6.7 Hz, H-7'), 3.59 (1H, m, H-1'b), 3.90 (1H, ddd, J$_{5,4}$=9.7 Hz, J$_{5,6b}$=5.4 Hz, J$_{5,6a}$=2.3 Hz, H-5), 3.99 (1H, m, propylamine), 4.03 (1H, dd, J$_{6a,6b}$=12.3 Hz, J$_{6a,5}$=2.3 Hz, H-6a), 4.19 (1H, dd, J$_{6b,6a}$=12.3 Hz, J$_{6b,5}$=5.4 Hz, H-6a), 4.36 (2H, m, triazol-CH$_2$-propylamine), 4.53 (2H, bs O—CH$_2$-triazol), 4.72 (1H, d, J$_{1,2}$=1.6 Hz, H-1), 4.83 (1H, bs, NH), 5.15 (1H, dd, J$_{2,3}$=3.4 Hz, J$_{2,1}$=1.8 Hz, H-2), 5.19 (1H, dd, J$_{4,3}$=9.9 Hz, J$_{4,5}$=9.9 Hz, H-4), 5.32 (1H, dd, J$_{3,4}$=10.0 Hz, J$_{3,2}$=3.4 Hz, H-3), 7.50 (1H, bs, Triazol).

$^{13}$C NMR (100.6 MHz, CDCl$_3$): δ=20.47 (2×CH$_3$, 2×AcO), 20.50 (CH$_3$, AcO), 20.7 (CH$_3$, AcO), 25.8 (CH$_3$, propylamine), 28.1 (3×CH$_3$, N-Boc), 28.6-28.9 (4×CH$_2$), 29.4 (CH$_2$), 62.5 (CH, C-6), 64.1 (CH$_2$, O—CH$_2$-triazol), 64.3 (CH$_2$, triazol-CH$_2$, propylamine), 68.2 (CH, C-5), 68.3 (CH, C-1'), 68.9 (CH, C-4), 69.5 (CH, C-2), 70.5 (CH, propylamine), 70.8 (CH$_2$, C-7'), 97.3 (CH, C-1), 123.1 (CH, triazol), 145.2 (C, triazol), 154.9 (C, N-Boc), 169.5 (C, AcO), 169.7 (C, AcO), 169.9 (C, AcO), 170.4 (C, AcO).

MS (CI, NH$_3$): m/z 702 [M+H]$^+$

HRMS (MALDI, DHB): m/z calcd for C$_{32}$H$_{52}$N$_4$O$_{13}$Na [M+Na]$^+$: 723.3423. found: 723.3430.

Example 13: Compound 6'

To a solution of mannosyl alkine 3 (100 mg, 0.200 mmol) and 2-(azidomethy)pyridine (40 mg, 0.300 mmol) in a mixture of 3:1 of 1,4-dioxane-H$_2$O (4 ml) were added CuSO$_4$ (6 mg, 0.040 mmol) and VitC Na (16 mg, 0.080 mmol) and the mixture was warmed up at 50° C. After 8 h, the mixture was concentrated and the crude was purified by silica gel column chromatography (DCM→DCM/MeOH: 90/10 as eluents) to give the triazol 6' (120 mg, 0.191 mmol, 95%) as a colorless oil.

$[\alpha]_D$=+51.2 (c=0.91 in CHCl$_3$)

$^1$H NMR (300 MHz, CDCl$_3$): 1.28-1.35 (8H, m), 1.57 (21, m), 1.97 (3H, s, AcO), 2.02 (3H, s, AcO), 2.08 (3H, s, AcO), 2.13 (3H, s, AcO), 3.31 (1H, m, H-1'a), 3.49 (2H, t, J=6.7 Hz, H-7'), 3.64 (1H, m, H-1'b), 3.95 (1H, ddd, J$_{5,4}$=9.5 Hz, J$_{5,6b}$=5.3 Hz, J$_{5,6a}$=2.4 Hz, H-5), 4.08 (1H, dd, J$_{6a,6b}$=12.3 Hz, J$_{6a,5}$=2.3 Hz, H-6a), 4.26 (1H, dd, J$_{6b,6a}$=12.3 Hz, $J_{6b,5}$=5.3 Hz, H-6a), 4.59 (2H, s, O—CH$_2$-triazol), 4.67 (1H, d, $J_{1,2}$=1.7 Hz, H-1), 5.21 (1H, dd, $J_{2,3}$=3.3 Hz, $J_{2,1}$=1.7 Hz, H-2), 5.25 (1H, dd, $J_{4,3}$=10.0 Hz, $J_{4,5}$=9.8 Hz, H-4), 5.32 (1H, dd, $J_{3,4}$=10.0 Hz, $J_{3,2}$=3.3 Hz, H-3), 5.68 (2H, s, triazol-CH$_2$—Py), 7.17 (1H, bd, J=7.8 Hz, Py), 7.25 (1H, ddd, J=7.6 Hz, J=4.9 Hz, J=1.1 Hz, Py), 7.67 (1H, ddd, J=7.8 Hz, J=7.8 Hz, J=1.8 Hz, Py), 7.68 (1H, bs, Triazol), 8.57 (1H, ddd, J=4.9 Hz, J=1.8 Hz, J=0.9 Hz, Py).

$^{13}$C NMR (100.6 MHz, CDCl$_3$): δ=20.65 (2×CH$_3$, 2×AcO), 20.68 (CH$_3$, AcO), 20.9 (CH$_3$, AcO), 25.9-29.5 (5×CH$_2$), 55.6 (CH$_2$, triazol-CH$_2$—Py), 62.5 (CH, C-6), 64.3 (CH$_2$, O—CH$_2$-triazol), 66.2 (CH, C-4), 68.3 (CH, C-5), 68.4 (CH, C-1'), 69.1 (CH, C-3), 69.7 (CH, C-2), 70.8 (CH$_2$, C-7'), 97.5 (CH$_2$, C-1), 122.4 (CH, Py), 122.9 (CH, triazol), 123.4 (CH, Py), 137.3 (CH, Py), 145.8 (C, triazol), 149.7 (CH, Py), 154.4 (C, Py), 169.7 (C, AcO), 169.8 (C, AcO), 170.0 (C, AcO), 170.6 (C, AcO).

MS (CI, NH$_3$): m/z 635 [M]$^+$

HRMS (MALDI, DHB): m/z calcd for C$_{30}$H$_{42}$N$_4$O$_{11}$Na [M+Na]$^+$: 657.2742. found: 657.2725.

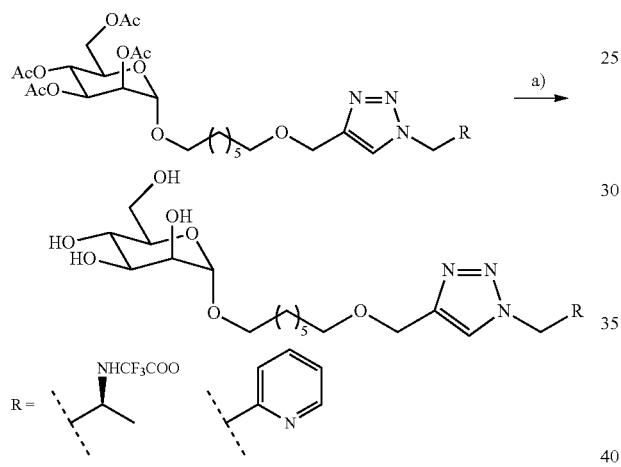

i. NaOMe, MeOH, rt, ii. Amberlite IR120 (H), iii. TFA—DCM, 0° C. (for N—Boc protected 5').

Example 14: Compound 7'

According to the general procedure B and C, using the triazol 5' (253 mg, 0.361 mmol) as starting material, the derivative 7' was obtained after lyophilization (193 mg, 0.353 mmol, 98%), in form of trifluoroacetate salt, as an amorphous white solid.

[α]$_D$=+61.3 (c=0.31 in MeOH)

$^1$H NMR (300 MHz, MeOD): 1.31-1.66 (13H, m), 3.43 (1H, m, H-1'a), 3.49-3.98 (10H, m), 4.62 (2H, s, O—CH$_2$-triazol), 4.69 (2H, m, triazol-CH$_2$), 4.76 (1H, bs, H-1), 8.09 (1H, bs, Triazol).

$^{13}$C NMR (100.6 MHz, MeOD): δ=16.36 (CH$_3$, propylamine), 27.1 (CH$_2$), 27.2 (CH$_2$), 30.2 (CH$_2$), 30.4 (CH$_2$), 30.5 (CH$_2$), 53.4 (CH$_2$, O—CH$_2$-triazol), 62.5 (CH, C-6), 64.5 (CH$_2$, triazol-CH$_2$-propylamine), 68.4 (CH), 68.6 (CH$_2$, C-1'), 71.8 (CH), 72.2 (CH), 72.6 (CH), 74.4 (CH$_2$, C-7'), 101.5 (CH, C-1), 118.3 (C, q, $J_{C,F}$=289.8 Hz, TFA), 126.2 (CH, triazol), 146.6 (C, triazol), 163.1 (C, q, $J_{C,F}$=33.7 Hz, TFA).

MS (CI, NH$_3$): m/z 433 [M−TFA]$^+$

Example 15: Compound 8'

According to the general procedure B, using the triazol 6' (100 mg, 0.157 mmol) as starting material, the pyridin derivative 8' was obtained after lyophilization (72 mg, 0.154 mmol, 98%) as an amorphous white solid.

[α]$_D$=+36.3 (c=0.41 in MeOH)

$^1$H NMR (300 MHz, MeOD): 1.29-1.41 (6H, m), 1.53-1.62 (4H, m), 3.40 (1H, m, H-1'a), 3.50 (2H, t, J=6.6 Hz, H-7'), 3.54-3.75 (6H, m), 3.81 (1H, bd, $J_{2,3}$=3.8 Hz, H-2), 4.58 (2H, s, O—CH$_2$-triazol), 4.74 (1H, bs, H-1), 4.95 (2H, s, OH), 4.97 (1H, s, OH), 5.72 (2H, s, triazol-CH$_2$—Py), 7.33 (1H, bd, J=8.0 Hz, Py), 7.38 (1H, dd, J=7.8 Hz, J=5.3 Hz, Py), 7.84 (1H, ddd, J=7.8 Hz, J=7.8 Hz, J=1.5 Hz, Py), 8.06 (1H, bs, Triazol), 8.54 (1H, bd, J=4.5 Hz, Py).

$^{13}$C NMR (100.6 MHz, MeOD): δ=27.1 (CH$_2$), 27.3 (CH$_2$), 30.2 (CH$_2$), 30.5 (CH$_2$), 30.6 (CH$_2$), 56.0 (CH$_2$, triazol-CH$_2$—Py), 62.7 (CH, C-6), 64.6 (CH$_2$, O—CH$_2$-triazol), 68.5 (CH$_2$, C-1'), 68.6 (CH), 71.6 (CH$_2$, C-7'), 72.3 (CH, C-2), 72.7 (CH), 74.5 (CH), 101.6 (CH, C-1), 123.9 (CH, Py), 124.9 (CH, Py), 125.7 (CH, triazol), 139.2 (CH, Py), 146.5 (C, triazol), 150.6 (CH, Py), 155.9 (C, Py).

MS (CI, NH$_3$): m/z 467 [M]$^+$

HRMS (MALDI, DHB): m/z calcd for C$_{22}$H$_{34}$N$_4$O$_7$Na [M+Na]$^+$: 489.2320. found: 489.2314.

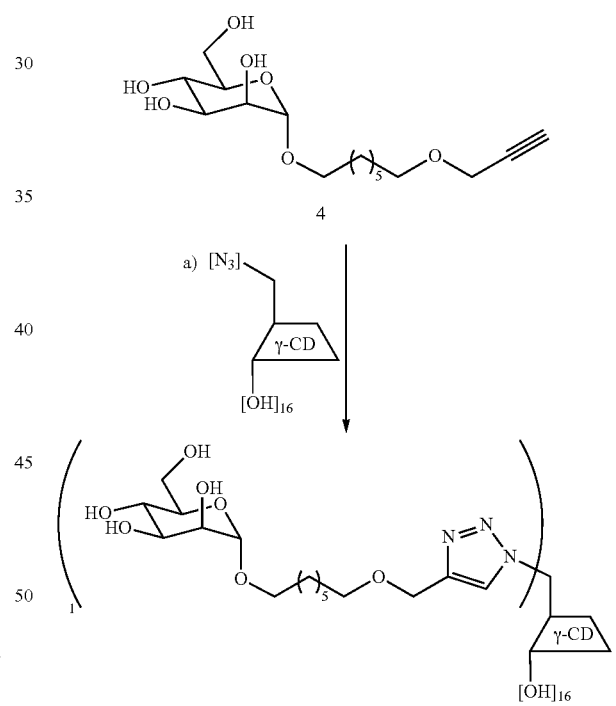

a) CuSO$_4$, VitC Na, DMF—H$_2$O, 70° C. b) i. NaOMe, MeOH, rt, ii. Amberlite IR120 (H).

Example 16: Compound 10'

Alkynyl-saccharide 4 (87 µmol) and mono-7-azido-7-deoxy-gamma-cyclodextrin (43 µmol) were dissolved in a DMF/H$_2$O mixture (2/0.5 mL). Copper sulfate (43 µmol) and sodium ascorbate (86 µmol) were added and the mixture was stirred at 70° C. for 30 minutes under µW irradiation.

Ethylenediamine tetraacetic acid trisodium salt (127 μmol) was added and the mixture was stirred for 10 minutes at rt. The mixture was evaporated under reduced pressure and the residue purified by preparative HPLC leading to compound 10' as a white powder after lyophilisation.

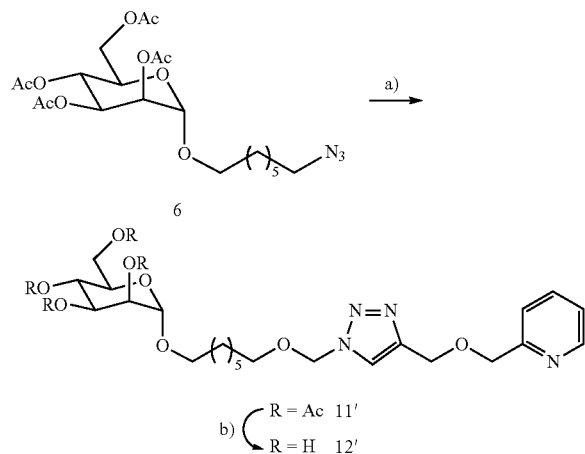

a) Pyridinmethyl propargyl ether, CuSO₄, VitC Na, 1,4-dioxane-H₂O, 50° C.
b) NaOMe, MeOH.

Example 18: Compound 11'

To a solution of mannosyl azide 6 (100 mg, 0.205 mmol) and pyridinmethyl propargyl ether (36 mg, 0.246 mmol) in a mixture of 3:1 of 1,4-dioxane-H₂O (4.1 ml) were added CuSO₄ (7 mg, 0.041 mmol) and VitC Na (16 mg, 0.082 mmol) and the mixture was warmed up at 65° C. After 8 h, the mixture was concentrated and the crude was purified by silica gel column chromatography (AcOEt→AcOEt/MeOH: 90/10 as eluents) to give the triazol 11' (128 mg, 0.202 mmol, 98%) as a colorless oil.

$[α]_D$=+37.9 (c=0.83 in CHCl₃)

¹H NMR (300 MHz, CDCl₃): 1.29-1.41 (6H, m), 1.58 (2H, m), 1.91 (2H, m), 1.99 (3H, s, AcO), 2.04 (3H, s, AcO), 2.09 (3H, s, AcO), 2.15 (3H, s, AcO), 3.42 (1H, m, H-1'a), 3.67 (1H, m, H-1'b), 3.96 (1H, ddd, $J_{5,4}$=9.3 Hz, $J_{5,6b}$=5.3 Hz, $J_{5,6a}$=2.4 Hz, H-5), 4.10 (1H, dd, $J_{6a,6b}$=12.3 Hz, $J_{6a,5}$=2.3 Hz, H-6a), 4.28 (1H, dd, $J_{6b,6a}$=12.3 Hz, $J_{6b,5}$=5.3 Hz, H-6a), 4.35 (2H, t, J=7.3 Hz, H-7'), 4.72 (2H, s, O—CH₂-triazol), 4.77 (2H, s, O—CH₂—Py), 4.79 (1H, d, $J_{1,2}$=1.7 Hz, H-1), 5.22 (1H, dd, $J_{2,3}$=3.3 Hz, $J_{2,1}$=1.7 Hz, H-2), 5.27 (1H, dd, $J_{4,3}$=10.1 Hz, $J_{4,5}$=9.7 Hz, H-4), 5.34 (1H, dd, $J_{3,4}$=10.1 Hz, $J_{3,2}$=3.3 Hz, H-3), 7.19 (1H, dd, J=7.4 Hz, J=5.2 Hz, Py), 7.55 (1H, bd, J=7.8 Hz, Py), 7.59 (1H, bs, Triazol), 7.69 (1H, ddd, J=7.8 Hz, J=7.8 Hz, J=1.8 Hz, Py), 8.56 (1H, bd, J=4.8 Hz, Py).

¹³C NMR (100.6 MHz, CDCl₃): δ=20.73-20.88 (4×CH₃, 4×AcO), 25.9 (CH₂), 26.7 (CH₂), 28.7 (CH₂), 29.1 (CH₂), 30.2 (CH₂), 50.3 (CH₂, C-7'), 62.5 (CH, C-6), 64.4 (CH₂, O—CH₂-triazol), 66.2 (CH, C-4), 68.35 (CH, C-1'), 68.40 (CH, C-5), 69.1 (CH, C-3), 69.7 (CH, C-2), 73.3 (CH₂, O—CH₂—Py), 97.5 (CH₂, C-1), 121.7 (CH, Py), 122.4 (CH, Py), 122.5 (CH, triazol), 136.7 (CH, Py), 144.8 (C, triazol), 149.2 (CH, Py), 157.9 (C, Py), 169.7 (C, AcO), 169.9 (C, AcO), 170.1 (C, AcO), 170.6 (C, AcO).

MS (MALDI): m/z 657 [M+Na]⁺

HRMS (MALDI, DHB): m/z calcd for C₃₀H₄₂N₄O₁₁ [M]⁺: 635.2923. found: 635.2944.

Example 19: Compound 12'

According to the general procedure B, using the triazol 11' (110 mg, 0.173 mmol) as starting material, the pyridin derivative 12' was obtained after lyophilization (7 mg, 0.154 mmol, 98%) as an amorphous white solid.

$[α]_D$=+51.2 (c=0.49 in MeOH)

¹H NMR (300 MHz, MeOD): 1.38 (6H, m), 1.58 (2H, m), 1.93 (2H, m), 1.99 (3H, s, AcO), 3.41 (1H, m, H-1'a), 3.48-3.85 (7H, m), 4.43 (2H, t, J=7.1 Hz, H-7'), 4.69 (2H, s, O—CH₂-triazol), 4.77 (3H, bs, O—CH₂—Py, H-1), 7.37 (1H, dd, J=7.3 Hz, J=5.1 Hz, Py), 7.56 (1H, bd, J=7.9 Hz, Py), 7.86 (1H, ddd, J=7.8 Hz, J=7.8 Hz, J=1.8 Hz, Py), 8.06 (1H, s, Triazol), 8.50 (1H, bd, J=4.8 Hz, Py).

¹³C NMR (100.6 MHz, MeOD): δ=27.1 (CH₂), 27.3 (CH₂), 29.8 (CH₂), 30.4 (CH₂), 31.2 (CH₂), 51.3 (CH₂, C-7'), 62.8 (CH, C-6), 64.7 (CH₂, O—CH₂-triazol), 68.4 (CH, C-1'), 68.6 (CH), 72.3 (CH), 72.7 (CH), 73.4 (CH₂, O—CH₂—Py), 74.6 (CH), 101.5 (CH, C-1), 123.4 (CH, Py), 124.2 (CH, Py), 125.2 (CH, Py), 138.9 (CH, triazol), 145.6 (C, triazol), 149.6 (CH, Py), 159.0 (C, Py).

MS (CI, NH₃): m/z 467 [M+H]⁺

C. Synthesis of Mannosyl-S-Heptylamides

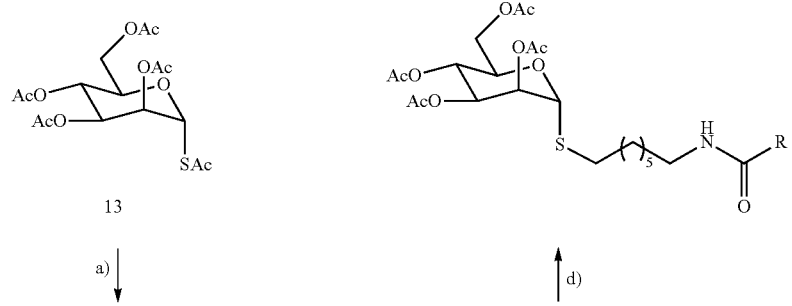

a) ↓          ↑ d)

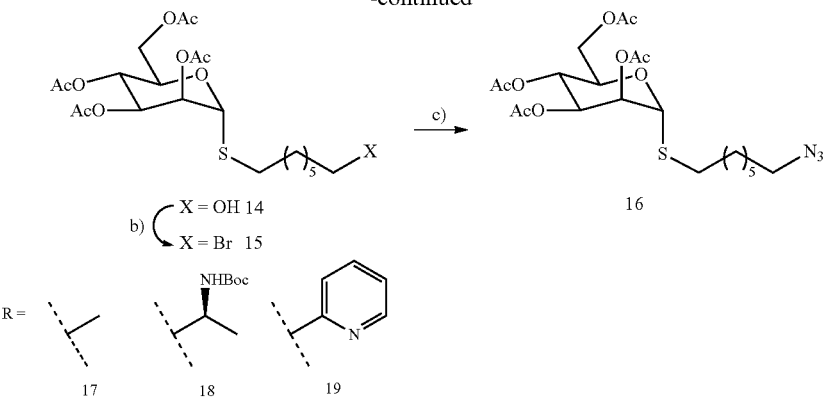

a) 7-bromo-1-heptanol, Et$_2$NH, DMF, rt. b) CCl$_4$, Ph$_3$P, DCM, 0° C. → rt. c) NaN$_3$, DMF, 70° C.
d) Carboxylic acid, HOBt, DIC, PH$_3$P, THF, 0° C. → rt

Example 21: Compound 15

A solution of 14 (1.35 g, 2.82 mmol) and carbon tetrabromide (1.03 g, 3.10 mmol) in dry DCM (15 mL), cooled to 0° C. was added Ph$_3$P (812 mg, 3.10 mmol) in portions over 30 min with vigorous stirring. Upon addition of the phosphine, the colorless solution turned a pale brown color and was stirred for an additional 2 h at room temperature. The mixture was concentrated and the crude was purified by silica gel column chromatography (Hexanes/EtOAc, 80:20) to give the product 15 (1.41 g, 2.61 mmol, 93%) as an amorphous white solid.

$[\alpha]_D$=+83.8 (c=0.79 in CHCl$_3$)

$^1$H NMR (300 MHz, CDCl$_3$): 1.34 (6H, m), 1.62 (2H, m), 1.85 (2H, m), 1.99 (3H, s, AcO), 2.05 (3H, s, AcO), 2.09 (3H, s, AcO), 2.16 (3H, s, AcO), 2.61 (2H, m, H-1'), 3.40 (2H, t, J=6.8 Hz, H-7'), 4.08 (1H, dd, J$_{6a,6b}$=11.9 Hz, J$_{6a,5}$=1.9 Hz, H-6a), 4.32 (1H, dd, J$_{6b,6a}$=11.9 Hz, J$_{6b,5}$=5.3 Hz, H-6a), 4.38 (1H, m, H-5), 5.25 (1H, d, J$_{1,2}$=1.4 Hz, H-1), 5.24-5.35 (2H, m, H-3, H-4), 5.35 (1H, dd, J$_{2,3}$=2.8 Hz, J$_{2,1}$=1.4 Hz, H-2).

$^{13}$C NMR (100.6 MHz, CDCl$_3$): δ=20.5 (CH$_3$, AcO), 20.6 (CH$_3$, AcO), 20.63 (CH$_3$, AcO), 20.8 (CH$_3$, AcO), 27.9 (CH$_2$), 28.1 (CH$_2$), 28.4 (CH$_2$), 29.1 (CH$_2$), 31.1 (CH$_2$, C-1'), 32.5 (CH$_2$), 33.7 (CH$_2$, C-7'), 62.3 (CH, C-6), 66.2 (CH, C-3 or C-4), 68.8 (CH, C-5), 69.3 (CH, C-3 or C-4), 71.1 (CH, C-2), 82.4 (CH, C-1), 169.6 (C, AcO), 169.7 (C, AcO), 169.9 (C, AcO), 170.5 (C, AcO).

MS (CI, NH$_3$): m/z: [M+NH$_3$]$^+$560

HRMS (MALDI, DHB): m/z calcd for C$_{21}$H$_{33}$BrO$_9$SNa [M+Na]$^+$: 563.0921. found: 563.0932.

Example 22: Compound 16

A solution of 15 (560 mg, 1.037 mmol) in DMF (10 mL) was added NaN$_3$ (135 mg, 2.074 mmol) and the resulting mixture was stirred at 70° C. overnight. The mixture was diluted with Et$_2$O and washed with H$_2$O and brine. The crude was purified by silica gel column chromatography (Hexanes/EtOAc, 70:30) to give the azide 16 (498 mg, 0.990 mmol, 96%) as a colorless oil.

$[\alpha]_D$=+73.3 (c=0.67 in CHCl$_3$)

$^1$H NMR (300 MHz, CDCl$_3$): 1.25-1.65 (10H, m), 1.99 (3H, s, AcO), 2.05 (3H, s, AcO), 2.09 (3H, s, AcO), 2.16 (3H, s, AcO), 2.60 (2H, m, H-1'), 3.26 (2H, t, J=6.9 Hz, H-7'), 4.08 (1H, dd, J$_{6a,6b}$=11.9 Hz, J$_{6a,5}$=2.0 Hz, H-6a), 4.32 (1H, dd, J$_{6b,6a}$=11.9 Hz, J$_{6b,5}$=5.2 Hz, H-6a), 4.38 (1H, m, H-5), 5.23-5.35 (3H, m, H-1, H-3, H-4), 5.33 (1H, dd, J$_{2,3}$=2.9 Hz, J$_{2,1}$=1.5 Hz, H-2).

$^{13}$C NMR (100.6 MHz, CDCl$_3$): δ=20.6 (CH$_3$, AcO), 20.7 (CH$_3$, AcO), 20.73 (CH$_3$, AcO), 20.9 (CH$_3$, AcO), 26.5 (CH$_2$), 28.5 (CH$_2$), 28.6 (CH$_2$), 28.7 (CH$_2$), 29.2 (CH$_2$), 31.2 (CH$_2$, C-1'), 51.3 (CH$_2$, C-7'), 62.4 (CH, C-6), 66.2 (CH, C-3 or C-4), 68.9 (CH, C-5), 69.4 (CH, C-3 or C-4), 71.1 (CH, C-2), 82.4 (CH, C-1), 169.7 (C, AcO), 169.72 (C, AcO), 169.9 (C, AcO), 170.5 (C, AcO).

MS (CI, NH$_3$): m/z: [M+NH$_3$]$^+$521

HRMS (MALDI, DHB): m/z calcd for C$_{21}$H$_{33}$N$_3$O$_9$SNa [M+Na]$^+$: 526.1830. found: 526.1836.

Example 23: Compound 17

According to the general procedure A, mannosyl azide 16 (50 mg, 0.096 mmol), acetic acid (11 mg, 0.173 mmol, 1.8 equiv.), HOBt (23 mg, 0.173 mmol, 1.8 equiv.), DIC (27 μL, 0.173 mmol, 1.8 equiv.) and Ph$_3$P (45 mg, 0.173 mmol, 1.8 equiv.) were allowed to react in THF (2.4 mL). The crude product was purified by silica gel column chromatography (EtOAc/petroleum ether, 70:30→EtOAc as eluents) to give the amide 17 (39 mg, 0.075 mmol, 78%) as an oil.

$[\alpha]_D$=+69.5 (c=0.81 in CHCl$_3$)

$^1$H NMR (300 MHz, CDCl$_3$): 1.27-1.65 (10H, m), 1.96 (3H, s, AcO), 1.98 (3H, s, AcO), 2.04 (3H, s, AcO), 2.09 (3H, s, AcO), 2.15 (3H, s, AcO), 2.59 (2H, m, H-1'), 3.21 (2H, q, J=6.8 Hz, H-7'), 4.08 (1H, dd, J$_{6a,6b}$ b=12.0 Hz, J$_{6a,5}$=2.1 Hz, H-6a), 4.30 (1H, dd, J$_{6b,6a}$=12.0 Hz, J$_{6b,5}$=5.1 Hz, H-6a), 4.36 (1H, m, H-5), 5.22-5.34 (3H, m, H-1, H-3, H-4), 5.32 (1H, dd, J$_{2,3}$=3.0 Hz, J$_{2,1}$=1.6 Hz, H-2), 5.57 (1H, bs, NH).

$^{13}$C NMR (100.6 MHz, CDCl$_3$): δ=20.6 (CH$_3$, AcO), 20.70 (CH$_3$, AcO), 20.75 (CH$_3$, AcO), 20.9 (CH$_3$, AcO), 23.3 (CH$_3$, acetamide), 26.7 (CH$_2$), 28.5 (CH$_2$), 28.7 (CH$_2$), 29.1 (CH$_2$), 29.5 (CH$_2$), 31.2 (CH$_2$, C-1'), 39.5 (CH$_2$, C-7'), 62.4 (CH, C-6), 66.2 (CH, C-3 or C-4), 68.9 (CH, C-5), 69.4 (CH, C-3 or C-4), 71.2 (CH, C-2), 82.4 (CH, C-1), 169.7 (C, acetamide), 169.8 (C, AcO), 169.96 (C, AcO), 169.99 (C, AcO), 170.6 (C, AcO).

MS (CI, NH$_3$): m/z: [M]$^+$520

HRMS (MALDI, DHB): m/z calcd for C$_{27}$H$_{38}$N$_2$O$_{10}$SNa [M+Na]$^+$: 542.2036. found: 542.2028.

Example 24: Compound 18

According to the general procedure A, mannosyl azide 16 (150 mg, 0.289 mmol), N-Boc-L-alanine (98 mg, 0.520 mmol, 1.8 equiv.), HOBt (70 mg, 0.520 mmol, 1.8 equiv.), DIC (80 μL, 0.520 mmol, 1.8 equiv.) and Ph$_3$P (136 mg, 0.520 mmol, 1.8 equiv.) were allowed to react in THF (27.3 mL). The crude product was purified by silica gel column chromatography (EtOAc/petroleum ether, 50:50→EtOAc as eluents) to give the amide 18 (97 mg, 0.149 mmol, 52%) as an oil.

[α]$_D$=+39.9 (c=1.27 in CHCl$_3$)

$^1$H NMR (300 MHz, CDCl$_3$): δ=1.11-1.63 (10H, m), 1.34 (3H, d, J=7.1 Hz, CH$_3$-alanine), 1.42 (9H, s, N-Boc), 1.98 (3H, s, AcO), 2.04 (3H, s, AcO), 2.07 (3H, s, AcO), 2.15 (3H, s, AcO), 2.53 (2H, m, H-1'), 2.99 (2H, m, H-7'), 4.04-4.38 (4H, m, H-5, H-6a, H-6b, CH-alanine), 4.21-4.29 (3H, m, H-1, H-3, H-4), 5.32 (1H, dd, J$_{2,3}$=3.0 Hz, J$_{2,1}$=1.7 Hz, H-2), 5.36 (1H, bs, NH), 5.66 (1H, bs, NH).

$^{13}$C NMR (100.6 MHz, CDCl$_3$): δ=20.5 (CH$_3$, AcO), 20.60 (CH$_3$, AcO), 20.63 (CH$_3$, AcO), 20.8 (CH$_3$, AcO), 26.5 (CH$_3$, alanine), 28.2 (3×CH$_3$, N-Boc), 28.5 (CH$_2$), 28.6 (CH$_2$), 29.1 (CH$_2$), 29.3 (CH$_2$), 30.2 (C, N-Boc), 31.1 (CH$_2$), 39.3 (CH$_2$, C-7'), 41.8 (CH$_2$, C-1'), 62.3 (CH, C-6), 68.8 (CH), 69.4 (CH), 71.1 (CH, C-2), 82.4 (CH, C-1), 157.1 (C, amide), 169.6 (C, AcO), 169.7 (C, AcO), 169.9 (C, AcO), 170.5 (C, AcO), 172.5 (C, N-Boc).

MS (CI, NH$_3$): m/z: [M]$^+$ 649

HRMS (MALDI, DHB): m/z calcd for C$_{29}$H$_{48}$N$_2$O$_{12}$SNa [M+Na]$^+$: 671.2820. found: 671.2803.

Example 25: Compound 19

According to the general procedure A, mannosyl azide 16 (100 mg, 0.193 mmol), picolinic acid (43 mg, 0.347 mmol, 1.8 equiv.), HOBt (47 mg, 0.347 mmol, 1.8 equiv.), DIC (54 μL, 0.347 mmol, 1.8 equiv.) and Ph$_3$P (91 mg, 0.347 mmol, 1.8 equiv.) were allowed to react in DMF (5 mL). The crude product was purified by silica gel column chromatography (DCM→DCM/MeOH, 90:10 as eluents) to give the amide 19 (83 mg, 0.142 mmol, 74%) as an oil.

[α]$_D$=+55.7 (c=1.01 in CHCl$_3$)

$^1$H NMR (300 MHz, CDCl$_3$): 1.36-1.68 (10H, m), 1.98 (3H, s, AcO), 2.04 (3H, s, AcO), 2.09 (3H, s, AcO), 2.16 (3H, s, AcO), 2.60 (2H, m, H-1'), 3.46 (2H, q, J=6.8 Hz, H-7'), 4.08 (1H, dd, J$_{6a,6b}$=11.9 Hz, J$_{6a,5}$=1.9 Hz, H-6a), 4.31 (1H, dd, J$_{6b,6a}$=11.9 Hz, J$_{6b,5}$=5.2 Hz, H-6a), 4.37 (1H, m, H-5), 5.23-5.30 (3H, m, H-1, H-3, H-4), 5.33 (1H, dd, J$_{2,3=2.8}$ Hz, J$_{2,1}$=1.6 Hz, H-2), 7.41 (1H, ddd, J=7.7 Hz, J=4.9 Hz, J=1.3 Hz, picolinic), 7.84 (1H, ddd, J=7.6 Hz, J=7.6 Hz, J=1.7 Hz, picolinic), 8.05 (1H, bs, NH), 8.19 (1H, bd, J=7.8 Hz, picolinic), 8.54 (1H, ddd, J=4.7 Hz, J=1.7 Hz, J=0.9 Hz, picolinic).

$^{13}$C NMR (100.6 MHz, CDCl$_3$): δ=20.53 (CH$_3$, AcO), 20.60 (CH$_3$, AcO), 20.63 (CH$_3$, AcO), 20.8 (CH$_3$, AcO), 26.7 (CH$_2$), 28.5 (CH$_2$), 28.7 (CH$_2$), 29.2 (CH$_2$), 29.5 (CH$_2$), 31.1 (CH$_2$, C-1'), 39.2 (CH$_2$, C-7'), 62.3 (CH, C-6), 66.2 (CH, C-3 or C-4), 68.8 (CH, C-5), 69.4 (CH, C-3 or C-4), 71.1 (CH, C-2), 82.4 (CH, C-1), 122.1 (CH, picolinic acid), 126.0 (CH, picolinic acid), 137.2 (CH, picolinic acid), 147.9 (CH, picolinic acid), 149.9 (C, picolinic acid), 164.1 (C, amide), 169.6 (C, AcO), 169.7 (C, AcO), 169.9 (C, AcO), 170.5 (C, AcO).

MS (CI, NH$_3$): m/z: [M+NH$_3$]$^+$583

HRMS (MALDI, DHB): m/z calcd for C$_{27}$H$_{38}$N$_2$O$_{10}$SNa [M+Na]$^+$: 605.2139. found: 605.2129.

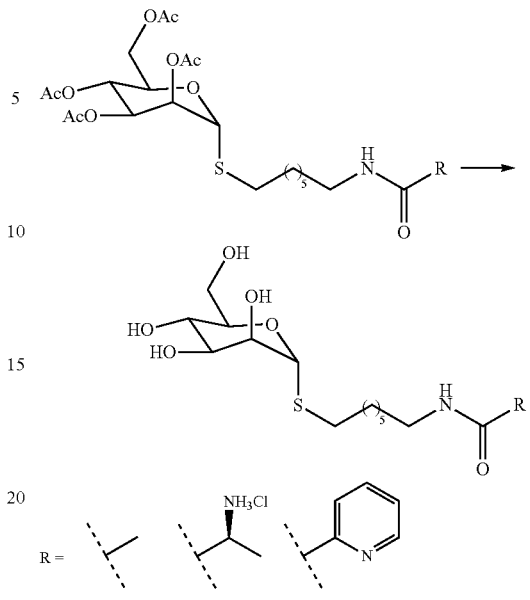

i. NaOMe, MeOH, rt, ii. Amberlite IR120 (H), iii. TFA-DCM, 0° C. vi. HCl ac. (for N——Boc protected compound 18).

Example 26: Compound 20

According to the general procedure B, using the amide 17 (20 mg, 0.038 mmol) as starting material, the derivative 20 was obtained after lyophilization (17 mg, 0.037 mmol, 98%) as an amorphous white solid.

[α]$_D$=+53.9 (c=0.69 in MeOD).

$^1$H NMR (300 MHz, MeOD): δ=1.29-1.71 (10H, m), 1.92 (3H, s, acetamide), 2.64 (2H, m, H-7'), 3.15 (2H, t, J=6.9 Hz, H-1'), 3.64-3.92 (6H, m), 5.21 (1H, d, J$_{1,2}$=1.3 Hz, H-1).

$^{13}$C NMR (100.6 MHz, MeOD): δ=22.5 (CH$_3$, acetamide), 27.8 (CH$_2$), 29.7 (CH$_2$), 29.9 (CH$_2$), 30.3 (CH$_2$), 30.6 (CH$_2$), 31.8 (CH$_2$, C-1'), 40.5 (CH$_2$, C-7'), 62.7 (CH, C-6), 68.9 (CH), 73.1 (CH), 73.8 (CH, C-5), 74.9 (CH, C-2), 86.4 (CH, C-1), 173.2 (C, acetamide).

MS (CI, NH$_3$): m/z 352 [M+H]$^+$

HRMS (ESI): m/z calcd for C$_{15}$H$_{29}$O$_6$NSNa [M+Na]$^+$: 374.1613. found: 374.1615.

Example 27: Compound 21

According to the general procedure B and C, using the amide 18 (51 mg, 0.078 mmol) as starting material, the alanine derivative 21 was obtained after lyophilization (31 mg, 0.074 mmol, 95%), in form of ammonium chloride salt, as an amorphous white solid.

[α]$_D$=61.3 (c=0.61 in D$_2$O).

$^1$H NMR (300 MHz, D$_2$O): δ=1.12-1.48 (10H, m), 1.36 (3H, d, J=7.1 Hz, CH$_3$-alanine), 2.63 (2H, m, H-7'), 3.42 (2H, m, H-1'), 3.31-3.87 (7H, m), 4.64 (1H, bs, H-1).

$^{13}$C NMR (100.6 MHz, D$_2$O): δ=16.6 (CH$_3$, alanine), 24.9 (CH$_2$), 25.2 (CH$_2$), 25.9 (CH$_2$), 28.0 (CH$_2$), 31.2 (CH$_2$), 61.8 (CH, C-1'), 39.5 (CH$_2$, C-7'), 60.9 (CH, C-6), 66.8 (CH, alanine), 67.9 (CH), 70.1 (CH), 70.7 (CH), 72.7 (CH, C-2), 85.9 (CH, C-1), 170.5 (C, amide).

MS (CI, NH$_3$): m/z 417 [M]$^+$

HRMS (ESI): m/z calcd

Example 28: Compound 22

According to the general procedure B, using the amide 19 (32 mg, 0.055 mmol) as starting material, the derivative 22 was obtained after lyophilization (22 mg, 0.053 mmol, 96%) as an amorphous white solid.

[α]$_D$=+53.9 (c=0.69 in MeOD).

$^1$H NMR (300 MHz, MeOD): δ=1.28-1.69 (10H, m), 2.63 (2H, m, H-7'), 3.42 (2H, m, H-1'), 3.64-3.93 (6H, m), 5.21 (1H, d, J$_{1,2}$=1.0 Hz, H-1), 7.41 (1H, ddd, J=7.6 Hz, J=4.8 Hz, J=1.3 Hz, picolinic), 7.53 (1H, ddd, J=7.6 Hz, J=4.8 Hz, J=1.3 Hz, picolinic), 7.95 (1H, ddd, J=7.7 Hz, J=7.7 Hz, J=1.7 Hz, picolinic), 8.09 (1H, ddd, J=7.8 Hz, J=1.1 Hz, J=1.1 Hz, picolinic), 8.62 (1H, ddd, J=4.7 Hz, J=1.7 Hz, J=1.1 Hz, picolinic).

$^{13}$C NMR (100.6 MHz, MeOD): δ=27.9 (CH$_2$), 29.7 (CH$_2$), 29.9 (CH$_2$), 30.5 (CH$_2$), 30.6 (CH$_2$), 31.8 (CH$_2$, C-1'), 40.4 (CH$_2$, C-7'), 62.7 (CH, C-6), 68.9 (CH), 73.2 (CH), 73.8 (CH, C-5), 74.9 (CH, C-2), 86.4 (CH, C-1), 123.0 (CH, picolinic), 127.6 (CH, picolinic), 138.8 (CH, picolinic), 149.8 (CH, picolinic), 151.1 (C, picolinic), 166.6 (C, amide).

MS (CI, NH$_3$): m/z 415 [M+H]$^+$

HRMS (ESI): m/z calcd for C$_{19}$H$_{30}$N$_2$O$_6$SNa [M+Na]$^+$: 437.1722. found: 437.1735.

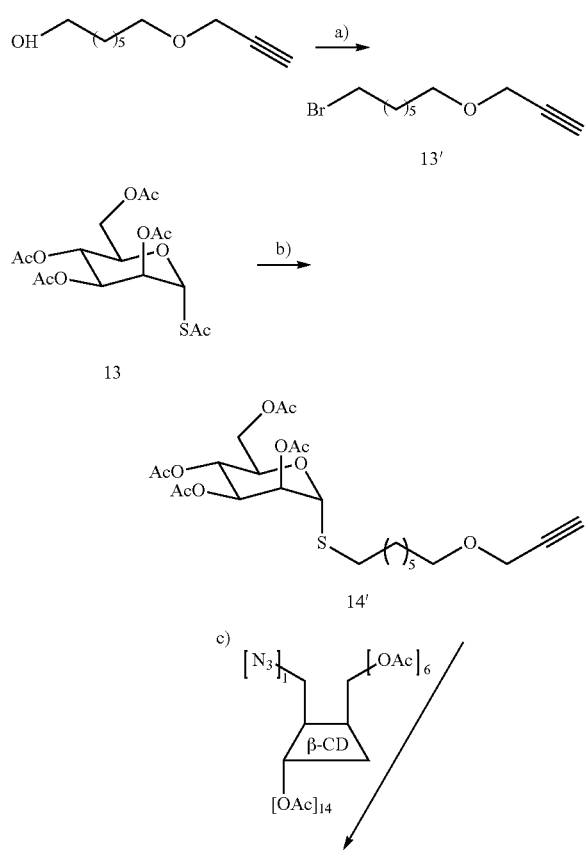

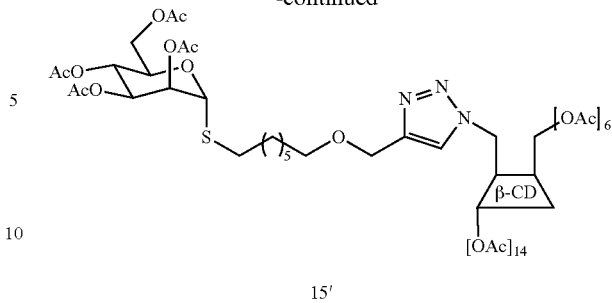

a) CBr$_4$, Ph$_3$P, DCM, 0° C. → rt. b) 1-bromo-7-propargyloxyheptane (13'), Et$_2$NH, DMF, rt. c) CuSO$_4$, VitC Na, DMF—H$_2$O, 70° C. d) CuSO$_4$, VitC Na, DMF—H$_2$O, 70° C.

Example 29: Compound 13'

A solution of 7-O-propargylheptanediol (500 mg, 2.941 mmol) and carbon tetrabromide (1.07 g, 3.235 mmol) in dry DCM (15 mL), cooled to 0° C. was added Ph$_3$P (848 mg, 3.235 mmol) in portions over 30 min with vigorous stirring. Upon addition of the phosphine, the colorless solution turned a pale brown color and was stirred for an additional 3 h at room temperature. The mixture was concentrated and the crude was purified by silica gel column chromatography (Hexanes/EtOAc, 70:30) to give the product 13' (625 mg, 2.682 mmol, 91%) as a colorless oil.

$^1$H NMR (300 MHz, CDCl$_3$): δ=1.30-1.48 (6H, m), 1.59 (2H, m), 1.86 (2H, m), 2.41 (1H, t, J=2.4 Hz, CH-propargyl), 3.40 (2H, t, J=6.8 Hz), 3.51 (2H, t, J=6.5 Hz), 4.13 (2H, d, J=2.4 Hz, CH$_2$-propargyl).

$^{13}$C NMR (100.6 MHz, CDCl$_3$): δ=25.9 (CH$_2$), 28.1 (CH$_2$), 28.5 (CH$_2$), 29.4 (CH$_2$), 32.7 (CH$_2$), 33.9 (CH$_2$), 58.0 (CH$_2$, CH$_2$-propargyl), 70.1 (CH$_2$), 74.1 (CH, CH-propargyl), 77.2 (C, C-propargyl).

Example 30: Compound 14'

To a solution of acetylated 1-thiosugar 13 (944 mg, 2.325 mmol) and 1-bromo-7-propargyloxyheptane 13' (650 mg, 2.789 mmol, 1.2 equiv) in DMF (93 mL) at rt under a nitrogen atmosphere, was added diethylamine (4.8 mL, 46.500 mmol, 20 equiv). After stirring for 8 hours, diethylamine and DMF were removed in vacuo. The crude product was purified by silica gel column chromatography (Hexanes/EtOAc, 80:20) to give the product 14' (1026 mg, 1.984 mmol, 85%) as a colorless oil.

[α]$_D$=+47.2 (c=0.28 in CHCl$_3$)

$^1$H NMR (300 MHz, CDCl$_3$): 1.18-1.36 (8H, m), 1.53 (2H, m), 1.99 (3H, s, AcO), 2.05 (31H, s, AcO), 2.10 (3H, s, AcO), 2.16 (3H, s, AcO), 2.42 (1H, t, J=2.4 Hz, propargyl), 2.60 (2H, m, H-1'), 3.50 (2H, t, J=3.5 Hz, H-7'), 4.08 (1H, dd, J$_{6a,6b}$=11.9 Hz, J$_{6a,5}$=2.0 Hz, H-6a), 4.13 (2H, d, J=2.4 Hz, propargyl), 4.32 (1H, dd, J$_{6b,6a}$=11.9 Hz, J$_{6b,5}$=5.3 Hz, H-6b), 4.38 (1H, m, H-5), 5.25 (1H, d, J$_{1,2}$=1.4 Hz, H-1), 5.27-5.34 (3H, m, H-2, H-3, H-4).

$^{13}$C NMR (100.6 MHz, CDCl$_3$): δ=20.4 (CH$_3$, AcO), 20.47 (CH$_3$, AcO), 20.50 (CH$_3$, AcO), 20.7 (CH$_3$, AcO), 25.74 (CH$_2$), 28.5 (CH$_2$), 28.6 (CH$_2$), 29.1 (CH$_2$), 29.2 (CH$_2$), 31.1 (C-1', CH$_2$), 31.5 (CH$_2$), 57.8 (CH$_2$, CH$_2$-propargyl), 62.2 (CH$_2$, C-6), 66.1 (CH, C-3 or C-4), 68.7 (CH, C-5), 69.2 (CH, C-3 or C-4), 69.8 (CH$_2$, C-7'), 70.9 (CH, C-2), 73.9 (CH, CH-propargyl), 79.8 (C, C-propargyl), 82.3 (CH, C-1), 169.5 (C, AcO), 169.5 (C, AcO), 169.7 (C, AcO), 170.3 (C, AcO).

MS (CI, NH$_3$): m/z: [M+NH$_3$]$^+$ 534
HRMS (MALDI, DHB): m/z calcd for C$_{24}$H$_{36}$O$_{10}$S [M+Na]$^+$: 539.1921. found: 539.1945.

Example 31: Compound 15'

To a solution of 6'-azido-2,3,6-O-acetyl-β-Cyclodextrin (150 mg, 0.075 mmol) and alkyne 14' (47 mg, 0.090 mmol) in a mixture DMF-H$_2$O (3:1, 3.8 ml) were added CuSO$_4$ (2 mg, 0.015 mmol) and VitC Na (6 mg, 0.030 mmol) and the mixture was warmed up at 60° C. After 12 h, the mixture was diluted with water, extracted with AcOEt, dried, concentrated and the crude was purified by silica gel column chromatography (AcOEt→AcOEt/MeOH: 95/5 as eluents) to give the monovalent derivative 15' (128 mg, 0.051 mmol, 68%) as a colorless solid.

[α]$_D$=+101.7 (c=0.21 in CHCl$_3$)

$^1$H NMR (400 MHz, CDCl$_3$) δ=1.22-1.44 (6H, m), 1.60 (4H, m), 1.97-2.15 (78H, m, 26×AcO), 2.59 (2H, m, H-1'), 3.50 (2H, t, J=6.7 Hz, H-7'), 3.54-3.78 (8H, m), 4.03-4.70 (18H, m), 4.72-4.86 (6H, m, 6×H-2 CD), 4.94 (1H, dd, J=8.4 Hz, J=3.6 Hz, H-2 CD), 5.00-5.13 (6H, m, 6×H-1 CD), 5.15-5.38 (12H, m), 5.64 (1H, d, J=3.9 Hz, H-1 CD), 7.59 (1H, s, triazol).

$^{13}$C NMR (125 MHz, CDCl$_3$): δ=20.3-20.7 (24×CH$_3$, AcO), 25.8 (CH$_2$), 28.8 (CH$_2$), 29.9 (CH$_2$), 29.3 (CH$_2$), 29.4 (CH$_2$), 31.2 (CH$_2$, C-1' thioglycoside), 50.4 (CH$_2$, C-6 CD), 59.5-82.9 (9CH$_2$, 32CH), 82.6 (CH, C-1 thioglycoside), 96.0-96.6 (7×CH, C-1 CD), 125.5 (CH, triazol), 145.8 (C, triazol), 169.1-171.2 (24×C, AcO).

HRMS (ESI): m/z calcd for C$_{106}$H$_{145}$N$_3$O$_{64}$SNa$_2$ [M+2Na]$^{2+}$: 1280.8844. found: 1280.8864.

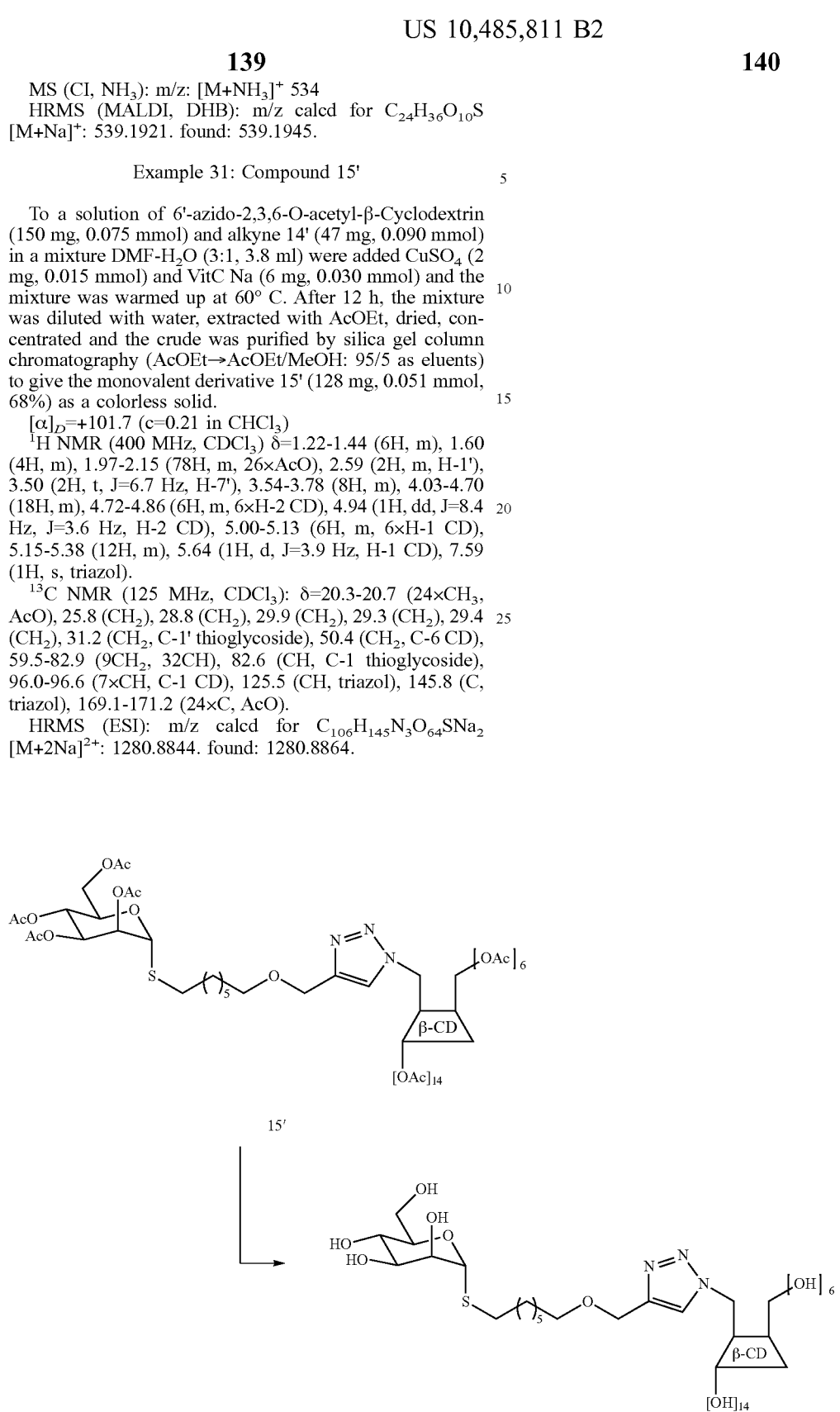

i. NaOMe, MeOH, rt, ii. Amberlite IR120 (H)

Example 32: Compound 16'

According to the general procedure B, using the derivative 15' (55 mg, 0.029 mmol) as starting material, the derivative 16' was obtained after lyophilization (39 mg, 0.026 mmol, 89%) as an amorphous white solid.

$[\alpha]_D = +161$ (c=1.12, MeOH)

$^1$H NMR (400 MHz, D$_2$O) δ=1.14-1.74 (10H, m), 2.77 (2H, m, H-1'), 3.15 (1H, bd, $J_{6a,6b}$=11.8 Hz, H-6a thioglycoside), 3.38-4.18 (51H, m), 5.11 (1H, d, J=3.5 Hz, H-1 CD), 5.17 (5H, m, H-1 CD), 5.31 (1H, d, J=3.5 Hz, H-1 CD), 5.42 (1H, d, J=1.1 Hz, H-1 thioglycoside), 8.04 (1H, s, triazol).

$^{13}$C NMR (125 MHz, D$_2$O): δ=25.3 (CH$_2$), 27.4 (CH$_2$), 27.5 (CH$_2$), 28.2 (CH$_2$), 28.4 (CH$_2$), 30.5 (CH$_2$, C-1' thioglycoside), 51.5 (CH$_2$, C-6 CD), 58.9-83.2 (9CH$_2$, 32CH), 85.2 (CH, C-1 thioglycoside), 101.9-102.3 (7×CH, C-1 CD), 123.8 (CH, triazol), 146.2 (C, triazol).

HRMS (MALDI, DHB): m/z calcd for C$_{58}$H$_{97}$N$_3$O$_{40}$SNa [M+Na]$^+$: 1530.5261. found: 1530.5252.

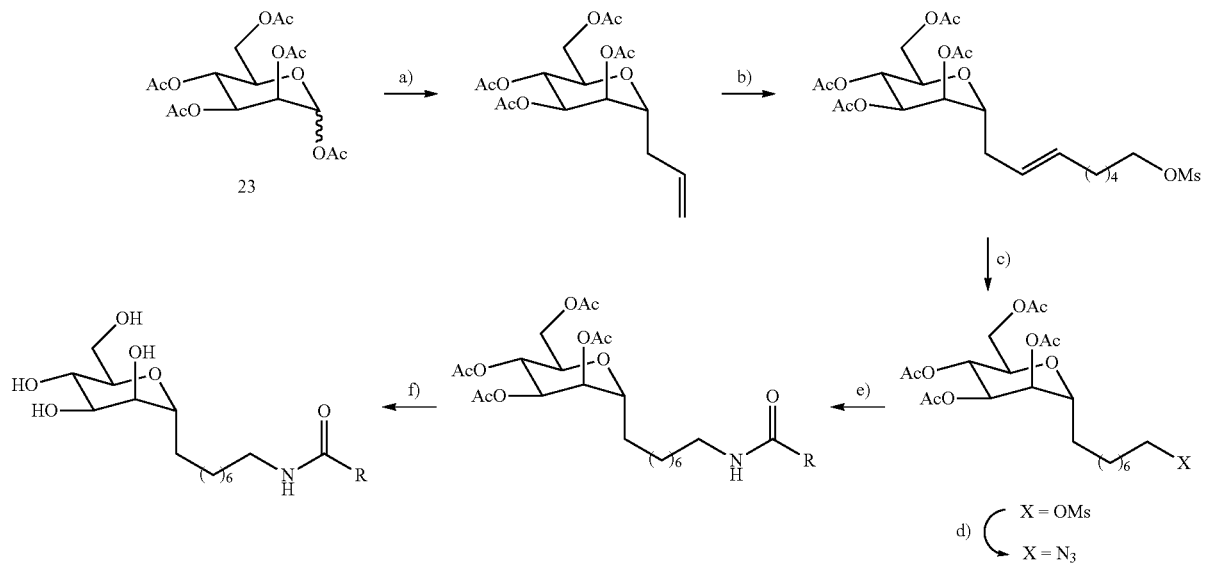

a) ATMS, Et$_2$O·BF$_3$, ACN, 0° C. → rt. b) Grubb's 2° generation cat., DCM, reflux. c) H$_2$, Pd(OH)$_2$, MeOH.
d) NaN$_3$, DMF, 80° C. e) Carboxylic acid, HOBt, DIC, Ph$_3$P, THF, 0° C. → rt. f) NaOMe, MeOH.

D. Synthesis of Mannosyl-C-Heptylamides

Mannosyl-C-heptylamides are obtained from compound 23 through reaction with allyl trimethylsilane (ATMS, step a)), olefin metathesis (step b)), hydrogenation (step c)), displacement of the mesylate using sodium azide (step d)), Staudinger-amide coupling (step e)) and deprotection (step f)).

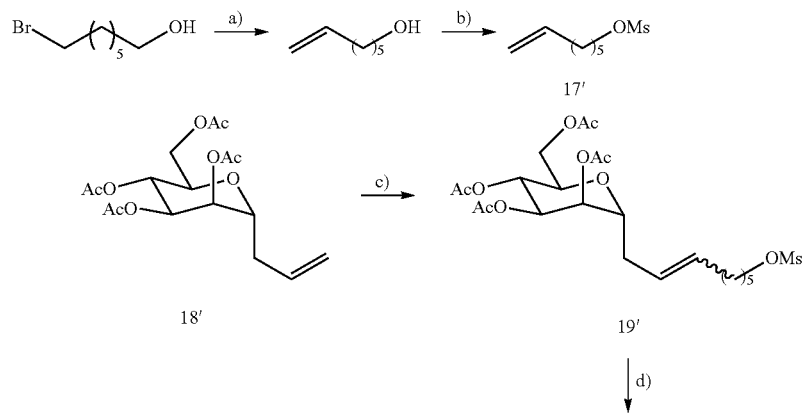

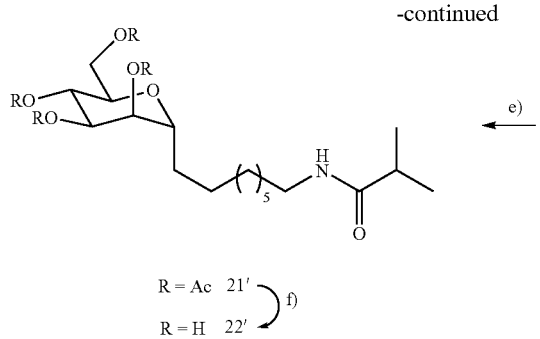 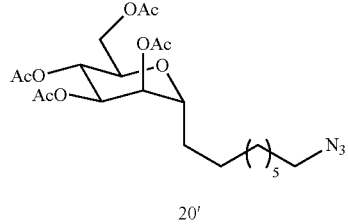

a) ᵗBuOK, THF, 0° C. b) MsCl, Et₃N, DMAP, DCM, 0° C. → rt. c) 17', Grubbs catalyst second generation, DCM, 43° C.
d) i. H₂, Pd/C, MeOH. ii. NaN₃, DMF, 80° C. e) i. Ph₃P, THF—H₂O, 60° C. ii. Isobutyric chloride, DMAP, DCM, rt.
f) i. NaOMe, MeOH, rt, ii. Amberlite IR120 (H).

Example 33: Compound 17'

To a solution of 7-bromo-1-heptanol (2.00 mg, 8.439 mmol) in dry THF (240 mL), cooled at 0° C., was added tBuOK (2.08 g, 18.565 mmol). After stirring at 0° C. for 30 min, 10 ml of H₂O were added and the solvent was evaporated in vacuo.

To a solution of the crude in dry DCM (40 ml) was added MsCl (715 μl, 9.283 mmol), Et₃N (1.76 ml, 12.659 mmol) and DMAP (100 mg). The mixture was stirred for 3 h at rt, washed with saturated solution of NaHCO₃, concentrated under vacuum and the crude was purified by silica gel column chromatography (Hexanes/EtOAc, 70:30) to give the product 17' (1.35 g, 7.089 mmol, 84%) as a colorless oil.

$^1$H NMR (300 MHz, CDCl₃): δ=1.43 (4H, m), 1.76 (2H, m), 2.07 (2H, m), 3.00 (3H, s, MsO), 4.22 (2H, t, J=6.5 Hz), 4.93-5.04 (2H, m, CH₂-alkene), 5.79 (1H, m, CH-alkene).

$^{13}$C NMR (100.6 MHz, CDCl₃): δ=24.8 (CH₂), 28.2 (CH₂), 28.9 (CH₂), 33.4 (CH₂), 37.3 (CH₂), 70.0 (CH₃, MsO), 114.7 (CH₂, CH₂-alkene), 138.4 (CH₂, CH-alkene).

MS (CI, NH₃): m/z: [M+NH₃]⁺210

Example 34: Compound 19'

The Grubbs second-generation catalyst (206 mg, 0.242 mmol, 100/% mol) was added under argon to a mixture of terminal alkenes 18' (as described by Pawel et al., *J. Am. Chem. Soc.* 2008, 130, 2928-2929; 900 mg, 2.421 mmol) and 17' (1.15 g, 6.053 mmol) in deoxygenated dry DCM (36 ml). The resulting solution was stirred at reflux for 8 h. Removal of the solvent in vacuo gave a brown oil, which could be purified by silica gel column chromatography (Hexanes/EtOAc, 80:20) to give the product 19' (703 mg, 1.304 mmol, Z/E: 8/2, 54%) as a colorless oil.

$^1$H NMR (300 MHz, CDCl₃): major isomer 1.39 (4H, m), 1.74 (2H, m), 2.02 (3H, s, AcO), 2.06 (3H, s, AcO), 2.08 (2H, m), 2.09 (3H, s, AcO), 2.12 (3H, s, AcO), 2.42 (2H, m), 3.00 (3H, s, MsO), 3.89 (1H, m, H-5), 3.97 (1H, m, H-1), 4.09 (1H, dd, $J_{6a,6b}$=12.1 Hz, $J_{6a,5}$=2.9 Hz, H-6a), 4.22 (2H, t, J=6.6 Hz, H-7'), 4.32 (1H, dd, $J_{6b,6a}$=12.1 Hz, $J_{6b,5}$=6.0 Hz, H-6b), 5.18-5.28 (3H, m), 5.37 (1H, m, alkene), 5.57 (1H, m, alkene).

MS (CI, NH₃): m/z: [M+NH₃]⁺ 554
HRMS (ESI): m/z calcd for C₂₃H₃₆O₁₂SNa [M+Na]⁺: 559.1819. found: 539.1807.

Example 35: Compound 20'

The mixture Z/E of the metathesis product 19' (458 mg, 0.854 mmol) and 10% palladium on carbon (80 mg) in MeOH (15 mL) were stirred under a hydrogen atmosphere (1 atm) at room temperature for 4 h. The reaction mixture was filtered through a pad of Celite and the solvent was evaporated in vacuo.

A solution of the crude in DMF (26 mL) was added NaN₃ (83 mg, 1.280 mmol) and the resulting mixture was stirred at 70° C. overnight. The mixture was diluted with Et₂O and washed with H₂O and brine. The crude was purified by silica gel column chromatography (Hexanes/EtOAc, 70:30) to give the azide 20' (407 mg, 0.837 mmol, 98%) as a colorless oil.

$[\alpha]_D$=+86.5 (c=0.91 in CHCl₃)

$^1$H NMR (300 MHz, CDCl₃): 1.27-1.46 (10H, m), 1.59 (3H, m), 1.77 (1H, m), 2.02 (3H, s, AcO), 2.05 (3H, s, AcO), 2.10 (3H, s, AcO), 2.13 (3H, s, AcO), 3.26 (2H, t, J=6.9 Hz, H-8'), 3.84 (1H, ddd, $J_{5,4}$=8.8 Hz, $J_{5,6a}$=6.1 Hz, $J_{5,6b}$=2.7 Hz, H-5), 3.94 (1H, ddd, J=10.0 Hz, J=4.6 Hz, J=2.6 Hz, H-1), 4.09 (1H, dd, $J_{6a,6b}$=12.2 Hz, $J_{6a,5}$=2.8 Hz, H-6a), 4.30 (1H, dd, $J_{6b,6a}$=12.2 Hz, $J_{6b,5}$=6.1 Hz, H-6a), 5.16-5.26 (3H, m, H-2, H-3, H-4).

$^{13}$C NMR (100.6 MHz, CDCl₃): δ=20.3 (CH₃, AcO), 20.36 (CH₃, AcO), 20.40 (CH₃, AcO), 20.44 (CH₃, AcO), 25.6 (CH₂), 26.8 (CH₂), 28.7 (CH₂), 28.9 (CH₂), 29.1 (CH₂), 29.3 (CH₂), 29.6 (CH₂), 51.3 (CH₂, C-8'), 62.7 (CH, C-6), 67.6 (CH), 69.6 (CH), 71.1 (CH), 71.2 (CH), 75.0 (CH, C-1), 169.4 (C, AcO), 169.8 (C, AcO), 169.9 (C, AcO), 170.0 (C, AcO).

MS (CI, NH₃): m/z: [M+NH₃]⁺ 503
HRMS (ESI): m/z calcd for C₂₂H₃₅N₃O₉N₃Na [M+Na]⁺: 508.2265. found: 508.2257.

Example 36: Compound 21'

A mixture of 20' (350 mg, 0.720 mmol) and 10% palladium on carbon (35 mg) in MeOH (7 mL) were stirred under a hydrogen atmosphere (1 atm) at room temperature for 10 h. The reaction mixture was filtered through a pad of Celite and the solvent was evaporated in vacuo. To a solution of the amine crude in dry DCM (14 ml) was added isobutyric chloride (114 μl, 1.080 mmol) and DMAP (264 mg, 2.160 mmol) at 0° C. under N₂ atmosphere. The mixture was stirred for 5 h at rt, concentrated under vacuum and the crude was purified by silica gel column chromatography (DCM/MeOH, 90:10) to give the product 21' (253 mg, 0.477 mmol, 66% from 20') as a colorless oil.

$[\alpha]_D$=+59.2 (c=0.75 in CHCl₃)

$^1$H NMR (300 MHz, CDCl₃): δ=1.11 (6H, d, J=6.9 Hz, 2×CH₃-isobutyric acid), 1.22-1.57 (13H, m), 1.74 (1H, m), 1.98 (3H, s, AcO), 2.02 (3H, s, AcO), 2.06 (3H, s, AcO), 2.10 (3H, s, AcO), 2.29 (1H, m, CH, isobutyric acid), 3.19 (2H, m, H-8'), 3.77 (1H, m, H-5), 3.87 (1H, ddd, J=10.0 Hz, J=4.6 Hz, J=2.6 Hz, H-1), 4.10 (1H, dd, $J_{6a,6b}$=12.1 Hz, $J_{6a,5}$=2.6 Hz, H-6a), 4.04 (1H, dd, $J_{6b,6a}$=12.1 Hz, $J_{6b,5}$=5.9 Hz, H-6a), 5.09-5.20 (3H, m, H-2, H-3, H-4), 5.53 (1H, bs, NH).

$^{13}$C NMR (100.6 MHz, CDCl$_3$): δ=19.6 (2×CH$_3$, isobutyric acid), 20.2 (CH$_3$, AcO), 20.65 (CH$_3$, AcO), 20.67 (CH$_3$, AcO), 20.9 (CH$_3$, AcO), 25.2 (CH$_2$), 26.7 (CH$_2$), 28.3 (CH$_2$), 28.9 (CH$_2$), 29.0 (CH$_2$), 29.2 (CH$_2$), 29.6 (CH$_2$), 35.6 (CH, isobutyric acid), 39.2 (CH$_2$, C-8'), 62.6 (CH, C-6), 66.8 (CH), 69.0 (CH), 69.9 (CH), 70.8 (CH), 75.2 (CH, C-1), 169.6 (C, AcO), 169.9 (C, AcO), 170.3 (C, AcO), 170.6 (C, AcO), 176.8 (C, amide).

MS (CI, NH$_3$): m/z: [M+H]$^+$ 530

HRMS (ESI): m/z calcd for $C_{26}H_{44}O_{10}N$ [M+H]$^+$: 530.2959. found: 530.2955.

Example 37: Compound 22'

According to the general procedure B, using the amide 21' (50 mg, 0.094 mmol) as starting material, the derivative 22' was obtained after lyophilization (33 mg, 0.091 mmol, 97%) as an amorphous white solid.

[α]$_D$=+26.6 (c=0.81 in MeOH).

$^1$H NMR (300 MHz, MeOD): δ=1.12 (6H, d, J=6.9 Hz, 2×CH$_3$-isobutyric acid), 1.31-1.79 (14H, m), 2.44 (1H, m, CH-isobutyric acid), 3.17 (2H, q, J=6.3 Hz, C-8'), 3.42 (1H, m, H-5), 3.61-3.89 (6H, m), 7.85 (1H, bs, NH).

$^{13}$C NMR (100.6 MHz, MeOD): δ=19.9 (2×CH$_3$, 2×CH$_3$-isobutyric acid), 26.9-30.5 (7×CH$_2$), 36.3 (CH, CH-isobutyric acid), 40.2 (CH$_2$, C-8'), 63.1 (CH, C-6), 69.3 (CH), 72.8 (CH), 73.1 (CH), 75.5 (CH), 78.9 (CH, C-1), 179.9 (C, amide).

MS (CI, NH$_3$): m/z 362 [M+H]$^+$

HRMS (MALDI, DHB): m/z calcd for $C_{18}H_{35}O_6NaN$ [M+Na]$^+$: 384.2357. found: 384.2354.

Example 38: Adhesion Ability of Adherent-Invasive E. coli to Intestinal Epithelial Cells in Presence of Monovalent Compounds: Pre-, Co- and Post-Incubation Experiments Bacterial Strain and Cell Line E. coli strain LF82 was isolated from a chronic ileal lesion of a patient with Crohn's disease (CD). Bacteria were grown routinely in Luria-Bertani (LB) broth overnight at 37° C. Intestinal epithelial cells T84 derived from colonic adenocarcinoma were maintained in an atmosphere containing 5% CO2 at 37° C. in DMEM/F12 (50/50) medium supplemented with 10% (v/v) heat-inactivated fetal calf serum (FCS), 1% L-glutamine, 100 000 U·l$^{-1}$ penicillin, 100 mg·l$_{-1}$ streptomycin, 25 μg·l$^{-1}$ amphotericin B.

Adhesion Ability of Adherent-Invasive E. coli to Intestinal Epithelial Cells in Presence of Monovalent Compounds.

T84 were seeded in 48-well plates at a concentration of 1.5×10$^5$ cells per well and grown for 48 h. AIEC LF82 bacteria were incubated 1 h with monovalent compounds prior the cell infection (pre-incubation protocol) or they were added simultaneously onto the cells (co-incubation protocol) in complete medium without antibiotics, containing heat inactivated fetal calf serum (FCS). Monovalent compound 10 was tested at a dose of 100; 10; 1 (and 0.1) M, compound 5 was tested at a dose of 500; 100; 10 and 1 μM and D-mannose was tested at a dose of 10 000; 1 000; 100 or 10 μM. Cells were infected with AIEC LF82 bacteria at a multiplicity of infection (MOI) of 10 bacteria per cell for 3 h at 37° C.

For the post-incubation protocol, monovalent compounds (same doses than in the pre- and co-incubation assays) were incubated with cells for 3 h after bacterial infection. A washing step was realized before this post-incubation to eliminate non-adherent bacteria.

Monolayers were washed in phosphate-buffered saline (PBS; pH 7.2) and cells were then lysed with 1% Triton X-100 in deionized water. Samples were diluted and plated onto Luria Bertani agar plates to determine the number of colony-forming units (CFU) recovered from the lysed monolayers. Results were expressed as percentages of residual adhesion, considering adhesion level of AIEC LF82 without mannosides treatment as 100%.

Results

Figure 1A:
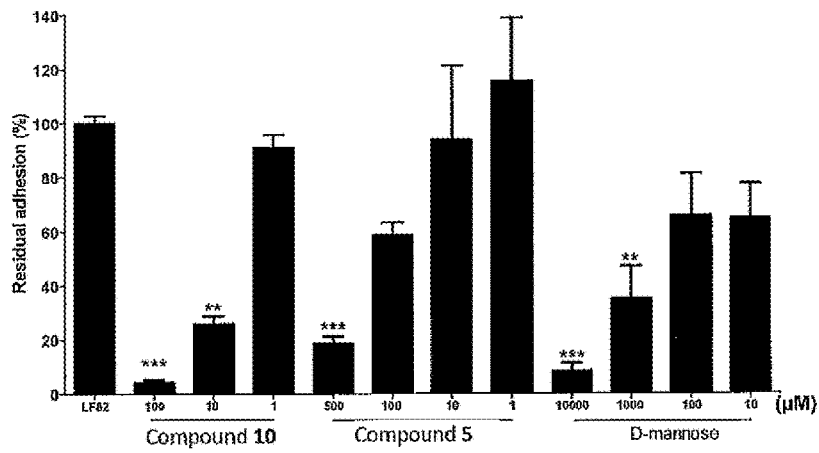
FIG. 1 presents the adhesion levels of Adherent-Invasive E. coli strain LF82 to intestinal epithelial cells T84 in the presence of increasing doses of compounds 5 and 10 or D-mannose, using co-, pre- and post-incubation protocols (respectively FIGS. 1A, 1B and 1C). Results are expressed in percentages of residual adhesion, considering 100% as the LF82 adhesion level in absence of any compound (means±sem). *: $p<0.05$; : $p<0.01$; *: $p<0.00$ (t test).
Figure 1B:
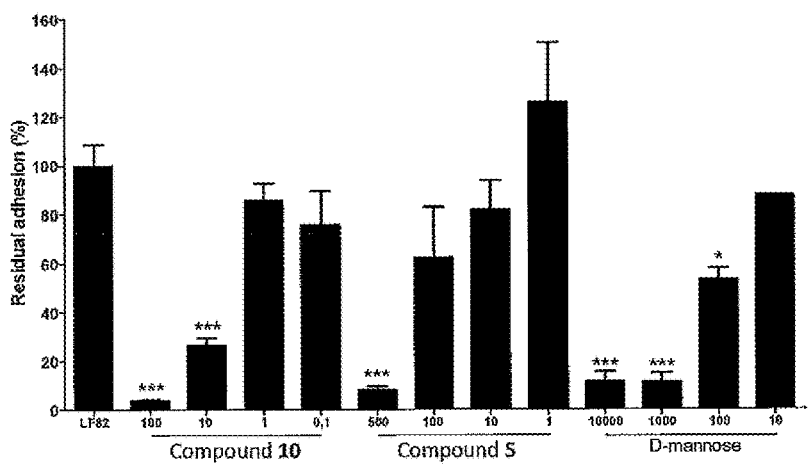
Figure 1C:
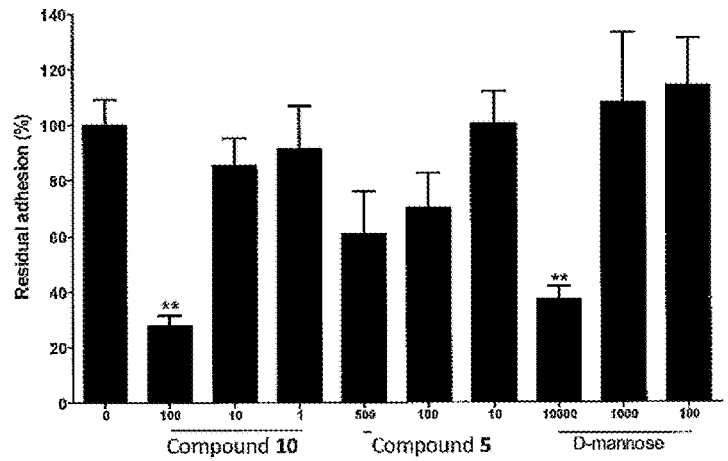

D-mannose, compounds 5 and 10 were assessed as putative inhibitors to compete the interaction of CEACAM6 expressed by T84 intestinal epithelial cells with the adhesin FimH of AIEC bacteria following three different protocols: pre-, co- and post-incubation experiments (FIG. 1).

For co-incubation experiments, results clearly indicated that monovalent compound 10 possessed the best inhibitory effect, with a 50-fold increased potency in comparison with the compound 5 and a 100-fold increased potency in comparison with D-Mannose. Significant decreases in the bacterial adhesion levels were obtained at 10 μM for compound 10, at 500 μM for compound 5 and at 1 000 μM for D-Mannose. Using the pre-incubation protocol, D-mannose showed a significant inhibitory effect on the bacterial adhesion at 100 μM, whereas similar results than those observed with the co-incubation protocol were obtained for compounds 5 and 10. Finally, in post-incubation experiments, D-mannose decreased adhesion at a high dose of 10 mM, compound 5 was not able to decrease bacterial adhesion even at 500 μM, and compound 10 showed a significant inhibitory effect at 100 μM. These data indicated that monovalent compound 10 is a good inhibitor to detach bacteria adhering to intestinal epithelial cells at a dose of 100 μM.

Example 39: Adhesion Ability of Adherent-Invasive E. Coli Strains to Intestinal Mucosa of Transgenic Mice Expressing CEACAM6 in the Presence of Monovalent Compounds Bacterial Strain and Transgenic Mouse Model E. coli strain LF82 was isolated from a chronic ileal lesion of a patient with Crohn's disease (CD). Bacteria were grown routinely in Luria-Bertani (LB) broth overnight at 37° C.

The transgenic mouse model CEABAC10 expressing the human CEACAM6 protein is available in the UMR Inserm/ Université d'Auvergne 1071 led by Professor Arlette Darfeuille-Michaud at Clermont-Ferrand. This model is particularly suitable to mimic the abnormal colonization of gut mucosa by AIEC bacteria through the interaction of CEACAM6 abnormally expressed in the ileal mucosa of Crohn's disease and FimH adhesin of AIEC.

Adhesion Assays of Adherent-Invasive E. Coli Strains to Colonic Loops from CEABAC10 Mice in Presence of Monovalent Compounds.

Three colonic loops were performed in anesthetized CEABAC10 mice. A volume of 100 μl of a bacterial suspension containing 2.5×10$^7$ bacteria/mL in the presence or absence of monovalent compounds was injected into the loops (here, compound 10 at a concentration of 100 μM). After an incubation period of 4 h, mice were euthanized and each loop was longitudinally opened, extensively washed in phosphate buffer and homogenized to numerate adherent LF82 bacteria. Bacterial adhesion levels were expressed as colony forming units (CFU) per gram of colonic tissue in the FIG. 2 (100% corresponds to the LF82 adhesion in absence of any compound).

Results

Figure 2:
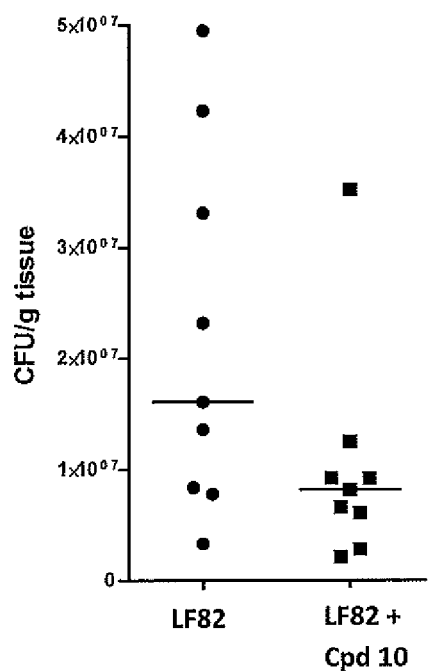
FIG. 2 presents the adhesion levels of Adherent-Invasive E. coli strain LF82 to colonic mucosa from CEABAC10 mice, in presence of compound 10 at a concentration of 100 μM. Infections were performed with 100 μL of a bacterial suspension of AIEC LF82 at $2.5 \times 10^7$ bacteria/mL. Results are expressed in CFU/g of tissue, each point represents result for LF82 adhesion in one colonic loop (horizontal bars=median).

A-two fold decrease in the number of LF82 bacteria adhering to colonic mucosa was observed in the presence of the monovalent compound 10 at a concentration of 100 μM (FIG. 2).

Example 40: Effect of Orally Administered Monovalent Compounds to Adherent-Invasive *E. coli* LF82-Infected Transgenic Mice Expressing CEACAM6

Bacterial Strain and Transgenic Mouse Model

*E. coli* strain LF82 was isolated from a chronic ileal lesion of a patient with Crohn's disease (CD). Bacteria were grown routinely in Luria-Bertani (LB) broth overnight at 37° C.

The transgenic mouse model CEABAC10 expressing the human CEACAM6 protein is available in the UMR Inserm/ Université d'Auvergne 1071 led by Professor Arlette Darfeuille-Michaud at Clermont-Ferrand. This model is particularly suitable to mimic the abnormal colonization of gut mucosa by AIEC bacteria through the interaction of CEACAM6 abnormally expressed in the ileal mucosa of Crohn's disease and FimH adhesin of AIEC.

AIEC Colonization Assessment in CEABAC10 Mice Treated with Monovalent Compounds.

To mimic curative treatment, compounds were analyzed for their anti-adhesive effect on a pre-established LF82 colonization in CEABAC10 mice. CEABAC10 mice were given 0.5% of DSS in drinking water. Two days later, mice were treated per os with streptomycin sulfate, 5 mg/mouse. Twenty four hours later, (corresponding to day "0"), a five-hour culture of AIEC LF82 bacteria in LB broth was concentrated to reach $5 \times 10^9$ bacteria/mL and was administered by gavage 2 h after the intragastric administration of cimetidine at 50 mg/kg in order to ablate gastric secretion. Oral administration of monovalent compounds at a range from 1 to 1000 μg/mouse (=0.04 to 40 mg/kg) was realized 2 h after LF82 infection. A second administration of the compounds was realized 18 h later (cimetidine was also given 2 h before administration of the compounds). Body weight and signs of colitis were followed for 4 days. Stools were collected from day 1 to day 4 post-infection to assess bacterial colonization. Mice were euthanized at day +4 and the entire intestine was collected to assess the number of AIEC bacteria associated with the gut mucosa, to measure pro-inflammatory cytokine secretion, to measure myeloperoxidase activity as indicator of neutrophil infiltration in the intestinal tissue, to determine the disease activity index and to estimate histological damages of the mucosa.

Similar protocol was realized in testing a prophylactic administration of the compounds (administration of similar doses of monovalent compounds 5 h before infection). Compounds were compared for their efficacy, depending on the dose and on the preventive or curative effect. To analyze whether the inhibitory effects could be related to toxicity effects, the absence of cell death of intestinal epithelial cells or bacteria was assessed at the highest dose of each compound.

CEABAC10 mice were infected with $10^9$ bacteria at day 0 (D0) and then orally treated two times with 10 mg/kg of compounds 5 and 10 ("curative treatment"). Body weight was followed during 3 days before LF82 infection and until day 4 post-infection. Bacterial loads in feces and signs of colitis were followed at day 1, 3 and 4 after infection as well as the severity of colitis, assessed by establishment of the Disease Activity Index score (DAI). The numbers of bacteria associated to the intestinal mucosa were assessed at day 4 post-infection. Intestinal tissues were sampled to measure the levels of pro-inflammatory cytokines and to analyze damages of mucosa (HES staining of colonic slices). Finally, spleen were collected and weighted.

Results

Figure 3:
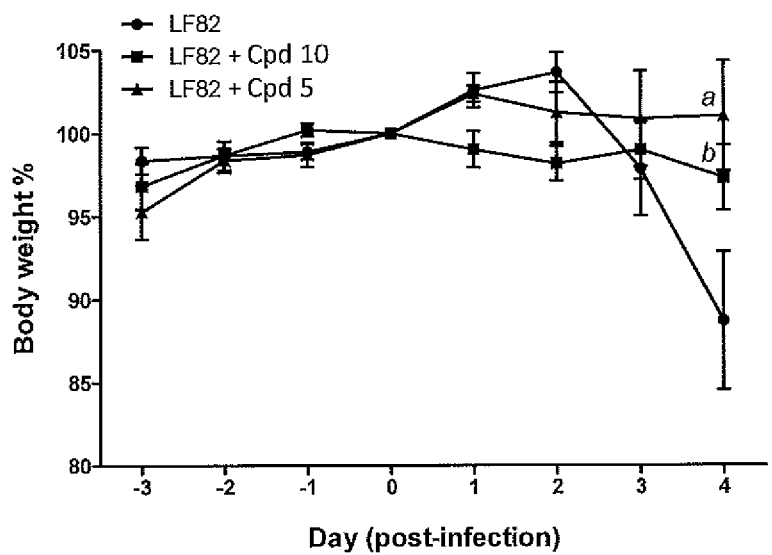
FIG. 3 presents the body weight of CEABAC10 mice infected with $10^9$ AIEC LF82 bacteria at day 0, after two oral administrations of the monovalent compounds 5 and 10 at a dose of 10 mg/kg. Each point represents the mean±sem of body weights for each group of mice. Results are expressed as percentages, day 0 (LF82 infection) being considered as 100%. NI: non-infected. a: $p<0.001$; b: $p<0.01$ compared to LF82-infected mice (t test).

The body weight mean of the LF82-infected mice strongly decreased between day 0 and day 4 post-infection, compared to the non-infected group. LF82-infected mice treated with compound 5 or 10 did not show any decrease in the body weight (FIG. 3). Compared to LF82-infected mice, LF82-infected mice treated with monovalent compounds 5 or 10 showed very low DAI scores at day 3 and 4 post-infection, similar to that of non-infected mice (FIG. 4 D). The LF82 colonization levels were strongly decreased in the feces of LF82-infected mice treated with 5 and 10 (with less than $10^4$ bacteria/g of feces), in comparison with LF82-infected but non treated mice (more than $10^6$ bacteria/g of feces) (FIGS. 4A, 4B and 4C). Similar decreased colonization in the presence of compounds 5 and 10 was observed for the number of bacteria associated to the ileum and the colon (0 CFU/g of intestinal tissue) compared to $5 \times 10^3$ and $1 \times 10^4$ CFU/g of tissue for ileum and colon, respectively, in the absence of any compounds (FIG. 5). Compared to the non-infected mice, increased spleen weight was observed in LF82-infected mice. This was no longer observed when mice were treated with monovalent compounds 5 and 10 (FIG. 6). Finally, in that infection model, LF82 was able to increase the levels of pro-inflammatory cytokines IL-23, KC and TNF-α secreted, compared to non-infected mice. When mice were treated with monovalent compound, 5 and 10 the levels of pro-inflammatory cytokines secreted were decreased compared to non-treated mice. Decreases were significant for the three IL-23, KC and TNF-α cytokines in the presence of compound 10 but not in the presence of compound 5 (FIG. 7).

Example 41: In Vitro Screening of Anti-FimH Molecules

Molecules were screened for their inhibition effect on the adhesion of the AIEC LF82 strain to intestinal epithelial T84 cells.

The molecules tested were the O-glycosides 10 and 5, the S-glycoside 16' and the C-glycoside 22'.

Post-Incubation Protocol with Undifferentiated T84 Cells:

The AIEC LF82 strain was incubated with T84 cells and then the tested molecule was added.

The Protocol is as follows:

Cells: T84, 48 h culture, in 48 wells plate at $1.5 \times 10^5$ cells/well;

Bacteria: AIEC LF82 strain, Culture ON;

Inhibitor compounds in mother solutions (10, 20, 50 or 100 mM);

Measure the OD(620) of the bacterial culture;

Prepare the bacterial suspension at $6 \times 10^6$ bact/mL in DMEM/F12/SVF dec 10% medium;

Wash twice the cellular layer with PBS;

Add 250 μl/well of bacteria suspension, id. $1.5 \times 10^6$ bact/well (MOI=10);

Incubate 3 hours at 37° C.;

Prepare inhibitor compounds at the wished final concentration in DMEM/F12/SVF dec 10% medium and filtrate at 0.2 µl filter;
Wash 5 times the cellular layer with PBS;
Add 250 µL of inhibitor compounds/well;
Incubate 3 hours at 37° C.;
Wash 5 times the cellular layer with PBS;
Add 250 µL of Triton X-100 at 1%, incubate 5 min at room temperature then add Triton in each well;
Take the entire content of each well and transfer it in an Eppendorf tube of 1.5 mL;
Perform serial dilutions in physiological water: 50 µl of sample in 450 µl of physiological water;
(NB: Prepare physiological water+2% D-mannose if difficulty met to get isolated colonies)
Spread 25 µl of dilution on LB-agar gelose;
Incubate overnight at 37° C.
For this experiment, all compounds have been tested at a final concentration of 100 µM.

Criteria of Evaluation:
The criteria of evaluation is the residual adhesion (level of colonization/decolonization of AIEC measured on cells) expressed in percentage.

Results: Dose Effect with Tested Molecule at Different Concentrations:
Pre incubation experiments and post incubation experiments (FIG. 8) provide consistent results with respect to 10/22' and 5/16'.

Example 42: In Vivo Testing of Anti-Adhesive Effect of Molecules on AIEC LF82 Colonization in CEABAC10 Mice Molecules tested: 10 (1 mg/kg and 10 mg/kg), 22' (10 mg/kg), 16' (10 mg/kg), 5 (10 mg/kg) The aim was to test different compounds given per os to CEABAC10 mice infected by AIEC LF82 strains by assessing their ability to decrease bacterial colonization and related colitis.

Protocol:
Mice CEABAC10 (8 weeks-old males) were given DSS 0.5% in water for all the time of experiment.
Two days later, mice were treated p.o. with Streptomycin sulfate, 5 mg/mouse (in water).
The following day (=D0), LB broth was inoculated (1/100$^{th}$) with an ON culture of AIEC LF82 and incubated at 37° C. with shaking in order to obtain a D0=0.5 or 0.6 maximum. Bacteria were concentrated at $1.5 \times 10^{10}$ bacteria/mL and 0.2 mL was administered intra-gastrically to mice (=$3 \times 10^9$ bact/mouse) 2 h after oral administration of cimetidine at 50 mg/kg in order to ablate gastric secretion (6.25 mg/mL in water, 0.2 mL/mouse).
Tested molecules were orally given twice at a dose of 250 µg/mouse (=10 mg/kg) or 25 µg/mouse (=1 mg/kg) in PBS, 2 h and 18 h after infection (cimetidine was given 2 h before each administration of the compounds).
Body weight were followed for 3 (for ANR5) to 4 (for ANR3) days.
Stools were collected at day+1 (ANR3 and ANR5), day+3 post-infection (ANR5), day+4 post-infection (ANR3) to assess bacterial colonization.
Mice were euthanized at day+4 for ANR3 and day+3 for ANR5 and entire intestine was collected to assess the bacterial colonization at the mucosa (ileum+colon), to measure pro-inflammatory cytokine secretions, to assess the neutrophil infiltration into the tissues (myeloperoxidase activity), to assess the disease activity index.

ANR3: Groups of male mice (32 mice in total):
A. Non-infected (NI) mice; n=8
B. LF82-Infected mice without treatment; n=8
C. LF82-Infected mice+10 at 10 mg/kg; n=8
D. LF82-Infected mice+5 at 10 mg/kg; n=8
ANR5: Groups of male mice (48 mice in total):
E. Non-infected (NI) mice; n=12
F. LF82-Infected mice without treatment; n=12
G. LF82-Infected mice+22' at 10 mg/kg; n=12
H. LF82-Infected mice+16' at 10 mg/kg; n=12

Criteria of Evaluation:
1. Body weight
2. Disease activity index (DAI)
3. Bacterial colonization in stools
4. Bacterial colonization at the mucosa
5. Pro-inflammatory cytokine secretions
6. Neutrophil infiltration into the tissues (myeloperoxidase activity)

Result:
The evolution of the weight of CEABAC10 transgenic mice uninfected or infected with AIEC LF82 was followed after administration of various molecules to be tested (FIG. 9). Infection of mice with AIEC LF82 leads to a decrease in the weight of mouse. The administration of molecules 10, 22' and 16' prevents weight loss induced by infection with the AIEC LF82 strain (FIGS. 9A and 9B). This observation correlates with decreased of disease activity index (DAI score) 3 days after infection following administration of molecules 10, 22' and 16' in mice infected with AIEC LF82 (FIG. 10). To assess the ability of molecules to reduce the colonization of the intestinal mucosa by AIEC strains, the amount of AIEC bacteria present in the feces, which reflects the amount of AIEC bacteria associated with intestinal mucosa, was measured. As control, one day post-infection, the amount of AIEC bacteria present in feces was comparable irrespective of the administration of molecules tested, indicating a similar level of colonization in all the batches from the experiment. Interestingly, administration of molecule 22' lead to a decrease in the amount of AIEC LF82 bacteria in the feces of infected mice at 3 and 4 days post-infection, showing the effectiveness of these molecules to decrease the ability of the AIEC LF82 to colonize the mouse intestine (FIG. 11). In addition, the count of AIEC LF82 bacteria associated with ileal or colonic mucosa at 4 day post-infection shows that the molecules 22' and 16' decolonized AIEC bacteria very effectively at the ileal and colonic mucosa (FIG. 12). Various inflammatory parameters were measured at 3 or 4 days post-infection. First, the myeloperoxidase (MPO) activity, which reflects the infiltration of the intestinal mucosa by neutrophils, was measured. Interestingly, administration of molecules 10, 5, 22' led to a decrease in MPO activity (FIG. 13). In addition, the quantification of the pro-inflammatory cytokines IL23 (FIG. 14) and IL-1beta (FIG. 15) was performed at the level of mucosa from infected mice. The administration of the molecules 10, 5, 16' resulted in a reduction of the cytokine IL23 level and administration of the molecules 10, 5 led to a decrease in the release of IL1-beta.

All of these in vivo results obtained in the transgenic mouse model CEABAC10 infected with AIEC LF82 shows that different molecules tested either reduced the activity of the disease (weight and score DAI), the level of colonization of mucosa or inflammatory parameters (MPO activity and production of pro-inflammatory cytokines), suggesting that these molecules are potentially useful in the treatment of Crohn's disease patients colonized by AIEC strains.

Example 43: Ex Vivo Protocol

The ex vivo model of explant cultures from human colonic mucosa is used to examine the interactions of the AIEC strain LF82 with human colonic mucosa (controls) cells and the decolonization of AIEC from mucosa cells thanks to the FimH antagonists molecules (treated).

Human Colonic Mucosa Explants.

The mucosa is carefully stripped from the underlying compartment. Fragments of 40 mg are maintained in culture overnight in RPMI-BSA 0.01% supplemented with gentamicin to get rid of commensal bacteria, and fungizone washed twice in RPMI, and then incubated for 4 h with or without bacterial cultures (LF82-GFP) in 2 ml culture medium without antibiotics. The explants are maintained at 37° C. in a 95% oxygen, 5% carbon dioxide humid atmosphere on a rocking platform at low speed. In each experiment, at least three explants are cultured for each condition. The supernatants are centrifuged and aliquots are stored at −80° C. for further analysis.

Bacterial Strains and Media.

The prototype AEC strain LF82-GFP is used (UMR 1071 Inserm/Universite d'Auvergne, Clermont-Ferrand, France). The strains are stored at −20° C. in cryotubes. Before the experiments, the bacteria are cultivated on TS agar at 37° C. for 24 h after thawing. For each experiment, bacteria are subcultured in LB broth at 37° C. for 18 h with shaking. The bacteria are then centrifuged for 10 min at 800 g. The pellet is washed twice with sterile PBS, and the suspension is adjusted to $0.5 \times 10^1$ or $0.5 \times 10^9$ bacteria per milliliter, in culture medium (RPMI/BSA 0.01% without antibiotics).

The explant cultures, left to stabilize overnight in culture medium with antibiotics, were co-incubated with LF82-green fluorescent protein (GFP) ($10^8$ or $10^9$ bacteria per explant) without antibiotics for 4 h. LF82 bacteria, detected by immunoperoxidase using an anti-GFP antibody on paraffin sections, are found adhering to the apical pole of a few epithelial cells of the surface and crypt base, scattered or sometimes focally clustered.

Example 44: Pharmacokinetic Study Following Administration of 2 Compounds by Oral and Intravenous Administration to Male Sprague Dawley Rats These in vivo and analytical experiments are conducted to:

Estimate the plasma concentration level after oral and intravenous administrations of 2 compounds to male Sprague Dawley rats;

Calculate the bioavailability;

Estimate the amount of unchanged compounds in the faeces.

Two substances are tested (previously stored at room temperature in the dark).

For analysis, the molecules are dissolved in DMSO at 1 mg/mL.

| Compounds | Weight tube (mg) |
|---|---|
| 10, 22' | 2 * 1 mg for the analytical part<br>15 mg for the in vivo part |

1. Analytical Test

Before the beginning of the in vivo part, an analytical test for each compound are performed in the two matrices.

The molecular and daughter ions are selected for each compound by direct infusion into the MS-MS system.

At least 8 point calibration standards are run using standard conditions which consist to LC-MS/MS system with C18 column after precipitation of proteins before the start of the analytical test.

Blank rat faeces are homogeneized with 3 volumes of UHQ water until obtention of a paste. Then 100 μL of the homogenate are spiked with the molecules and precipitated with 300 μL of acetonitrile.

For the plasma, 100 μL of blank rat plasma are directly spiked with the compounds before being precipitate with 300 μL of acetonitrile.

The corresponding correlation coefficient (r) is calculated and should be higher than 0.75 to continue with the in vivo test.

The concentration ranges tested are:

0.5 ng/mL to 1000 ng/mL for plasma, 4 to 2000 ng/g for faeces, corresponding to 1 to 500 ng/mL of faeces homogenate.

2. In-Life Part 2.1. Characteristics, Housing and Handling of Animals 30 male Sprague Dawley rats around 6-7 week old are used.

At reception, the animals are housed in makrolon cages with stainless steel wire lids with catches. A label on each cage indicates the reception date, the rat strain, sex and weight. Temperature and humidity are continually monitored. The animal room conditions is kept as follows:

Temperature: 22° C.±2° C. Exceptionally, upper or lower values can be tolerated.

Light/dark cycle: 12 h/12 h (07:00 h-19:00 h).

After administration and over the experiment duration, the animals are placed individually in metabolic cages (tecniplast).

Animals have free access to food and water during the experiment.

2.2. Design

| Compounds | Route | vehicle | Dose (mg/kg) | Concentration | Volume of administration (mL/kg) |
|---|---|---|---|---|---|
| 10, 22' | IV | 100% DMSO | 1 | 1 mg/mL | 1 |
|  | PO | 100% DMSO | 10 | 2 mg/mL | 5 |

2.3. Sampling

For each test substance

| Molecule | Administration route | Rat name | Blood sampling Time | Faeces sampling Time |
|---|---|---|---|---|
| 10, 22' | IV | IV1, IV2, IV3 | 5 min<br>30 min<br>2 h<br>6 h<br>24 h | 0-24 h |
|  | PO | PO4, PO5, PO6 | 30 min<br>1 h<br>2 h<br>6 h<br>24 h | 0-24 h |

After administration, the animals are placed in individual metabolic cages in order to collect faeces samples during 24 hours.

2.4. Blood Sampling

At prescribed times, blood will be collected. Animals are briefly anaesthetised with Isoflurane® using an anaesthetic system (Équipement Vétérinaire Minerve) during blood samplings.

Site of collection: sinus retro-orbital using a capillary tube
Volume of blood collected: 0.3 mL per time-point
Anticoagulant: Heparin Lithium Exact sampling times are noted for each blood sampling.

Blood samples are centrifuged at 2500 rpm at +4° C. (between 0 and 9° C.), the plasma is removed and placed into labelled polypropylene tubes. Individual plasma samples is stored frozen at −20° C. (target temperature) until analysis.

3. Analysis 3.1. Analysis of Plasma Samples

100 µL of the plasma sample are taken and 300 µL of acetonitrile are added. After protein precipitation, analysis are performed using LC-MS/MS determination according to previous analytical test results.

3.2. Analysis of Faeces Samples

Faeces samples are collected over the 24 hours of the experiment.

They are precisely weighed and 3 volumes of UHQ water are added.

The mixture is homogenized until obtention of a paste. Then 100 µL of the homogenate are taken and extracted with 300 µL of Acetonitrile.

Analysis is performed using LC-MS/MS determination according to previous analytical test results.

3.3. Determination of the Concentrations

Concentrations of the samples are calculated directly from chromatograms after automatic integration by Analyst® 1.5.1 and expressed as ng/mL.

Mean plasma concentrations are calculated (when calculable, i.e. n≥2) using individual concentration and are expressed with the corresponding standard deviation value and variation coefficient (when calculable, i.e. n≥3)

$$\left(\text{with } CV(\%) = \frac{SD}{\text{mean}} \times 100\right).$$

The individual plasma concentrations are tabulated for each rat and scheduled sampling time. Concentrations below the LLOQ are indicated by BLQ. All BLQ concentrations are substituted by zero for calculation of the descriptive statistics of the concentrations.

4. Results

The results is provided with plasma concentration/time curves, as well as the tabulated concentrations results obtained for each plasma and faeces time point.

Estimation of PK parameters is performed using Kinetica® (Version 4.3—Thermo Electron Corporation—Philadelphia—USA). An independent model method is used. The following parameters are estimated:

Cmax (ng/mL): maximal plasma concentration
Tmax (h): first time to reach Cmax
$AUC_t$ (ng/mL*h): area under the plasma concentration-time curve from administration up to the last quantifiable concentration at time t
Absolute bioavailabilty:

$$F(\%) = \frac{AUC\ PO/\text{dose } PO}{AUC\ IV/\text{dose } IV} \times 100$$

Example 45: Testing of Resistance to Mannosidases

Compounds are testing for degradation by intestinal enzymes like mannosidases, known to preferentially induce breakage between mannose and O-linkage. To avoid such degradation, several analogues have been designed, for example 22' ($CH_2$-analogue of 10), 16' (S analogue of 5).

Each compound is incubated with mannosidase and with or without inhibitors of mannosidase. Mass spectrometry experiments are performed to detect native and degraded compounds.

Example 46: In Vitro Toxicity Studies

The cytotoxic activity of compounds 10 and 22' against normal cell lines using MTS assay was determined.

Materials and Methods

Compounds 10 and 22' were extemporaneously dissolved at 100 mM in water to obtain a stock solution.

The final concentrations of compounds 10 and 22' were 100 nM, 19 µM, 10 µM, 100 µM and 1 mM within wells.

The cell lines that were used are detailed in the table hereafter.

| Cell line | Type | Species | Origin |
|---|---|---|---|
| HUV-EC-C | Umbilical vein endothelial cells | Human | Millipore |
| CCD-18Co | Colon normal fibroblast | Human | ATCC ® CRL-1459 ™ |
| MRC-5 | Normal foetal lung fibroblast | Human | ATCC ® CCL-171 ™ |
| PWR-1E | Normal prostate cells | Human | ATCC ® CRL-11611 ™ |

The 4 cell lines were plated at optimal density per well in 96-well plates. Plates were incubated at 37° C. for 24 hours before treatment, in drug-free culture medium.

Cell lines were then incubated for 96 hours at 37° C. under 5% $CO_2$ with the 5 concentrations of compounds 10 or 22' in 1:10 dilution steps. Each concentration was done in triplicate.

Control cells were treated with vehicle alone (water).

At the end of the treatment, the cytotoxic activity of compounds 10 and 22' was assessed by MTS assay.

The in vitro cytotoxic activity of compounds 10 and 22' was revealed by a MTS assay using tetrazolium compound (MTS, 3-(4,5-dimethylthiazol-2-yl)-5-(3-carboxymethoxyphenyl)-2-(4-sulfophenyl)-2H-tetrazolium) and an electron coupling reagent named PMS (phenazine methosulfate).

The dose response for index of cytotoxicity (IC) is expressed as following:

$$IC = \frac{OD_{drug\text{-}exposed\ wells}}{OD_{vehicule\text{-}exposed\ wells}} \times 100$$

The OD values are the mean of 3 experimental measurements.

$IC_{50}$ represents the drug concentration required to obtain 50% of cellular cytotoxicity. The $IC_{50}$ determination values were calculated from semi-log curves.

Results

Cytotoxicity studies have shown that compounds 10 and 22' do not present an acute toxicity towards the above-mentioned four cell lines.

The values obtained for Docetaxel (control compound) are consistent with known values of inherent toxicity, thus validating these experiments.

The invention claimed is:
1. A pharmaceutical composition comprising, in combination with a pharmaceutically acceptable vehicle:
(i) at least one compound of the following formula (I-0):

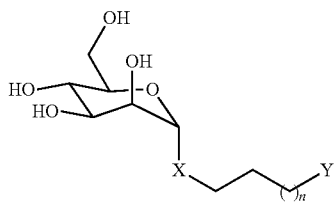

wherein:
X represents NH, O, S or $CH_2$;
n represents an integer comprised from 3 to 7;
Y represents a group selected from:

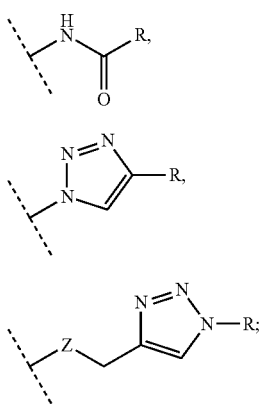

Z representing O, S or NH;
R representing a moiety selected from the group consisting of:
H
a linear or branched $(C_1-C_7)$-alkyl,
a group of formula $—(CH_2)_i—X'—(CH_2)_j—H$, wherein X' represents O, S or NH, i is an integer from 1 to 7, and j is an integer from 0 to 7,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, said aryl being an aromatic or heteroaromatic group,
an alkyl aryl, wherein the aryl is an aromatic or heteroaromatic group,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
$CF_3$,
adamantyl,
CHRa—$NH_2$, wherein Ra represents the side chain of a proteinogenic amino acid, and
a cyclodextrin,
said $(C_1-C_7)$-alkyl, group of formula —$(CH_2)_i$—X'—$(CH_2)_j$—H, $(C_2-C_7)$-alkenyl, $(C_2-C_7)$-alkynyl, $(C_3-C_7)$-cycloalkyl, $(C_5-C_7)$-cycloalkenyl, $C_3-C_7$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$-alkyl, aryl, alkyl aryl, CO-aryl and cyclodextrin being optionally substituted by one or more substituent(s), each independently selected from the group consisting of:
a linear or branched $(C_1-C_7)$-alkyl,
a linear or branched $(C_2-C_7)$-alkenyl,
a linear or branched $(C_2-C_7)$-alkynyl,
a $(C_3-C_7)$-cycloalkyl,
a $(C_5-C_7)$-cycloalkenyl,
a $(C_3-C_7)$-heterocycloalkyl,
a $(C_5-C_7)$-heterocycloalkenyl,
an aryl, wherein the aryl is an aromatic or heteroaromatic group
an alkyl aryl, wherein the aryl is an aromatic or heteroaromatic group,
a CHO,
a CO—$(C_1-C_7)$-alkyl,
a CO-aryl, wherein aryl is an aromatic or heteroaromatic group,
a $CO_2H$,
a $CO_2$—$(C_1-C_7)$-alkyl,
a CONH—$(C_1-C_7)$-alkyl,
a halogen selected from the group consisting of F, Cl, Br, and I,
$CF_3$,
$OR_a$, wherein $R_a$ represents:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NR_bR_c$, wherein $R_b$ and $R_c$ represent independently from each other:
H, a linear or branched $(C_1-C_7)$-alkyl, a $(C_3-C_7)$-cycloalkyl, CO—$(C_1-C_7)$-alkyl, or CO-aryl, wherein aryl is an aromatic or heteroaromatic group,
$NO_2$,
CN,
$SO_3H$ or a salt thereof; and
pharmaceutically acceptable salts thereof,
provided that when R represents CHRa—$NH_2$, then Y can only represent the following group (a):

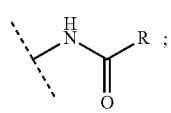

with the proviso that said compound is not of the following structure:

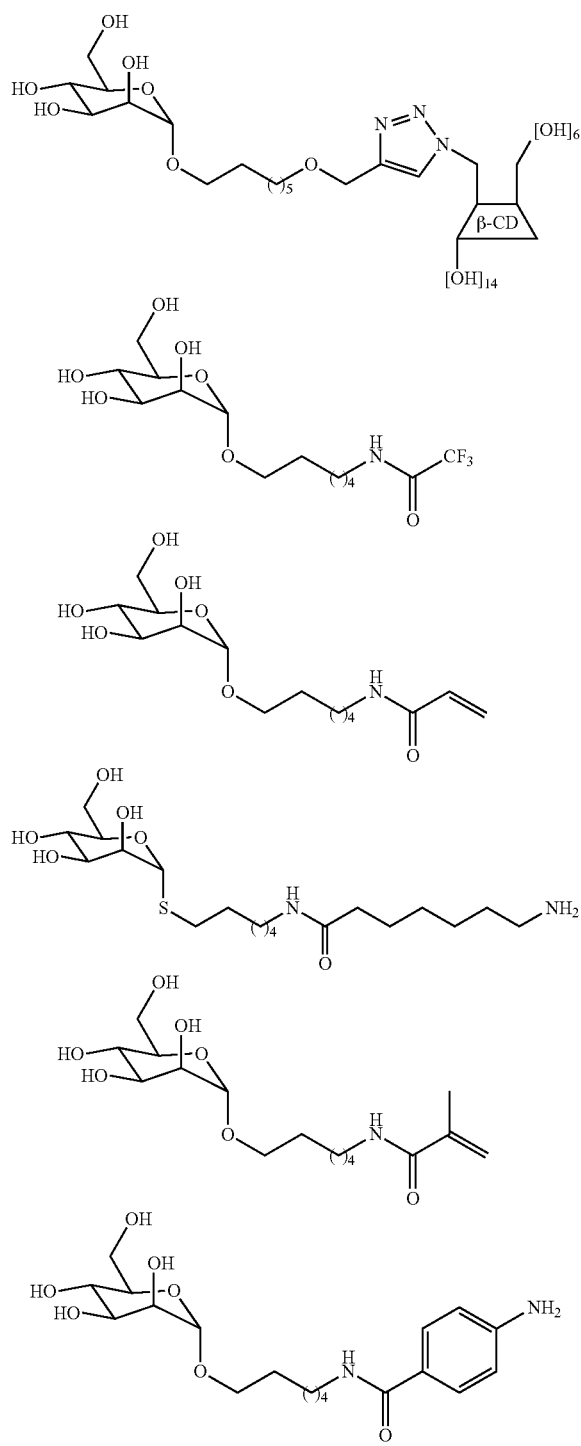

and salts thereof; and
(ii) at least one compound selected from the group consisting of antibiotics, anti-inflammatory compounds, glucocorticoids, immunosuppressive compounds and anti-TNF-alpha therapies,
said pharmaceutical composition being used for simultaneous or separate use or use spread over time intended for the treatment of inflammatory bowel disease.

2. The pharmaceutical composition according to claim 1, wherein said at least one compound of the formula (I-0) is of the following formula (I-1):

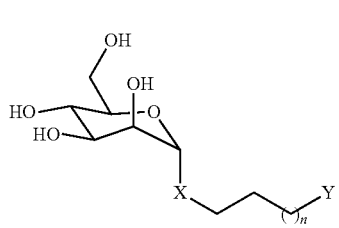

(I-1)

wherein:
X represents NH, O, S or $CH_2$;
n represents an integer comprised from 3 to 7;
Y represents a group selected from the group consisting of:

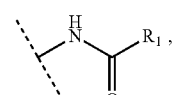

(a)

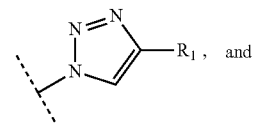

(b)

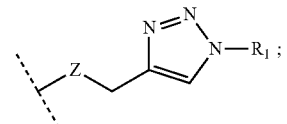

(c)

Z representing O, S or NH;
$R_1$ representing:
  H
  a linear or branched $(C_1-C_7)$-alkyl,
  a linear or branched $(C_2-C_7)$-alkenyl,
  a linear or branched $(C_2-C_7)$-alkynyl,
  a $(C_3-C_7)$-cycloalkyl,
  a $(C_5-C_7)$-cycloalkenyl,
  a $(C_3-C_7)$-heterocycloalkyl,
  a $(C_5-C_7)$-heterocycloalkenyl,
  an aryl, said aryl being an aromatic or heteroaromatic group,
  an alkyl aryl, wherein the aryl is an aromatic or heteroaromatic group,
  a CO—$(C_1-C_7)$-alkyl,
  a CO-aryl, wherein aryl is an aromatic or heteroaromatic group,
  a $CO_2H$,
  a $CO_2$—$(C_1-C_7)$-alkyl,
  a CONH—$(C_1-C_7)$-alkyl,
  $CF_3$,
  adamantyl,
  CHRa—$NH_2$, wherein Ra represents the side chain of a proteinogenic amino acid,
said $(C_1-C_7)$-alkyl, $(C_2-C_7)$-alkenyl, $(C_2-C_7)$-alkynyl, $(C_3-C_7)$-cycloalkyl, $(C_5-C_7)$-cycloalkenyl, $(C_3-C_7)$-heterocycloalkyl, $(C_5-C_7)$-heterocycloalkenyl, CO—$(C_1-C_7)$-alkyl, $CO_2$—$(C_1-C_7)$-alkyl, CONH—$(C_1-C_7)$- alkyl, aryl, alkyl aryl and CO-aryl being optionally substituted by one or more substituent(s), each independently selected from the group consisting of:

a linear or branched $(C_1\text{-}C_7)$-alkyl, a linear or branched $(C_2\text{-}C_7)$-alkenyl, a linear or branched $(C_2\text{-}C_7)$-alkynyl, a $(C_3\text{-}C_7)$-cycloalkyl, a $(C_5\text{-}C_7)$-cycloalkenyl, a $(C_3\text{-}C_7)$-heterocycloalkyl, a $(C_5\text{-}C_7)$-heterocycloalkenyl, an aryl, wherein the aryl is an aromatic or heteroaromatic group, an alkyl aryl, wherein the aryl is an aromatic or heteroaromatic group, a CHO, a CO—$(C_1\text{-}C_7)$-alkyl, a CO-aryl, wherein aryl is an aromatic or heteroaromatic group, a $CO_2H$, a $CO_2$—$(C_1\text{-}C_7)$-alkyl, a CONH—$(C_1\text{-}C_7)$-alkyl, a halogen selected from the group consisting of F, Cl, Br, and I, $CF_3$, $OR_a$, wherein $R_a$ represents:

H, a linear or branched $(C_1\text{-}C_7)$-alkyl, a $(C_3\text{-}C_7)$-cycloalkyl, CO—$(C_1\text{-}C_7)$-alkyl, or CO-aryl, wherein aryl is an aromatic or heteroaromatic group, $NR_bR_c$, wherein $R_b$ and $R_c$ represent independently from each other:

H, a linear or branched $(C_1\text{-}C_7)$-alkyl, a $(C_3\text{-}C_7)$-cycloalkyl, CO—$(C_1\text{-}C_7)$-alkyl, or CO-aryl, wherein aryl is an aromatic or heteroaromatic group, $NO_2$, CN; and pharmaceutically acceptable salts thereof, provided that when $R_1$ represents $CHR_a$—$NH_2$, then Y can only represent the following group (a):

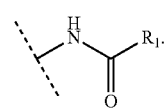

(a)

3. The pharmaceutical composition according to claim 2, wherein:

Y represents

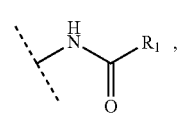

(a)

said at least one compound of the formula (I-0) being of following formula (I-1a):

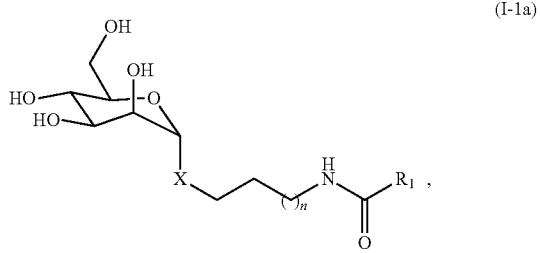

(I-1a)

X, n and $R_1$ being as previously defined;

or

Y represents

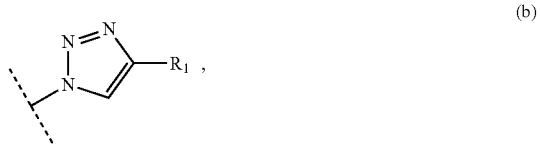

(b)

said at least one compound of the formula (I-0) being of following formula (I-1b):

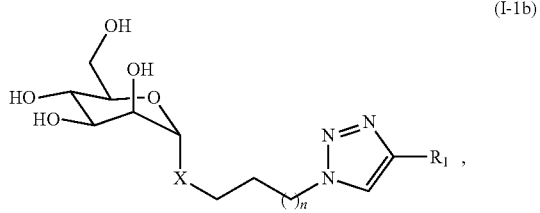

(I-1b)

X, n and $R_1$ being as previously defined;

or

Y represents

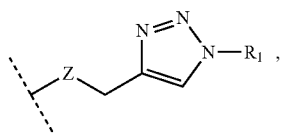

(c)

said at least one compound of the formula (I-0) being of following formula (I-1c):
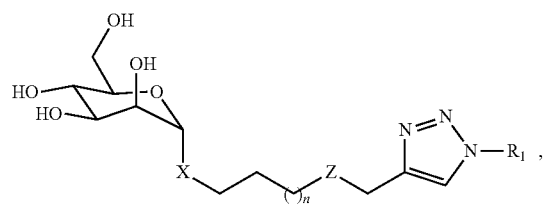
(I-1c)
X, n, Z and R₁ being as previously defined.
4. A compound selected from the group consisting of:
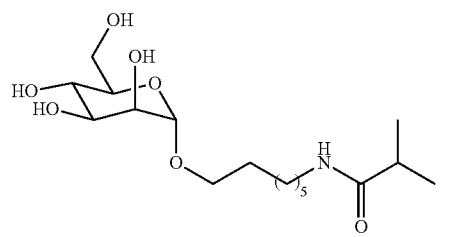
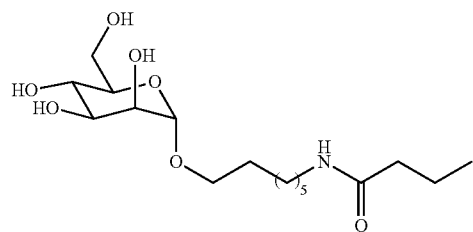
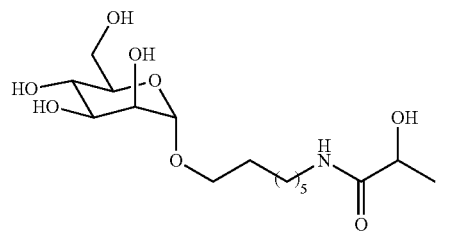
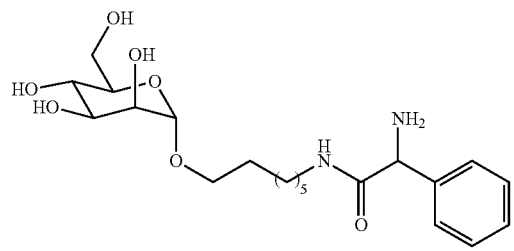
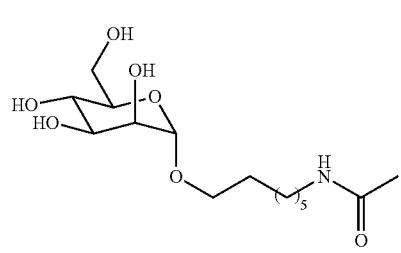
-continued
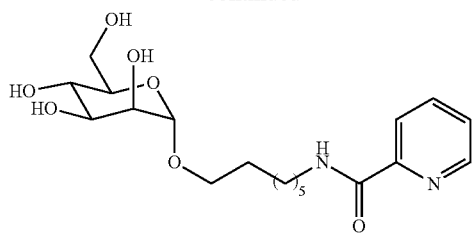
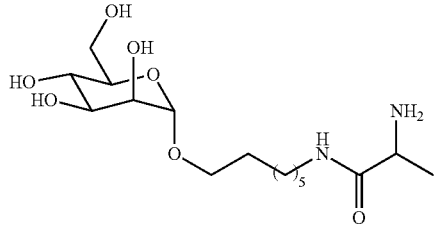
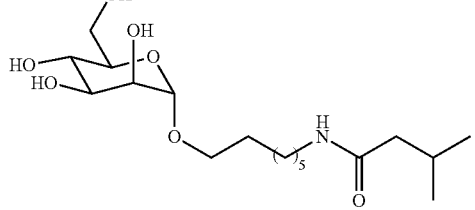
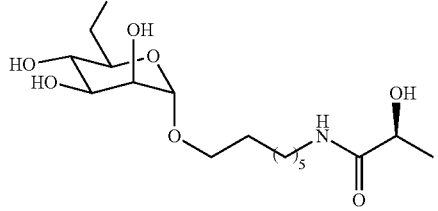
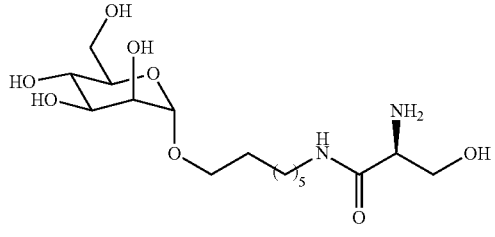
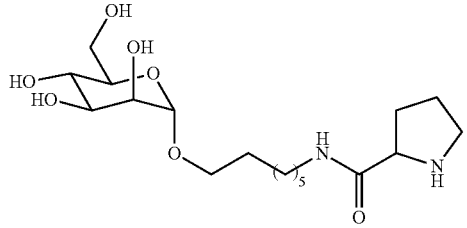
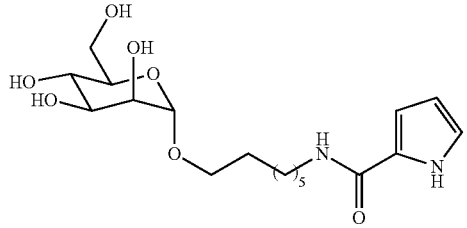

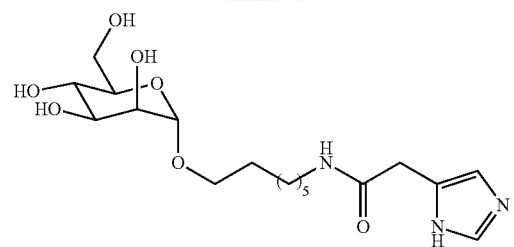
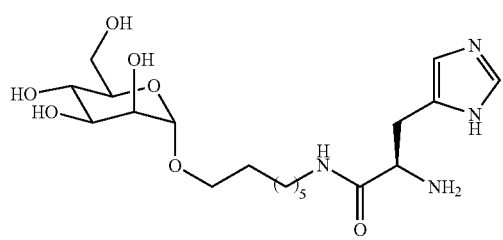
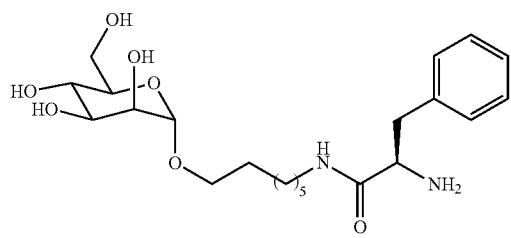
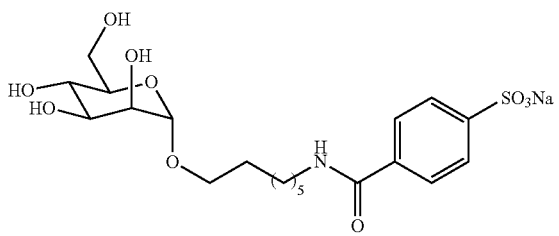
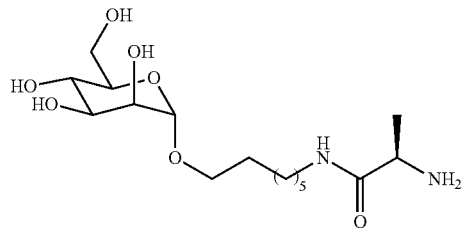
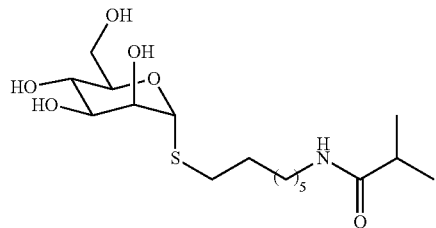
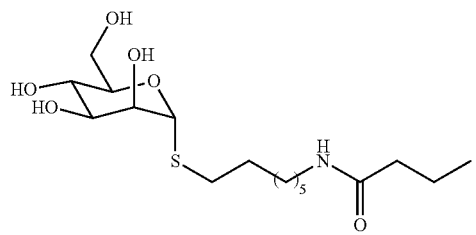
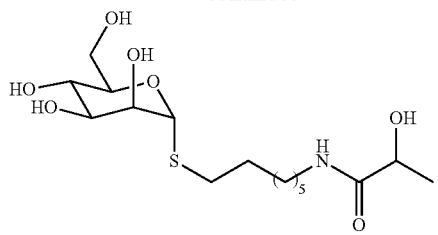
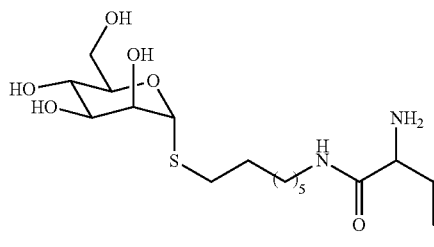
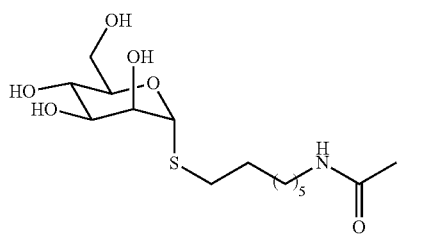
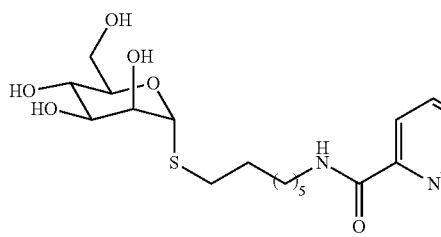
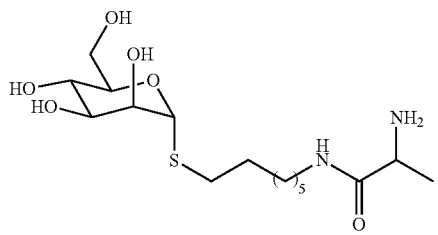
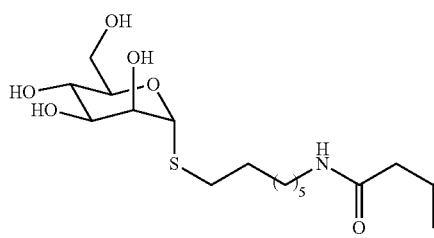
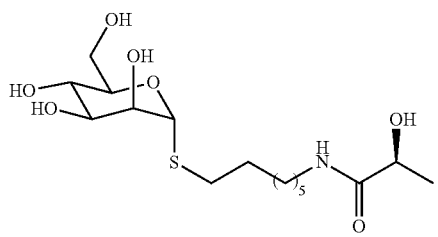

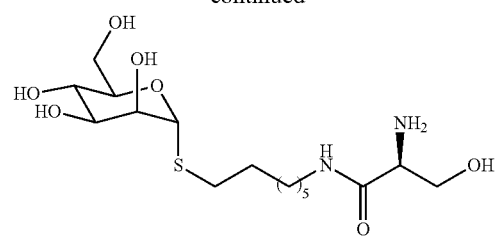
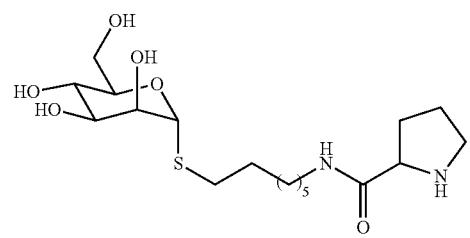
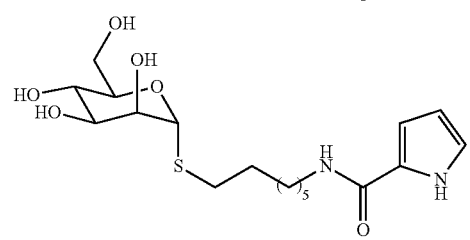
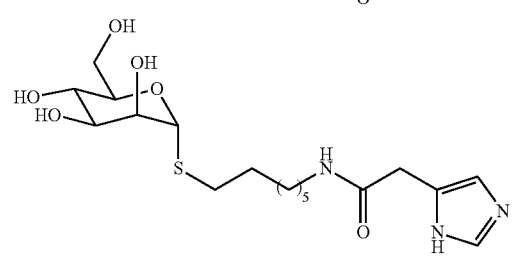
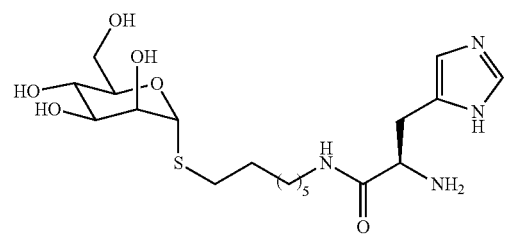
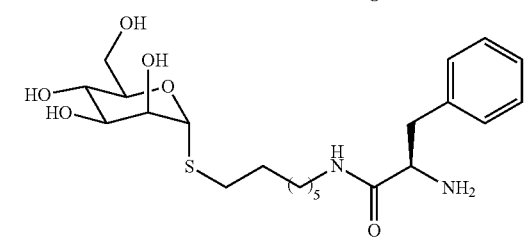
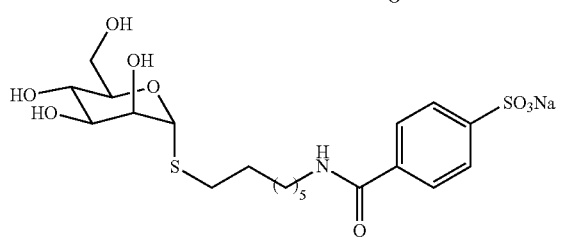
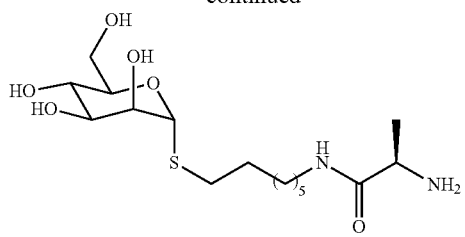
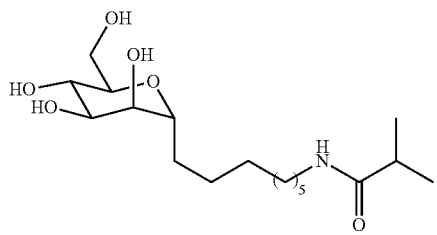
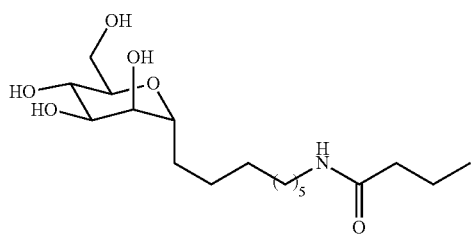
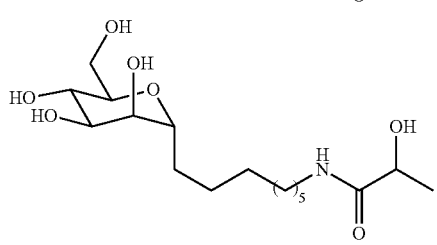
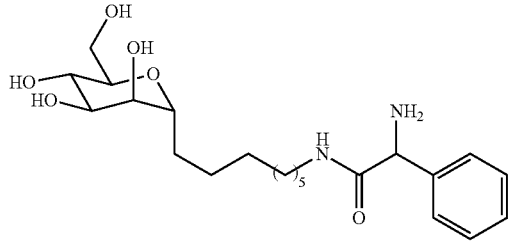
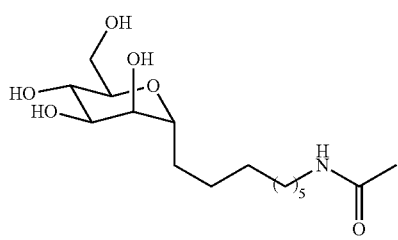
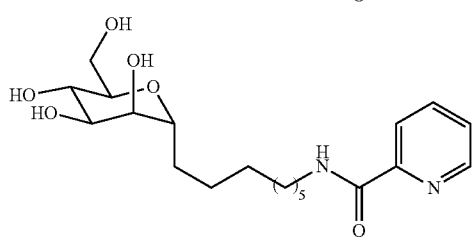

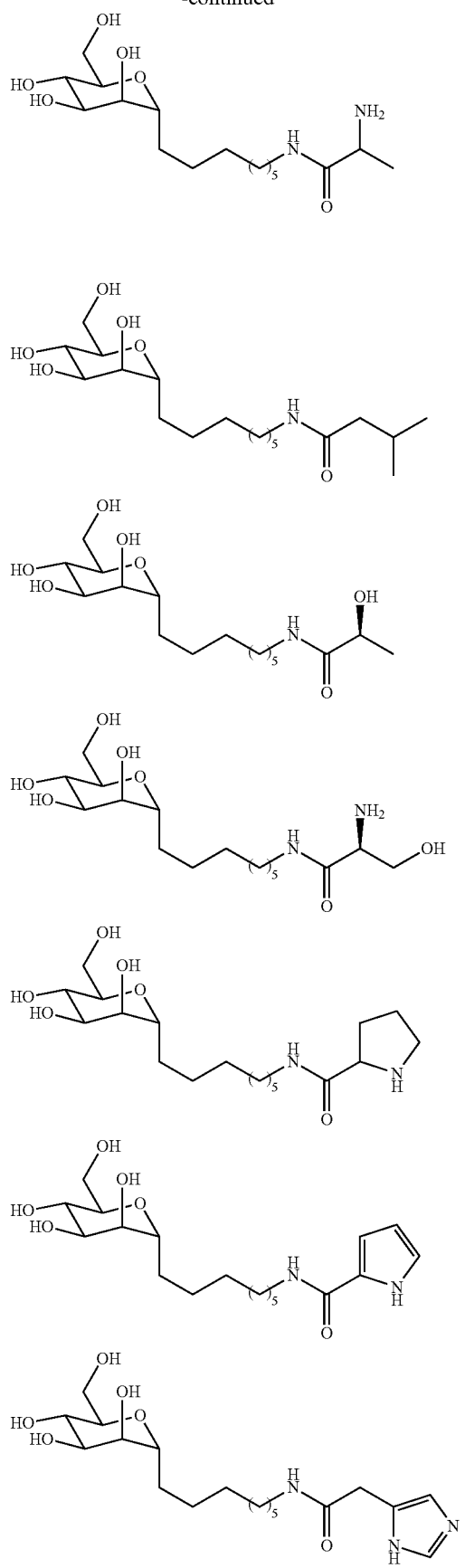
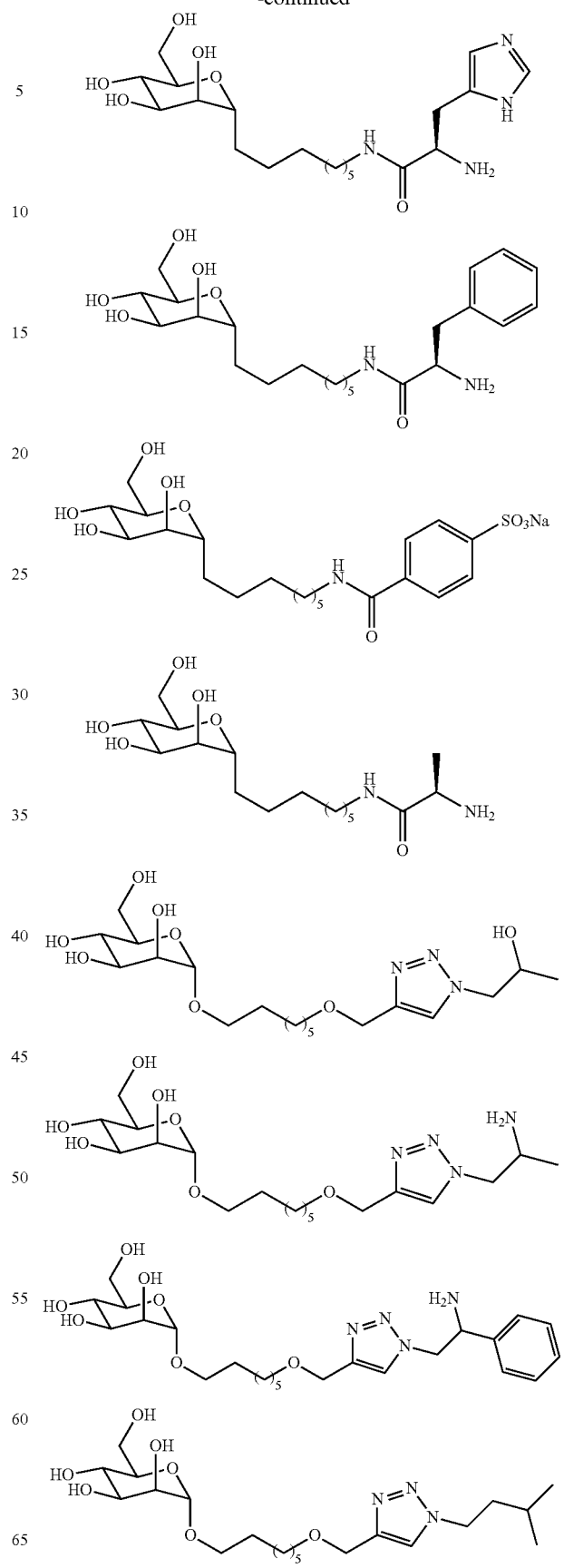

169
-continued
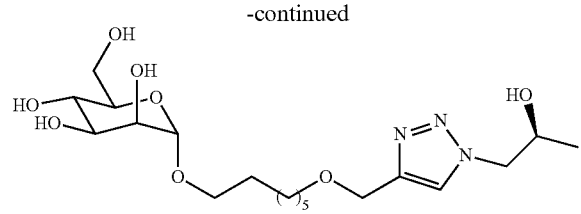
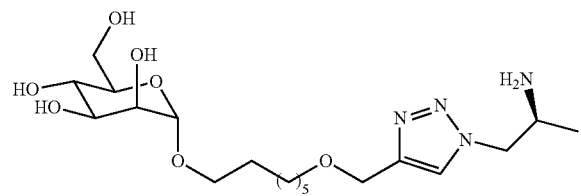
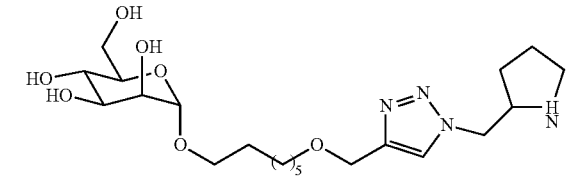
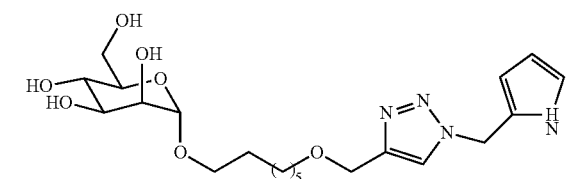
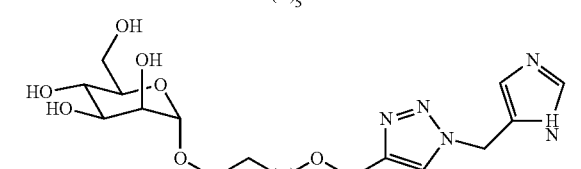
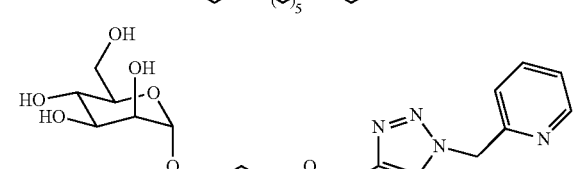
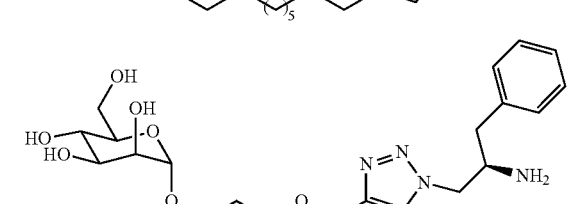
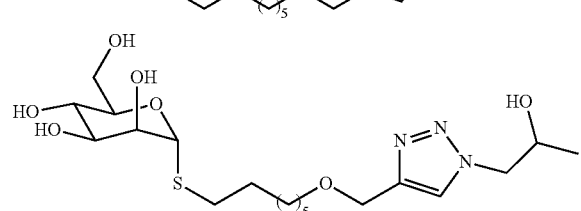
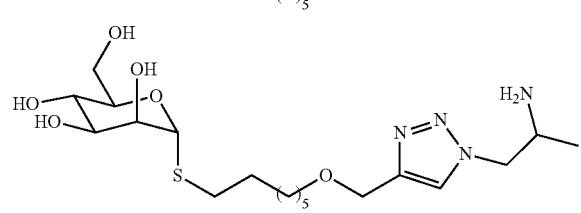
170
-continued
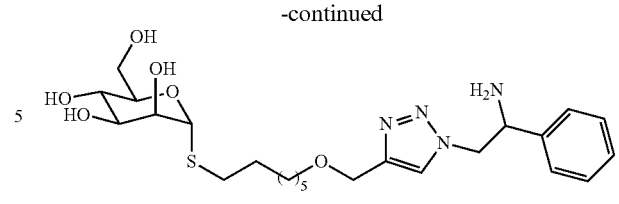
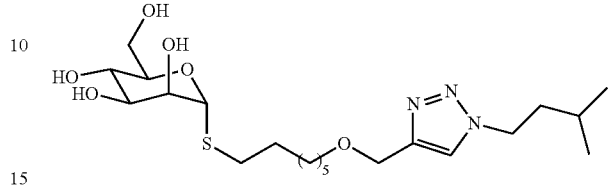
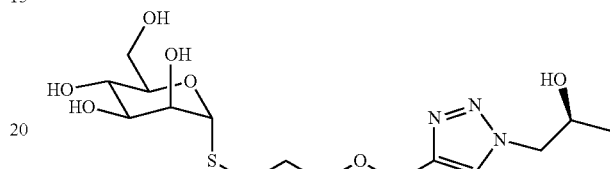
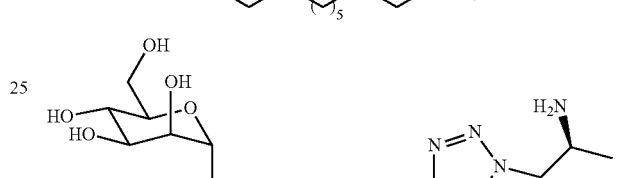
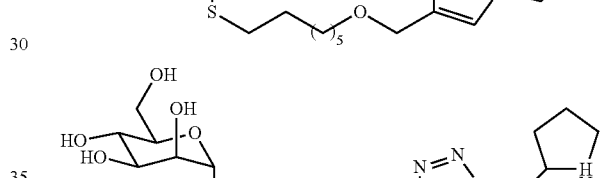
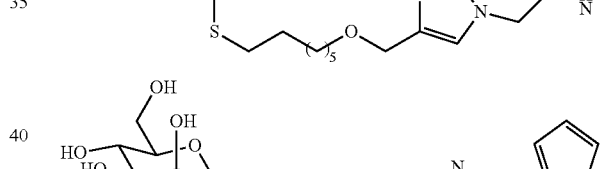
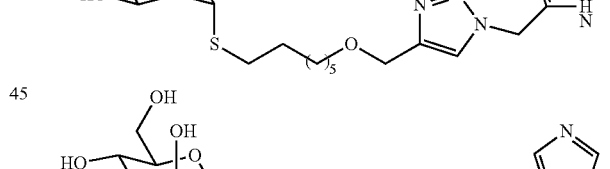
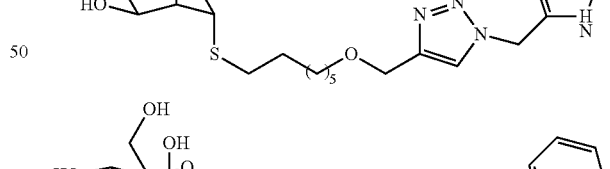
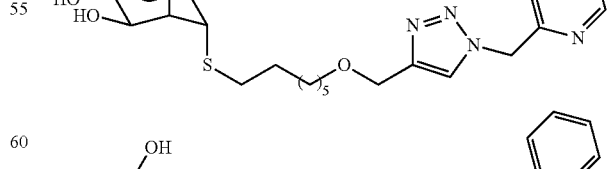
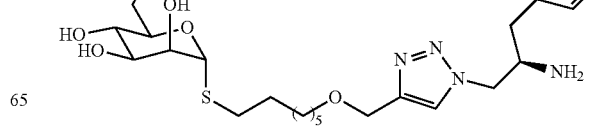

171
-continued
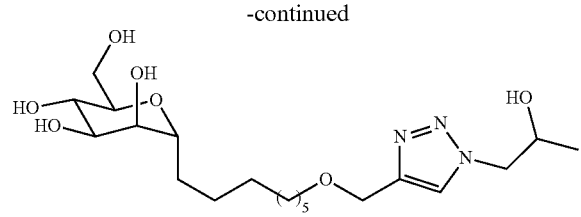
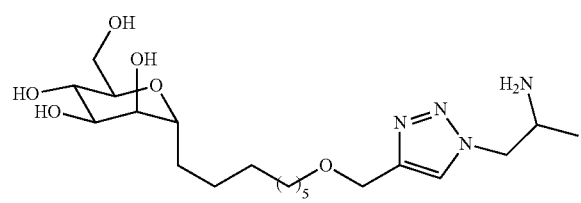
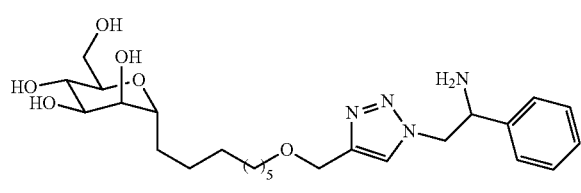
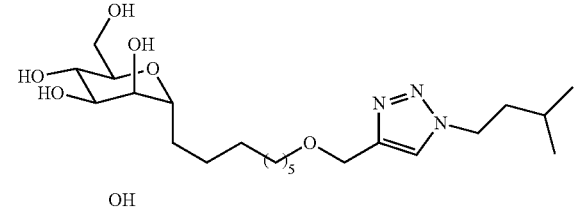
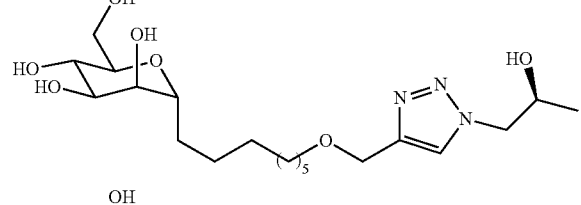
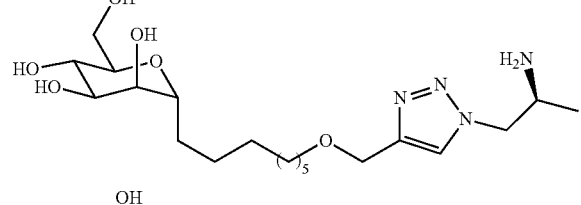
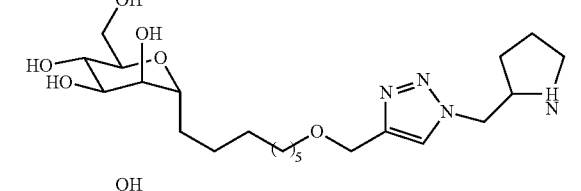
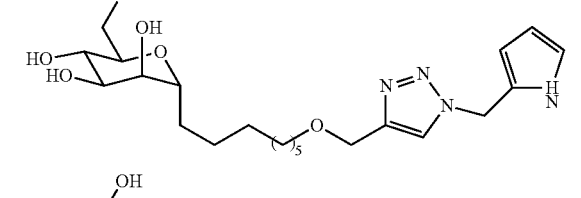
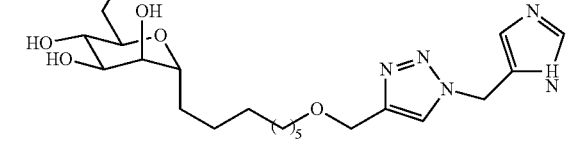
172
-continued
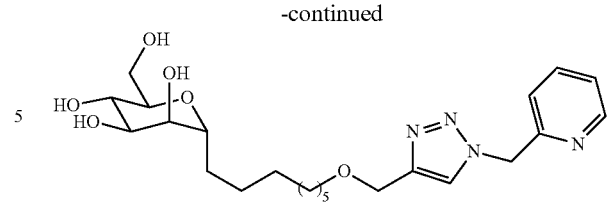
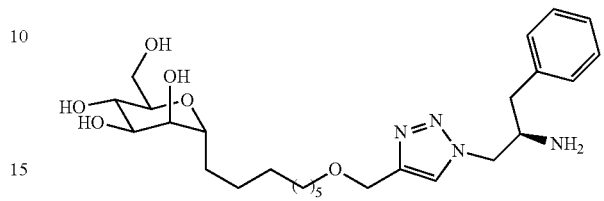
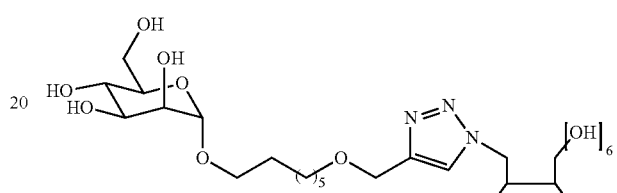
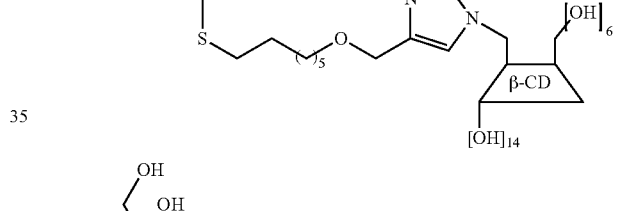
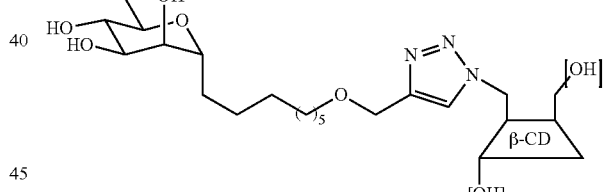
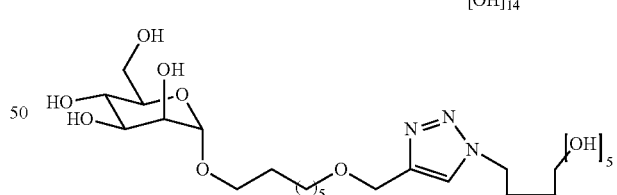
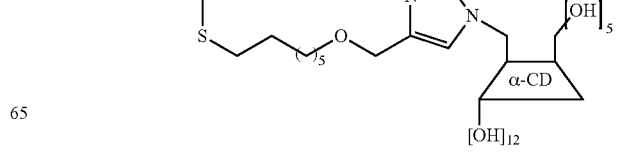

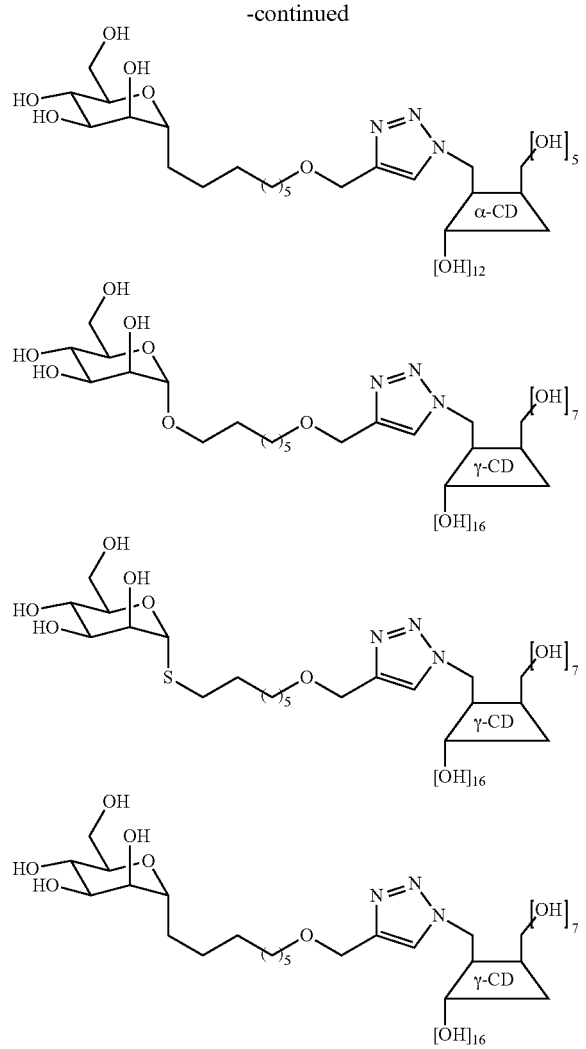

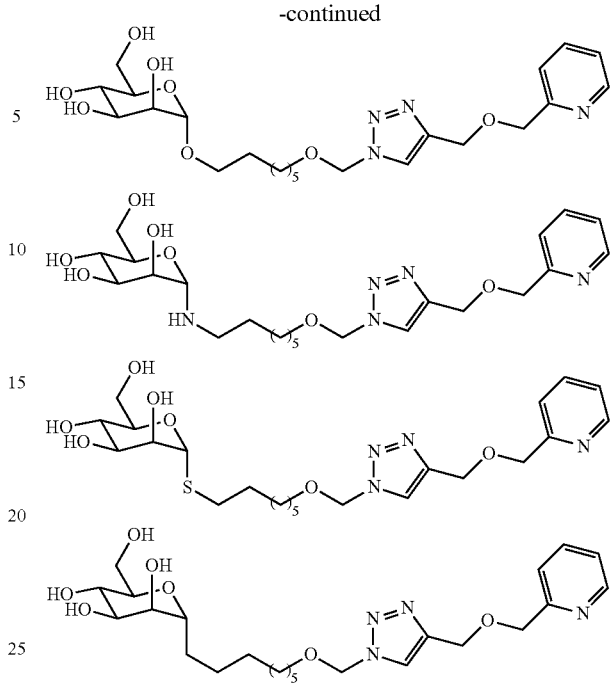

and salts thereof.

5. A pharmaceutical composition comprising, in combination with a pharmaceutically acceptable vehicle:
- at least one compound according to claim 4, and
- at least one compound selected from the group consisting of antibiotics, anti-inflammatory compounds, glucocorticoids, immunosuppressive compounds and anti-TNF-alpha therapies,
- said pharmaceutical composition being used for simultaneous or separate use or use spread over time intended for the treatment of inflammatory bowel disease.

* * * * *